US011524062B2

(12) United States Patent
Matoba et al.

(10) Patent No.: US 11,524,062 B2
(45) Date of Patent: *Dec. 13, 2022

(54) COMPOSITIONS AND METHODS FOR TREATING CANCER AND PROMOTING WOUND HEALING

(71) Applicant: University of Louisville Research Foundation, Inc., Louisville, KY (US)

(72) Inventors: Nobuyuki Matoba, Louisville, KY (US); Keegan Baldauf, Louisville, KY (US); Joshua Royal, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 147 days.

This patent is subject to a terminal disclaimer.

(21) Appl. No.: 16/997,186

(22) Filed: Aug. 19, 2020

(65) Prior Publication Data

US 2021/0038708 A1  Feb. 11, 2021

Related U.S. Application Data

(63) Continuation of application No. 15/740,622, filed as application No. PCT/US2016/040041 on Jun. 29, 2016, now Pat. No. 10,758,605.

(60) Provisional application No. 62/246,367, filed on Oct. 26, 2015, provisional application No. 62/186,151, filed on Jun. 29, 2015.

(51) Int. Cl.
| | |
|---|---|
| *A61K 31/74* | (2006.01) |
| *A61K 39/108* | (2006.01) |
| *A61K 39/187* | (2006.01) |
| *A61K 39/00* | (2006.01) |
| *A61K 39/38* | (2006.01) |
| *A61K 39/02* | (2006.01) |
| *C07K 14/28* | (2006.01) |
| *A61K 39/39* | (2006.01) |

(52) U.S. Cl.
CPC ............ *A61K 39/107* (2013.01); *A61K 39/39* (2013.01); *C07K 14/28* (2013.01); *A61K 2039/542* (2013.01); *A61K 2039/55544* (2013.01); *A61K 2039/58* (2013.01); *A61K 2039/82* (2018.08)

(58) Field of Classification Search
CPC .. A61K 39/0011; A61K 38/00; A61K 39/107; C07K 2319/00
See application file for complete search history.

(56) References Cited

U.S. PATENT DOCUMENTS

| | | | |
|---|---|---|---|
| 2,909,462 A | 10/1959 | Warfield et al. | |
| 4,464,763 A | 8/1984 | Mohler | |
| 5,888,789 A | 3/1999 | Rodriguez | |
| 6,218,864 B1 | 4/2001 | Young et al. | |
| 6,395,964 B1 | 5/2002 | Arntzen et al. | |
| 6,777,546 B2 | 8/2004 | Langridge et al. | |
| 7,041,296 B1 | 5/2006 | Stober et al. | |
| 7,556,806 B2 | 7/2009 | Wang | |
| 10,160,789 B2 | 12/2018 | Matoba et al. | |
| 10,758,605 B2 * | 9/2020 | Matoba | A61K 39/107 |
| 2002/0055618 A1 | 5/2002 | Langridge et al. | |
| 2003/0021803 A1 | 1/2003 | Langridge et al. | |
| 2003/0165543 A1 | 9/2003 | Langridge et al. | |
| 2003/0191076 A1 | 10/2003 | Wesselingh et al. | |
| 2004/0043003 A1 | 3/2004 | Chen et al. | |
| 2005/0044588 A1 | 2/2005 | Langridge et al. | |
| 2005/0186219 A1 | 8/2005 | Langridge et al. | |
| 2005/0241024 A1 | 10/2005 | Langridge et al. | |
| 2005/0244424 A1 | 11/2005 | Wang | |
| 2005/0277635 A1 | 12/2005 | Bornemann et al. | |
| 2006/0199778 A1 | 9/2006 | Ellis-Behnke et al. | |
| 2006/0211087 A1 | 9/2006 | Roosild et al. | |
| 2006/0286096 A1 | 12/2006 | Swain et al. | |
| 2007/0041981 A1 | 2/2007 | Howard et al. | |
| 2007/0192905 A1 | 8/2007 | Piller et al. | |
| 2008/0060092 A1 | 3/2008 | Dickey et al. | |
| 2008/0233083 A1 | 9/2008 | Ansari et al. | |
| 2008/0279877 A1 | 11/2008 | Yusibov et al. | |
| 2009/0081256 A1 | 3/2009 | Langridge et al. | |
| 2009/0155297 A1 | 6/2009 | Mrsny | |
| 2009/0214570 A1 | 8/2009 | Mrsny et al. | |
| 2010/0303835 A1 | 12/2010 | Gocke et al. | |

(Continued)

FOREIGN PATENT DOCUMENTS

| | | |
|---|---|---|
| WO | 91002071 A2 | 2/1991 |
| WO | 95006128 A3 | 3/1995 |

(Continued)

OTHER PUBLICATIONS

Final Office Action for U.S. Appl. No. 16/201,585, entitled "Polypeptides Having Immunoactivating Activity and Methods of Producing the Same," dated Nov. 12, 2021.

(Continued)

*Primary Examiner* — Gary B Nickol
*Assistant Examiner* — Lakia J Jackson-Tongue
(74) *Attorney, Agent, or Firm* — Hamilton, Brook, Smith & Reynolds, P.C.

(57) ABSTRACT

Protein complex variants, compositions, and methods of use thereof are provided. The protein complex variant includes a cholera toxin B subunit variant having one or more modifications thereto. The method of use thereof includes treating a disease by administering an effective amount of a composition including a cholera toxin B subunit variant to a subject in need thereof.

20 Claims, 80 Drawing Sheets

Specification includes a Sequence Listing.

(56) References Cited

U.S. PATENT DOCUMENTS

| | | |
|---|---|---|
| 2012/0100171 A1 | 4/2012 | Henry |
| 2012/0100609 A1 | 4/2012 | Crawford et al. |
| 2014/0286986 A1 | 9/2014 | Matoba |
| 2019/0085036 A1 | 3/2019 | Matoba |
| 2019/0111123 A1 | 4/2019 | Matoba et al. |

FOREIGN PATENT DOCUMENTS

| | | |
|---|---|---|
| WO | 98016247 A1 | 4/1998 |
| WO | WO 2012/125720 A2 | 9/2012 |
| WO | WO 2013/148258 A1 | 10/2013 |
| WO | WO 2017/004168 A1 | 1/2017 |

OTHER PUBLICATIONS

Bauldauf, K.J., et al., "Cholera Toxin B: One Subunit with Many Pharmaceutical Applications", Toxins 2015, 7, 974-996.

Boirivant M., et al., "Oral Administration of Recombinant Cholera Toxn Subunit B Inhibits IL-12-Mediated Murine Experimental (Trinitrobenzene Sulfonic Acide) Colitis", The Journal of Immunology, 166(5): 3522-2532, Mar. 1, 2001.

Coccia, E.M., et al., "Cholera toxin subunit B inhibits IL-12 and IFN-γ production and signaling in experimental colitis and Crohn's disease", GUT, 54(11): 1558-1564, Nov. 1, 2005.

Fensterle, J., et al., "Cancer immunotherapy based on recombinant *Salmonella enterica* serovar Typhimurium aroA strains secreting prostate-specific antigen and cholera toxin subunit B", Cancer Gene Therapy, (2008) 15, 85-93.

Hamorsky, K.T., et al., N-Glycosylation of cholera toxin B subunit in Nicotiana benthamiana: impacts on host stress response, production yeield and vaccine potential, Scientific Reports, 5 (1): 1-9, Jan. 23, 2015.

Hamorsky, K.T., et al., "Rapid and Scalable Plant-based Production of a Cholera Toxin B Subunit Variant to Aid in Mass Vaccination against Cholera Outbreaks", PLOS Neglected Tropical Diseases, 7(3): p. e2046, Mar. 7, 2013.

Stal, P., et al., "Clinical trial: the safety and short-term efficacy of recombinant cholera toxin B subunit in the treatment of active Crohns' disease", Alimentary Pharmacology & Therapeutics, 31:3 387-395, Feb. 1, 2010.

Supplemental European Search Report for EP Application No. 16818658, "Compositions and Methods for Treating Cancer and Promoting Wound Healing", dated Dec. 19, 2018.

J. Sanchez, J. Holmgren, Cholera toxin structure, gene regulation and pathophysiological and immunological aspects. CellMol Life Sci 65, 1347-1360 (2008).

R. G. Zhang et al, The 2.4 A crystal structure of cholera toxin B subunit pentamer: choleragenoid. Journal of molecular biology 251, 550-562 (1995).

T. Jelinek, H. Kollaritsch, Vaccination with Dukoral against travelers' diarrhea (ETEC) and cholera. Expert Rev Vaccines 7, 561-567 (2008).

J. Clemens, S. Shin, D. Sur, G. B. Nair, J. Holmgren, New-generation vaccines against cholera. Nature reviews. Gastroenterology & hepatology 8, 701-710 (2011).

J. Holmgren et al., Mucosal adjuvants and anti-infection and anti-immunopathology vaccines based on cholera toxin, cholera toxin B subunit and CpG DNA. Immunology letters 97, 181-188 (2005).

J. B. Sun, C. Czerkinsky, J. Holmgren, Mucosally induced immunological tolerance, regulatory T cells and the adjuvant effect by cholera toxin B subunit. Scand J Immunol 71, 1-11 (2010).

H. H. Smits et al, Cholera toxin B suppresses allergic inflammation through induction of secretory IgA. Mucosal Immunol 2, 331-339 (2009).

M. Stanford et al., Oral tolerization with peptide 336-351 linked to cholera toxin B subunit in preventing relapses of uveitis in Behcet's disease. Clin Exp Immunol 137, 201-208 (2004).

M. H. Kothary, E. F. Claverie, M. D. Miliotis, J. M. Madden, S. H. Richardson, Purification and characterization of a Chinese hamster ovary cell elongation factor of Vibrio hollisae. Infection and immunity 63, 2418-2423 (1995).

K. Gloudemans et al, The mucosal adjuvant cholera toxin B instructs non-mucosal dendritic cells to promote IgA production via retinoic acid and TGF-beta. PLoS One 8, e59822 (2013).

L. Guo et al., Prophylactic and therapeutic efficacy of the epitope vaccine CTB-UA against Helicobacter pylori infection in a BALB/c mice model. Applied microbiology and biotechnology 95, 1437-1444 (2012).

D. M. Gonzalez, D. Medici, Signaling mechanisms of the epithelial-mesenchymal transition. Science signaling 7, re8 (2014).

P. Biancheri et al., The role of transforming growth factor (TGF)-beta in modulating the immune response and fibrogenesis in the gut. Cytokine Growth Factor Rev 25, 45-55 (2014).

Sturm, A. U. Dignass, Epithelial restitution and wound healing in inflammatory bowel disease. World J Gastroenterol 14, 348-353 (2008).

P. Balogh, S. Katz, A. L. Kiss, The role of endocytic pathways in TGF-beta signaling. Pathol Oncol Res 19, 141-148 (2013).

G. Jego, A. Hazoume, R. Seigneuric, C. Garrido, Targeting heat shock proteins in cancer. Cancer Lett 332, 275-285 (2013).

G. D. Lianos et al., The role of heat shock proteins in cancer. Cancer Lett 360, 114-118 (2015).

T. Kayashima et al., Consumption of vitamin B6 reduces colonic damage and protein expression of HSP70 and HO-1, the anti-tumor targets, in rats exposed to 1,2-dimethylhydrazine. Oncol Lett 2, 1243-1246 (2011).

V. Khattar, J. Fried, B. Xu, J. V. Thottassery, Cks1 proteasomal degradation is induced by inhibiting Hsp90-mediated chaperoning in cancer cells. Cancer Chemother Pharmacol 75, 411-420 (2015).

J. S. Chen et al, Secreted heat shock protein 90alpha induces colorectal cancer cell invasion through CD91/LRP-1 and NF-kappaB-mediated integrin alphaV expression. The Journal of biological chemistry 285, 25458-25466 (2010).

S. Baindur-Hudson, A. L. Edkins, G. L. Blatch, Hsp70/Hsp90 organising protein (hop): beyond interactions with chaperones and prion proteins. Subcell Biochem 78, 69-90 (2015).

F. F. Anhe et al, A polyphenol-rich cranberry extract protects from diet-induced obesity, insulin resistance and intestinal inflammation in association with increased *Akkermansia* spp. population in the gut microbiota of mice. Gut 64, 872-883 (2015).

F. Gutierrez-Orozco et al, Intestinal microbial dysbiosis and colonic epithelial cell hyperproliferation by dietary alpha-mangostin is independent of mouse strain. Nutrients 7, 764-784 (2015).

P. Desreumaux, S. Ghosh, Review article: mode of action and delivery of 5-aminosalicylic acid—new evidence. Aliment Pharmacol Ther 24 Suppl 1, 2-9 (2006).

G. Bamias, G. Kaltsa, S. D. Ladas, Cytokines in the pathogenesis of ulcerative colitis. DiscovMed 11, 459-467 (2011).

M. H. Zaki, M. Lamkanfi, T. D. Kanneganti, The Nlrp3 inflammasome: contributions to intestinal homeostasis. Trends Immunol 32, 171-179 (2011).

J. Dabritz et al., Reprogramming of monocytes by GM-CSF contributes to regulatory immune functions during intestinal inflammation. J Immunol 194, 2424-2438 (2015).

D. C. Lacey et al., Defining GM-CSF- and macrophage-CSF-dependent macrophage responses by in vitro models. J Immunol 188, 5752-5765 (2012).

Matos, A. F. Bento, R. Marcon, R. F. Claudino, J. B. Calixto, Preventive and therapeutic oral administration of the pentacyclic triterpene alpha,beta-amyrin ameliorates dextran sulfate sodium-induced colitis in mice: the relevance of cannabinoid system. Mol Immunol 54, 482-492 (2013).

S. Wirtz, C. Neufert, B. Weigmann, M. F. Neurath, Chemically induced mouse models of intestinal inflammation. Nature protocols 2, 541-546 (2007).

N. A. Williams, T. R. Hirst, T. O. Nashar, Immune modulation by the cholera-like enterotoxins: from adjuvant to therapeutic. Immunology today 20, 95-101 (1999).

(56) References Cited

OTHER PUBLICATIONS

N. A. Williams, Immune modulation by the cholera-like enterotoxin B-subunits: from adjuvant to immunotherapeutic. International journal of medical microbiology: IJMM 290, 447-453 (2000).
D'Ambrosio, M. Colucci, O. Pugliese, F. Quintieri, M. Boirivant, Cholera toxin B subunit promotes the induction of regulatory T cells by preventing human dendritic cell maturation. JLeukoc Biol 84, 661-668 (2008).
V. Burkart et al, Cholera toxin B pretreatment of macrophages and monocytes diminishes their proinflammatory responsiveness to lipopolysaccharide. J Immunol 168, 1730-1737 (2002).
M. Kaplan, B. B. Mentes, E. Tatlicioglu, B. Kayhan, C. Aybay, Effect of mucosal immunomodulation with fed cholera toxin on healing of experimental colonic anastomosis. Diseases of the colon and rectum 45, 819-825 (2002).
P. H. Kim, L. Eckmann, W. J. Lee, W. Han, M. F. Kagnoff, Cholera toxin and cholera toxin B subunit induce IgA switching through the action of TGF-beta 1. J Immunol 160, 1198-1203 (1998).
Hameedaldeen, J. Liu, A. Batres, G. S. Graves, D. T. Graves, FOXO1, TGF-beta regulation and wound healing. International journal of molecular sciences 15, 16257-16269 (2014).
Y. Jung, M. E. Rothenberg, Roles and regulation of gastrointestinal eosinophils in immunity and disease. J Immunol 193, 999-1005 (2014).
Y. Wang et al, Tumor-derived GM-CSF promotes inflammatory colon carcinogenesis via stimulating epithelial release of VEGF. Cancer Res 74, 716-726 (2014).
R. Cutroneo, TGF-beta-induced fibrosis and SMAD signaling: oligo decoys as natural therapeutics for inhibition of tissue fibrosis and scarring. Wound Repair Regen 15 Suppl 1, S54-60 (2007).
W. Liu et al, A novel benzo[d]imidazole derivate prevents the development of dextran sulfate sodium-induced murine experimental colitis via inhibition of LRP3 inflammasome. Biochem Pharmacol 85, 1504-1512 (2013).
A. Dieleman et al, Chronic experimental colitis induced by dextran sulphate sodium (DSS) is characterized by Th1 and Th2 cytokines. Clin Exp Immunol 114, 385-391 (1998).
Yue, Z. Shen, C. H. Yu, H. Ye, Y. M. Li, The therapeutic role of oral tolerance in dextran sulfate sodium-induced colitis via Th1-Th2 balance and gammadelta T cells. Journal of digestive diseases 14, 543-551 (2013).
K. Karlinger, T. Gyorke, E. Mako, A. Mester, Z. Tarjan, The epidemiology and the pathogenesis of inflammatory bowel disease. European journal of radiology 35, 154-167 (2000).
G. Latella, C. Papi, Crucial steps in the natural history of inflammatory bowel disease. World J Gastroenterol 18, 3790-3799 (2012).
A. Engel, M. Khalil, M. F. Neurath, Highlights in inflammatory bowel disease—from bench to bedside. Clinical chemistry and laboratory medicine: CCLM / FESCC 50, 1229-1235 (2012).
G. Monteleone, R. Caruso, F. Pallone, Targets for new immunomodulation strategies in inflammatory bowel disease. Autoimmun Rev 13, 11-14 (2014).
Geremia, P. Biancheri, P. Allan, G. R. Corazza, A. Di Sabatino, Innate and adaptive immunity in inflammatory bowel disease. Autoimmun Rev 13, 3-10 (2014).
M. Globig et al., Comprehensive intestinal T helper cell profiling reveals specific accumulation of IFN-gamma IL-17 coproducing CD4+ T cells in active inflammatory bowel disease. Inflamm Bowel Dis 20, 2321-2329 (2014).
R. Siegel, D. Naishadham, A. Jemal, Cancer statistics, 2012. CA Cancer J Clin 62, 10-29 (2012).
P. Munkholm, Review article: the incidence and prevalence of colorectal cancer in inflammatory bowel disease. Aliment Pharmacol Ther 18 Suppl 2, 1-5 (2003).
Doulberis et al., Cholera-toxin suppresses carcinogenesis in a mouse model of inflammation-driven sporadic colon cancer. Carcinogenesis 36, 280-290 (2015).
K. Bulut et al., Glucagon-like peptide 2 improves intestinal wound healing through induction of epithelial cell migration in vitro-evidence for a TGF—beta-mediated effect. RegulPept 111, 137-143 (2004).
H. S. Cooper, S. N. Murthy, R. S. Shah, D. J. Sedergran, Clinicopathologic study of dextran sulfate sodium experimental murine colitis. Laboratory investigation; a journal of technical methods and pathology 69, 238-249 (1993).
Ordas, I, Eckmann, L., Talamini, M., Baumgart, DC, & Sandborn, WJ. Ulcerative Colitis. Lancet. 380(9853), 1606-19 (2012).
E. Ruckova, P. Muller, R. Nenutil, B. Vojtesek. Alterations of the Hsp70/Hsp90 chaperone and the HOP/CHIP co-chaperone system in cancer. Cell Mol Biol Lett 17. 446-458 (2012).
Y. L. Jones-Hall, M. B. Grisham. Immunopathological characterization of selected mouse models of inflammatory bowel disease: Comparison to human disease. Pathophysiology 21. 267-288 (2014).
J. B. Sun, C. Czerkinsky, J. Holmgren. B Lymphocytes Treated In Vitro with Antigen Coupled to Cholera Toxin B Subunit Induce Antigen-Specific Foxp3(+) Regulatory T Cells and Protect against Experimental Autoimmune Encephalomyelitis. Journal of Immunology '188. 1686-1697 (2012).
D. Ma, D. Wolvers, A. M. Stanisz, J. Bienenstock. Interleukin-10 and nerve growth factor have reciprocal upregulatory effects on intestinal epithelial cells. Am J Physiol Regul Integr Comp Physiol ' 284. R1323-1329 (2003).
A. Phipps, M. R. Stanford, J. B. Sun, B. G. Xiao, J. Holmgren, T. Shinnick, A. Hasan, Y. Mizushima, T. Lehner. Prevention of mucosally induced uveitis with a HSP60-derived peptide linked to cholera toxin B subunit. Eur J Immunol 33. 224-232 (2003).
J. B. Sun, B. G. Xiao, M. Lindblad, B. L. Li, H. Link, C. Czerkinsky, J. Holmgren. Oral administration of cholera toxin B subunit conjugated to myelin basic protein protects against experimental autoimmune encephalomyelitis by inducing transforming growth factor-beta-secreting cells and suppressing chemokine expression. Int Immunol 12. 1449-1457 (2000).
J. B. Sun, B. L. Li, C. Czerkinsky, J. Holmgren. Enhanced immunological tolerance against allograft rejection by oral administration of allogeneic antigen linked to cholera toxin B subunit. Clin Immunol 97 (2). 130-139 (2000).
Aspord, C. Thivolet. Nasal administration of CTB-insulin induces active tolerance against autoimmune diabetes in non-obese diabetic (NOD) mice. Clin Exp Immunol 130. 204-211 (2002).
M. F. Neurath. New targets for mucosal healing and therapy in inflammatory bowel diseases. Mucosal Immunol 7. 6-19 (2014).
H. Oshima, M. Nakayama, T. S. Han, K. Naoi, X. Ju, Y. Maeda, S. Robine, K. Tsuchiya, T. Sato, H. Sato, M. M. Taketo, M. Oshima. Suppressing TGFbeta signaling in regenerating epithelia in an inflammatory microenvironment is sufficient to cause invasive intestinal cancer. Cancer Res 75. 766-776 (2015).
M. Stahle-Backdahl, J. Maim, B. Veress, C. Benoni, K. Bruce, A. Egesten. Increased presence of eosinophilic granulocytes expressing transforming growth factor-beta1 in collagenous colitis. Scand J Gastroenterol 35. 742-746 (2000).
K. Suzuki, X. Sun, M. Nagata, T. Kawase, H. Yamaguchi, V. Sukumaran, Y. Kawauchi, H. Kawachi, T. Nishino, K. Watanabe, H. Yoneyama, H. Asakura. Analysis of intestinal fibrosis in chronic colitis in mice induced by dextran sulfate sodium. Pathol Int 61. 228-238 (2011).
J. M. Davies, M. T. Abreu. The innate immune system and inflammatory bowel disease. Scand J Gastroenterol 50. 24-33 (2015).
M. Gross, T. M. Salame, S. Jung. Guardians of the Gut—Murine Intestinal Macrophages and Dendritic Cells. Frontiers in immunology 6. 254 (2015).
G. Leoni, P. A. Neumann, R. Sumagin, T. L. Denning, A. Nusrat. Wound repair: role of immune-epithelial interactions. Mucosal Immunol 8. 959-968 (2015).
J. E. Quails, H. Tuna, A. M. Kaplan, D. A. Cohen. Suppression of experimental colitis in mice by CD1 1c+ dendritic cells. Inflamm Bowel Dis 15 236-247 (2009).
T. Lysakova-Devine, C. O'Farrelly. Tissue-specific NK cell populations and their origin. JLeukoc Biol 96. 981-990 (2014).

(56) References Cited

OTHER PUBLICATIONS

Kiesler, I. J. Fuss, W. Strober. Experimental Models of Inflammatory Bowel Diseases. Cell Mol Gastroenterol Hepatol 1. 154-170 (2015).
Bezzio, F. Furfaro, R. de Franchis, G. Maconi, A. K. Asthana, S. Ardizzone. Ulcerative colitis: current pharmacotherapy and future directions. Expert Opin Pharmacother 15. 1659-1670 (2014).
F. Furfaro, C. Bezzio, S. Ardizzone, A. Massari, R. de Franchis, G. Maconi. Overview of biological therapy in ulcerative colitis: current and future directions. J Gastrointestin Liver Dis 24. 203-213 (2015).
B. P. Vaughn, S. Shah, A. S. Cheifetz. The role of mucosal healing in the treatment of patients with inflammatory bowel disease. Curr Treat Options Gastroenterol 12. 103-117 (2014).
A. Irizarry, B. Hobbs, F. Collin, Y. D. Beazer-Barclay, K. J. Antonellis, U. Scherf, T. P. Speed. Exploration, normalization, and summaries of high density oligonucleotide array probe level data. Biostatistics 4. 249-264 (2003).
Emedicine health, https://www.emedicinehealth.com/colon_cancer_symptoms_vs_ulcerative_colitis/topic-guide.htm, accessed on Dec. 18, 2019 (Year: 2019).
Yuki et al., "Oral MucoRice expressing double-mutant cholera toxin A and B subunits induces toxin-specific neutralizing immunity", Vaccine, 2009; 27: 5982-5988 (Year: 2009).
International Search Report for International Application No. PCT/US2016/040041, entitled "Compositions and Methods for Treating Cancer and Promoting Wound Healing," consisting of 4 pages, dated Dec. 5, 2016.
International Preliminary Report on Patentability and Written Opinion for International Application No. PCT/US2016/040041, entitled "Compositions and Methods for Treating Cancer and Promoting Wound Healing," dated Dec. 5, 2016.
Non-Final Office Action for U.S. Appl. No. 15/740,622, entitled "Compositions and Methods for Treating Cancer and Promoting Wound Healing," dated May 13, 2019.
Final Office Action for U.S. Appl. No. 15/740,622, entitled "Compositions and Methods for Treating Cancer and Promoting Wound Healing," dated Dec. 26, 2019.
Notice of Allowance for U.S. Appl. No. 15/740,622, entitled "Compositions and Methods for Treating Cancer and Promoting Wound Healing," dated Apr. 3, 2020.
Mishra et al, "Ubiquitin fusion enhances cholera toxin B subunit expressionin transgenic plants and the plant-expressed protein binds GM1 receptors more efficiently," (Journal of Biotechnology, 2006, 127(1): 95-108) (2006).
Jiang et al, "Cholera toxin B protein in transgenic tomato fruit induces immune response in mice," (Transgenic Res., 2007, 16:169-175) (2007).
GenBank® accession No. P48978; Retrieved Jul. 28, 2021.
Sola et al, "Glycosylation of Therapeutic Proteins: An Effective Strategy to Optimize Efficacy," (Biodrugs, 2010, 24(1): 9-21) (2010).
Balzarini J. "Targeting the glycans of glycoproteins: a novel paradigm for antiviral therapy" Nat Rev Microbiol. 5(8): 583-97 (2007).
Irache JM, et al., "Mannose-targeted systems for the delivery of therapeutics," Expert Opin Drug Deliv. 5(6): 703-24 (2008).
Gleba Y, et al. "Magnifection—a new platform for expressing recombinant vaccines in plants" Vaccine 23 (17-18): 2042-8 (2005).
Keler T, et al. "Mannose receptor-targeted vaccines" Expert opinion on biological therapy, 4(12): 1953-62 (2004).
Marillonnet S, et al. "In planta engineering of viral RNA replicons: efficient assembly by recombination of DNA modules delivered by Agrobacterium". Proc Natl Acad Sci U S A., 101(18): 6852-7 (2004).
Matoba N, et al. "A mucosally targeted subunit vaccine candidate eliciting HIV-1 transcytosis-blocking Abs". Proc Natl Acad Sci U S A.; 101(37): 13584-9 (2004).

Matoba N, et al. :Transcytosis-blocking Abs elicited by an oligomeric immunogen based on the membrane proximal region of HIV-1 gp41 target non-neutralizing epitopes. Curr HIV Res.; 6(3): 218-29 (2008).
Matoba N, et al. "Recombinant Protein Expression in Nicotiana". Methods Mol Biol.; 701: 199-219 (2011).
Matoba N, et al. "Humoral immune responses by prime-boost heterologous route immunizations with CTB-MPR (649-684), a mucosal subunit HIV/AIDS vaccine candidate". Vaccine; 24(23): 5047-55 (2006).
Matoba N, et al :"Biochemical and immunological characterization of the plant-derived candidate human immunodeficiency virus type 1 mucosal vaccine CTB-MPR(649-684)". Plant Biotechnol J.; 7(2): 129-45 (2009).
Sheng KC, et al.. "Delivery of antigen using a novel mannosylated dendrimer potentiates immunogenicity in vitro and in vivo". Eur J Immunol.; 38(2): 424-36 (2008).
GenBank® Accession No. AAC60441; Retrieved Jul. 28, 2021.
Arakawa, et al. "Expression of cholera toxin B subunit oligomers in transgenic potato plants," Transgenic Research, vol. 6, pp. 403-413 (1997).
ISA/KR, International Preliminary Report on Patentability and Written Opinion issued in related international application No. PCT/US2012/029072, dated Sep. 17, 2013.
ISA/KR, International Search Report issued in related international application No. PCT/US2012/029072, dated Sep. 24, 2012.
Mikschofsky, et al. "Cholera toxin B (CTB) is functional as an adjuvant for cytoplasmic proteins if directed to the endoplasmic reticulum (ER), but not to the cytoplasm of plants," Plant Science, vol. 177, pp. 35-42 (2009).
Kang et al. "Modification of the cholera toxin B subunit coding sequence to enhance expression in plants", Molecular Breeding 13: 143-153 (2004).
Lebens, M. "Synthesis of Hybrid Molecules between Heat-Labile Enterotoxin and Cholera Toxins B Subunits: Potential for Use in a Broad Spectrum Vaccine", Infection and Immunity, 2144-2150 (1996).
GenBank Accession No. AAD51360.1 (published Nov. 1999).
GenBank Accession No. CAA00098.1 (published Dec. 2005).
NCBI, GenBank accession No. CAA00066.1 (Dec. 1, 2005).
Office Action for U.S. Appl. No. 14/005,388, "Polypeptides Having Immunoactivating Activity and Methods of Producing the Same" dated Dec. 19, 2016.
Final Office Action for U.S. Appl. No. 14/005,388, "Polypeptides Having Immunoactivating Activity and Methods of Producing the Same" dated Apr. 7, 2017.
Office Action for U.S. Appl. No. 14/005,388, "Polypeptides Having Immunoactivating Activity and Methods of Producing the Same" dated Jan. 25, 2018.
Notice of Allowance for U.S. Appl. No. 14/005,388, "Polypeptides Having Immunoactivating Activity and Methods of Producing the Same" dated Aug. 9, 2018.
Office Action for U.S. Appl. No. 16/201,585, "Polypeptides Having Immunoactivating Activity and Methods of Producing the Same," dated Apr. 29, 2021.
PCT International Search Report and Written Opinion for International Application No. PCT/US2012/029072, entitled "Polypeptides Having Immunoactivating Activity and Methods of Producing the Same," dated Sep. 24, 2012.
PCT International Preliminary Report on Patentability for International Application No. PCT/US2012/029072, entitled "Polypeptides Having Immunoactivating Activity and Methods of Producing the Same," dated Sep. 17, 2013.
GenBank® accession No. P27932; Retrieved Jul. 29, 2021.
GenBank® accession No. Z71395; Retrieved Jul. 28, 2021.
GenBank® accession No. U25679, nucleotide 1 to 63; Retrieved Jul. 28, 2021.
GenBank® accession No. CAX51374; Retrieved Jul. 28, 2021.
GenBank® Accession No. AY475128; Retrieved Jul. 28, 2021.

\* cited by examiner

| Up Regulated Pathways | p Value | Gene Ratio |
|---|---|---|
| Cell Adhesion ECM Remodeling | 5.97E-07 | 10/52 |
| Development TGFβ-dependent induction of EMT via SMADs | 2.07E-06 | 8/35 |
| Development Regulation of epithelial to mesenchymal transition (EMT) | 4.37E-06 | 10/64 |
| Development MicroRNA-dependent inhibition of EMT | 7.11E-06 | 5/12 |
| Development TGFβ-dependent induction of EMT via via RhoA, PI3K and ILK | 1.80E-05 | 8/46 |
| Normal and pathological TGFβ-mediated regulation of cell proliferation | 1.61E-04 | 6/33 |
| Development TGFβ-dependent induction of EMT via MAPK | 1.70E-04 | 7/47 |
| Cell adhesion Chemokines and adhesion | 2.24E-04 | 10/100 |
| Immune response Function of MEF2 in T Lymphocytes | 2.87E-04 | 7/51 |
| Cholesterol and Sphingolipid transport / Recycling to plasma membrane in lung (normal and CF) | 2.97E-04 | 5/24 |

FIG. 4C

| Down Regulated Pathways | p Value | Gene Ratio |
|---|---|---|
| Androstenedione and testosterone biosynthesis and metabolism p.2/Rodent version | 6.838e-6 | 7/36 |
| Oxidative phosphorylation | 9.240e-6 | 11/105 |
| CFTR folding and maturation (normal and CF) | 5.341e-5 | 5/21 |
| Androstenedione and testosterone biosynthesis and metabolism p.2 | 6.763e-5 | 6/35 |
| Regulation of metabolism Bile acids regulation of glucose and lipid metabolism via FXR | 9.363e-5 | 6/37 |
| Regulation of lipid metabolism PPAR regulation of lipid metabolism | 1.941e-4 | 6/42 |
| Role of Diethylhexyl Phthalate and Tributyltin in fat cell differentiation | 2.729e-4 | 5/29 |
| Apoptosis and survival Granzyme A signaling | 3.221e-4 | 5/30 |
| Mechanisms of deltaF508 CFTR activation by S-nitrosoglutathione | 3.650e-4 | 6/47 |
| Pyruvate metabolism/ Rodent version | 3.803e-4 | 7/66 |

FIG. 4D

|   | Domain | Phylum |
|---|---|---|
|   | Bacteria | Bacteroidetes |
|   | Bacteria | Firmicutes |
|   | Bacteria | Tenericutes |
|   | Bacteria | Actinobacteria |
|   | Bacteria | Proteobacteria |
|   | Bacteria | Verrucomicrobia |
|   | Bacteria | Unclassified |
|   | Bacteria | Acidobacteria |
|   | Bacteria | Deferribacteres |

FIG. 7A

|   | Domain | Phylum | Class | Order | Family | Genus | Species |
|---|---|---|---|---|---|---|---|
|   | Bacteria | Bacteroidetes | Bacteroidia | Bacteroidales | S24-7 | 94otu11032 | 97otu53444 |
|   | Bacteria | Bacteroidetes | Bacteroidia | Bacteroidales | S24-7 | 94otu7438 | 97otu87775 |
|   | Bacteria | Bacteroidetes | Bacteroidia | Bacteroidales | S24-7 | 94otu11032 | unclassified |
|   | Bacteria | Firmicutes | Clostridia | Clostridiales | unclassified | unclassified | unclassified |
|   | Bacteria | Firmicutes | Bacilli | Lactobacillales | Lactobacillaceae | Lactobacillus | 97otu71944 |
|   | Bacteria | Firmicutes | Clostridia | Clostridiales | 91otu13759 | 94otu11810 | 97otu90453 |
|   |   |   |   |   |   |   | other |

FIG. 7B

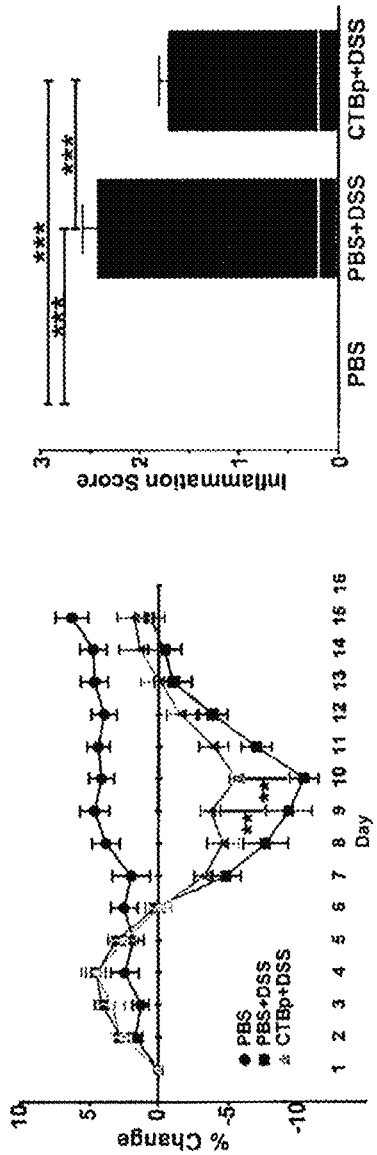
FIG. 9A
FIG. 9B
FIG. 9C

Normal Tissue 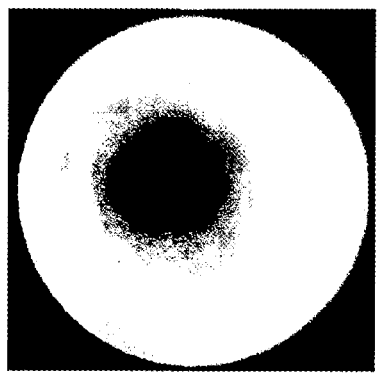
Grade 1 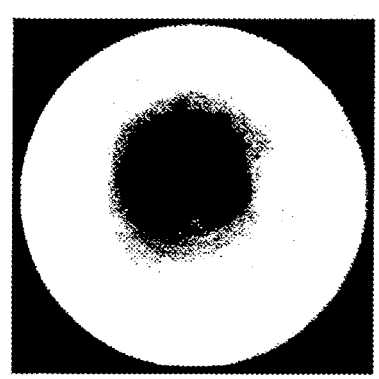
Grade 2 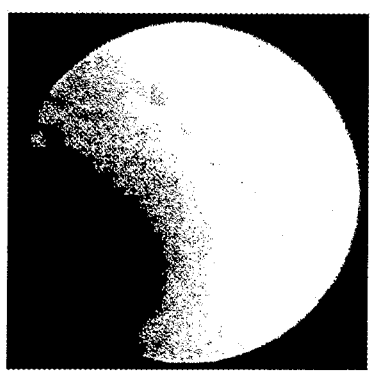
Grade 3 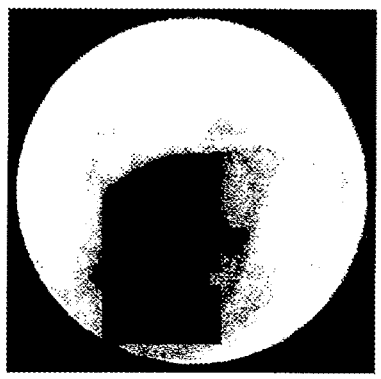
Grade 4 
Grade 5 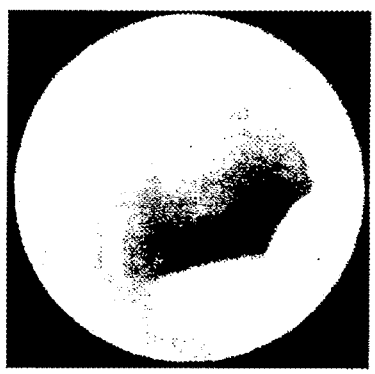
FIG. 16

Find an optimal dosage of CTBp

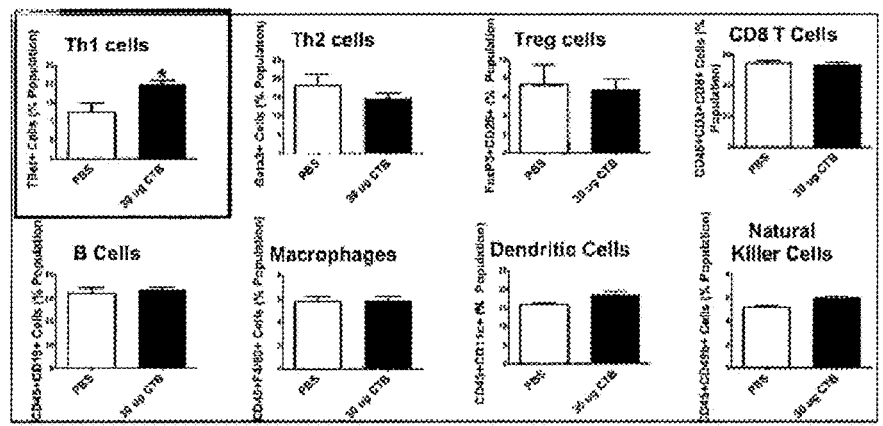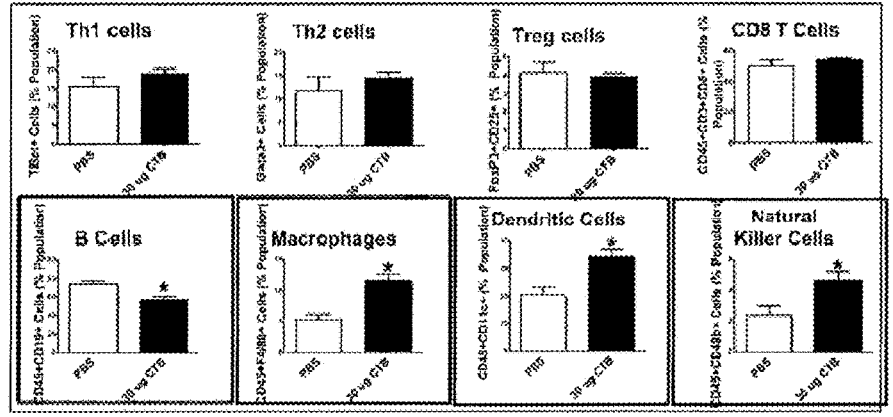
FIG. 22

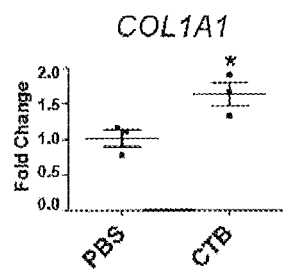 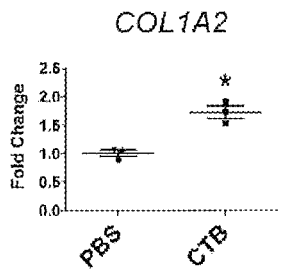 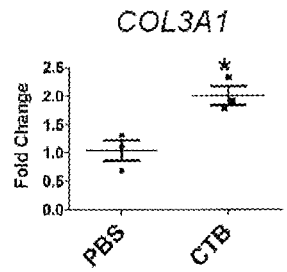 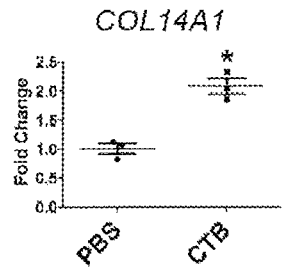
FIG. 23A     FIG. 23B     FIG. 23C     FIG. 23D
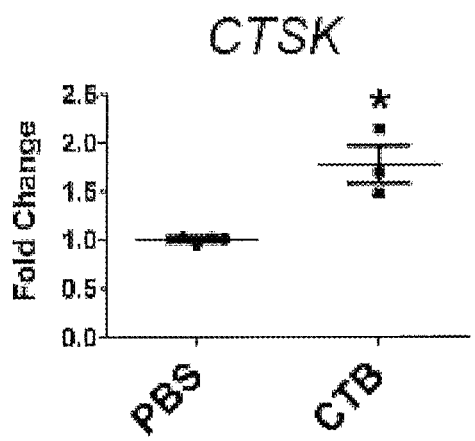 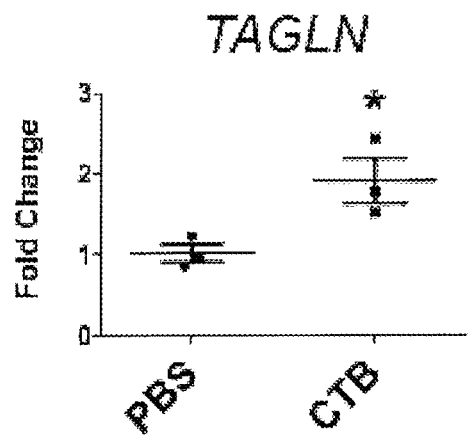
FIG. 24A     FIG. 24B

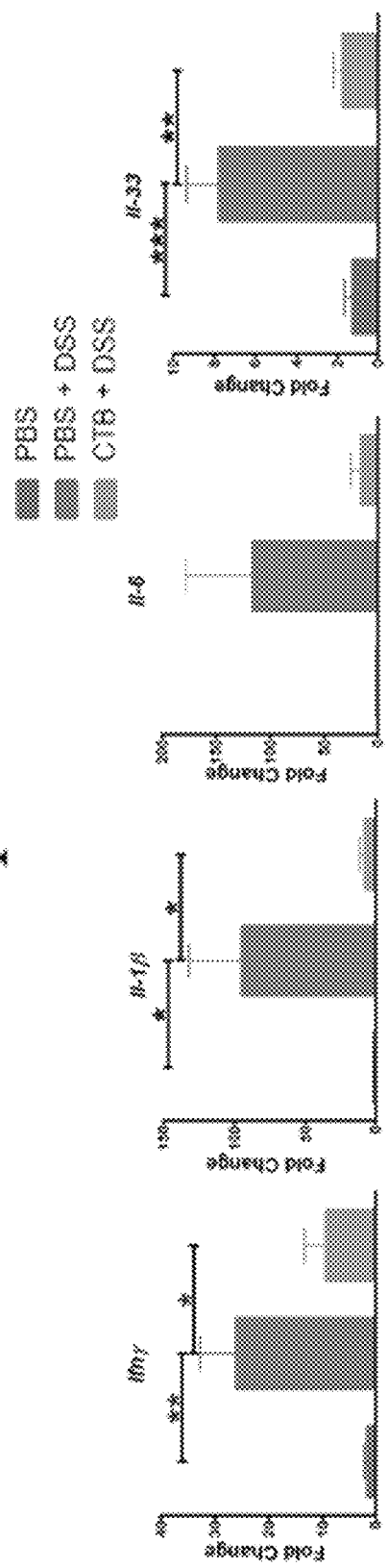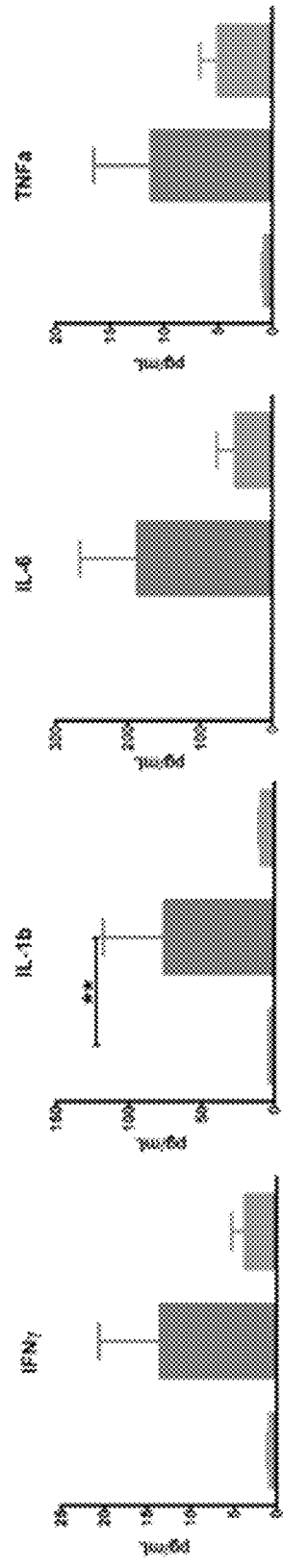
FIG. 25

| Up Regulated Pathways | P Value | Gene Ratio | Down Regulated Pathways | P Value | Gene Ratio |
|---|---|---|---|---|---|
| Cell Adhesion Extracellular Matrix Remodeling (ECM) Remodelling | 5.97E-07 | 10/52 | Androstenedione and Testosterone biosynthesis and metabolism (Rodent version) | 6.838e-6 | 7/36 |
| TGFβ-dependent induction of Epithelial to Mesenchymal Transition (EMT) via SMADs | 2.07E-06 | 8/35 | Oxidative phosphorylation | 9.240e-6 | 11/105 |
| Regulation of EMT | 4.37E-06 | 10/64 | Cystic Fibrosis Transmembrane Conductance Regulator (CFTR) folding and maturation | 5.341e-5 | 5/21 |
| MicroRNA-dependent inhibition of EMT | 7.11E-06 | 5/12 | Androstenedione and Testosterone biosynthesis and metabolism | 6.763e-5 | 6/35 |
| Development TGFβ-dependent induction of EMT via RhoA, PI3K and ILK | 1.80E-05 | 8/46 | Regulation of Glucose and Lipid metabolism via FXR | 9.363e-5 | 6/37 |
| Normal and pathological TGFβ-mediated regulation of cell proliferation | 1.6E-04 | 6/33 | Regulation of Lipid metabolism PPAR regulation of Lipid metabolism | 1.941e-4 | 6/42 |
| TGFβ-dependent induction of EMT via MAPK | 1.70E-04 | 7/47 | Role of Diethylhexyl Phthalate and Tributyltin in fat cell differentiation | 2.729e-4 | 5/29 |
| Cell adhesion Chemokines | 2.24E-04 | 10/100 | Granzyme A signaling | 3.221e-4 | 5/30 |
| Immune response Function of MEF2 in T Lymphocytes | 2.87E-04 | 7/51 | DeltaF508-CFTR activation by S-nitrosoglutathione | 3.630e-4 | 6/47 |
| Cholesterol and Sphingolipid transport Recycling to plasma membrane in lung (normal and Cystic Fibrosis) | 2.97E-04 | 5/24 | Pyruvate metabolism (Rodent version) | 3.803e-4 | 7/66 |

FIG. 38C

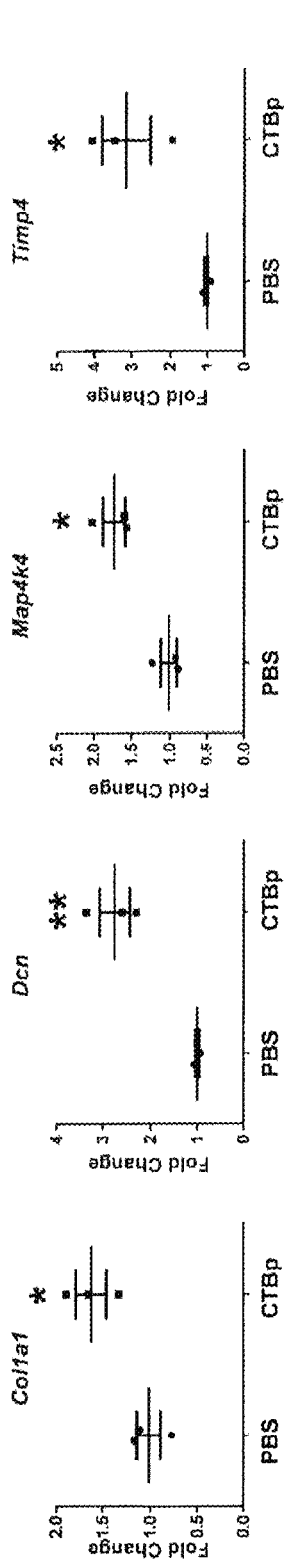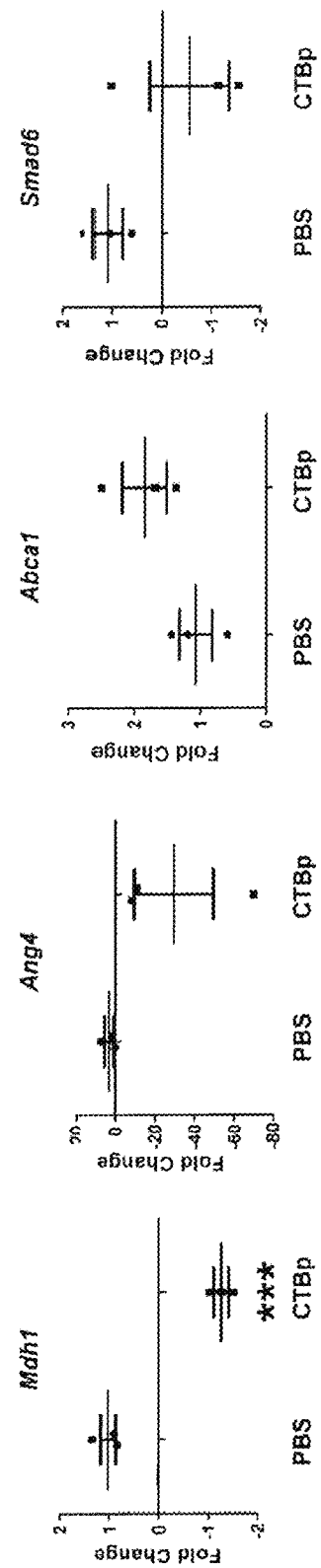

COMPOSITIONS AND METHODS FOR TREATING CANCER AND PROMOTING WOUND HEALING

RELATED APPLICATIONS

This application is a continuation of U.S. application Ser. No. 15/740,622, filed on Jun. 29, 2016, which is a U.S. National Stage of International Application No. PCT/US2016/040041, filed on Jun. 29, 2016, published in English, which claims priority to U.S. Provisional Application Ser. No. 62/186,151, filed Jun. 29, 2015, and U.S. Provisional Application Ser. No. 62/246,367, filed Oct. 26, 2015. The entire teachings of the above applications are incorporated herein by reference.

GOVERNMENT INTEREST

This invention was made with government support under grant no. W81WH-10-2-0082-CLIN 2 awarded by U.S. Department of Defense. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:
   a) File name: 56001001002_SEQUENCELISTING.txt; created Jul. 9, 2020, 22 KB in size.

TECHNICAL FIELD

The presently-disclosed subject matter relates to compositions and methods for treating cancer and promoting wound healing. In particular, the presently-disclosed subject matter relates to compositions and methods for treating cancer and promoting wound healing that make use of a plant produced cholera-toxin B subunit (CTBp) variant.

BACKGROUND

Cholera toxin (CT), a virulence factor of *Vibrio cholerae*, induces an acute diarrheal response in the gut. Two major subunits make up CT, the toxic ADP-ribosylating CTA subunit and the non-toxic, GM1-ganglioside-binding CTB subunit. The CTB subunit consists of a pentameric structure with a molecular mass of approximately 55 kD and is currently used in World Health Organization (WHO)-prequalified oral cholera vaccines due to its capacity to induce CT-neutralizing antibodies. Additionally, CTB is often used as an adjuvant or a molecular scaffold of subunit vaccines because of its strong mucosal immunogenicity.

It is further appreciated that CTB may induce anti-inflammatory and regulatory T cell responses and suppress immunopathological reactions in allergy and autoimmune diseases. For example, the airway administration of CTB ameliorated experimental asthma in a murine model. In a Phase I/II clinical trial, oral administration of CTB, chemically cross-linked to a peptide from the human 60 kDa heat shock protein, blunted uveitis of Behcet's disease. CTB was also shown to blunt the intestinal inflammation of Crohn's disease in mice and humans. These findings indicate the potential of CTB, in addition to its use as a cholera vaccine, as an oral immunotherapeutic agent to blunt intestinal inflammation in Inflammatory Bowel Disease (IBD). However, a comprehensive investigation of CTB's effect on the gastrointestinal (GI) tract has not been done, thus leading to some debate on the protein's usefulness.

In previous studies, a non-glycosylated variant of CTB (CTBp) was rapidly and efficiently manufactured in *Nicotiana benthamiana* plants. CTBp showed comparable GM1 binding affinity, physicochemical stability and immunogenicity to native (*E. coli* produced) CTB. Additionally, antibodies elicited by oral administration of CTBp in mice were able to neutralize the cholera holotoxin. These results indicated that CTBp provides a viable alternative to the recombinant protein antigen included in DUKORAL® oral cholera vaccines, potentially facilitating reactive mass vaccination to respond to cholera outbreaks.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently disclosed subject matter includes protein complex variants, compositions, and methods of use thereof. In some embodiments, the presently-disclosed subject matter relates to methods of treating a disease, comprising administering to a subject in need thereof an effective amount of a composition including a cholera toxin B subunit variant having one or more modifications. In some embodiments, the one or more modification to the cholera toxin B subunit variant increases the expression of the polypeptide in a plant cell. In one embodiment, the modification reduces N-glycosylation. In another embodiment, the modification facilitates recombinant production of the variant. In some embodiments, the cholera toxin B subunit variant is substantially immunologically identical to a cholera toxin B subunit.

Suitable modifications include, but are not limited to, sequence modifications and/or mutations, sequence attachments, or a combination thereof. For example, in some embodiments, the modification includes an Asn4 to Ser mutation. In some embodiments, the modification includes an attached C-terminal hexapeptide sequence. In one embodiment, the attached C-terminal hexapeptide sequence provides endoplasmic reticulum (ER) retention. In some embodiments, the cholera toxin B subunit variant comprises the sequence of SEQ ID NO: 4, SEQ ID NO: 6, or SEQ ID NO: 25. In some embodiments, the one or more modifications comprise a secretory signal peptide selected from the group consisting of a rice alpha-amylase secretory signal peptide, a *Nicotiana plumbagenfolia* calreticulin secretory signal peptide, an apple pectinase secretory signal peptide, and a barley alpha-amylase secretory signal peptide. In some embodiments, the one or more modifications comprise a secretory signal peptide having an amino acid sequence selected from the group consisting of SEQ ID NOS: 18, 20, 22, and 24. In some embodiments, the secretory signal peptide comprises the rice alpha-amylase secretory signal peptide. In some embodiments, the polypeptide comprises an amino acid sequence selected from the group consisting of SEQ ID NOS: 26-29. In some embodiments, the one or more modifications comprise an endoplasmic reticulum retention signal having the amino acid sequence KDEL or HDEL. In some embodiments, the KDEL or HDEL sequence is attached directly to the cholera toxin polypeptide without the use of a linker sequence. In some embodiments, the cholera toxin B subunit variant includes two or more N-linked glycosylation sequons. For example, in one embodiment, the cholera toxin B subunit variant comprises the amino acid sequence of SEQ ID NO: 8, SEQ ID NO: 10, SEQ ID NO: 12, or SEQ ID NO: 14.

In some embodiments, the disease includes an inflammatory disorder and/or cancer. In one embodiment, the cancer is colon cancer. In another embodiment, the cancer is colitis associated colon cancer. In one embodiment, the inflammatory disorder is an inflammatory bowel disease, such as, but not limited to, ulcerative colitis or Crohn's disease. In another embodiment, the inflammatory disorder is a gastrointestinal inflammation and/or injury, such as, but not limited to, celiac disease, irritable bowel syndrome, radiation-induced colitis, or infection-induced colitis. In another embodiment, the inflammatory disorder is a mucosal inflammation and/or injury, such as, but not limited to, asthma, airway burns, corneal injury, or vaginosis.

The method of treating a disease includes administering the composition by any suitable route. For example, in one embodiment, the method includes oral administration of the composition. In some embodiments, the method includes administering the composition to the subject without substantially changing a fecal microbiome of the subject. In some embodiments, administering the composition decreases protein levels of tumor promoting cytokines. In some embodiments, administering the composition increases the innate immune cell populations in the subject's colon. In one embodiment, administering the composition increases the innate immune cell populations without producing substantial effect on adaptive immune cell populations. In some embodiments, administering the composition provides an increased effect on colon gene expression as compared to small intestine gene expression.

In some embodiments, the presently-disclosed subject matter relates to methods of enhancing wound healing, comprising administering to a subject in need thereof an effective amount of a composition including a cholera toxin B subunit variant having one or more modifications. In some embodiments, the wound healing comprises mucosal wound healing. In some embodiments, the one or more modification to the cholera toxin B subunit variant increases the expression of the polypeptide in a plant cell. In one embodiment, the modification reduces N-glycosylation. In another embodiment, the modification facilitates recombinant production of the variant. Suitable modifications include, but are not limited to, an Asn4 to Ser mutation, an attached C-terminal hexapeptide sequence, or a combination thereof. In one embodiment, the modification provides endoplasmic reticulum (ER) retention. In some embodiments, the cholera toxin B subunit variant is substantially immunologically identical to a cholera toxin B subunit.

In some embodiments, the presently-disclosed subject matter relates to cholera toxin B subunit variants. In some embodiments, the cholera toxin B subunit variants are immunologically identical to natural cholera toxin B subunits. In some embodiments, the cholera toxin B subunit variants include one or more modification to increase the expression of the polypeptide in a plant cell, reduce N-glycosylation, and/or facilitate recombinant production. In some embodiments, the cholera toxin B subunit variants are produced by recombinant production in plants, *E. coli*, yeast, insect cells, mammalian cells, or a combination thereof.

Suitable modifications of the cholera toxin B subunit variants include, but are not limited to, sequence modifications and/or mutations, sequence attachments, or a combination thereof. For example, in some embodiments, the modification includes an Asn4 to Ser mutation. In some embodiments, the modification includes an attached C-terminal hexapeptide sequence. In one embodiment, the attached C-terminal hexapeptide sequence provides endoplasmic reticulum (ER) retention. In some embodiments, the cholera toxin B subunit variant comprises the sequence of SEQ ID NO: 4, SEQ ID NO: 6, or SEQ ID NO: 25. In some embodiments, the one or more modifications comprise a secretory signal peptide selected from the group consisting of a rice alpha-amylase secretory signal peptide, a *Nicotiana plumbagenfolia* calreticulin secretory signal peptide, an apple pectinase secretory signal peptide, and a barley alpha-amylase secretory signal peptide. In some embodiments, the one or more modifications comprise a secretory signal peptide having an amino acid sequence selected from the group consisting of SEQ ID NOS: 18, 20, 22, and 24. In some embodiments, the secretory signal peptide comprises the rice alpha-amylase secretory signal peptide. In some embodiments, the polypeptide comprises an amino acid sequence selected from the group consisting of SEQ ID NOS: 26-29. In some embodiments, the one or more modifications comprise an endoplasmic reticulum retention signal having the amino acid sequence KDEL or HDEL. In some embodiments, the cholera toxin B subunit variant includes two or more N-linked glycosylation sequons. For example, in one embodiment, the cholera toxin B subunit variant comprises the amino acid sequence of SEQ ID NO: 8, SEQ ID NO: 10, SEQ ID NO: 12, or SEQ ID NO: 14.

Further features and advantages of the present invention will become evident to those of ordinary skill in the art after a study of the description, figures, and non-limiting examples in this document.

BRIEF DESCRIPTION OF THE DRAWINGS

FIGS. 4C and 4D are diagrams describing pathways affected by CTBp oral administration.

FIGS. 7A-7C include schematic diagrams and graphs showing gut microbiome analysis of mice administered with CTBp or PBS at the phylum and species levels. Fecal samples were collected from each mouse 2 weeks after the second dose of PBS or CTBp. Following bacterial DNA isolation samples were analyzed. (FIG. 7A) A representative sample of the phylum level abundance analysis. (FIG. 7B) Representative samples of the species level abundance analysis and top 6 represented species in the samples. (FIG. 7C) Operational Taxonomic Units (OTUs) representing the lowest p-values as determined by ANOVA. CTBp did not significantly affect the overall composition of the gut microbiota, but the abundance of several minor species in the Firmicutes phylum was significantly altered.

FIGS. 9A-9E include graphs and images illustrating CTBp's effects in an acute DSS colitis model one week after DSS exposure. (FIG. 9A) A graph illustrating weight loss as percent change body weight for mice administered PBS, PBS+DSS, and CTBp+DSS. (FIG. 9B) A graph illustrating inflammation score for mice administered PBS, PBS+DSS, and CTBp+DSS. (FIG. 9C) Representative photomicrographs of tissue from mice administered PBS, PBS+DSS, and CTBp+DSS. (FIG. 9D) Graphs illustrating various gene expression levels for mice administered PBS, PBS+DSS, and CTBp+DSS. (FIG. 9E) Graphs illustrating various protein levels for mice administered PBS, PBS+DSS, and CTBp+DSS.

(FIG. 10A) Representative photomicrographs of tissue from mice administered PBS, CTBp, PBS+DSS, MES+DSS, and CTBp+DSS. (FIG. 10B) A graph illustrating inflammation score for mice administered PBS, CTBp, PBS+DSS, MES+DSS, and CTBp+DSS. (FIG. 10C) Graphs illustrating various gene expression levels for mice administered PBS, PBS+DSS, and CTBp+DSS.

(FIG. 11A) A graph showing disease activity index for mice administered various different compositions. The graph illustrates CTBp's effects on disease activity index in a chronic colitis/colon cancer model. (FIG. 11B) Representative images of various tumor grades. (FIG. 11C) A graph showing tumor numbers for mice administered various different compositions. The graph illustrates CTBp's effects on tumor number in a chronic colitis/colon cancer model. (FIG. 11D) A graph showing total tumor score for mice administered various different compositions. The graph illustrates CTBp's effects on tumor score in a chronic colitis/colon cancer model.

FIG. 16 includes representative photomicrographs of various tumor grades.

FIG. 22 includes graphs showing cell levels in colon lamina propria.

FIGS. 23A-23D include graphs illustrating how extracellular matrix components are significantly increased by CTBp administration.

FIGS. 24A-24B include graphs illustrating how remodeling enzymes are significantly increased by CTBp administration.

FIG. 25 includes graphs illustrating gene expression data and tissue protein levels. *, , *$P<0.05$, 0.01, 0.001 compared to PBS-DSS, One-way ANOVA with Bonferroni's multiple comparison tests.

(FIG. 37A) Innate immune cell populations in the colon lamina propria. (FIG. 37B) Adaptive immune cell populations in the colon lamina propria. (FIG. 37C-37E) Immunohistochemistry analysis of macrophage ($F4/80^+$) cells in the distal colon lamina propria isolated from mice 2 weeks post second CTBp oral administration. Paraffin embedded colon sections were incubated with F4/80 primary antibody (1:100 dilution) and a biotinylated secondary antibody. After addition of a horseradish peroxidase (HRP) and 3,3'-diaminobenzidine tetrahydrochloride (DAB) solution, positive cells were counted in 10 high power fields per section and averaged for each colon. Mean±SEM is shown. Unpaired t test was performed with *P<0.05 compared to PBS group. Animals per group: PBS (n=6) and 30 µg CTBp (n=7).

FIGS. 38A-38C include graphs and schematic diagrams showing TGFβ-dependent pathways are significantly altered by CTBp in the colon. PBS or CTBp was administered twice to mice at a two week interval. Two weeks after the final dose animals were sacrificed and the small intestine and colon were removed for RNA purification. Total RNA was amplified and labeled, and then whole transcript expression analysis was performed. (FIG. 38A) Heat map showing differentially expressed genes in the small intestine (SI) and colon (COL) following PBS or CTBp administration. (FIG. 38B) Number of significantly altered genes in the colon and small intestine following PBS or CTBp administration. Significance was determined at P<0.01.

(FIG. 38C) Ten most significantly enhanced and suppressed pathways by CTBp administration in the colon as determined by METACORE™ ontologies enrichment analysis using P<0.01 and a fold change of <−1.2 or >1.2.

(FIG. 39A) Photomicrographs of wounded Caco2 cells. (FIG. 39B) Analysis of in vitro wound closure after 24 and 48 h by wound area measurement. Means±SEM of four independent experiments are shown. P<0.01, and *P<0.001; one-way ANOVA with Bonferroni's multiple comparison tests. (FIG. 39C) Analysis of in vitro wound closure after 24 h by wound area measurement after incubation with PBS or an anti-TGFβ1,2,3 antibody coincubated with 1.0 µM CTBp or 0.2 nM TGFβ1. Means±SEM of four independent experiments are shown. *P<0.05, P<0.01, and *P<0.001; one-way ANOVA with Bonferroni's multiple comparison tests. (d) Protein concentrations in Caco2 cell supernatants. Means±SEM of four independent experiments are shown. *P<0.05, P<0.01, and *P<0.001; one-way ANOVA with Bonferroni's multiple comparison tests.

(FIG. 40A) Percent change of body weights. Animals were weighed daily and just prior to the initiation of DSS exposure. Percent change was based on the initial body weight. **P<0.01 between DSS-exposed, CTBp- and PBS-administered groups; two-way ANOVA with Bonferroni's multiple comparison tests. (FIG. 40B) Colon inflammation scoring. Paraffin embedded tissue sections were scored after staining with Hematoxylin and Eosin (H&E). Scoring was based on a 0 to 4 scale. (FIG. 40C) Representative 4× (left) and 20× (right) photomicrographs of colons from treatment groups. (FIGS. 40D-40E) Immunohistochemistry staining of $F4/80^+$ cells in distal colon tissue. Means±SEM of positive cells from 10 individual microscope fields per sample (FIG. 40D) and representative photographs (FIG. 40E) are shown. (FIG. 40F) Representative photomicrographs of colons following Masson's Trichrome Stain. (FIG. 40G) qRT-PCR analysis of cytokine gene expression in mouse colon tissue. Mean±SEM is shown for each group (N=5). One-way ANOVA with Bonferroni's multiple comparison test was used for (b, d, g). *P<0.05, P<0.01, *P<0.001.

(FIG. 41A) Representative photomicrographs of colons from the treatment groups and colon inflammation scoring. Paraffin embedded tissue sections were scored after staining with H&E. Scoring was based on a 0 to 4 scale. Mean±SEM is shown for each group. Animals per group: PBS (n=8), 30 µg CTBp+DSS (n=8), MES+DSS (n=9) and PBS+DSS (n=7). (FIG. 41B) qRT-PCR analysis of cytokine gene expression in mouse colon tissue. Mean±SEM is shown for each group (N=5). (FIG. 41C) Cytokine concentrations in colon tissue lysate. N=5 per group. One-way ANOVA with Bonferroni's multiple-comparison post-test (b) or Kruskal-Wallis test with Dunn's multiple-comparison post-test were used to compare groups. *P<0.05, P<0.01 and *P<0.001.

(FIG. 42A) Disease activity index (DAI) scores. Body weight loss, fecal consistency and occult blood were scored at the time of sacrifice. (FIG. 42B) Colon length. (FIG. 42C) Colon inflammation scoring. Paraffin embedded tissue sections were scored after staining with H&E. Scoring was based on a 0 to 4 scale. Mean±SEM is shown for each group. *P<0.05, P<0.01 and *P<0.001; one-way ANOVA with Bonferroni's multiple comparison tests. (d) Representative 4× (top) and 20× (bottom) photomicrographs of H&E-stained distal colon tissues from each group.

(FIG. 43A) DAI. Body weights, fecal consistency and occult blood were scored daily. *P<0.05 compared to PBS+DSS group; a repeated-measures ANOVA with Bonferroni Correction. (FIG. 43B) Representative tumor scoring. Tumors were scored from 0 to 5 with 0 being normal tissue and 5 being greater than 50% of colon circumference tumor invasion. Red arrows indicate representative tumors. (FIG. 43C) Tumor scoring results. Tumors were scored based on the scale in b. ##P<0.01 and ###P<0.001 compared to PBS and **P<0.01 compared to PBS+DSS; a repeated-measures ANOVA with Bonferroni Correction. (FIG. 43D) Tumor score vs tumor number. Total tumor number is the X axis and total tumor grade is the Y axis. A dot represents each mouse. Mice with no tumors are at the axis intersection. Mean±SEM is shown (n=5 for PBS group and all other groups n=10). (FIG. 43E) qRT-PCR analysis of cytokine gene expression in mouse colon tissue. Mean±SEM is shown for each group (N=5). (FIG. 43F) Cytokine concentrations in colon tissue lysate. N=5 per group. For e and f, a Kruskal-Wallis test with Dunn's multiple-comparison post-test was used. *P<0.05 and **P<0.01.

FIGS. 47A-47H include graphs showing qRT-PCR analysis of representative genes that were shown to be induced by CTBp administration in microarray analysis. RNA samples from the distal colon tissue were isolated using the Qiagen RNEASY® Microarray Tissue Mini Kit and analyzed by APPLIED BIOSYSTEMS™ TAQMAN® Array 96-Well FAST plate in an APPLIED BIOSYSTEMS™ 7500 Fast Real-Time PCR System. N=3 per group. *P<0.05, P<0.01 and *P<0.001; unpaired t test. (FIGS. 47A-47D) Microarray-identified significantly induced genes including: Col1a1, Dcn, Map4k4 and Timp4. (FIGS. 47E-47F) Microarray identified suppressed genes including: Mdh1 and Ang4. (FIGS. 47G-47H) Unchanged genes in microarray analysis including: Abca1 and Smad6.

FIGS. 48A-48G are graphs showing wound healing pathway-focused qRT-PCR analysis of colon gene expression. Two weeks post administration, RNA samples were isolated using the Qiagen RNEASY® Microarray Tissue Mini Kit and analyzed by RT2 Profiler PCR Mouse Wound Healing Array (Qiagen, Cat. No. PAMM-121Z) in an APPLIED BIOSYSTEMS™ 7500 Fast Real-Time PCR System. N=3 per group. A 1.5 fold change from PBS cutoff was used to filter data prior to testing for significance. Seven significantly changed genes in: (FIGS. 48A-48C) extracellular matrix structural constituents; (FIGS. 48D-48E) extracellular matrix remodeling enzymes; (FIG. 48F) cytoskeleton regulators; and (FIG. 48G) growth factors, are shown. *P<0.05 and **P<0.01; unpaired t tests.

(FIG. 53A) A representative sample of the phylum level abundance analysis. (FIG. 53B) Representative samples of the species level abundance analysis and top 6 represented species in the samples. (FIG. 53C) Operational Taxonomic Units (OTUs) representing the lowest p-values as determined by ANOVA. CTBp did not significantly affect the overall composition of the gut microbiota, but the abundance of several minor species in the Firmicutes phylum was significantly altered.

BRIEF DESCRIPTION OF THE SEQUENCE LISTING

Figure 1:
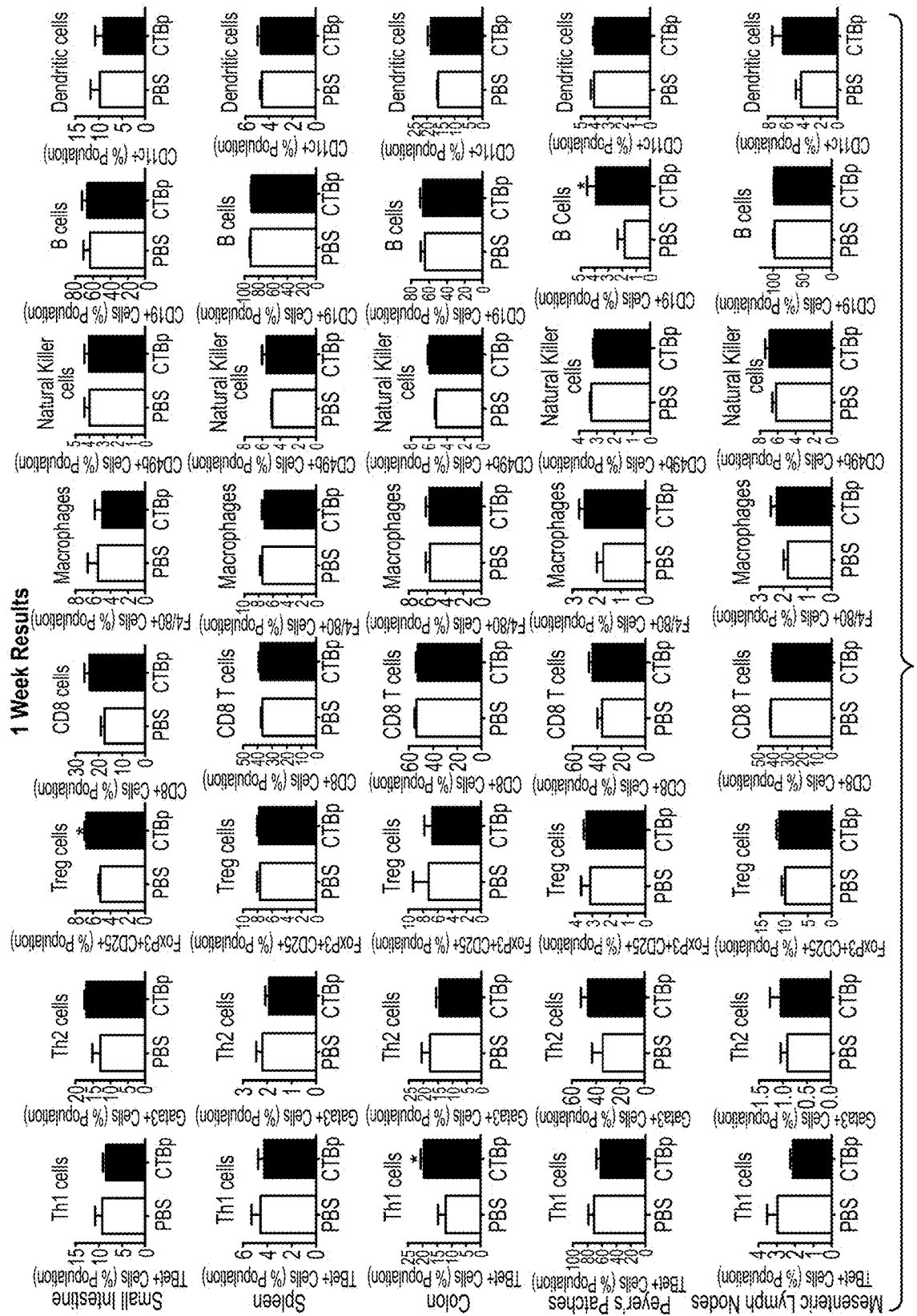
FIG. 1 includes graphs showing results of flow cytometry performed one week after CTBp administration.

SEQ ID NO: 1 is nucleic acid sequence of a wild-type cholera toxin B subunit from *Vibrio cholerae;*

SEQ ID NO: 2 is an amino acid sequence of a wild-type cholera toxin B subunit from *Vibrio cholerae;*

SEQ ID NO: 3 is nucleic acid sequence encoding a cholera toxin B subunit variant polypeptide modified to include a C-terminal endoplasmic reticulum signal and to include no N-linked glycosylation sequons at Asn4;

SEQ ID NO: 4 is an amino acid sequence of a cholera toxin B subunit variant polypeptide modified to include a C-terminal endoplasmic reticulum signal and to include no N-linked glycosylation sequons at Asn4;

SEQ ID NO: 5 is a nucleic acid sequence encoding a cholera toxin B subunit variant polypeptide modified to include a C-terminal endoplasmic reticulum retention signal and having one N-linked glycosylation sequon at Asn4;

SEQ ID NO: 6 is an amino acid sequence of a cholera toxin B subunit variant polypeptide modified to include a C-terminal endoplasmic reticulum retention signal and having one N-linked glycosylation sequon at Asn4;

SEQ ID NO: 7 is a nucleic acid sequence encoding a cholera toxin B subunit variant polypeptide modified to include a C-terminal endoplasmic reticulum retention signal and to include two N-linked glycosylation sequons at Asn4 and Asn103;

SEQ ID NO: 8 is an amino acid sequence of a cholera toxin B subunit variant polypeptide modified to include a C-terminal endoplasmic reticulum retention signal and to include two N-linked glycosylation sequons at Asn4 and Asn103;

SEQ ID NO: 9 is a nucleic acid sequence encoding another cholera toxin B subunit variant polypeptide modified to include a C-terminal endoplasmic reticulum retention signal and to include two N-linked glycosylation sequons at Asn4 and Asn21;

SEQ ID NO: 10 is an amino acid sequence of another cholera toxin B subunit variant polypeptide modified to include a C-terminal endoplasmic reticulum retention signal and to include two N-linked glycosylation sequons at Asn4 and Asn21;

SEQ ID NO: 11 is a nucleic acid sequence encoding a cholera toxin B subunit variant polypeptide modified to include a C-terminal endoplasmic reticulum retention signal and to include three N-linked glycosylation sequons at Asn4, Asn21, and Asn103;

SEQ ID NO: 12 is an amino acid sequence of a cholera toxin B subunit variant polypeptide modified to include a C-terminal endoplasmic reticulum retention signal and to include three N-linked glycosylation sequons at Asn4, Asn21, and Asn103;

SEQ ID NO: 13 is a nucleic acid sequence encoding another cholera toxin B subunit variant polypeptide modified to include a C-terminal endoplasmic reticulum retention signal and to include three N-linked glycosylation sequons at Asn4, Asn21, and Asn103;

SEQ ID NO: 14 is an amino acid sequence of another cholera toxin B subunit variant polypeptide modified to include a C-terminal endoplasmic reticulum retention signal and to include three N-linked glycosylation sequons at Asn4, Asn21, and Asn103;

SEQ ID NO: 15 is a nucleic acid sequence encoding a cholera toxin B subunit variant polypeptide with an N-terminal secretory signal from *Vibrio cholerae* and a C-terminal endoplasmic reticulum retention signal;

SEQ ID NO: 16 is an amino acid sequence of a cholera toxin B subunit variant polypeptide including an N-terminal secretory signal from *Vibrio cholerae* and a C-terminal endoplasmic reticulum retention signal;

SEQ ID NO: 17 is a nucleic acid sequence encoding a rice alpha-amylase secretory signal peptide;

SEQ ID NO: 18 is an amino acid sequence of a rice alpha-amylase secretory signal peptide;

SEQ ID NO: 19 is nucleic acid sequence encoding a *Nicotiana plumbagenfolia* calreticulin secretory signal peptide;

SEQ ID NO: 20 is an amino acid sequence of a *Nicotiana plumbagenfolia* calreticulin secretory signal peptide;

SEQ ID NO: 21 is a nucleic acid sequence encoding an apple pectinase secretory signal peptide;

SEQ ID NO: 22 is an amino acid sequence of an apple pectinase secretory signal peptide;

SEQ ID NO: 23 is a nucleic acid sequence encoding a barley alpha-amylase secretory signal peptide;

SEQ ID NO: 24 is an amino acid sequence encoding a barley alpha-amylase secretory signal peptide;

SEQ ID NO: 25 is an amino acid sequence of a cholera toxin B subunit variant polypeptide including a Ser26→Cys and an Ala102→Cys mutation;

SEQ ID NO: 26 is an amino acid sequence of a cholera toxin B subunit variant polypeptide including a rice alpha-amylase N-terminal secretory signal peptide and a C-terminal endoplasmic reticulum retention signal peptide;

SEQ ID NO: 27 is an amino acid sequence of a cholera toxin B subunit variant polypeptide including a *Nicotiana plumbagenfolia* calreticulin N-terminal secretory signal peptide and a C-terminal endoplasmic reticulum retention signal peptide;

SEQ ID NO: 28 is an amino acid sequence of a cholera toxin B subunit variant polypeptide including an apple pectinase N-terminal secretory signal peptide and a C-terminal endoplasmic reticulum retention signal peptide;

SEQ ID NO: 29 is an amino acid sequence of a cholera toxin B subunit variant polypeptide including a barley alpha-amylase N-terminal secretory signal peptide and a C-terminal endoplasmic reticulum retention signal peptide;

SEQ ID NO: 30 is an amino acid sequence of an exemplary endoplasmic reticulum retention signal peptide, KDEL, including a two amino acid linker, SE, preceding the KDEL sequence; and SEQ ID NO: 31 is an amino acid of the exemplary endoplasmic reticulum retention signal peptide, KDEL.

SEQ ID NO: 32 is an amino acid of the exemplary endoplasmic reticulum retention signal peptide, HDEL.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK®/GENPEPT® accession numbers. The sequences cross-referenced in the GENBANK®/GENPEPT® database are expressly incorporated by reference as are equivalent and related sequences present in GENBANK®/GENPEPT® or other public databases. Also expressly incorporated herein by reference are all annotations present in the GENBANK®/GENPEPT® database associated with the sequences disclosed herein. Unless otherwise indicated or apparent, the references to the GENBANK®/GENPEPT® database are references to the most recent version of the database as of the filing date of this Application.

Unless defined otherwise, all technical and scientific terms used herein have the same meaning as is commonly understood by one of skill in the art to which the invention(s) belong. All patents, patent applications, published applications and publications, GENBANK® sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Cholera toxin B subunit (CTB) is a pleiotropic mucosal immunomodulatory protein and currently used as an active component of an internationally licensed oral cholera vaccine. However, CTB's immunomodulatory effect on the gastrointestinal tract has not been fully investigated. To that end, the presently-disclosed subject matter is based, at least in part, on the discovery that oral administration of a CTB variant (CTBp) significantly altered the gene expression profile in the distal colon in mice while comparatively less change was noted in the small intestine. The alterations in gene expression indicated the activation of TGFβ-mediated pathways involved in mucosal epithelial integrity. Additionally, immune cell populations in the colon lamina propria were significantly altered by CTBp, whereby macrophages, dendritic cells, and natural killer cells were increased, while B cells were decreased. Meanwhile, the fecal microbiome remained largely unchanged upon CTBp oral administration, indicating that the changes in colonic gene expression and immune cell populations are not mediated by gut microflora.

Given that CTBp induced TGFβ-mediated pathways and increased phagocytic innate immune cells in the colonic mucosa, and without wishing to be bound by any particular theory, it was believed that CTBp could enhance mucosal wound healing in the colon. That belief was, at least in part, then demonstrated in an in vitro mucosal wound healing model employing Caco2 cells, in which CTBp increased wound healing in a TGFβ-dependent manner. Interestingly, CTBp exhibited more effective wound healing activity than native CTB. Again, without wishing to be bound by theory, the increased wound healing provided by CTBp as compared to native CTB is believed to be due to the amino acid sequence modification introduced to the former resulting in prolonged retention in the epithelial cells. CTBp's wound healing capacity was further demonstrated in a dextran sodium sulfate (DSS) acute colitis model in mice. CTBp protected against epithelial damage as manifested by mitigating body weight loss, decreasing pathological symptoms in the colon epithelia, and blunting the escalation of inflammatory cytokine levels. Notably, biweekly oral administration of CTBp significantly reduced tumorigenesis in the azoxymethane/DSS model of colon cancer. Together, the results demonstrated CTBp's ability to enhance mucosal wound healing, and highlighted its potential for application in ulcerative colitis oral immunotherapy.

The presently-disclosed subject matter thus includes compositions and methods for treating cancer, enhancing wound healing, and/or treating an inflammatory disorder. In some embodiments, a method of treating a cancer is provided, the method including administering to a subject in need thereof an effective amount of a composition including a cholera toxin B subunit variant. In some embodiments, the cholera toxin B subunit variant includes one or more modifications as compared to a native cholera toxin B subunit. Such variants are referred to herein as a CTB variant (CTBp) or a cholera toxin B subunit variant polypeptide.

The term "cancer" refers to all types of cancer or neoplasm or malignant tumors found in a subject, including leukemias, lymphomas, myelomas, carcinomas, melanomas, teratomas, and sarcomas. Examples of cancers include cancer of the liver, pancreas, esophagus, brain, bladder, breast, central nervous system (e.g., spine), cervix, colon, rectum, head and neck, kidney, lung, ovary, prostate, sarcoma, stomach, uterus, leukemias, lymphomas, myelomas, and melanomas. In one embodiment, the cancer includes colon cancer. In another embodiment, the colon cancer includes colitis-associated colon cancer.

In some embodiments, a method of enhancing wound healing is provided, the method including administering to a subject in need thereof an effective amount of a composition including a cholera toxin B subunit variant. In one embodiment, the enhanced wound healing includes enhanced mucosal wound healing. As used herein, the term "mucosal wound" refers to any injury to tissue that includes a mucosal membrane and that may be capable of producing mucus, such as, but not limited to, digestive tissue, genital tissue, and/or urinary tract tissue.

In some embodiments, a method of treating an inflammatory disorder is provided, the method including administering to a subject in need thereof an effective amount of a composition including a cholera toxin B subunit variant. The term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cancer, or other agents or conditions.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories.

Exemplary inflammatory disorders include, but are not limited to atherosclerosis; arthritis; asthma; autoimmune uveitis; adoptive immune response; dermatitis; multiple sclerosis; diabetic complications; osteoporosis; Alzheimer's disease; cerebral malaria; hemorrhagic fever; autoimmune disorders; and inflammatory bowel disease. In embodiments, the term "inflammatory disorder" is further inclusive of inflammation-promoted cancers, such that the term "inflammatory disorder" can be used to refer to cancers caused or promoted by inflammation, such as colon cancer. In some embodiments, the inflammatory disorder is selected from the group consisting of sepsis, septic shock, colitis, colon cancer, and arthritis. For example, in one embodiment, the method of treating an inflammatory disorder includes treating an inflammatory bowel disease, such as, but not limited to, ulcerative colitis and/or Crohn's disease; a gastrointestinal inflammation and/or injury, such as, but not limited to, celiac disease, irritable bowel syndrome, radiation-induced colitis, and/or infection-induced colitis; a mucosal inflammation and/or injury, such as, but not limited to, asthma, airway burns, corneal injury, and/or vaginosis; or a combination thereof. The term "colitis" refers to an inflammation of the colon which may be acute or chronic.

As used herein, the terms "treatment" or "treating" relate to any treatment of a disease of a subject, including, but not limited to, prophylactic treatment and therapeutic treatment. As such, the terms treatment or treating include, but are not limited to: preventing a disease or the development of a disease; inhibiting the progression of a disease; arresting or preventing the development of a disease; reducing the severity of a disease; ameliorating or relieving symptoms associated with a disease; and causing a regression of the disease or one or more of the symptoms associated with the disease.

As would be recognized by those of ordinary skill in the art, cholera toxin is an oligomeric protein complex, which is secreted by the bacterium *Vibrio cholerae* and is thought to be responsible for the enteric symptoms characteristic of a cholera infection. The cholera toxin itself is generally composed of six protein subunits, namely a single copy of the A subunit, which is thought to be the toxic portion of the molecule responsible for its enzymatic action; and five copies of the B subunit, which form a pentameric ring and are thought to comprise the non-toxic portions of the molecule responsible for binding to receptors, such as the GM1 ganglioside receptor, which contains a glycosphingolipid (e.g., a ceramide and oligosaccharide) with one sialic acid and which is attached to the surface of a host cell. As such, the term "cholera toxin B subunit" is used herein to refer to a single B subunit of the cholera toxin as well as to B subunits of the cholera toxin in the form of multimers (e.g., in a pentameric form). Exemplary nucleic acid and amino acid sequence of a native cholera toxin B subunit polypeptide from wild-type *Vibrio cholerae* are provided herein in SEQ ID NOS: 1 and 2 in the Sequence Listing appended hereto.

The terms "polypeptide," "protein," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a gene product. Thus, exemplary polypeptides include gene products, naturally occurring or native proteins, homologs, orthologs, paralogs, fragments and other equivalents, variants, and analogs of the foregoing. The term "native," when used with reference to a polypeptide, refers to a polypeptide that is encoded by a gene that is naturally present in the genome of an untransformed cell.

The terms "polypeptide fragment" or "fragment," when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

A fragment can also be a "functional fragment," in which case the fragment retains some or all of the activity of the reference polypeptide as described herein. For example, in some embodiments, a functional fragment of a cholera toxin B subunit polypeptide can refer to a polypeptide in which amino acid residues have been deleted as compared to the full-length cholera toxin B subunit polypeptide, but which retains some or all of the ability of the full-length cholera toxin B subunit polypeptide to bind to a GM1 ganglioside and/or some or all of the ability of the full-length cholera toxin B subunit polypeptide to attach to a glycan.

The terms "modified amino acid," "modified polypeptide," and "variant" are used herein to refer to an amino acid sequence that is different from the reference polypeptide by one or more amino acids, e.g., one or more amino acid substitutions or additions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. For example, in some embodiments, the cholera toxin B subunit variant polypeptides described herein include amino acid sequences in which one or more amino acids have been added and/or replaced, but which nonetheless retain and/or enhance some or all of the ability of the full-length cholera toxin B subunit polypeptide to bind to a GM1 ganglioside and/or some or all of the ability of the full-length cholera toxin B subunit polypeptide to attach to a glycan.

As noted, in some embodiments of the presently-disclosed subject matter, an isolated polypeptide is utilized that comprises a cholera toxin B subunit variant polypeptide having one or more modifications. The CTBp may be produced by any suitable recombinant production platform, including, but not limited to, plants, *E. coli*, yeast, insect cells, mammalian cells, or a combination thereof. For example, in some embodiments, the one or more modifications increase the expression of the polypeptide in a plant cell.

In some embodiments, the one or more modifications to the CTBp include a C-terminal hexapeptide sequence attached to the CTB subunit. In some embodiments, the one or more modifications to the cholera toxin B subunit variant polypeptide include an endoplasmic reticulum retention signal having the amino acid sequence KDEL (SEQ ID NO: 31). In some embodiments, the KDEL sequence is linked to the cholera toxin by a two amino acid linker to comprise, in some embodiments, the signal: SEKDEL (SEQ ID NO: 30). In some embodiments, the cholera toxin B subunit variant polypeptide comprises the amino acid sequence of SEQ ID NO: 4, SEQ ID NO: 6, or SEQ ID NO: 25. In some embodiments, and without wishing to be bound by any particular theory, the addition of an endoplasmic reticulum retention signal, such as the amino acid sequence KDEL or HDEL or other similar sequence with similar functions, to a cholera toxin B subunit polypeptide enhances the variant polypeptide's wound healing, anti-inflammatory, and anti-cancer activity (e.g., anti-colon cancer activity), as described herein below. In some embodiments, the cholera toxin B subunit variant polypeptide comprises the cholera toxin B subunit variant polypeptide describe in, for example, Hamorsky, et al., "Rapid and Scalable Plant-based Production of a Cholera Toxin B Subunit Variant to Aid in Mass Vaccination against Cholera Outbreaks." PLoSNTD. March 2013. 7(3): e2046, which is incorporated herein by reference in its entirety.

In some embodiments of the presently-disclosed polypeptides, the one or more modifications to the cholera toxin B subunit variant polypeptide include the addition (e.g., an addition at the N-terminal of the cholera toxin B subunit variant polypeptide) of a secretory signal peptide capable of transferring or translocating the cholera toxin B subunit peptide such that the cholera toxin B subunit variant polypeptides is accumulated in a particular location in a plant tissue, such as in the apoplasts of plant cells. In some embodiments, the secretory signal peptide is selected from the group consisting of a rice (e.g., *Oryza sativa*) alpha-amylase secretory signal peptide (e.g., SEQ ID NO: 18), a *Nicotiana plumbagenfolia* calreticulin secretory signal peptide (e.g., SEQ ID NO: 20), an apple (e.g., *Malus domestica*) pectinase secretory signal peptide (e.g., SEQ ID NO: 22), and a barley (*Hordeum vulgare*) alpha-amylase secretory signal peptide (e.g., SEQ ID NO: 24). In some embodiments, the secretory signal peptide has an amino acid sequence selected from the group consisting of SEQ ID NOS: 18, 20, 22, and 24. In some embodiments, the secretory signal peptide comprises a rice alpha-amylase secretory signal peptide, such as the rice alpha-amylase secretory signal peptide of SEQ ID NO: 18.

In some embodiments, an isolated cholera toxin B subunit variant polypeptide is utilized that comprises a cholera toxin B subunit variant linked to a secretory signal peptide, such as those described herein above, and an endoplasmic reticulum retention signal. In some embodiments, the variant polypeptide comprises an amino acid sequence selected from the group consisting of SEQ ID NOS: 26-29.

With further regard to the polypeptides of the presently-disclosed subject matter, in some embodiments, a cholera toxin B subunit variant polypeptide used in accordance with the presently-disclosed subject matter includes one or more mutations so as to include a plurality of N-linked glycosylation sequons (i.e., Asn-X-Ser or Asn-X-Thr sequences) in the variant polypeptide sequences and thereby provide a mechanism to display multiple N-linked H-Man glycans and mimic a virus-like carbohydrate cluster. In some embodiments, about 1, about 2, about 3, about 4, about, 5, about 6, about 7, about 8, about 9, or about 10 N-linked glycosylation sequons are included in an exemplary cholera toxin B subunit variant polypeptide of the presently-disclosed subject matter. In some embodiments, a cholera toxin B subunit variant polypeptide is provided that comprises 2 N-linked glycosylation sequons, such as, in some embodiments, a cholera toxin B subunit variant polypeptide having the amino acid sequence of SEQ ID NO: 8 or SEQ ID NO: 10. In other embodiments, a cholera toxin B subunit variant polypeptide is provided that comprises 3 N-linked glycosylation sequons, such as, in some embodiments, a cholera toxin B subunit variant polypeptide having the amino acid sequence of SEQ ID NO: 12 or SEQ ID NO: 14. In some embodiments, the polypeptide comprises two or more N-linked glycosylation sequons, such as, in some embodiments, the polypeptides of SEQ ID NO: 8, SEQ ID NO: 10, SEQ ID NO: 12, or SEQ ID NO: 14.

In some embodiments, the presently-disclosed subject matter further provides a number of other benefits or advantages. For example, in some embodiments, and as determined by experimentation, the dosing regimen for the above-described CTBp-based therapy reduces the dose frequency and amount compared to current therapeutic options for ulcerative colitis patients. In some embodiments, the CTBp described herein has wound healing potential not reproducible with native CTB.

For administration of a therapeutic composition as disclosed herein (e.g., a composition comprising a cholera toxin B subunit variant polypeptide of the presently-disclosed subject matter and a pharmaceutically-acceptable vehicle, carrier, or excipient), conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kgx37 kg/sq m=3700 mg/m².

Suitable methods for administering a therapeutic composition in accordance with the methods of the presently-disclosed subject matter include, but are not limited to, systemic administration, parenteral administration (including intravascular, intramuscular, intraarterial administration), oral delivery, topical administration, buccal delivery, rectal delivery, vaginal delivery, subcutaneous administration, intraperitoneal administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180, 082). In some embodiments, such as those which include a pharmaceutical composition comprising a cholera toxin B subunit variant polypeptide of the presently-disclosed subject matter, the pharmaceutical composition can be administered orally to thereby elicit an immune response.

Regardless of the route of administration, the compounds of the presently-disclosed subject matter are typically administered in amount effective to achieve the desired response. As used herein, the terms "effective amount" and "therapeutically effective amount" refer to an amount of the therapeutic composition (e.g., a composition comprising a cholera toxin B subunit variant polypeptide of the presently-disclosed subject matter, and a pharmaceutically-acceptable vehicle, carrier, or excipient) sufficient to produce a measurable biological response (e.g., an increase in levels of IgA). Actual dosage levels of active ingredients in a therapeutic composition of the presently-disclosed subject matter can be varied so as to administer an amount of the active polypeptide(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902 and 5,234,933; PCT International Publication No. WO 93/25521; Berkow, et al., (1997) The Merck Manual of Medical Information, Home ed. Merck Research Laboratories, Whitehouse Station, N.J.; Goodman, et al., (2006) Goodman & Gilman's the Pharmacological Basis of Therapeutics, 11th ed. McGraw-Hill Health Professions Division, N.Y.; Ebadi. (1998) CRC Desk Reference of Clinical Pharmacology. CRC Press, Boca Raton, Fla.; Katzung, (2007) Basic & Clinical Pharmacology, 10th ed. Lange Medical Books/McGraw-Hill Medical Pub. Division, New York; Remington, et al., (1990) Remington's Pharmaceutical Sciences, 18th ed. Mack Pub. Co., Easton, Pa.; Speight, et al., (1997) Avery's Drug Treatment: A Guide to the Properties, Choice, Therapeutic Use and Economic Value of Drugs in Disease Management, 4th ed. Adis International, Auckland/Philadelphia; and Duch, et al., (1998) Toxicol. Lett. 100-101:255-263, each of which are incorporated herein by reference.

As used herein, the term "subject" includes both human and animal subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further described by the non-limiting examples shown below.

EXAMPLES

Materials and Methods for Examples 1-9

A non-glycosylated variant of CTB (CTBp; SEQ ID NOS: 3 and 4) can be rapidly and efficiently manufactured in *Nicotiana benthamiana* plants. That CTBp showed comparable GM1 binding affinity, physicochemical stability and immunogenicity to native (*E. coli* produced) CTB. Additionally, antibodies elicited by oral administration of CTBp in mice were able to neutralize the cholera holotoxin. Those results indicated that CTBp provides a viable alternative to the recombinant protein antigen included in DUKORAL® oral cholera vaccines, potentially facilitating reactive mass vaccination to respond to cholera outbreaks. Detailed investigation into the biological impacts of orally administered CTBp on the GI tract will not only bridge efforts in oral vaccine development, but also fill the aforementioned gap in our knowledge about one of the most potent mucosal immunomodulatory proteins known to date. In this regard, in Examples 1-9, the global impacts of CTBp oral vaccination on the small intestine and colon were characterized by elucidating changes in their immune cell populations and gene expression profiles as well as the gut microbiome. Cell culture and animal models were then used to investigate CTBp's oral immunotherapeutic effects. To this end, a Caco-2 wound healing assay was used to show enhanced wound healing with CTBp. Additionally, a dextran sulfate sodium (DSS) mouse model of intestinal wounding and ulcerative colitis was used, another major form of IBD to which CTB's impacts have not been reported before. As described below, the results revealed CTB's previously unidentified mucosal wound healing capacity and showed relevance as an oral immunotherapy for ulcerative colitis and colitis-associated colon cancer.

Animals. 8 week old C57BL/6J female mice were obtained from Jackson Laboratories (Bar Harbor, Me.) and allowed to acclimate for one week.

Induction of colitis and study design. For the acute DSS studies, animals were vaccinated with PBS or 30 μg plant-made cholera toxin B subunit (CTBp) two times prior to DSS exposure. Vaccinations occurred two weeks prior to and at the initiation of DSS exposure. The DSS exposure was slightly modified based on a previously published protocol. Animals were exposed to 4% DSS in drinking water for up to eight days and allowed up to a seven day recovery period in which the animals received normal drinking water. Mice were sacrificed using carbon dioxide inhalation followed by a thoracotomy. Serum, Fecal and Colon samples were taken for further analysis.

For the colon cancer study, Azoxymethane (AOM; 10 mg/kg) was administered by intraperitoneal injection one week after arrival. DSS exposure (2%) was initiated one week after the AOM injection for seven days and allowed to recover for 14 days following the DSS exposure period. The DSS exposure and recovery cycle was repeated three times and mice were sacrificed by Carbon Dioxide inhalation followed by thoracotomy following the 3.sup.rd cycle. This method was slightly modified from the published protocol. Colons were excised for further analysis. Animals were housed according to the University of Louisville's Institutional Animal Care and Use Committee standards.

RNA isolation. Sections from the Small Intestine and Distal colon were stored in RNALATER™ (Qiagen, Valencia, Calif.) at −20° C. until RNA was isolated. Colon Tissue (approximately 14 mg) was placed in QIAzol lysis reagent in a 2.0 mL conical bottom centrifuge tube with Zirconia/Silica beads. A Bead Beater was used to homogenize the tissue. An RNEASY® Microarray Tissue Kit from Qiagen (Catalog no. 73304) was used to purify the RNA from the tissue homogenate. RNA was stored at −80° C. until used.

Microarray gene expression analysis. Total RNA was amplified and labeled following the AFFYMETRIX™ (Santa Clara, Calif.) standard protocol for whole transcript expression analysis, followed by hybridization to AFFYMETRIX™ MOUSE GENE 2.0 ST® arrays. The arrays were processed following the manufacturer recommended wash and stain protocol on an AFFYMETRIX™ FS-450 fluidics station and scanned on an AFFYMETRIX™ GENECHIP® 7G scanner using Command Console 3.3. The resulting .cel files were imported into PARTEK® Genomics Suite 6.6 and transcripts were normalized on a gene level using RNA as normalization and background correction method. Contrasts in a 1-way ANOVA were set up to compare the treatments of interest.

Quantitative RT-PCR Gene expression analysis. Gene expression was carried out by quantitative RT-PCR using quality verified RNA samples obtained previously. First strand cDNA was obtained from reverse transcription of 150 ng RNA using a SUPERSCRIPT VILO cDNA synthesis kit (Life Technologies) according to the manufacturer's instructions. Optimal amounts of template cDNA were added to a reaction mixture containing 10 μl of 2× TAQMAN® Fast Advanced Master Mix (Life Technologies) and endonuclease free water to 20 μl and loaded in TAQMAN® Array Standard 96 well Plates (APPLIED BIOSYSTEMS™). Those plates contained pre-spotted individual TAQMAN® Gene Expression probes for detection of genes of interest as well as the house keeping genes 18 S, beta actin (ACTB), and GAPDH. PCR amplification was carried out using a 7900HT Fast Real-Time PCR System (APPLIED BIOSYSTEMS™) in the following conditions: 95° C., 20 min; 40 cycles (95° C., 1 min); 20 min at 60° C. The 7500 Software v2.0.6 (APPLIED BIOSYSTEMS™) was used to determine the cycle threshold (Ct) for each reaction and derive the expression Ratios.

Lymphocyte isolation. Eight week old C57BL/6J female mice were vaccinated according to the schedule in the Animals and Treatments section. One or two weeks following the second vaccination with PBS or CTBp the animals were sacrificed. Colons were removed for immune cell isolations. Lamina propria lymphocytes (LPLs) were isolated from the colons by using a series of washing steps and collagenase steps. Epithelial cells, mucus and fat tissue were removed by incubating with EDTA at 37° C. The colon and small intestine were cut into small pieces and incubated with collagenase at 37° C. Cell suspensions were separated using Percoll gradients and the middle layers, containing the lymphocytes, were isolated and counted. Cells were counted in a hemocytometer.

Flow Cytometry. Cells were stained using antibodies and a Cell staining kit from EBIOSCIENCES™, Inc. (San Diego, Calif.). Briefly, tubes containing $1\times10^6$ cells were washed with flow cytometry staining buffer 2 times. Fc Block was added to each tube in flow cytometry staining buffer for 10 minutes.

For adaptive immune cell populations, surface staining antibodies were then added to each tube (CD3-FITC, CD4-APC-Cy7, CD25-PerCP) and allowed to incubate at 4° C. for 30 minutes. After removing surface antibodies, fixation/permeabilization buffer was added to the tubes and incubated overnight. The following morning the tubes were washed with permeabilization buffer two times and again incubated for 10 minutes with Fc block. Internal cell antibodies (Gata3-PE, T-Bet-PE-Cy7, FoxP3-APC, IL-17-EFLUOR® 450) were added to each tube and incubated for 30 minutes at 4° C. The tubes were washed two times with permeabilization buffer and finally cells were suspended in flow cytometry staining buffer.

For innate immune cell populations, surface staining antibodies were added to each tube (CD19-APC, CD3-FITC, CD49b-PE, F4/80-PeCy7, CD11c-PerCP-Cy5.5, CD8-APC-EFLUOR® 780, and CD45-EFLUOR® 450) and allowed to incubate at 4° C. for 30 minutes. After removing surface antibodies, fixation buffer was added to the tubes and incubated overnight. The tubes were washed two times with flow cytometry staining buffer and suspended in flow cytometry staining buffer. Events ($1\times10^5$) were counted on a BD FACSCANTO™ II and analyzed with the BD FACS-DIVA™ Software v6.1.3.

Caco-2 Wound Healing Assay. The Caco-2 wound healing assay was performed using a modified method. Briefly, Caco-2 cells were seeded and grown to confluence in 6 well plates (THERMO SCIENTIFIC™ NUNC™ Cell-Culture Treated). The culture medium was discarded and 0.5-1.0 mm across linear wounds were made with a 200 μL sterile beveled pipette tip (USA Scientific) and cells were washed with PBS to remove loose cells. CTBp (0.3-1 μM), transforming growth factor-β (TGF-β; 5 ng/ml), or PBS were subsequently added in fresh serum-deprived medium to a total volume of 2 mL. Photomicrographs of the wounds were taken at 0 hours and 48 hours after the wounding using a 4× magnification. Quantification of the remaining cell-free area to the initial wound area was calculated as a mean percentage using the public domain software Image J.

Histology. Colons were removed and washed with PBS. A portion of the distal colon was fixed with paraformaldehyde overnight and stored in 70% ethanol until paraffin embedding, sectioning and routine H&E staining. Inflammation scoring was performed using a scale that has been previously published. Tissue sections from 8 mice were scored and averaged for each group. Statistics were performed comparing each group.

Protein Isolation and quantification. Distal colon sections were isolated at sacrifice and stored at −80° C. until the protein was isolated and analyzed. Briefly, tissue was frozen in liquid nitrogen and pulverized with a Bessman Tissue Pulverizer and placed in T-PER (Thermo Scientific) with a protease inhibitor cocktail (Sigma-Aldrich). Protein was isolated by gravity centrifugation of tissue fragments, removing the buffer containing isolated protein, and storing at −80° C. until analysis. Protein sample concentrations were determined using a NANODROP™ 1000 (Thermo Scientific). Protein was normalized for all samples prior to loading on a Mouse Cytokine/Chemokine Magnetic Bead Panel (EMD Millipore). The panel was analyzed with a MILLIPLEX® MAP Kit on a MAGPIX® with LUMINEX® XMAP® technology.

Disease Activity Index. Animals were scored on a daily basis which consisted of the following scoring rubric adapted from the literature. Weight loss: 0 for no weight loss, 1 for 1 to 5% weight loss, 2 for 6 to 10% weight loss, 3 for 11 to 15% weight loss and 4 for greater than 15% weight loss. Stool consistency: 0 for normal stools, 2 for loose stools and 4 for diarrhea. Occult blood: 0 for no blood, 1 for some occult blood, 2 for heavy positive occult blood, 3 for visible blood in stool with no anus clotting, or 4 for gross anus bleeding and clotting present.

Tumor Scoring. Tumors were scored via endoscopic analysis of the full length of the colon. Tumor scoring was based on the following rubric: 0 for no tumor, 1 is a very small but detectable tumor, 2 the tumor covers up to ⅛ colon circumference, 3 tumor covers ¼ of colon circumference, 4 tumor covers up to ½ of colon, and 5 tumor covers more than ½ of colon.

Statistics. Graphs were prepared and analyzed using Graphpad Prism version 5.0 (Graphpad Software). To compare two data sets, an unpaired, two-tailed Student's t test was conducted. To compare three or more data sets, a one-way ANOVA with a Bonferroni post-test was conducted. For body weight and DAI results, a Two-way ANOVA with a Bonferroni post-test was conducted.

Example 1—Colon Lymphocyte Profile was Significantly Altered by CTBP

Since CTB is a strong mucosal immunogen and induces a robust mucosal antibody response upon oral administration, the immune cell populations were characterized in various immune compartments in CTBp-vaccinated mice. Both innate and adaptive immune cell populations were evaluated in the small intestine lamina propria and colon lamina propria, mesenteric lymph node, Peyer's patches and spleen using flow cytometry. For this analysis, mice were given PBS or 30 μg CTBp, orally, twice over a two-week period, a standard regimen used for oral cholera vaccination, and sacrificed one or two weeks after the second dose. Small intestines and colons were excised and Peyer's patches were removed from the small intestines. Leukocytes were isolated from the small intestine and colon lamina propria, Peyer's patches, mesenteric lymph node and spleen, and were then stained with specific markers for adaptive and innate immune cell subsets.

Figure 2:
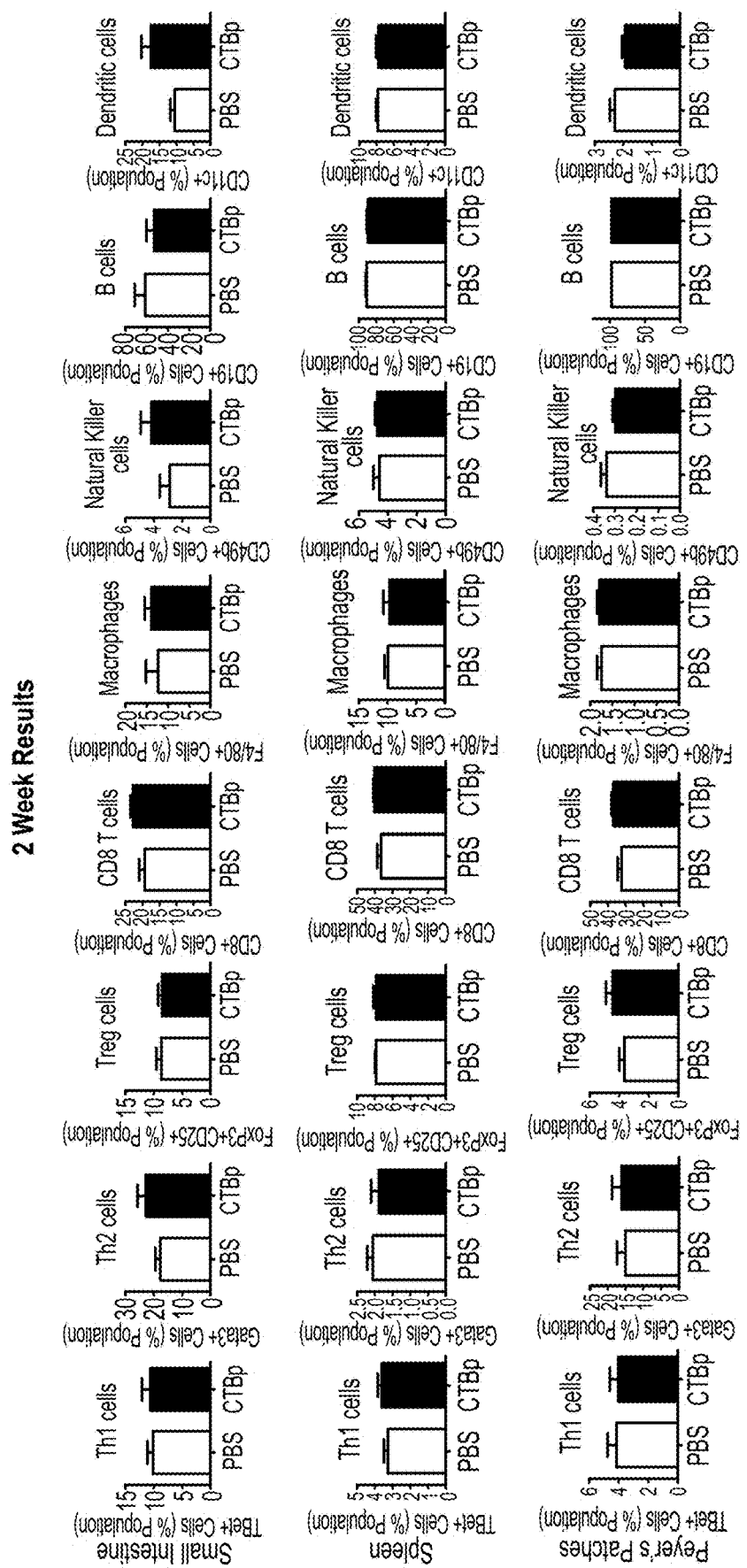
FIG. 2 includes graphs showing results of flow cytometry performed two weeks after CTBp administration.

T cell profiles were not significantly affected in the mesenteric lymph nodes or the spleen (FIGS. 1 and 2). A temporary significant increase of the B cell population (CD19+) within CD45+ cells was noted in Peyer's patches one-week post CTBp administration. For effector sites (lamina propria), an increased proportion of FoxP3+ CD25+ regulatory T (Treg) cells among total CD3+ CD4+ T cells was noted in the small intestine one week post vaccination, and there was also a trend of increase in CD8+ T cells (P=0.0667; FIG. 1). Meanwhile, a significantly increased proportion of $T_H1$ (TBet+) cells within CD3+ CD4+ cells was noted in the colon lamina propria one week post-CTBp administration (FIG. 1). In both small intestine and colon lamina propria, however, the changes in T cell populations did not sustain through the next week (FIG. 2), suggesting that CTBp oral administration has relatively short-term impacts on T cell profiles while inducing a robust and durable antibody response.

Figure 3:
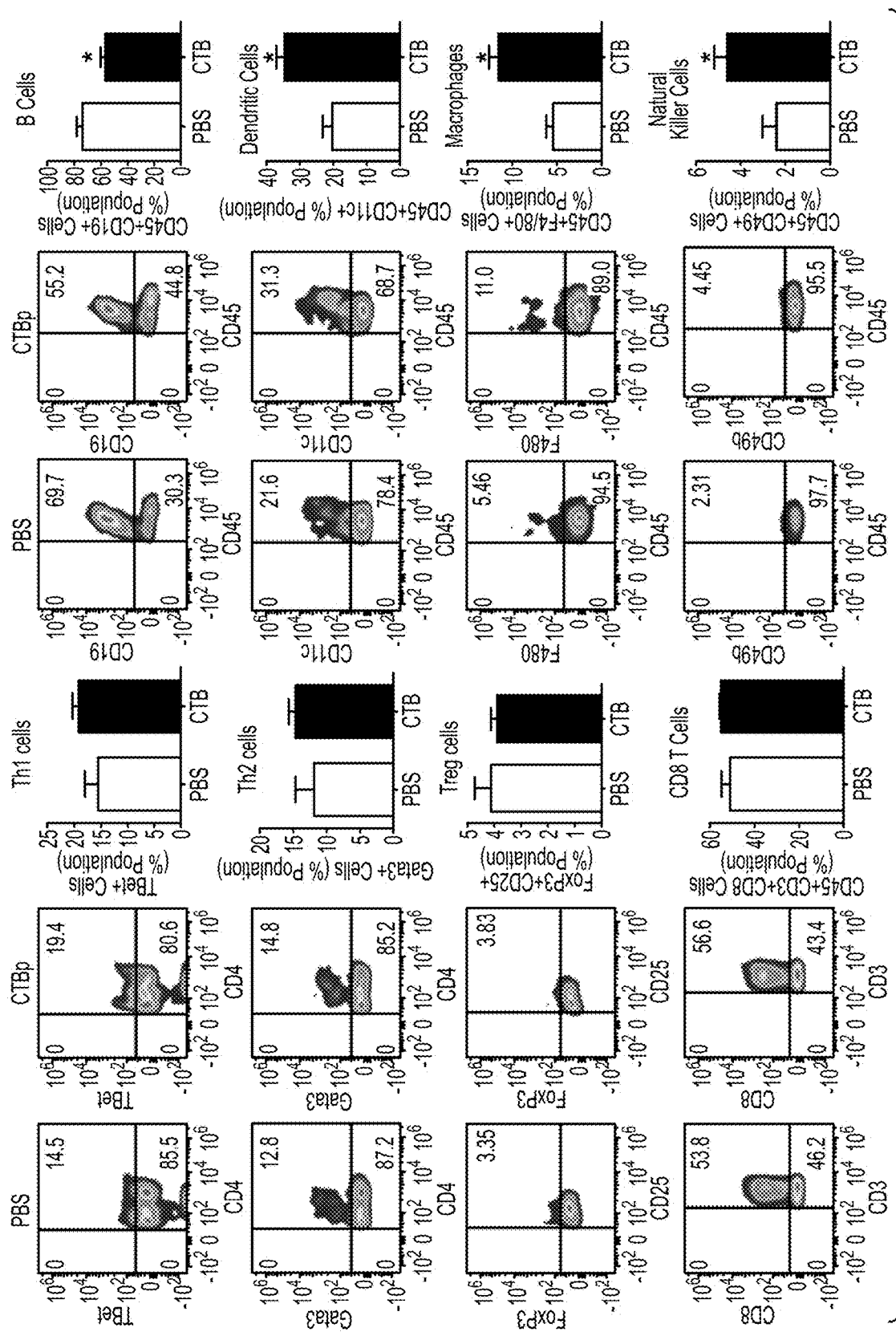
FIG. 3 includes graphs showing flow cytometry analysis of the colon lamina propria immune cell population.

Unexpectedly, more significant impacts were noted in innate immune cell populations in the lamina propria of colon, but not of small intestine, two week post CTBp oral administration (FIG. 3); macrophages (F4/80+), dendritic cells (CD11c+) and natural killer cells (CD49b+) were significantly increased within CD45+ cell populations when compared to the PBS group, which was associated with significant decrease in B cells. Immunohistochemistry analysis also revealed that the number of macrophages was increased in the colon lamina propria at the same time point after CTBp oral administration, compared to the PBS-fed control (FIG. 3). Hence, the results revealed an interesting effect of orally administered CTBp on the distal part of the GI tract two weeks after CTBp administration.

Example 2—Oral Ctbp Administration Affects Colon Gene Expression Profile More than Small Intestine's A microarray analysis of transcripts isolated from the small intestine and colon was performed to determine if CTBp affected gene expression in the GI tract, using a AFFYMETRIX™ MOUSE GENE 2.0 ST® array and PARTEK® Genomics Suite 6.6. A heat map was generated (FIG. 4A) to compare the gene expression profiles in the colon and small intestine. Mice were again given PBS or 30 µg CTBp twice over a two-week period and sacrificed two weeks after the second dose to further evaluate the time point of greatest change in immune cell populations.

Figure 4A:
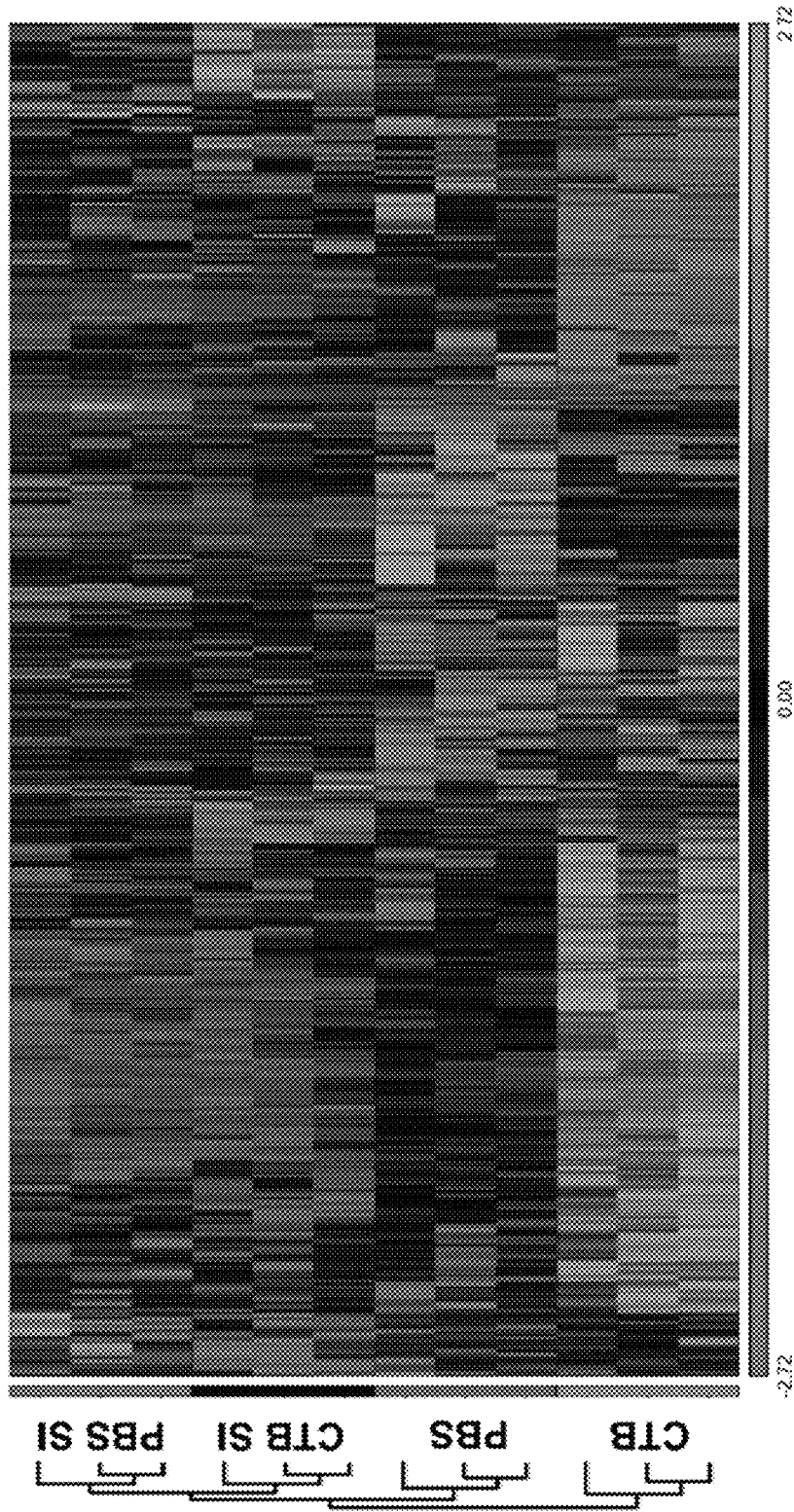
FIG. 4A is a heat map showing microarray analysis of gene expression in the colon epithelia.
Figure 4B:
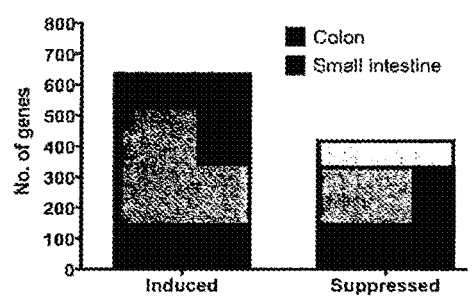
FIG. 4B is a transcriptome profile of intestinal genes after CTBp oral administration.

Orally administered CTBp had profound impacts on the gene expression of the entire intestinal epithelia (FIG. 4B). Interestingly, the gene expression profile in the small intestine clustered more closely together than that of the colon based on the heat map analysis. The gene expression patterns of the colons from PBS-fed mice were closely associated with those of the small intestine from both groups. However, the gene expression in colons from the CTB-treated mice was completely separated from the other samples in the heat map analysis (FIG. 4A). At a global level, 871 genes were significantly (p.ltoreq.0.01) altered following CTBp vaccination in the colon, while 184 genes were significantly altered in the small intestine (FIG. 4B). Of these significant genes, 539 were induced and 332 were suppressed in the colon. By comparison, the small intestine was fairly evenly split between induced and suppressed genes, 97 and 87, respectively.

Example 3—CTBP Enhances TGFB-Associated Gene Expression Pathways in the Colon

Figure 5:
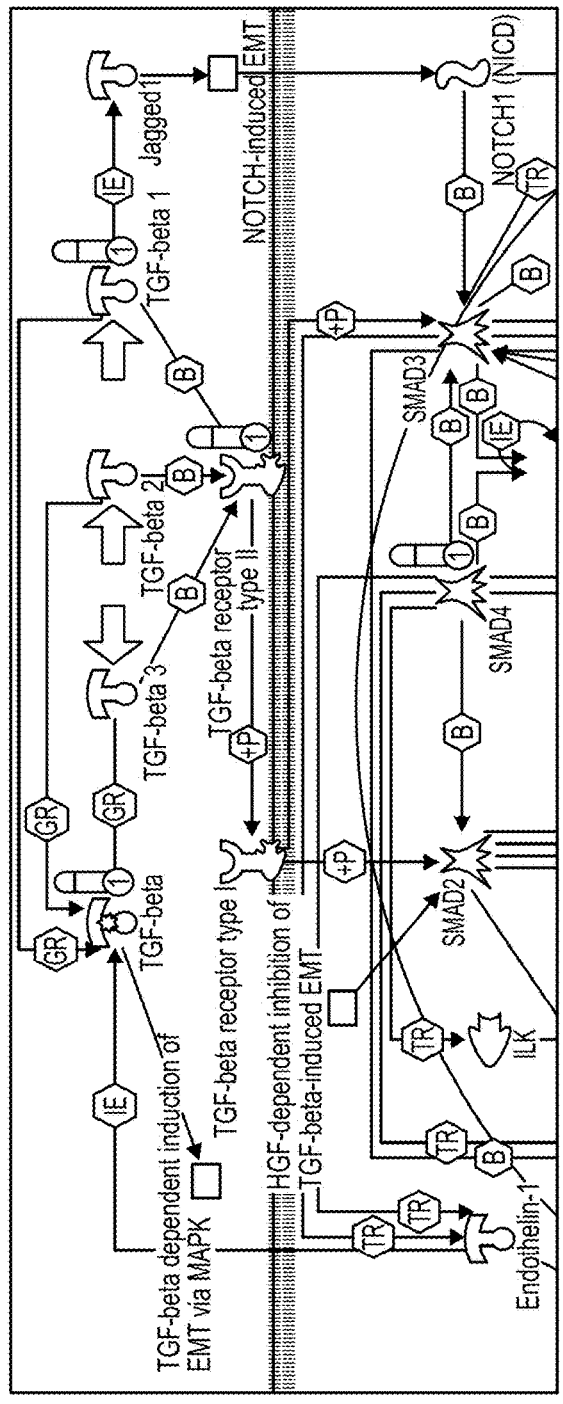
FIG. 5 is a schematic diagram showing a microarray TGFb pathway analysis.

Pathway analysis software in METACORE™ (version 6.22 build 67265) was used to dissect the gene expression alterations in the colon by CTBp administration. Interestingly, TGFβ-dependent pathways heavily populated the most significantly induced pathways following CTBp oral administration (FIGS. 4C-4D). Extracellular matrix remodeling pathways and epithelial to mesenchymal pathways were among the most significantly induced pathways by CTBp vaccination. Indeed, when evaluating individual gene expression from the microarray analysis Tgfβ1, TgfβII receptor, and Smad4 are significantly induced by CTBp oral administration (FIG. 5). These results indicated that CTBp can facilitate epithelial wound healing.

Figure 6A:
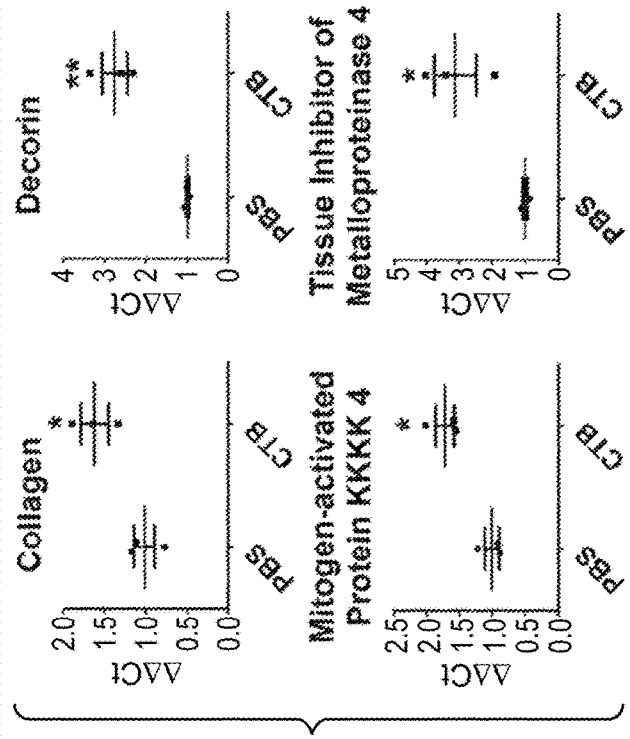
FIG. 6A includes graphs illustrating qPCR analysis of collagen, decorin, mitogen-activated protein KKKK4, and tissue inhibitor of metalloproteinase 4.
Figure 6B:
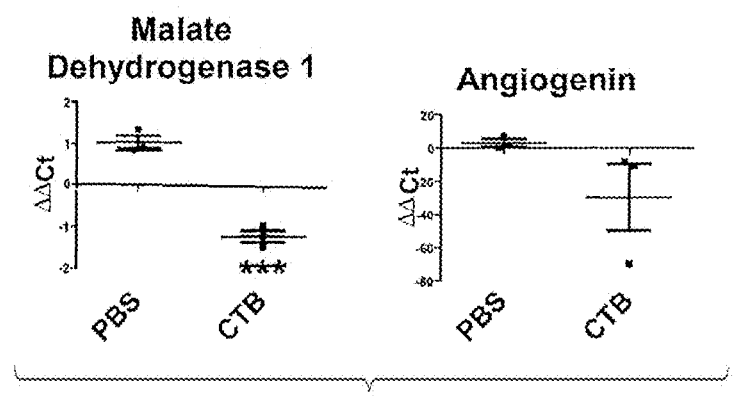
FIG. 6B includes graphs illustrating qPCR analysis of malate dehydrogenase 1 and angiogenin.
Figure 6C:
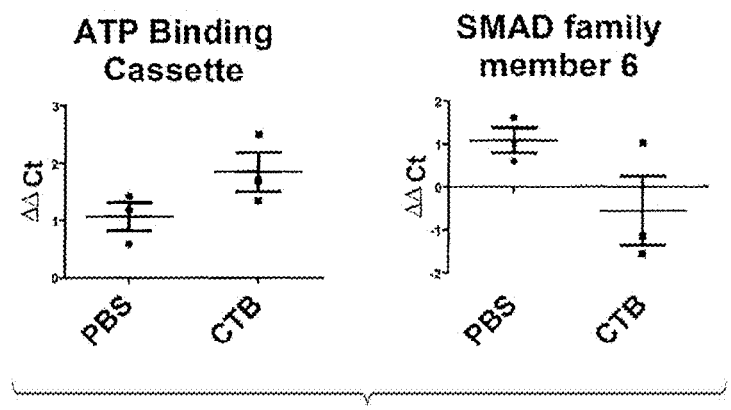
FIG. 6C includes graphs illustrating qPCR analysis of ATP binding cassette and SMAD family member 6.

By contrast, such strong induction of TGFβ-related pathways was not observed in the small intestine. Suppressed pathways in the colon epithelia included several metabolic pathways, cystic fibrosis transmembrane conductance regulator (CFTR) pathways, and an apoptosis associated pathway. Genes associated with lipid, bile acid, pyruvate, and androstenedione and testosterone metabolic pathways were significantly blunted by CTBp. Interestingly, Hsp70, Hsp90, Hsp90a, and St/1 were significantly suppressed in several of the pathways analyzed following CTBp oral administration, which are implicated in the progression of colon cancer. To confirm the results in our microarray analysis quantitative real-time-PCR (qPCR) analysis was performed on the transcripts of selected induced, suppressed, or unchanged genes. High agreement was found between the microarray and qPCR results (FIG. 6). Notably, a wound healing pathway-focused qPCR analysis revealed that many of the key genes in this pathway, including: Col14a, Mmp2, Col1a1, and Col3a1 are significantly upregulated by CTBp oral administration (FIGS. 6A-6C). Based on the changes in immune cell populations and gene expression it was hypothesized that the gut microbiome may also be altered.

Example 4—the Overall Microbiome Profile was Largely Unaltered by CTBP 2 Weeks after Administration With the changes in the gene expression of the colon and immune cell populations, a possible change in the microbiome profile was speculated. Fecal samples were collected prior to initial dosing with PBS or CTBp and at the time of sacrifice and sequencing of the V4 region of 16S ribosomal RNA was performed on fecal DNA.

Figure 7C:
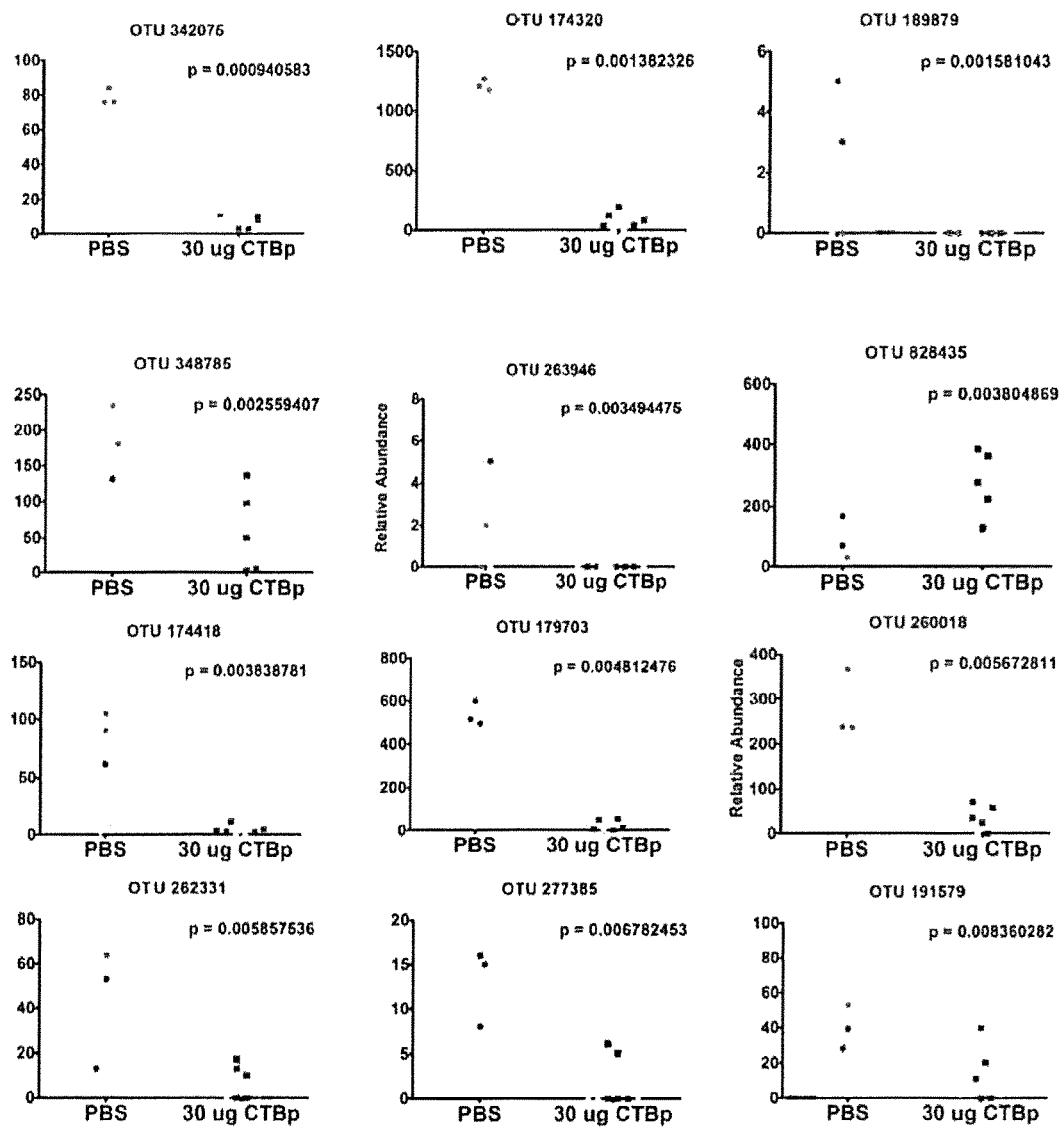

The overall microbiome profile was not significantly altered by CTBp oral administration after 2 weeks (FIG. 7A). Bacteroidetes and Firmicutes spp. dominated the abundance levels at the phylum level which is typical for C57BL/6J mice. Additionally, the six most common species were split evenly between Bacteroidetes and Firmicutes (FIG. 7B). However, there were minor subpopulations of gut flora that appeared to have been modified by CTBp administration; all belonging to the phylum Firmicutes. Of the 12 Operational Taxonomic Units (OTUs) significantly altered by CTBp administration, 11 were significantly downregulated compared to the PBS colon fecal samples (FIG. 7C). All 11 downregulated OTUs can be traced to the order Clostridiales of the Firmicutes phylum. The remaining OTU, which was induced, belonged to the order Erysipelotrichales of the Firmicutes phylum.

Example 5—Human Colonic Epithelial Cell Wound Healing was Significantly Enhanced by CTBP To investigate the mucosal wound healing potential of CTBp suggested by the gene expression analysis, the human colon epithelial cell line Caco-2 wound healing model was employed. In this assay, closure of wound after 24 hours in the presence of CTBp, TGFβ or PBS control was measured.

Figure 8A:
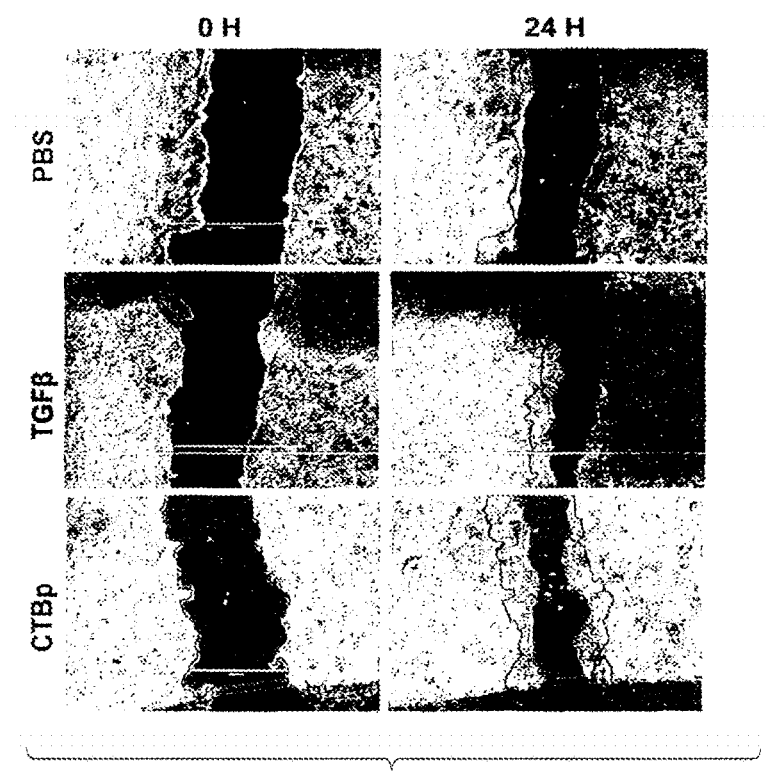
FIG. 8A includes photomicrographs of wounded CaCo2 cells, where the in vitro wound closure was recorded over 24 hours and microscopically analyzed.
Figure 8B:
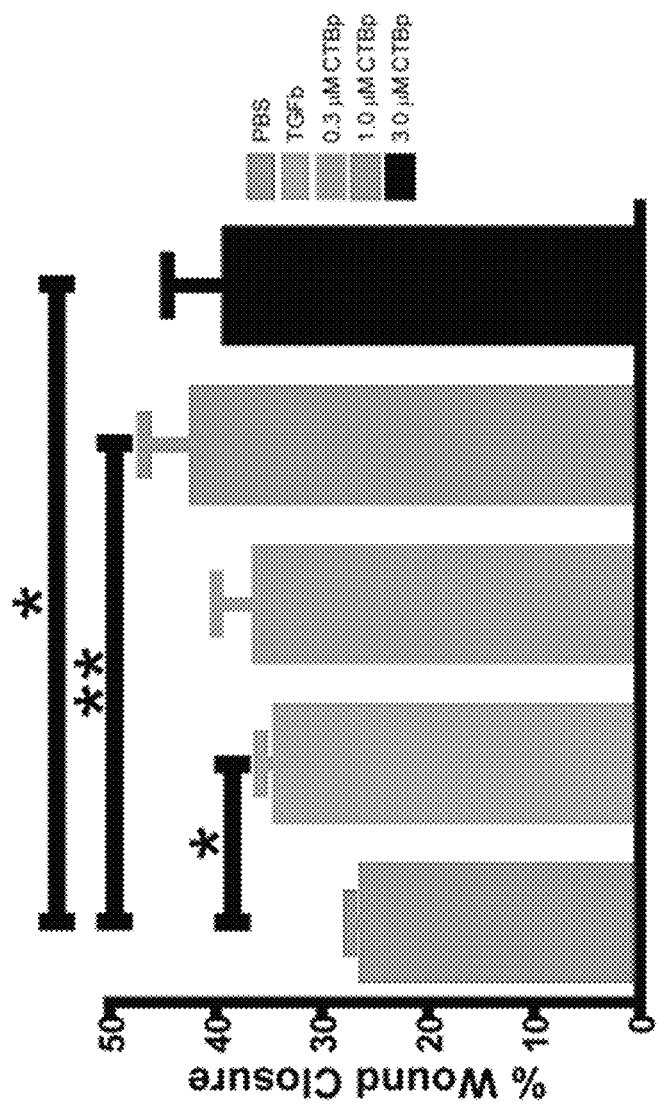
FIG. 8B is a graph illustrating analysis of in vitro wound closure after 24 hours by wound area measurement. Graphs represent percent wound closure after 24 hour (*,  *=$p<0.05$, 0.01, 0.001; One-way ANOVA with Bonferroni's multiple comparison tests).
Figure 8C:
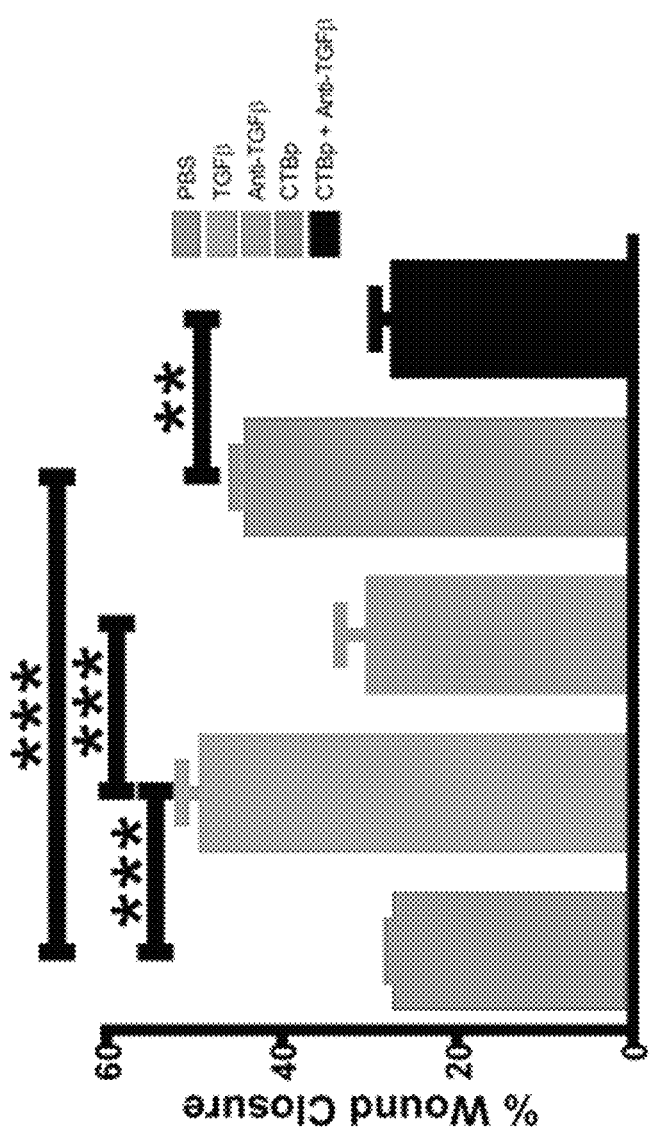
FIG. 8C is a graph showing that the enhancement of wound closure provided by TGFβ or 1 µM CTBp was inhibited by anti-TFGP antibody. Graphs represent percent wound closure after 24 hour (*, , *=$p<0.05$, 0.01, 0.001; One-way ANOVA with Bonferroni's multiple comparison tests).

As shown in FIGS. 8B-8C, CTBp (1.0 and 3.0 µM) significantly enhanced wound healing as compared to the PBS control, which was comparable to 5 ng/ml of TGFβ. Co-incubation of CTBp with an anti-TGFβ antibody (50 ng/mL) completely blunted the wound healing, demonstrating that CTBp's effect is mediated by TGFβ.

Example 6—CTBP Mitigated DSS-Induced Acute Colonic Injury and Inflammation

With the above data supporting a mucosal wound healing potential of CTBp, from both colon gene expression analysis after CTBp oral administration and an in vitro human colon epithelial wound model, it was next explored if this potential can be translated into a therapeutic effect in vivo. The DSS model of colitis induces injury in the distal colons of mice. PBS or 30 CTBp was orally administered twice to mice prior to DSS exposure and body weights were recorded daily. Distal colons were removed, paraffin embedded and stained with hematoxylin and eosin (H&E) for inflammation scoring.

DSS exposure resulted in significant body weight loss, a strong indicator of disease severity, when compared to control animal's at the most extreme point of weight loss (FIG. 9A). However, oral administrations of CTBp significantly blunted the weight loss during the end of the DSS exposure and early recovery period.

Histopathological examination was performed on the H&E-stained colon tissue sections to assess disease severity at the end of the DSS cycle and after a one-week recovery period. PBS administration resulted in aberrant loss of crypts with crypt regeneration, mild inflammatory infiltrates noted, and ulceration present in the colon sections after a 1 week recovery period. Oral administration of CTBp resulted in shortening of basal crypts and mild inflammatory infiltrates, but no loss of the epithelial surface following a one week recovery period. (FIGS. 9B and 9C). Importantly, CTBp administration appeared to have prevented the formation of fibrosis in the submucosa according to Masson's trichrome stain; on the contrary, fibrosis was evident in the PBS-administered control group (FIG. 9C).

Figure 10A:
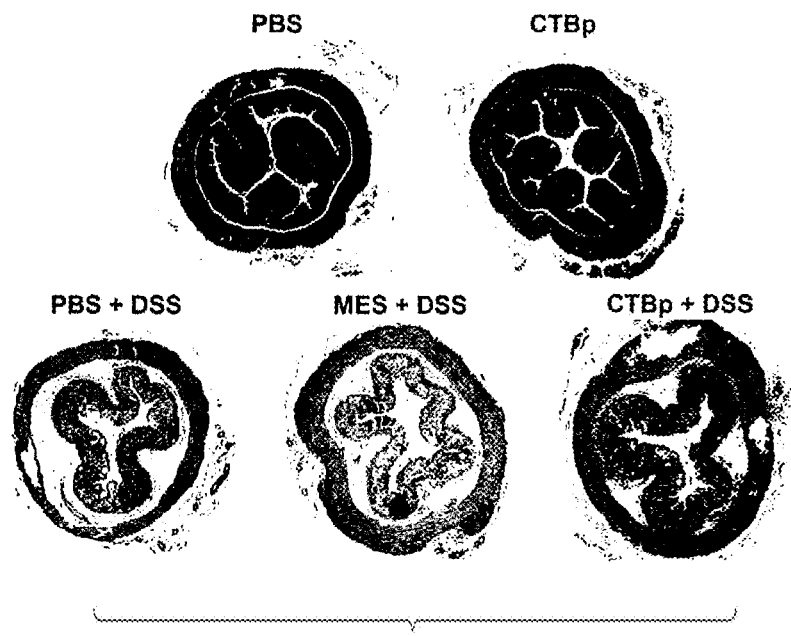
FIGS. 10A-10C are graphs and images illustrating CTBp's effects in an acute DSS colitis model immediately after DSS exposure.

Given that CTBp administration significantly improved the recovery from DSS-induced acute injury and inflammation in the colon, the effect at the maximum injury/inflammatory point immediately after DSS exposure was investigated next. Indeed, at this point the inflammation score was indicative of almost complete absence of crypts, moderate inflammatory cell infiltration in the mucosa and submucosa, and loss of the epithelial surface cells with PBS administration (FIG. 10A). Notably, CTBp administration significantly blunted the inflammation score; characterized by a shortening of the basal crypts, mild inflammatory infiltrates in the mucosa and submucosa, but retention of the epithelial cell surface. Meanwhile, daily oral administration of 100 µg mesalamine (MES) for 7 days during the DSS exposure, which simulates a current treatment for UC in humans, showed similar protection observed with the CTBp administration regimen employed here, demonstrating the effectiveness of CTBp against acute colonic injury and inflammation.

Figures 9D, 9E:
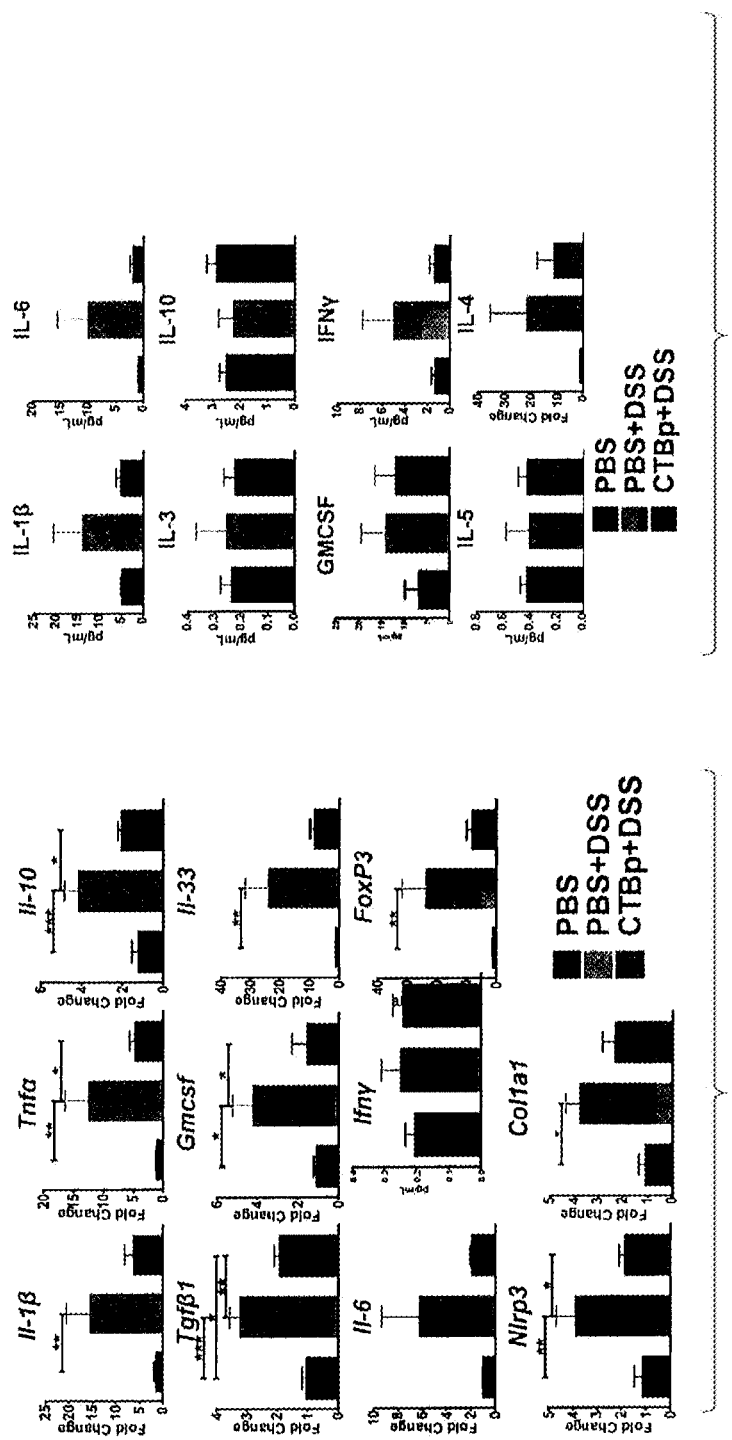

To further characterize CTBp's protective effect at the gene expression level, changes in ulcerative colitis-related genes were analyzed by quantitative real-time PCR analysis on total RNA isolates from the mouse colons. While the body weight has been mostly recovered at one week after the end of DSS exposure, classic ulcerative colitis cytokines, including Il-1β, Tnfα, and Il-33, were still significantly high at this time point in the PBS-administered group (FIG. 9D). Notably, CTBp administration blunted the expression of these genes to near baseline one week after the end of the DSS exposure (FIG. 9D). Nlrp3, crucial to gut homeostasis, gene expression was significantly induced by DSS exposure and CTBp administration significantly blunted the gene expression compared to PBS pretreated, DSS exposed mice after a one week recovery period. Gm-csf, which induces a proinflammatory cytokine profile from M1 macrophages, was significantly elevated by DSS exposure and CTBp administration significantly blunted Gm-csf expression.

Figure 10B:
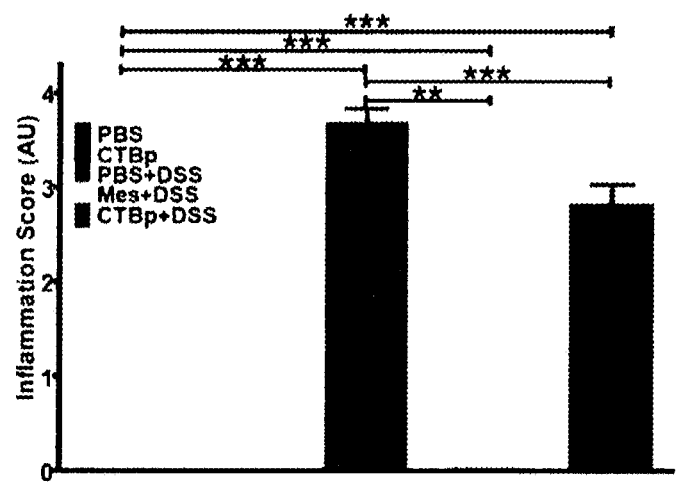

Overall similar trends were also noted at the maximal inflammatory time point; immediately following the end of DSS exposure, CTBp administration significantly blunted the increase of Il-1β, Il-33, Ifn.gamma., and Tnfα gene expression induced by DSS exposure (FIG. 10B). Though not statistically significant, CTBp also alleviated the massive increase of Il-6 induced by DSS exposure. Additionally, CTBp administration prevented the elevation of Gm-csf following DSS exposure (FIG. 10B).

Figure 10C:
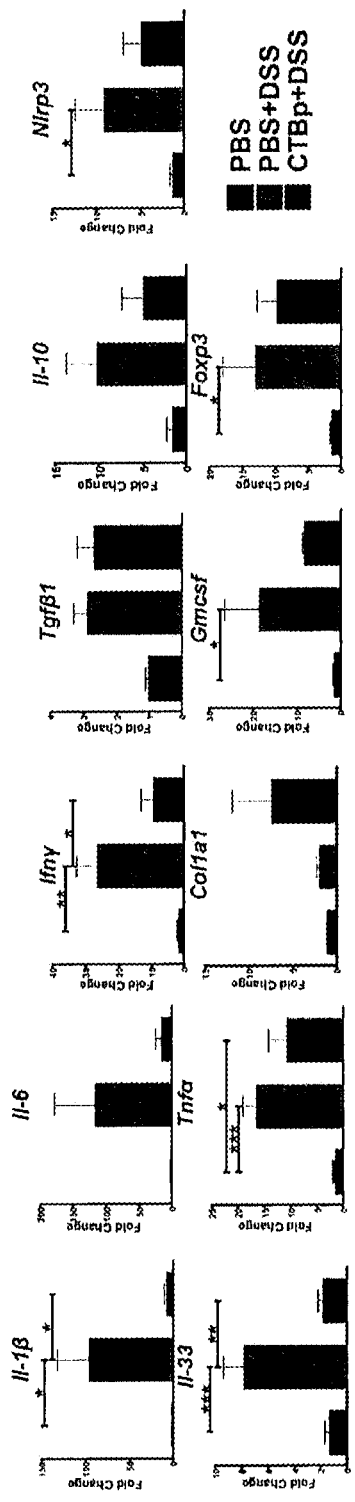
Figure 10D:
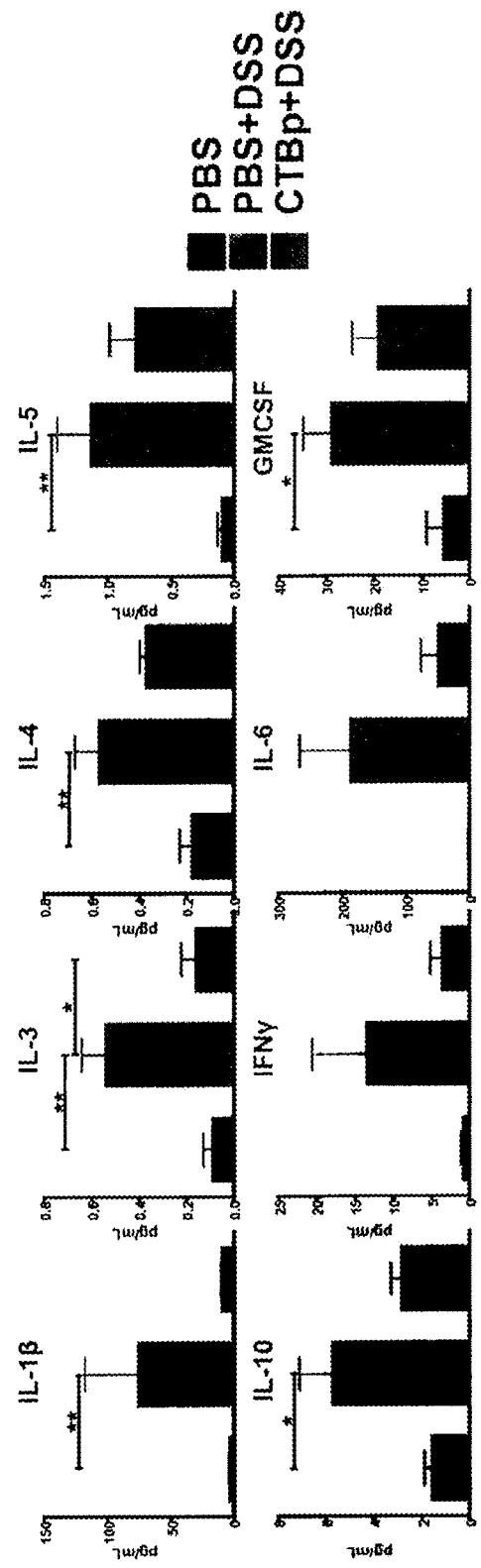
(FIG. 10D) Graphs illustrating various protein levels for mice administered PBS, PBS+DSS, and CTBp+DSS.

To confirm the gene expression results, soluble inflammatory markers were measured at the protein level in the distal colon using a MILLIPLEX® MAP Kit. Immediately following the end of the DSS exposure period, CTBp administration mitigated increases in major inflammatory proteins (IL-1β, IFN.gamma., IL-3, IL-4 and IL-5) and IL-3 following DSS exposure as well as a significant reduction in IL-3 (FIG. 10C). Interestingly, CTBp administration did not induce IL-10, which was significantly increased in the DSS exposed PBS pretreated group, suggesting that CTBp's anti-inflammatory activity is independent of the anti-inflammatory cytokine. By the end of the one-week recovery, all the elevated inflammatory markers induced by DSS exposure had returned to normal levels comparable to those of the non DSS-exposed control group. Hence, there was no noticeable effect of CTBp at the protein level at this time point (FIG. 9E).

Example 9—CTBP Oral Administration Protected Against Colon Cancer Development in an AOM/DSS Colitis Model The significant protection seen in the acute colitis/colon injury model prompted us to investigate if CTBp could also protect in a chronic model of ulcerative colitis and colitis-associated colon cancer. AOM was administered by intraperitoneal injection and one week later mice were exposed to DSS for one week. The DSS exposure was followed by a two-week recovery phase, and the DSS exposure/recovery cycle was repeated an additional two times. Upon completion of the third cycle, the mice were sacrificed and colons removed for analysis. Disease activity index was used as a metric to assess colitic activity in mice during the live phase of the experiment, in which occult blood, body weight, and fecal consistency were scored and averaged for each animal. At sacrifice, colons were analyzed for tumors with an endoscope and tumors were scored based on a previously developed rubric.

Figure 11A:
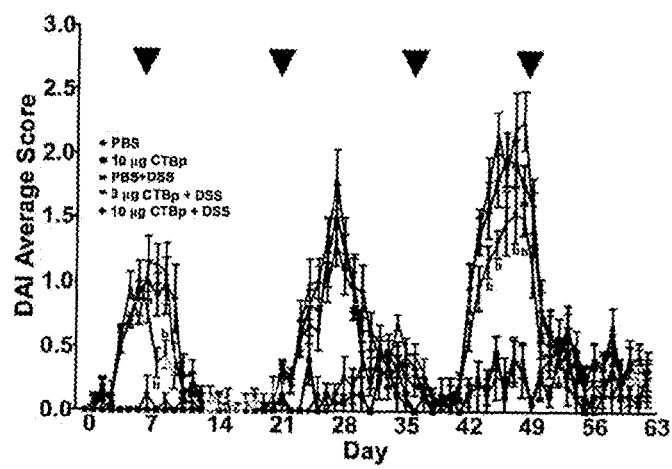
FIGS. 11A-11D are graphs and images illustrating CTBp's effects in a chronic colitis/colon cancer model.
Figure 11B:
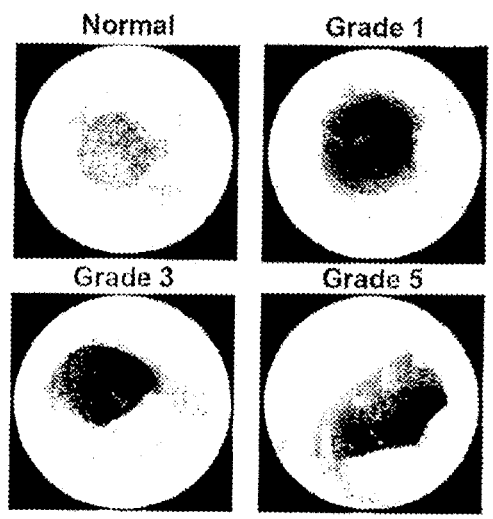
Figure 11C:
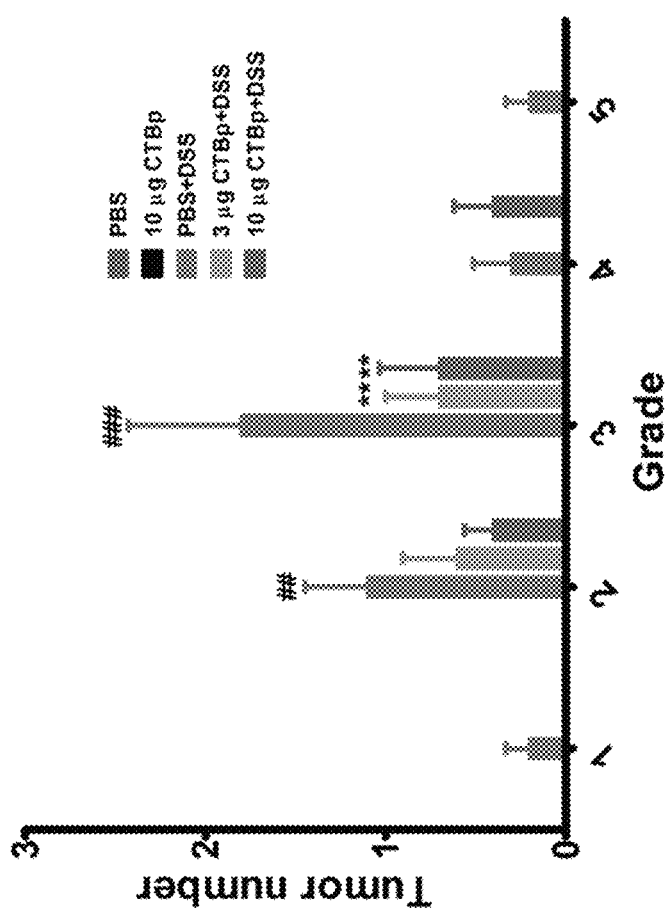
Figure 11D:
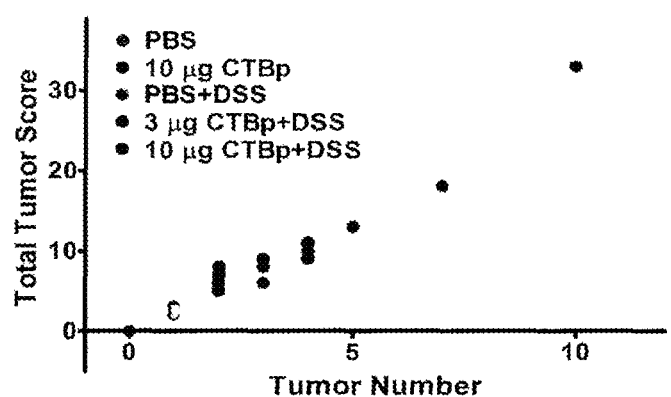

As shown in FIGS. 11A-11D, DSS exposure significantly and progressively increased the disease activity index score in mice over the 3 exposure periods in the chronic colitis model. Additionally, tumor numbers were significantly increased in mice exposed to DSS compared to controls. Notably, CTBp administration significantly decreased the disease activity index score immediately following the first dose of CTBp and more dramatically during the 3.sup.rd DSS exposure period (FIG. 11A). This decrease in disease activity index score was associated with a significantly reduced number and size of tumors in CTBp treated mice compared to PBS treated mice. DSS exposed mice developed on average four tumors per colon over the length of the study (FIG. 11C). CTBp administration significantly blunted the number of tumors to approximately one tumor per colon (FIG. 11C). Additionally, a significant increase of grade 2 and 3 tumors in DSS exposed mice was not seen in mice given CTBp. Of note, grade 4 and 5 tumors were found in DSS exposed mice, but no tumors above a grade 3 were found following CTBp administration (FIGS. 11C and 11D).

Discussion of Examples 1-9

The generation of CTBp, a novel CTB variant that was robustly produced in *N. benthamiana* while retaining key molecular properties of the original protein, has been previously reported. The plant-produced protein had Asn4→Ser mutation to avoid N-glycosylation and a C-terminal hexapeptide sequence attached for endoplasmic reticulum (ER) retention in plants to facilitate recombinant production. Notwithstanding those sequence modifications, CTBp had the GM1-ganglioside binding affinity and capacity to induce mucosal and systemic anti-CTB antibodies that were comparable to those of bacterially produced CTB, suggesting that they are immunologically identical. CTB's strong mucosal immunogenicity is appreciated. However, its detailed biological activities and impacts on the GI tract upon oral administration are not comprehensively described. Hence, the initial goal for this Example was to characterize what affect CTBp had on the GI tract following oral administration using a systems biology approach; by profiling gene expression changes and characterizing lymphocyte populations in relevant immune compartments. The Example also linked gene expression and immune cell population changes to the gut microbiota. To effectively reveal CTBp's impacts, mice were administered 30 μg CTBp twice over a two week period, since this dose induced the maximum antibody response that lasted over 6 months.

It has been previously suggested that CTB alters the T cell profile. In the present studies, some significant changes were observed in T.sub.H cell compositions in the lamina propria effector sites of the small intestine and the colon one week after the second oral dose of CTBp (i.e., increase of FoxP3+ CD25+ Treg cells in the small intestine and $T_H1$ cells in the colon; FIG. 1). However, these changes in $T_H1$ cell populations did not persist through the second week post CTBp oral administration despite a long-lasting intestinal and systemic anti-CTB antibody response induced by the same dosing regimen.

The most striking changes were noticed in the colon lamina propria 2 weeks after CTBp administration; interestingly, while T cell profiles were not affected, other immune cell types were significantly altered in the colon (FIG. 1). Dendritic cell, macrophage and natural killer cell ratios among the CD45+ cell population were significantly increased by CTBp administration. On the contrary, B cell composition was significantly reduced, although this may simply reflect the relative increase of the innate immune cell populations among CD45+ cells (B cells still represented the major fraction (>50%) of CD45+ cells). Such a finding on orally administered CTB's impacts on innate immune cells in the distal portion of the GI tract mucosa is unprecedented, representing one of the protein's yet to be uncovered immunomodulatory activities.

In vitro, it is appreciated that CTB affects dendritic cell maturation and diminishes the proinflammatory response of macrophages to lipopolysaccharide. However, whether these in vitro results are relevant to the present findings in vivo is elusive, and additional investigation is warranted for the detailed mechanism and the biological consequence of CTBp's impacts on innate immune cells in the colon. The results of this Example, however, showed that the alteration in immune cell populations in the colon was associated with dramatic changes in the gene expression pattern of the colonic epithelium (FIG. 4A), but it did not seem to be linked to gut microbiota (FIG. 7C).

The transcriptomic analysis revealed that CTBp oral administration dramatically altered gene expression profiles in the small intestine and colon of mice. However, of interest is the findings that the greatest change was noted in the colon and that genes affected by CTBp are compartmentalized between the two intestinal regions (FIG. 4B). As gene expression changes in the colon were deciphered, it was found that Tgfβ-mediated pathways were most significantly altered in the colon, but this was not observed in the small intestine. Additionally, a pathway focused qPCR analysis revealed significant upregulation of genes associated with wound healing (FIGS. 4C-4D).

In a model of colonic anastomosis in rabbits, CT was previously shown to enhance wound healing by inducing Tgfβ. The results of this Example suggest that the effect could have been mediated in part by the B subunit of CT in that model. Although recombinant CTB was previously shown to induce IgA class-switching through Tgβ1 stimulation, the foregoing studies were believed to be the first report showing that CTBp oral administration increased Tgβ1 expression in the colon epithelium. TGFβ is a pleiotropic cytokine involved in various biological activities, including wound healing pathways. The present data combined with these previous findings point to an anti-inflammatory potential as well as a major role for CTBp in altering TGFβ-driven pathways in the colon. Conversely, the results of this Example revealed CTBp's novel function to enhance wound healing, apart from eliciting a strong humoral immune response, via its capacity to induce Tgfβ expression.

Despite these changes to gene expression and innate immune cell populations, no overall change in the microbiome of mice treated with CTBp (FIG. 7C) was observed. However, there were changes at the species level in 12 OTU's with 11 being of the Clostridiales order. This suggests that CTBp may have a transient effect on specific gut microbiome subpopulations but overall, the familial populations are not affected, at least at the specific time point (two weeks post CTBp oral administration) analyzed in the present study. While a potential long term effect on the microflora is yet unknown, the results of this Example indicate that the drastic changes in the colon immune cell and gene expression profiles observed two weeks post CTBp oral administration resulted from the protein's direct impacts on the colonic mucosa.

Consistent with the gene expression pathway analysis of the microarray and qPCR results, an in vitro wound healing assay using the Caco-2 human colon epithelial cell line showed that CTBp could enhance TGFβ-mediated mucosal wound healing (FIGS. 8A-8C). This unique wound healing enhancement capacity of CTBp was further demonstrated in a DSS-mediated acute colitis model in mice. Hallmarks of decreased inflammation (decreased body weight loss and inflammation scoring) in the DSS colitis model were noted after CTBp administration (FIGS. 9A-9E). At the protein level, IL-3 IL-5, and GM-CSF are significantly elevated at the end of the DSS exposure period in PBS pretreated mice (FIGS. 10A-10D), which is indicative of eosinophil recruitment to the distal colon and increased inflammation. However, these proteins were not significantly increased in CTBp treated mice immediately following the end of the DSS exposure; suggesting CTBp is able to blunt inflammation in colitic mice. Elevated GM-CSF has also been shown to lead to enhanced tumorigenisis in the colon.

Notably, after one-week recovery from DSS exposure, genes associated with fibrosis were significantly blunted by CTBp administration (FIGS. 9A-9E). Tgfβ1, Il-1β, and Nlrp3 play significant roles in promoting collagen deposition leading to fibrosis, which results from increased expression of collagen 1 (Col1a1), the major fibrous collagen (32, 42). Also, Nlrp3 suppression has previously been shown to blunt injury in the DSS colitis model of ulcerative colitis. In fact, histological analysis demonstrated that CTBp administration facilitated recovery of the colonic epithelial damage (FIGS. 9A-9E) and prevented fibrosis induced by DSS exposure. It should be noted that the TGFβ- and collagen-inducing effects of CTBp observed under normal physiological conditions did not result in adverse effects in the acute colitis model, perhaps due to the dose used in the study was within a therapeutic range in which the protein did not overstimulate the activation of TGFβ pathways. In turn, these results revealed the therapeutic effects of CTBp for mucosal wound healing and colitis.

The DSS colitis model employed in the present study was a well-established method for the study of ulcerative colitis and wound healing in a mouse. IBD is composed of two main disease subcategories, Crohn's disease and ulcerative colitis, which have similarities pathologically but some important differences remain. Overall, differences exist in genetic susceptibility, environmental factors and lastly different T helper cell expression profiles. While the exact etiology of IBD remains elusive, Crohn's disease is generally accepted to be a $T_H1$ driven disease while ulcerative colitis is a $T_H2$ driven disease with Th17 cells appearing to have a role in both IBD subtypes. More recently, others have found that a subset of Th17 cells that coproduce IFN.gamma. and IL-17 were specifically enriched in both active Crohn's disease and ulcerative colitis; highlighting the uncertainty remaining in IBD pathogenesis.

Ulcerative colitis has become a growing concern in the developed world and colon cancer is the second leading cause of cancer-related death in the United States. Additionally, individuals with ulcerative colitis are at an enhanced risk for developing colon cancer. Extent and duration of the inflammation in the colon plays a clear role in the development of colorectal cancer, which suggests that, by decreasing the length of the inflammation period and severity of the inflammation, the incidence of colorectal cancer can be decreased. The findings that CTBp mitigated inflammation and enhanced wound healing in an acute DSS model suggested that the protein could also protect in a more chronic colitis state leading to colorectal cancer development.

In the chronic colitis/colon cancer model, disease activity index scoring revealed significant protection by CTBp immediately following dosing and during the third cycle of DSS exposure, suggesting that the protein's therapeutic effect took place relatively quickly after administration. This in turn provided an implication for optimal CTBp dosing schedule for potential immunotherapy against ulcerative colitis. Data indicated that CTBp most effectively induced anti-colitis activity when dosed at the time of ongoing, not prior to the onset of, inflammation. Most importantly, biweekly oral administration of CTBp during the induction of chronic colitis resulted in significant decrease in the tumor number and tumor score at the end of the study. These findings illustrate that CTBp's effect on the wound healing pathway not only protects against inflammation and enhances wound healing but also protects against the development of colon cancer.

Interestingly, the microarray analysis of colon gene expression in healthy mice (FIGS. 4A-4D) revealed that Hsp70 and Hsp90 were significantly suppressed by CTBp administration; increased expression of these stress proteins has been associated with poor outcomes in colon cancer. Consequently, there may be an additional mechanism for CTBp to slow the growth of tumors in colorectal cancer besides anti-inflammatory/wound healing effects against colitis. No major difference was observed between the two doses of CTBp (i.e., 3 and 10 µg per mouse) in tumor prevention activity. In fact, the disease activity index was slightly better (though not statistically significant) with the lower dose. The apparent lack of dose-dependent effect may be related to the therapeutic window of CTBp, although a more thorough study is necessary to derive a conclusion in this regard.

Recently, the whole CT molecule (not CTB) has been shown to protect against colon carcinogenesis in the DSS colitis model employing Balb/c mice. In that study, 10 µg of CT was orally administered at the first day of each of the three cycles of DSS exposure. Interestingly, the authors found that macrophages were upregulated by CT administration much like we found with CTBp administration. However, the authors observed upregulated regulatory T-cells and IL-10 in the colonic mucosa, while such an effect was not seen with CTBp. This suggests the distinct mechanisms of CT and CTB in colitis-associated colon cancer prevention. Since CTBp is not toxic, unlike CT, and the effective dose of CTBp seems to be comparable to that of CT (total 4 administrations of 3 and 10 µg CTBp vs. total 3 administrations of 10 µg CT), it appears that CTBp may be superior as a candidate drug against ulcerative colitis and colitis-associated colon cancer.

Taken together, these results show that oral administration of CTBp has profound impacts on the distal portion of the GI tract in innate immune cell and epithelial gene expression profiles, which led us to discover CTBp's unique potential as a novel mucosal wound healing agent. Coupled with the efficient recombinant production in plants, CTBp represents an orally active immunotherapeutic agent providing clinical benefits for patients with ulcerative colitis.

Example 10—Cholera Toxin B Subunit Protects Against Colitis-Associated Colon Cancer in a Mouse Model Inflammatory Bowel Disease (IBD) is a growing problem in the developed world and a significant risk factor for developing colorectal cancer (CRC). Cholera holotoxin (CT) is the causative agent of severe diarrhea upon infection with *Vibrio cholerae*. CT induces massive immune responses at exposed mucosa and is one of the most potent mucosal immunogens described to date. A well characterized model of Ulcerative Colitis (UC) in mice is the DSS model, which induces a similar response as human UC (T helper 2 mediated). In a chronic DSS model in BALB/cJ mice, CT has also been shown to suppress carcinogenesis. Additionally, the B Subunit of CT (CTB) is currently used as a component of an internationally licensed, World Health Organization (WHO)-prequalified oral cholera vaccine for human use (DUKORAL®, Crucell). In a Crohn's Disease mouse model, CTB has been shown to protect against inflammation. This work has led to a clinical trial in which CTB was able to blunt inflammation in humans as well. The instant inventors have generated, in plants (*Nicotiana benthamiana*), a robust recombinant production system for a non-glycosylated variant of CTB (CTBp). The potential for mass production of CTBp led the inventors to explore the anti-inflammatory and immunosuppressive activities demonstrated by original CTB. In this Example, whether CTBp could protect against colitis-associated colon cancer in a mouse model was investigated.

Figure 12:
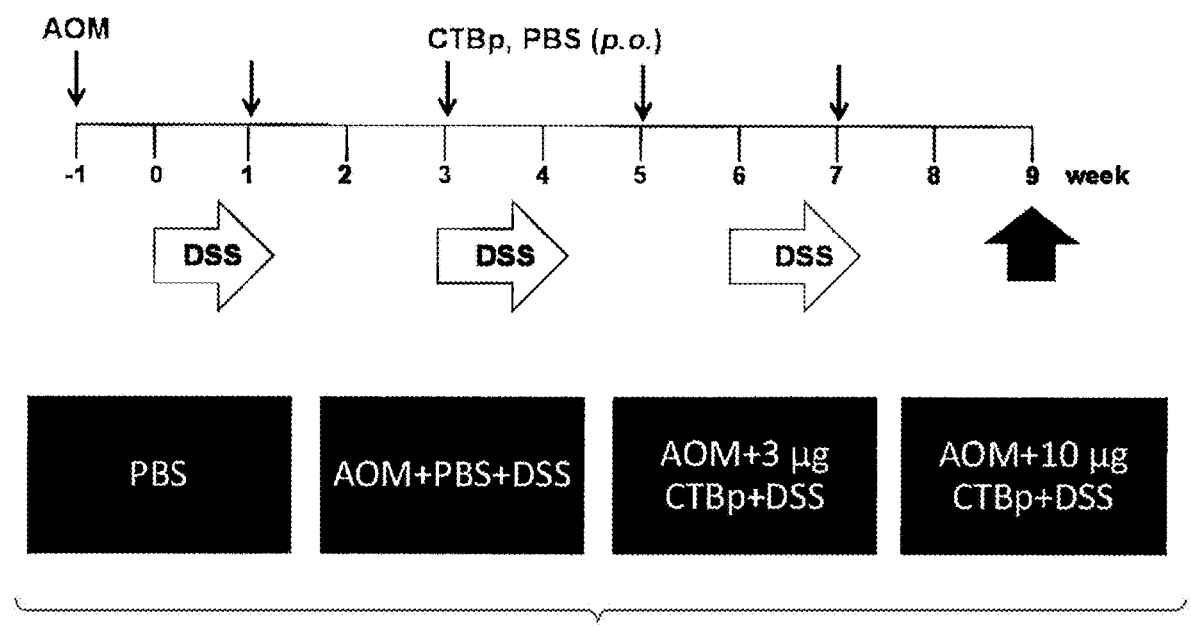
FIG. 12 is a schematic diagram of the experimental design according to an embodiment of the disclosure.

Animals and treatments. Eight week old female C57BL/6J mice were obtained from Jackson Laboratory (Bar Harbor, Me.). For the DSS experiment, animals were injected intraperitoneally (i.p.) with Azoxymethane (AOM) (10 mg/kg) one week prior to a one-week 2% dextran sulfate sodium (DSS) exposure period. The animals were given two weeks to recover from DSS exposure and the three-week cycle was repeated two more times. At the end of the first DSS exposure period mice were given oral (gavage) doses of CTBp (3 or 10 µg) or PBS and continued biweekly until the end of the study (FIG. 12). Body weights and Disease Activity Index (DAI) were determined daily. Following the last recovery period, the mice were sacrificed by $CO_2$ asphyxiation, the colons were excised, and the tumors were scored. Colon tissue was analyzed for inflammation, gene expression and inflammatory cytokine levels.

Hematoxylin and Eosin Staining. Tissue sections were collected from the distal colon and placed in 10% formalin for 18 H. The tissue was then placed in 70% Ethanol until the time of paraffin embedding. Paraffin embedding, cutting and H&E staining were performed by a trained professional. Tissue sections were scanned on an Aperio Scan Scope CS for analysis. Tissue sections were scored based on a modified prestablished rubric.

Disease Activity Index Scoring. Body weights and fecal samples were collected daily from the start of the first DSS exposure until study termination. The scoring rubric included a score for body weight loss: 0 for 0%, 1 for 1 to 5%, 2 for 5 to 10%, 3 for 10 to 15% and 4 for >15% weight loss. Additionally, fecal consistency was scored as: 0 for normal stool, 2 for loose stool and 4 for diarrhea. Finally occult blood was scored as: 0 for no blood, 1 for positive test, 2 for maximum positive test, 3 for visible blood in feces, 4 for gross anus bleeding and clotting present. The scores were added and averaged for each mouse and plotted.

Tumor Counting. At sacrifice, the colons were removed and an endoscope was inserted in the rectum and the entire length of the colon was scanned. Following the sacrifice the video was reviewed and tumors were scored based on the following rubric: 0=no tumor, 1=small but detectable, 2=covers up to ⅛ of colon, 3=covers up to ¼ of colon, 4=covers up to ½ of colon, and 5=covers over ½ of colon circumference.

Gene Expression. Sections from the Distal colon were stored in RNALATER™ (Qiagen, Valencia, Calif.) at −20° C. until RNA was isolated. RNA was isolated using a RNEASY® Microarray Tissue kit and cDNA was generated with TAQMAN® Fast Advanced Master Mix. Tissue sections were scanned on an Aperio Scan Scope CS for analysis. Gene expression was analyzed with a TAQMAN® array FAST plate and read with an APPLIED BIOSYSTEMS™ 7500 Fast Real-Time PCR System.

Protein Levels. Sections from the Distal colon were flash frozen and stored at −80° C. until the protein was isolated. Tissue was pulverized with a Besseman Tissue Pulverizer and placed in T-PER with a protease inhibitor cocktail. Gravity centrifugation removed the debris and the supernatant was collected and stored at 80° C. until analysis with an EMD Millipore mouse cytokine/chemokine magnetic bead panel.

Statistics. Summary data are means±SEM. Student T Test or ANOVA with Bonferroni's post-hoc test were used for the determination of statistical significance among treatment groups, as appropriate.

Figure 13A:
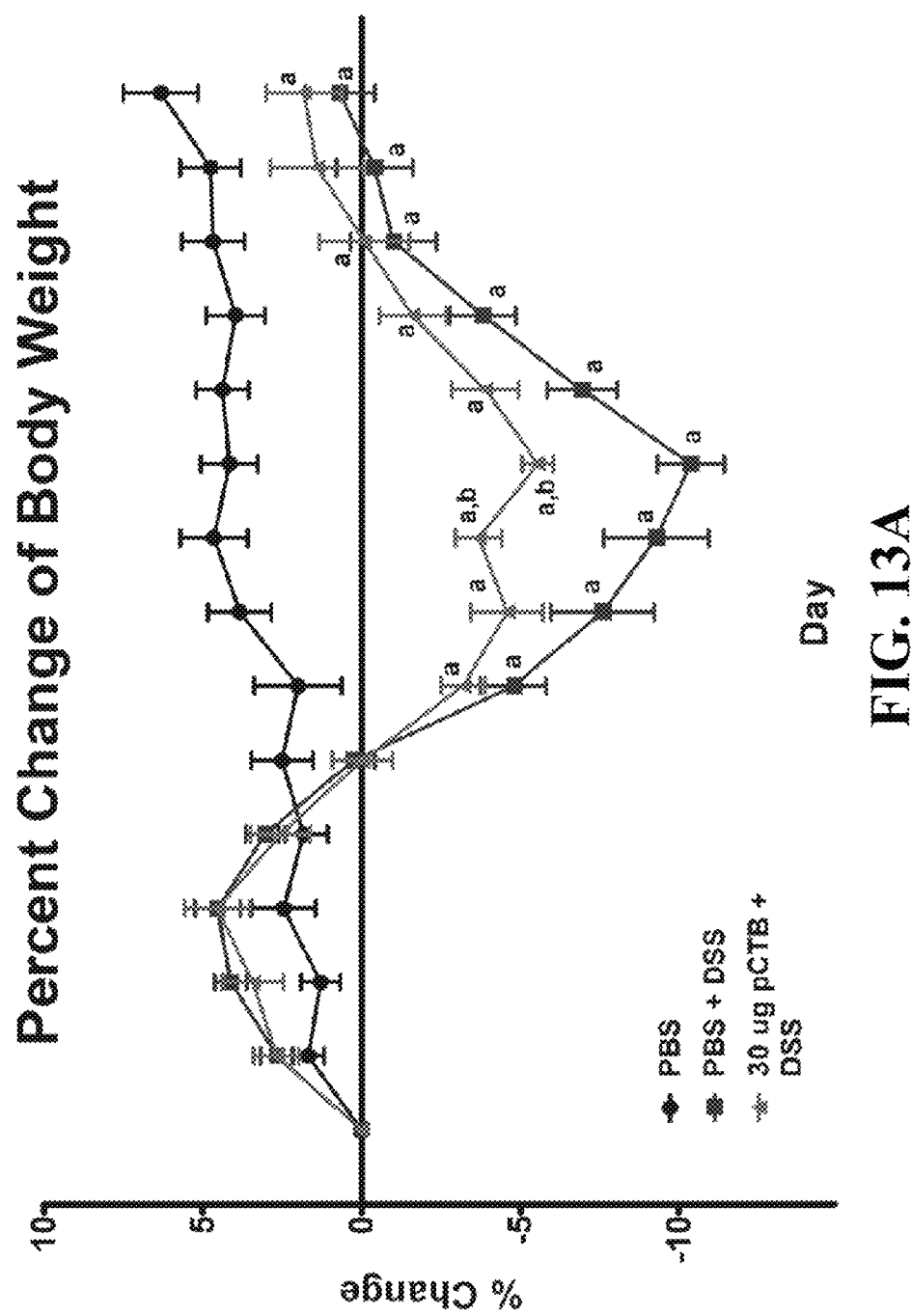
FIG. 13A is a graph illustrating percent body weight change in acute ulcerative colitis.
Figure 13B:
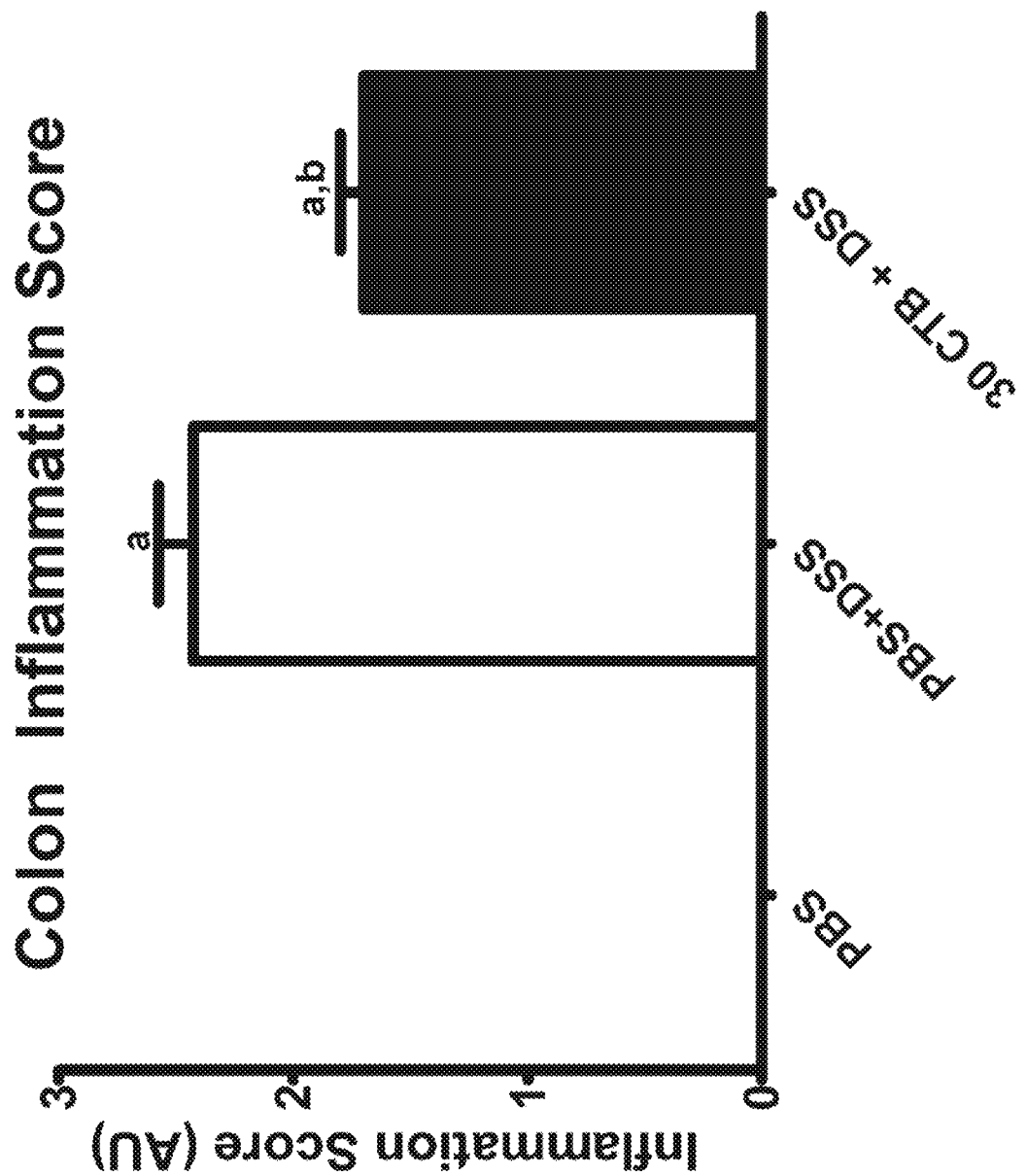
FIG. 13B is a graph illustrating colon inflammation scoring in acute ulcerative colitis.
Figure 13C:
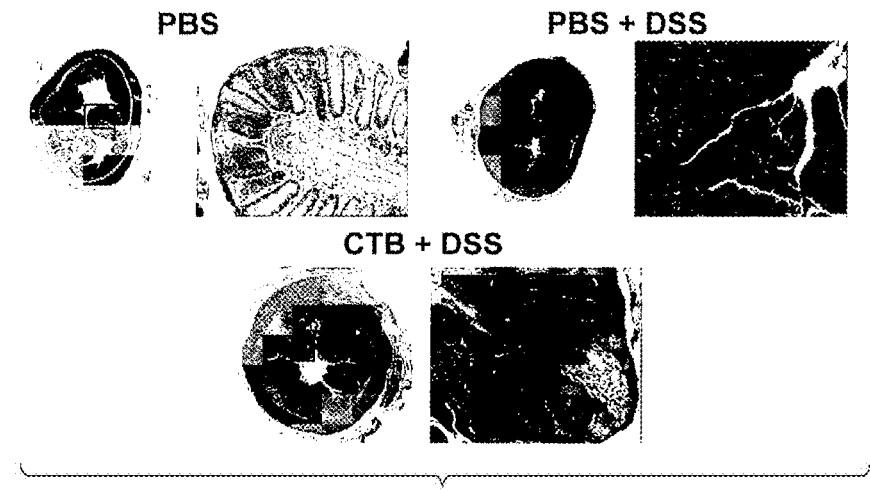
FIG. 13C includes representative composite photomicrographs depicting PBS, PBS+DSS, and CTBp+DSS.
Figure 14:
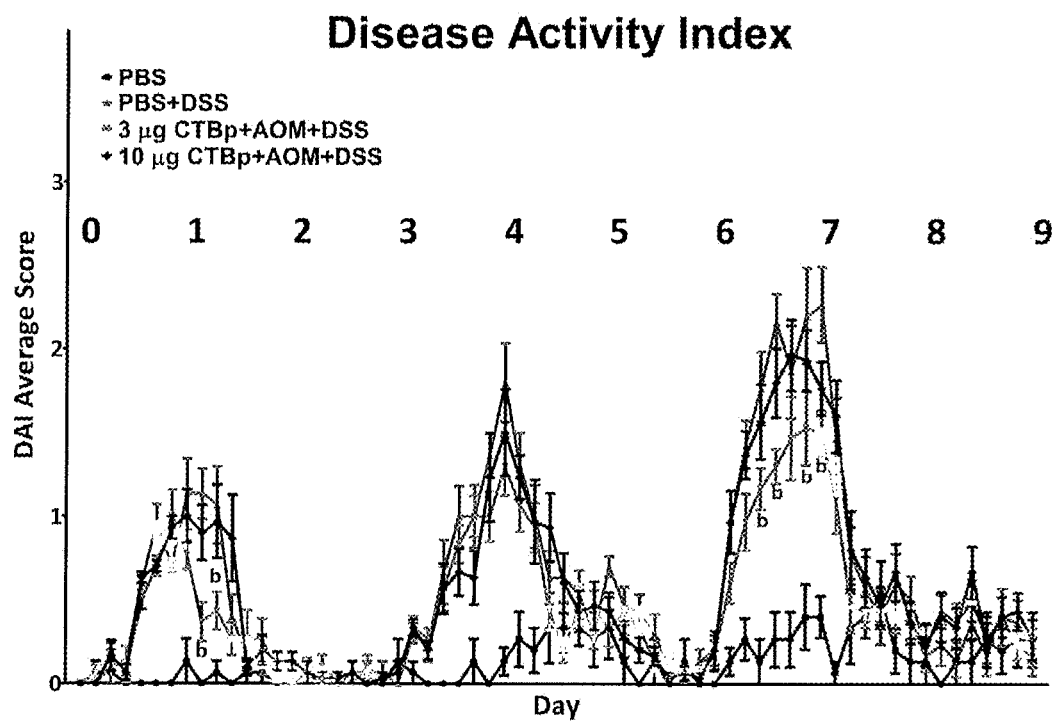
FIG. 14 is a graph illustrating disease activity index (DAI). Two way ANOVA was performed b=$p<0.05$ compared to PBS+AOM+DSS.

As illustrated in FIGS. 13A-13C, oral administration of CTBp blunted injury in acute ulcerative colitis. While DSS exposure resulted in significant weight loss in mice, the weight loss was blunted by CTBp pretreatment (FIG. 13A). Additionally, CTBp decreased inflammation in the tissue (approximately 1.7) compared to PBS+DSS group (approximately 2.5) (FIGS. 13B and 13C). Referring to FIG. 14, oral administration of CTBp blunted the disease activity index (DAI) score of mice exposed to DSS. The administration of CTBp significantly blunted the DAI score immediately following the first dose and throughout the third DSS exposure period. The DAI is composed of body weight, fecal consistency, and occult blood.

Figure 15A:
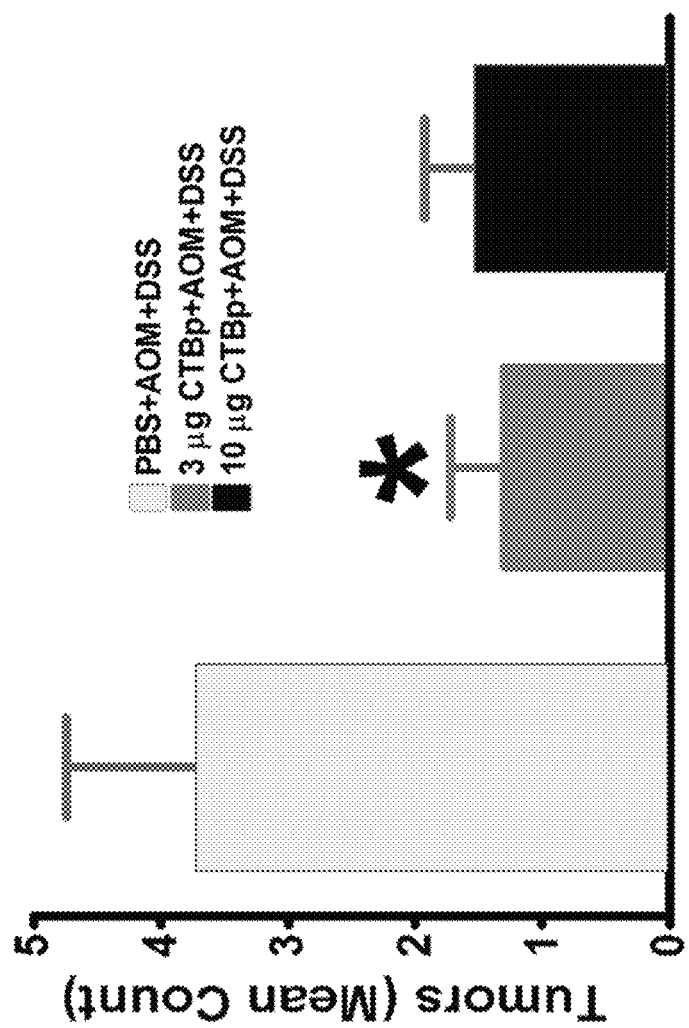
FIG. 15A is a graph showing average number of tumors per mouse.
Figure 15B:
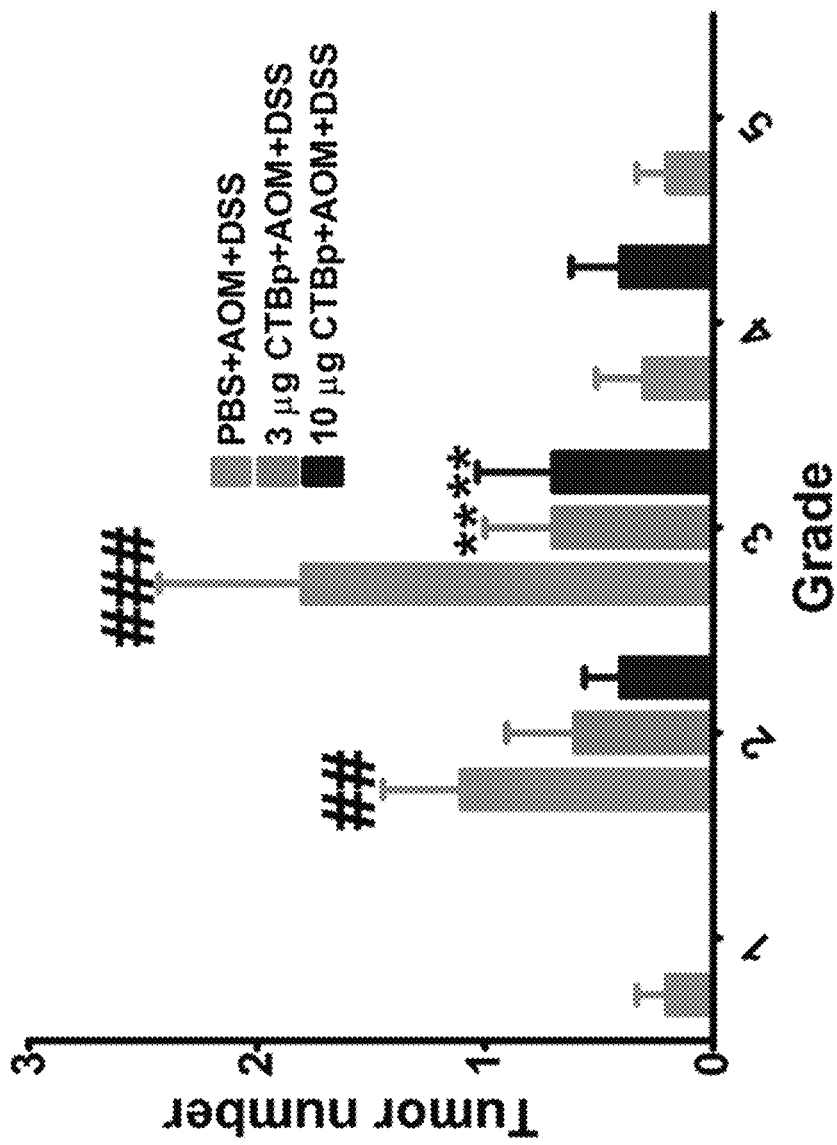
FIG. 15B is a graph showing the number of tumors per grade level.
Figure 15C:
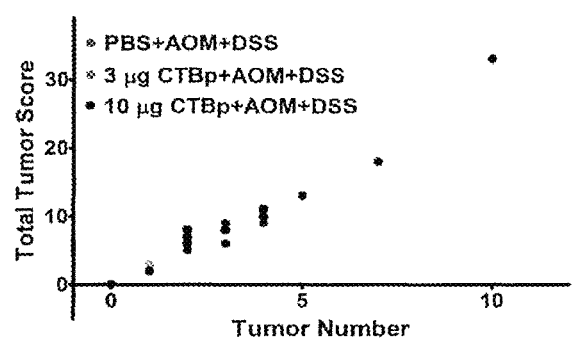
FIG. 15C is a graph showing total tumor score per mouse in relation to tumor number. ANOVA was performed, $p<0.05$ compared to PBS.

As illustrated in FIGS. 15A-15C, oral administration of CTBp also blunted the tumor numbers (FIG. 15A) and tumor grades (FIG. 15B) of mice exposed to DSS. Tumor numbers per mouse were significantly decreased by 3 µg CTBp and the tumor grades were significantly decreased by 3 and 10 µg CTBp. Additionally, a shift to lower tumor score (FIG. 15C) and numbers were noted with 3 and 10 µg CTBp. Tumor grades are shown in FIG. 16, and include grade 1—small but detectable; grade 2—covers up to 118.sup.th of colon; grade 3—covers up to ¼ of colon; grade 4—covers up to ½ of colon; and grade 5—covers over half of colon.

Figure 17:
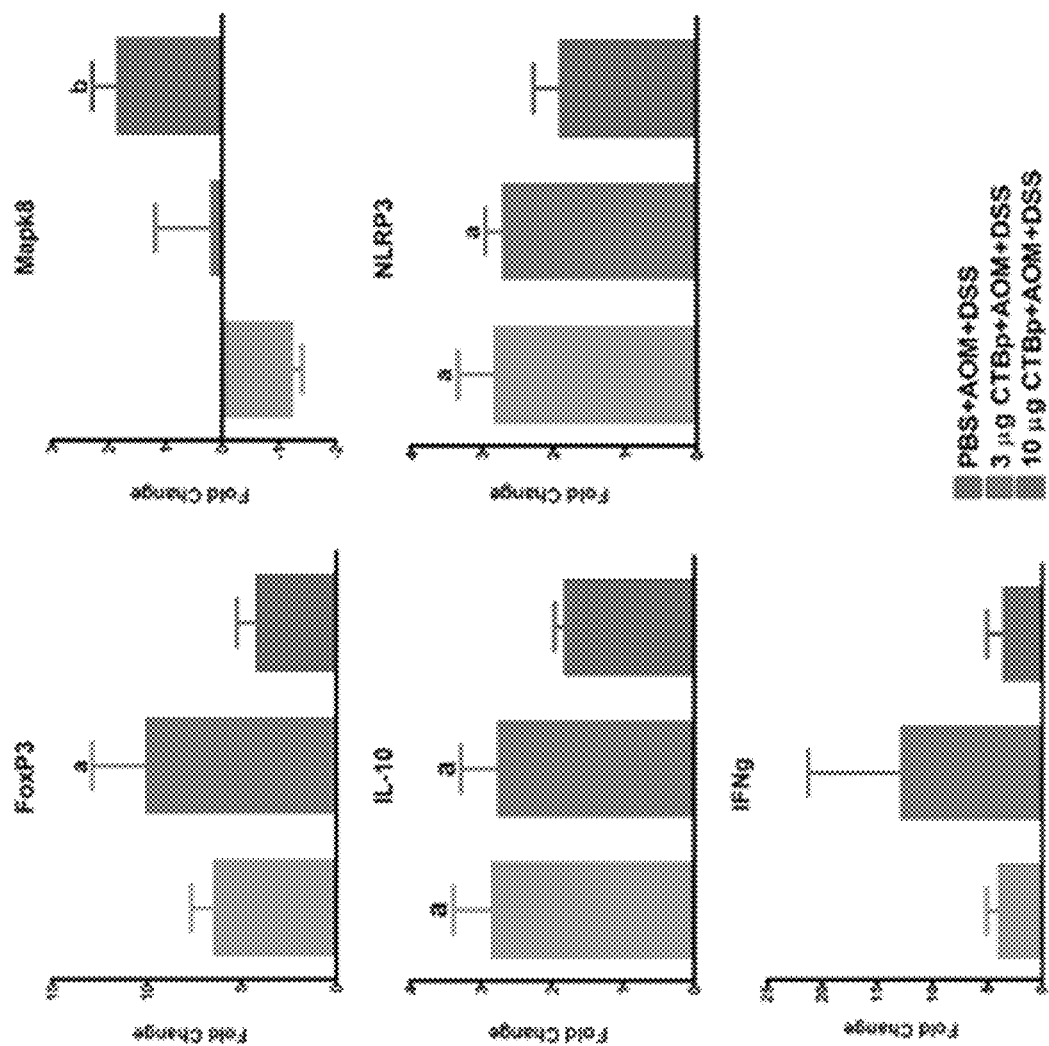
FIG. 17 includes graphs showing how CTBp significantly altered gene expression. ANOVA was performed a=$p<0.05$ compared to PBS and b=$p<0.05$ compared to PBS+AOM+DSS.
Figure 18:
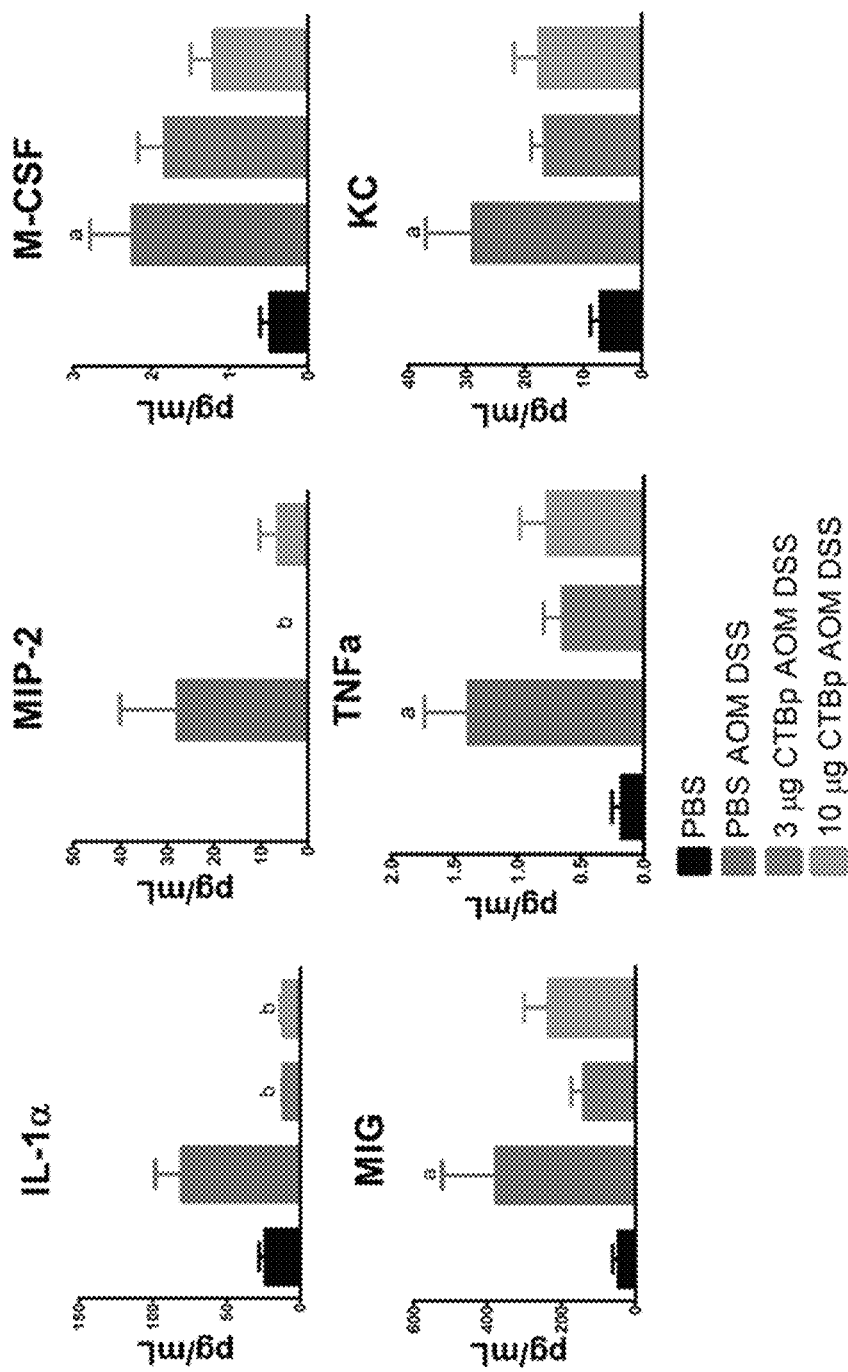
FIG. 18 includes graphs showing how CTBp significantly decreased inflammatory protein levels. ANOVA was performed a=$p<0.05$ compared to PBS and b=p, 0.05 compared to PBS+AOM+DSS.
Figure 19A:
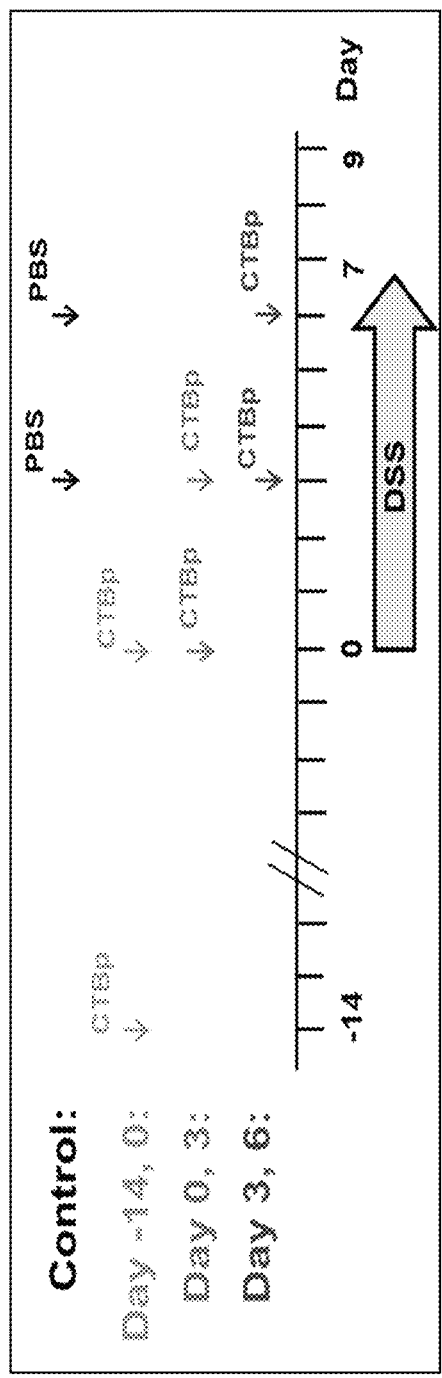
FIGS. 19A-19C include schematic diagrams and graphs showing experimental design, disease activity index, and inflammation score at various time points according to an embodiment of the disclosure. *$P<0.05$ compared to PBS-DSS, One-way ANOVA with Bonferroni's multiple comparison test.
Figure 19B:
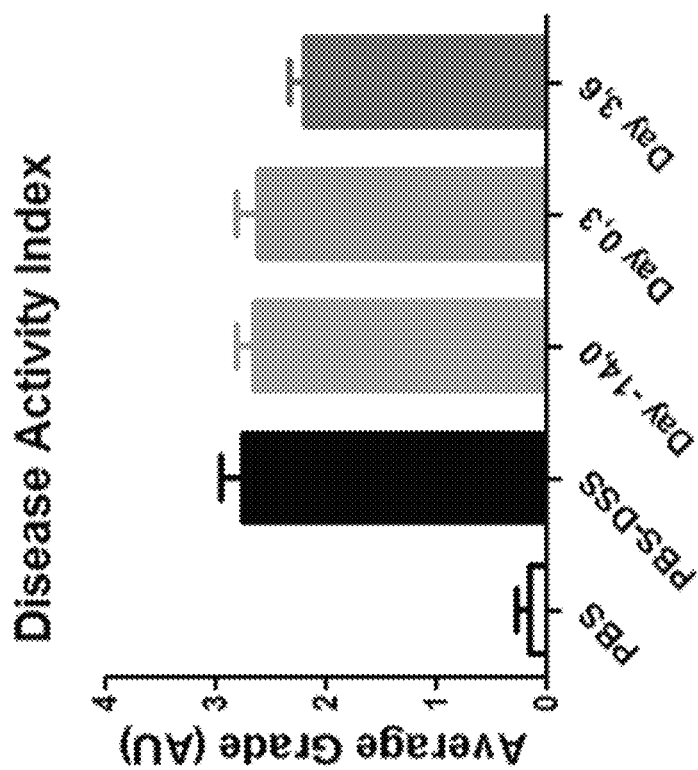
Figure 19C:
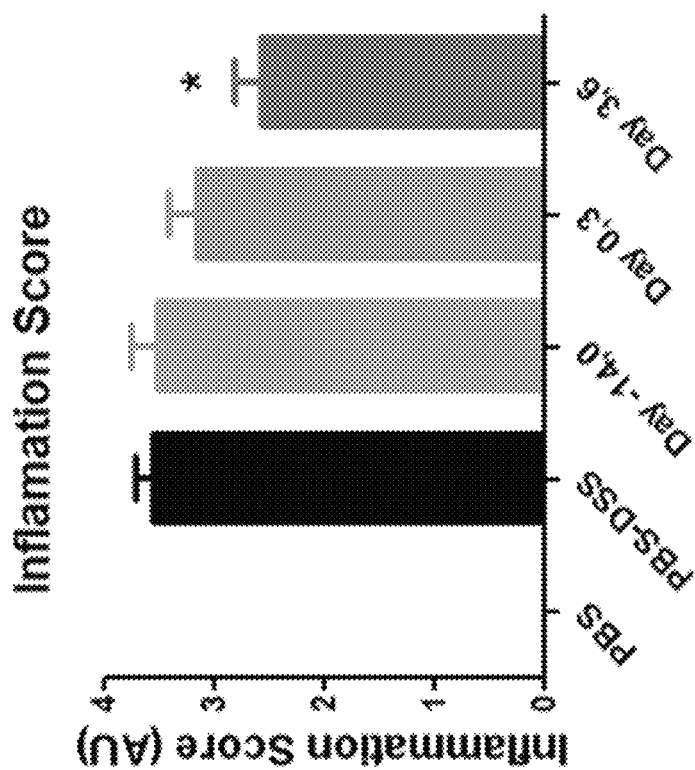
Figure 20A:
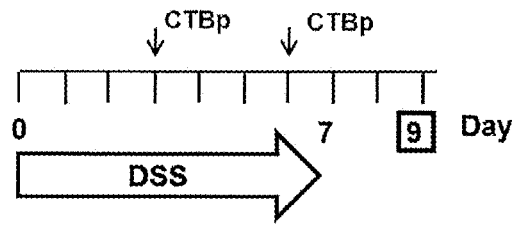
FIGS. 20A-20D include schematic diagrams and graphs showing experimental design, disease activity index, colon length, inflammation score at various dosage levels according to an embodiment of the disclosure. *, , *$P<0.05$, 0.01, 0.001 compared to PBS-DSS, One-way ANOVA with Bonferroni's multiple comparison tests.
Figure 20B:
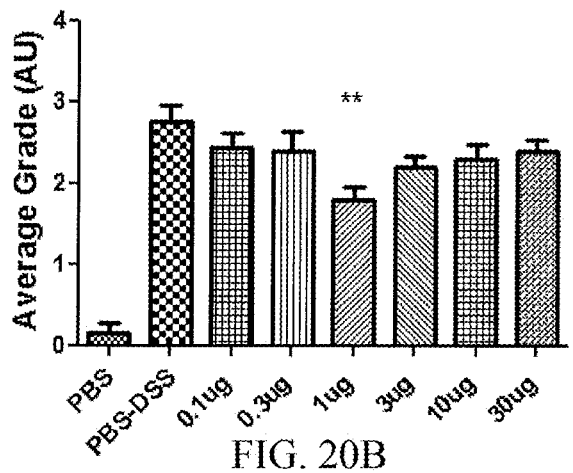
Figure 20C:
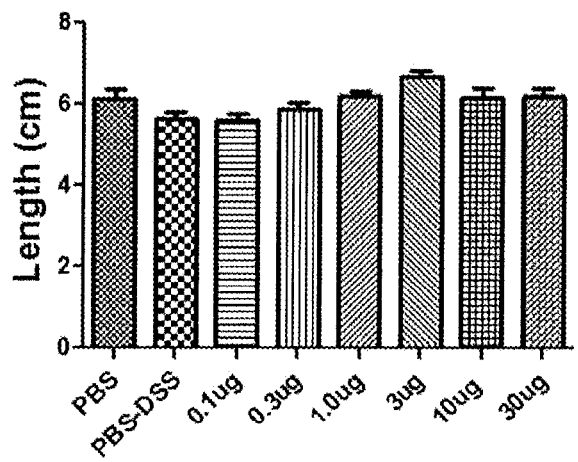
Figure 20D:
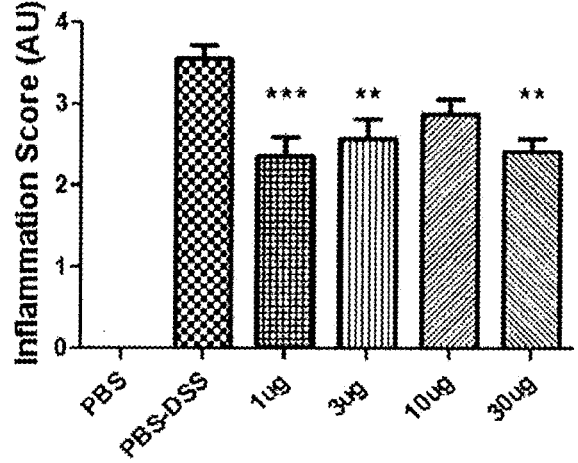

Oral administration of CTBp also significantly altered gene expression in mice exposed to DSS (FIG. 17). For example, 3 µg CTBp administration significantly increased FoxP3 expression following DSS exposure. Additionally, IFN.gamma. expression trended to significance and Mapk8 expression was significantly increased by 10 µg CTBp compared to PBS after DSS exposure. Furthermore, as illustrated in FIG. 18, protein levels of tumor promoting cytokines (GM-CSF and IL-1α) were blunted by CTBp administration in DSS exposed mice. 3 and 10 µg CTBp significantly blunted IL-1α protein levels following DSS exposure compared to PBS. MIP-2 was significantly blunted by 3 µg CTBp compared to PBS after DSS exposure. Interestingly, Interferon-.gamma., a tumor suppressor, was significantly elevated by CTBp administration. Gene expression analysis is currently underway to reveal additional protective factor(s).

In summary, oral administration of CTBp blunted CRC in the colons of mice. Additionally, oral administration of CTBp after induction of colitis blunted colon tumor development in mice. The protein may be developed as a novel oral immunotherapeutic agent against colitis and/or CRC.

Example 11—Plant-Made Cholera Toxin B Subunit as a Candidate Oral Immunotherapeutic Agent Against Ulcerative Colitis The anti-inflammatory potential of orally administered CTBp in a mouse model of ulcerative colitis was investigated. Briefly, C57BL/6J mice were exposed to dextran sodium sulfate (DSS) in drinking water for 7 days and allowed to recover for 2 or 7 days before sacrifice. Mice were orally administered twice with varying amounts of CTBp, dosed prior to or after the initiation of DSS exposure (prophylactic and therapeutic regimens, respectively). Upon sacrifice, body weights and fecal samples were analyzed for a Disease Activity Index (DAI). Colon was isolated and analyzed for inflammatory gene expression by quantitative PCR and histopathological scoring. Timing and dosage were selected based upon the information presented in FIGS. 19A-19C and 20A-20D, respectively.

Oral administration of CTBp significantly decreased the DAI, colon shrinkage, and histopathological scores. The maximum effect was observed when therapeutically dosed on Day 3 and 6, although the prophylactic regimen was also effective with higher dosages. The most effective dose of CTBp under the therapeutic regimen was determined to be 1-3 µg/mouse. Gene expression analysis revealed that CTBp significantly blunted the expression of inflammatory cytokines in the colon, including interleukin (IL)-1β, IL-6 and IL-33.

Figure 21:
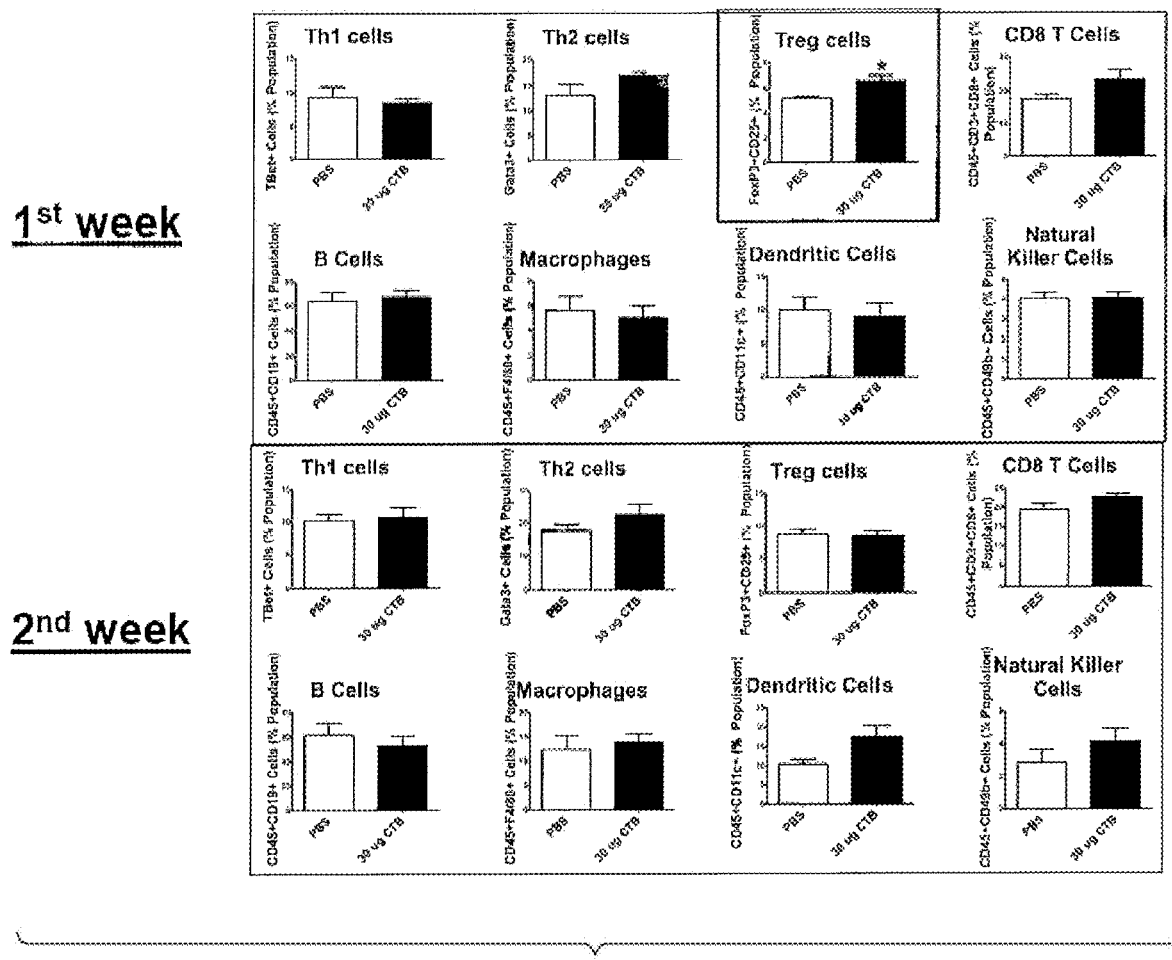
FIG. 21 includes graphs showing cell levels in small intestine lamina propria.
Figure 26:
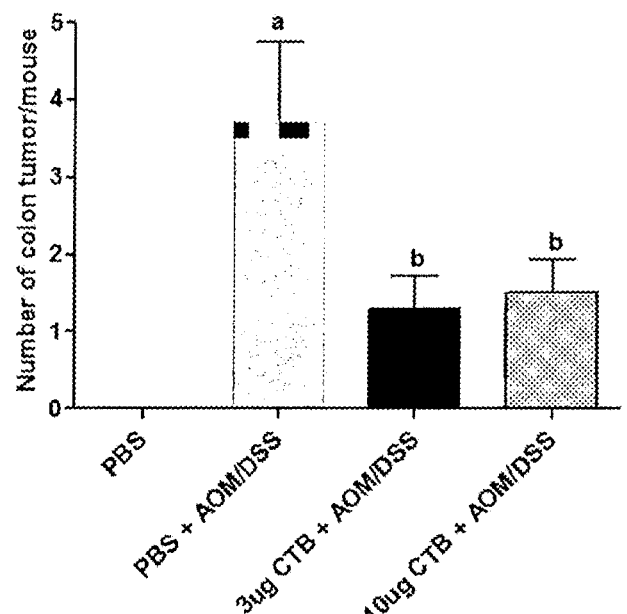
FIG. 26 is a graph illustrating the number of colon tumors per mouse. a=$p<0.05$ (vs PBS); b=$p<0.05$ (vs PBS+AOM/DSS), one-way ANOVA with Newman-Keuls Multiple Comparison Test.
Figure 27:
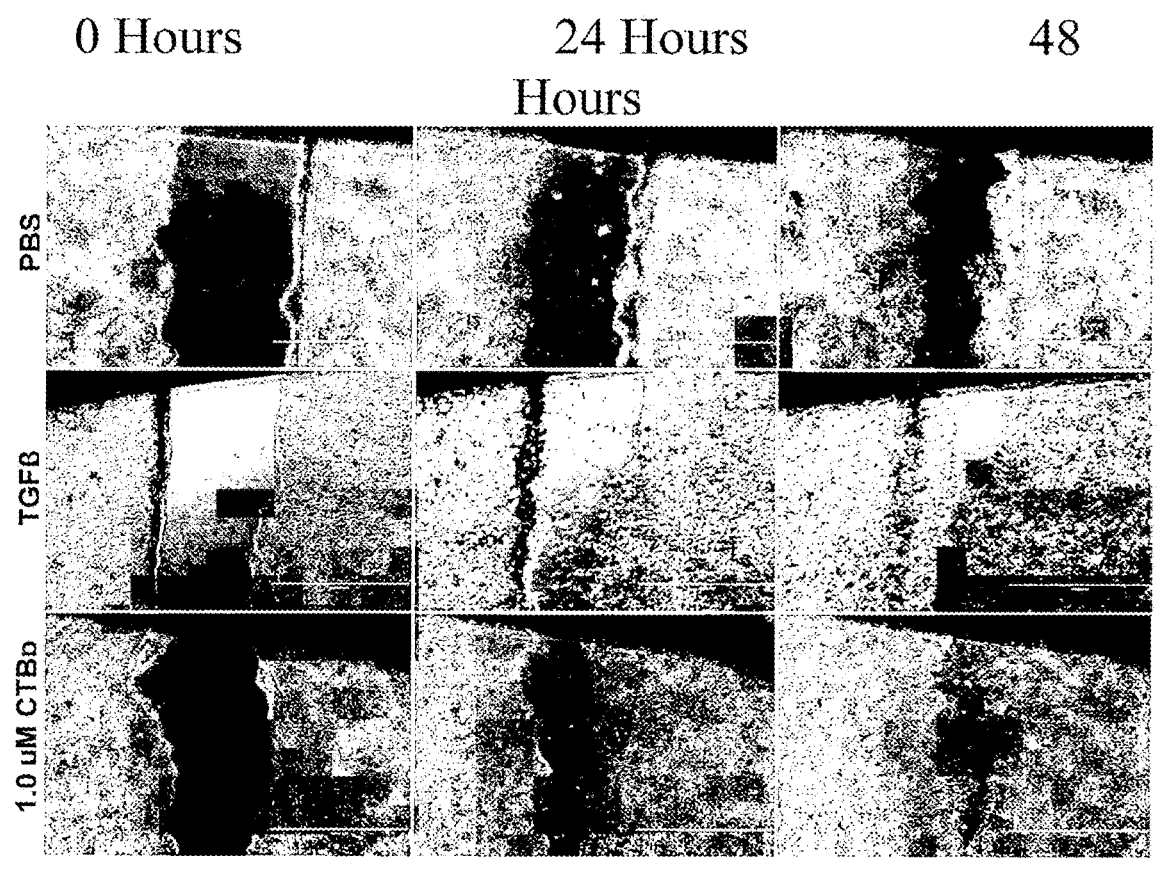
FIG. 27 includes representative images illustrating wound healing over a period of 48 hours for CaCO$_2$. *, , *$P<0.05$, 0.01, 0.001 compared to PBS; images were taken at ×4 magnification.
Figure 28:
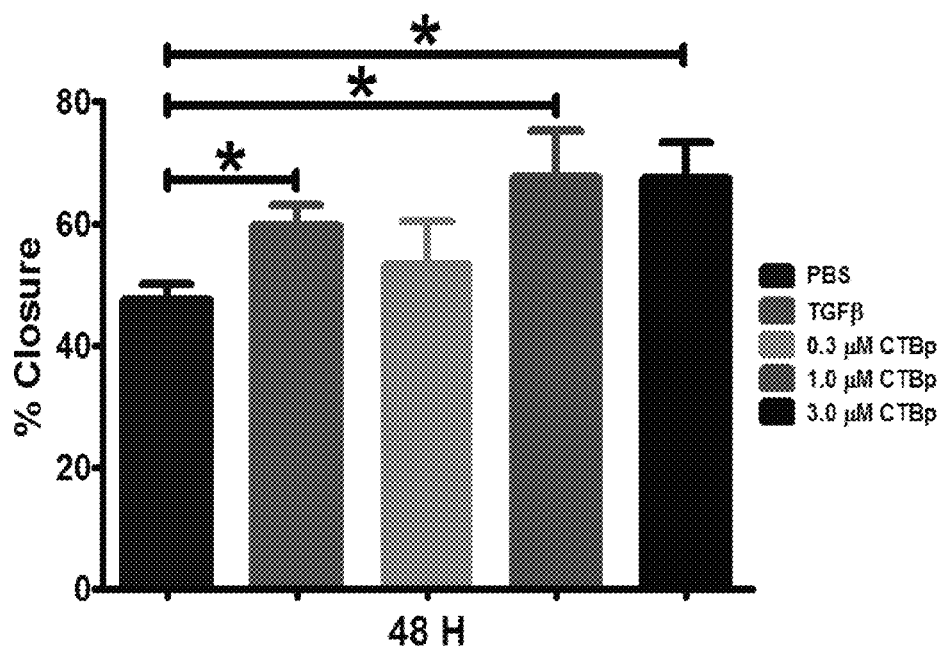
FIG. 28 is a graph illustrating percent wound closure.

As illustrated in FIGS. 21 and 22, CTBp administration increased the innate immune cell populations in the colon without producing notable effects on adaptive immune cell populations. Additionally, referring to FIGS. 23A-23D and 24A and 24B, various extracellular matrix components and remodeling enzymes were significantly increased by CTBp administration. Furthermore, as in Example 1, CTBp mitigated DSS-induced acute colitis (FIG. 25), prevented colitis-associated colon cancer development (FIG. 26, and facilitated wound healing (FIGS. 27-28)

The foregoing data demonstrated that oral administration of CTBp has therapeutic effects in chemically induced acute colitis in mice. More specifically, CTBp significantly altered the gene expression patterns in the GI tract, with higher impacts in the colon than in the small intestine and was found to be a mucosal wound healing molecule. Additionally, oral administration of CTBp mitigated chemically induced acute colitis in mice, in part by increasing epithelial barrier functions and/or wound healing. Oral administration of CTBp also reduced tumorigenesis in a mouse model of colitis-associated colon cancer. Furthermore, oral administration of CTBp did not change the overall composition of gut microbiota.

Example 12—a Plant-Produced Cholera Toxin B Subunit Prevents Acute Colitis in a Mouse Model Whether CTBp could also protect against acute colitis induced by dextran sulfate sodium (DSS) was also investigated. Briefly, a well characterized model of Ulcerative Colitis (UC) in mice is the DSS model, which induces a similar response as human UC (T helper 2 mediated).6 C57BL/6J mice were orally administered 30 µg pCTB 2 weeks before and the day of initiation of DSS exposure. Mice were exposed to 4% DSS water ad libitum for eight days and allowed to recover for six days before sacrifice.

Animals and treatments. Six week old female C57BL/6J mice were obtained from Jackson Laboratory (Bar Harbor, Me.). For the DSS experiment, sodium bicarbonate was administered orally to neutralize the stomach pH prior to oral (gavage) doses of pCTB (30 µg) or PBS, which was administered two weeks prior to and the day of the initiation of DSS exposure. 4% DSS was administered for up to eight-days, following which mice were put on laboratory water for up to a seven-day recovery period. Mice were sacrificed by $CO_2$ asphyxiation after the recovery period.

Figure 29:
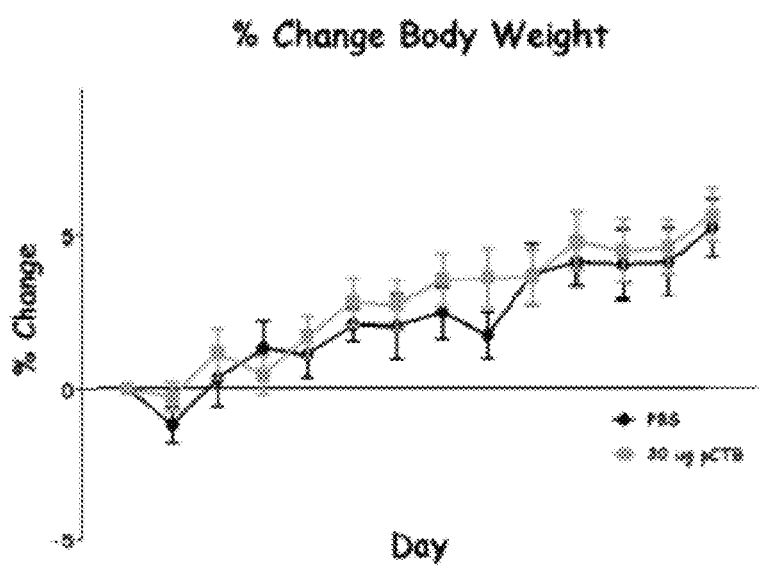
FIG. 29 is a graph comparing percent change body weight of PBS and CTBp.
Figure 30:
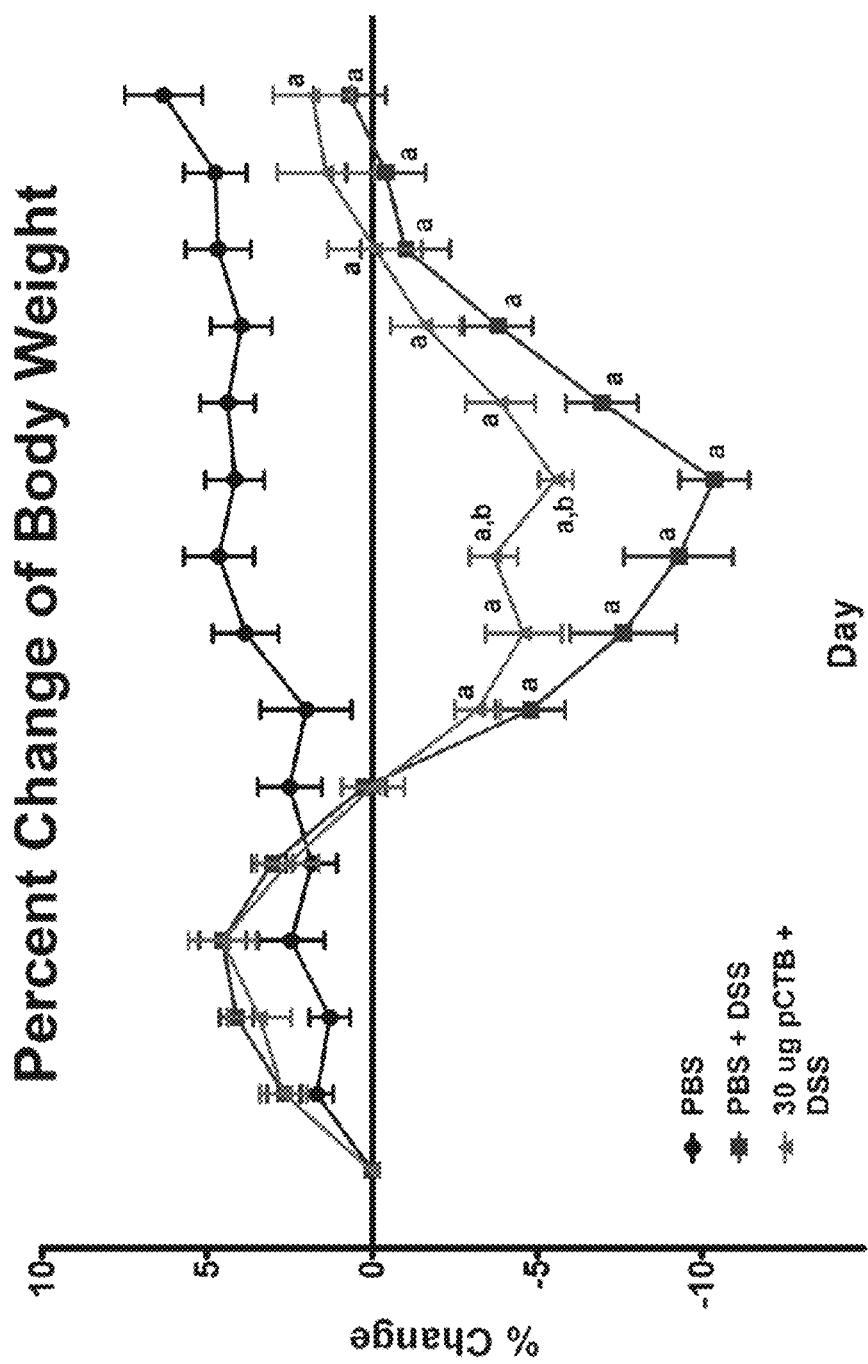
FIG. 30 is a graph comparing percent change body weight of PBS, PBS+DSS, and 30 µg CTBp+DSS. a=p<0.05 compared to PBS. b=p<0.05 compared to PBS+DSS.

Percent Body Weight Change. Initial body weights were collected immediately prior to the initiation of DSS exposure. The body weights were collected daily at similar times and percent change from baseline was calculated. Percent change body weight without DSS exposure is shown in FIG. 29 and percent change in body weight with exposure to DSS is shown in FIG. 30. There were no significant changes in body weight following administration of 30 µg pCTB as compared to PBS without DSS exposure (FIG. 29). While exposure to 4% DSS resulted in approximately 10% body weight loss, pCTB showed significant protection when administered prior to DSS exposure by increasing body weight during the recovery phase compared to DSS alone (FIG. 30).

Figure 31:
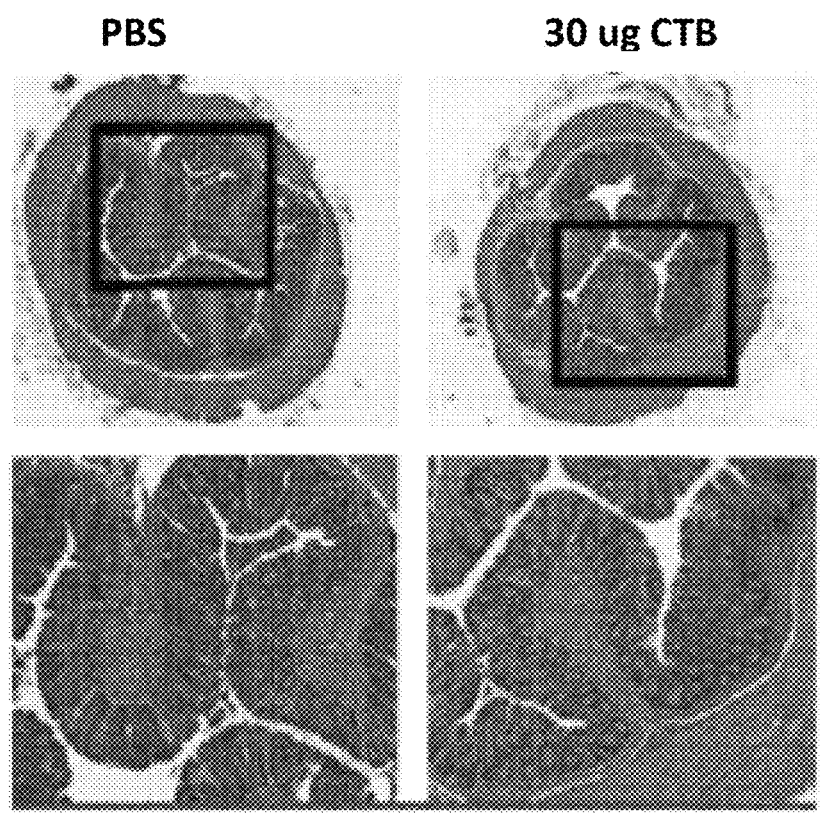
FIG. 31 includes representative images of hematoxylin and eosin staining.
Figure 32:
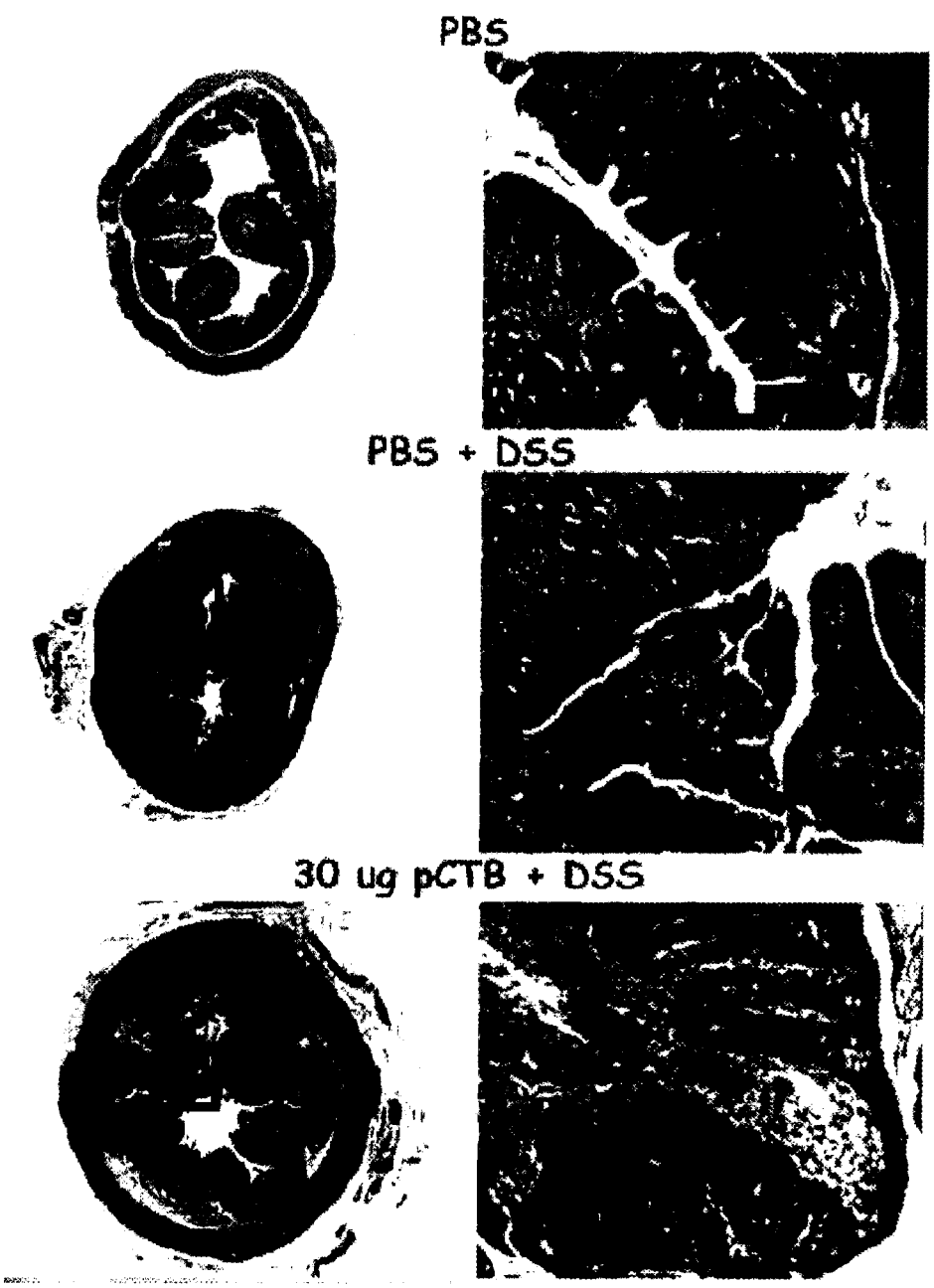
FIG. 32 includes representative images of hematoxylin and eosin staining.

Hematoxylin and Eosin Staining. Tissue sections were collected from the distal colon and placed in 10% formalin for 18 H. The tissue was then placed in 70% ethanol until the time of paraffin embedding. Paraffin embedding, cutting and H&E staining were performed by a trained professional. Tissue sections were scanned on an Aperio Scan Scope CS for analysis. Representative composite photomicrographs of tissue sections without exposure to DSS are illustrated in FIG. 31. Without DSS exposure, pCTB administration resulted in no morphological changes in mouse colons. Representative composite photomicrographs depicting PBS, PBS+DSS, and 30 µg pCTB+DSS are illustrated in FIG. 32. As shown in FIG. 32, DSS exposure resulted in loss of epithelial integrity, increased neutrophil infiltration, and ulceration, while CTB pre-treatment decreased the inflammatory injury seen in the DSS mice.

Figure 33:
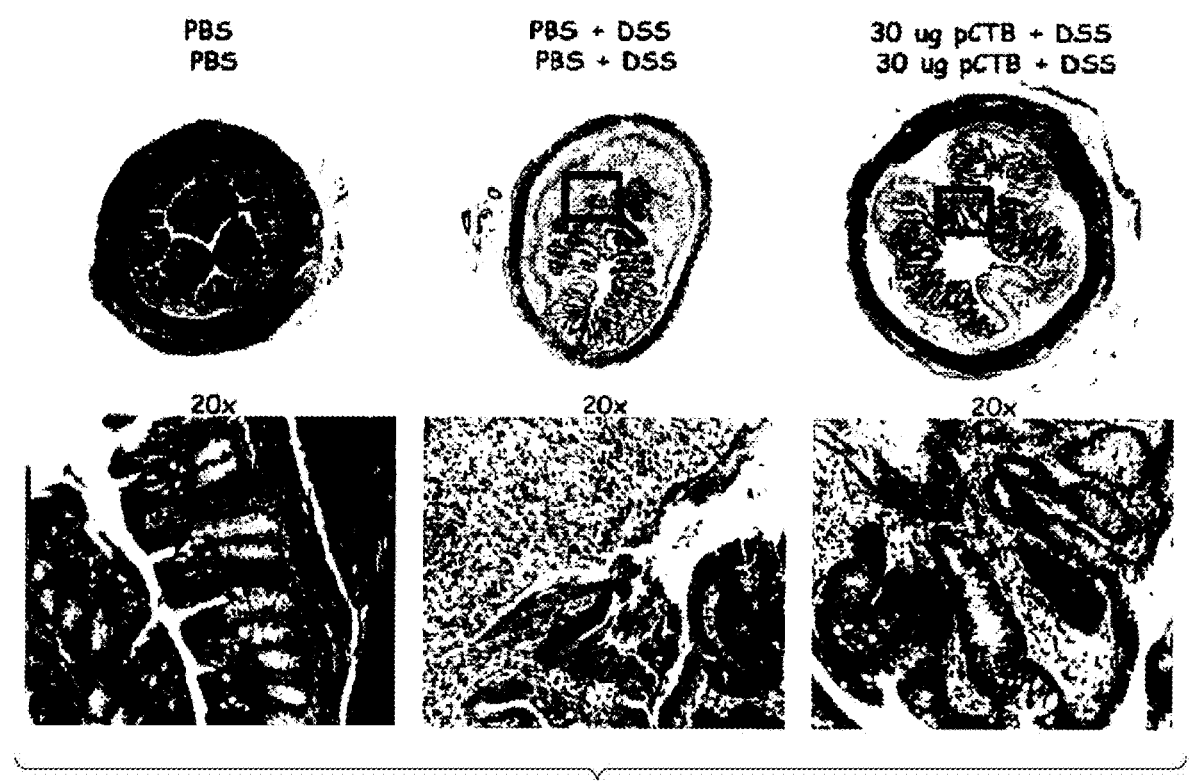
FIG. 33 includes representative images of trichrome stain.
Figure 34:
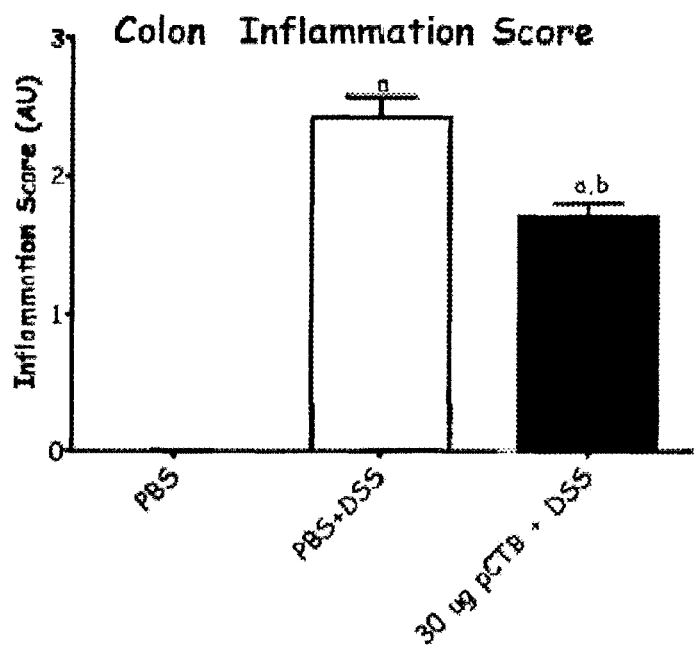
FIG. 34 is a graph illustrating inflammation scoring. a=p<0.05 compared to PBS; b=p<0.05 compared to PBS+DSS.
Figure 35:
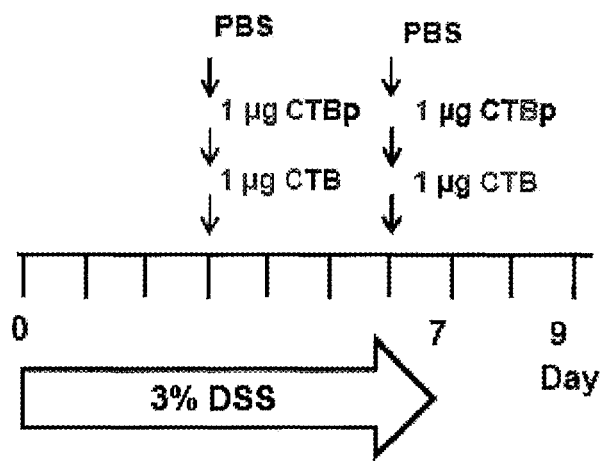
FIG. 35 is a schematic illustration of an experimental design according to an embodiment of the disclosure.

Masson's Trichrome Stain. Tissue sections were collected from the distal colon and placed in 10% formalin for 18 H. The tissue was then placed in 70% Ethanol until the time of paraffin embedding. Paraffin embedding and cutting were performed by a trained professional. Components of the Trichrome Stain were purchased from Electron Microscopy Sciences. Tissue section ere scanned on an Aperio Scan Scope CS for analysis. Representative composite photomicrographs depicting PBS, PBS+DSS, and pCTB+DSS are shown in FIG. 33. DSS exposure resulted in increased collagen deposition and loss of epithelial integrity while 30 µg pCTB blunted collagen deposition and protected epithelial integrity following DSS exposure, as compared to PBS+DSS.

Statistics. Summary data are means+/−SEM. ANOVA with Bonferroni's post-hoc test Mann-Whitney rank sum test was used for the determination of statistical significance among treatment groups, as appropriate.

CTBp Production in *N. benthamiana*. Tobamoviral vectors were vacuum infiltrated into *N. benthamiana* leaves. After 5 days in a growth room, leaves were harvested and CTBp was purified.

Figure 36:
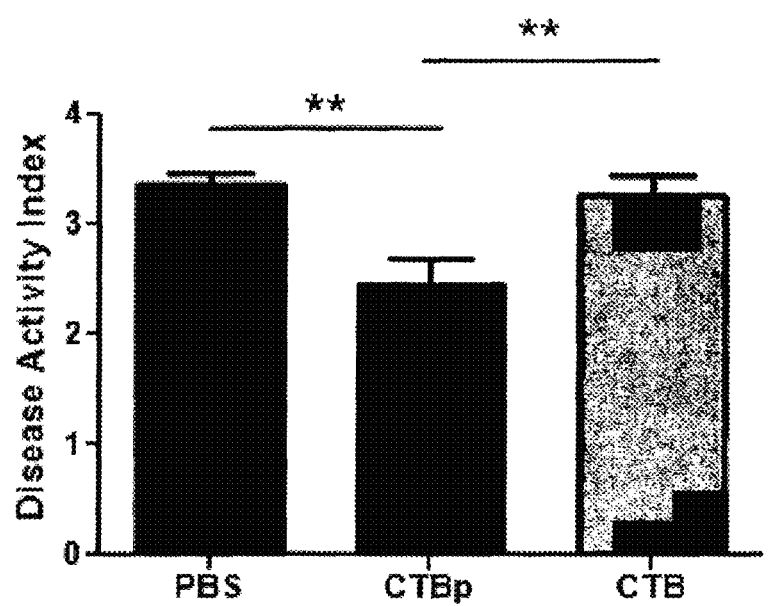
FIG. 36 is a graph illustrating disease activity index of PBS, CTBp, and CTB. **P<0.01; one-way ANOVA with Bonferroni's multiple comparison tests.

Upon analysis of the results from the experiments, it was observed that body weights decreased in mice exposed to 4% DSS in drinking water. This weight loss was significantly blunted by CTBp pretreatment. Additionally, histologically scored inflammation in the colon was significantly decreased (FIG. 33). More specifically, DSS exposure resulted in a score of approximately 2.5 while CTBp pretreatment significantly decreased the inflammatory score (approximately 1.6) seen in the DSS mice. Massons' Trichrome staining revealed decreased fibrosis in the CTBp-treated mice. Immunohistochemical analysis suggested a decreased T cell population in the inflamed tissue by CTBp pretreatment.

In summary, administering CTBp prior to exposure to 4% DSS protected mice from developing severe colitis. Additionally, pretreatment with CTBp protected against DSS-induced acute colitis by preventing inflammation and aberrant tissue regeneration. Furthermore, CTBp administration protected mice from DSS-associated weight loss; decreased inflammation in mice exposed to 4% DSS for 8 days; and completely blunted fibrosis in mice exposed to 4% DSS.

Example 13—an Acute Mucosal Injury/Colitis Study in C57B1/6 Mice

Referring to FIG. 35, colonic injury/inflammation was induced by 3% (w/v) dextran sodium sulfate (DSS) in drinking water on Day 0-7. PBS, 1 µg CTBp, or 1 µg CTB were orally administered on Day 3 and 6. On Day 9, Disease Activity Index (DAI; Qualis et al. Inflamm Bowel Dis 2009; 15:236-247) was used to evaluate the therapeutic effect of CTB and CTBp. As illustrated in FIG. 36, CTBp provided decreased DAI as compared to CTB as well as PBS alone.

Materials and Methods for Examples 14-19

The following studies describe the impacts of orally administered CTB on the GI tract in detail. As described below, a variant of CTB produced in *Nicotiana benthamiana* plants (CTBp; SEQ ID NOS: 3 and 4) was utilized, because the protein can be efficiently manufactured at scale while showing GM1 ganglioside-binding affinity, physicochemical stability and oral immunogenicity for anti-toxin antibody induction comparable to original CTB. Thus, CTBp provided a viable alternative to the vaccine antigen included in DUKORAL® and potentially facilitates other clinical applications as described above. The global impacts of CTBp oral administration on the small intestine and colon were first characterized by elucidating changes in their immune cell populations and gene expression profiles. The results led to the hypothesis that CTBp might induce TGFβ-mediated mucosal wound healing, which was subsequently demonstrated in an in vitro human colon epithelial model using the Caco2 cell line. To examine the clinical relevance of these findings, a dextran sulfate sodium (DSS) mouse model of intestinal wounding and ulcerative colitis was employed, another major form of inflammatory bowel disease (IBD) along with Crohn's disease, to which CTB's influences have not been reported before. Furthermore, as mucosal healing potentially lowered colorectal cancer risk in ulcerative colitis, the effect of CTBp treatment on ulcerative colitis-associated tumorigenesis was investigated in the azoxymethane (AOM)/DSS model. The data point to the potential utility of CTBp as an oral therapy for ulcerative colitis in addition to mass vaccination against cholera.

Animals. Eight-week-old C57BL/6J female mice were obtained from Jackson Laboratories (Bar Harbor, Me.). Animal studies were approved by the University of Louisville's Institutional Animal Care and Use Committee.

Study design. For all animal experiments, five to nine mice per group, randomly assigned, were used. For the characterization of the global impacts of CTBp oral administration, animals were gavaged with PBS or 30 µg CTBp twice at a 2-week interval after neutralization of stomach acids with a sodium bicarbonate solution, as described previously. CTBp was produced in *N. benthamiana* and purified to >95% homogeneity with an endotoxin level of <1 endotoxin units/mg, as described previously. Two weeks after the second dose, mice were sacrificed, and feces, colon, small intestine, spleen and Peyer's patches were collected. For the acute DSS "vaccination" study, animals were orally administered with PBS or 30 µg CTBp as described above. DSS exposure was initiated on the day of the second dosing (FIG. 50), using a method slightly modified from a previously published protocol. Body weights were measured at the initiation of DSS exposure as a baseline and every morning thereafter to determine percent change. To determine DAI, animals were scored on a daily basis with the scoring rubric adapted from the literature. Animals received 4% DSS (M.W. 36,000 to 50,000; MP Biomedicals, Santa Ana, Calif.) in drinking water for 8 days, and allowed to recover 6 days during which the animals received normal drinking water. For the therapeutic dose ranging study, mice were orally administered with PBS or 0.1-30 µg CTBp twice (day 3 and 6) during DSS exposure. Animals were exposed to 3% DSS for 7 days and allowed 2-day recovery. For the AOM/DSS study (FIG. 51), AOM (10 mg/kg) was administered by intraperitoneal injection. DSS exposure (2%) was initiated 1 week after the AOM injection for 7 days and allowed to recover for 14 days. The DSS exposure and recovery cycle was repeated 3 times and mice were sacrificed following the $3^{rd}$ cycle.

Immune cell isolation. Lamina propria lymphocytes were isolated from the colons and small intestines by a series of washing and collagenase digestion steps. Epithelial cells, mucus and fat tissue were removed by incubating with EDTA at 37° C. The intestinal tissues were cut into small pieces and incubated with collagenase at 37° C. Splenocytes were isolated by crushing the spleens on metal mesh and separating the supernatant. An ammonium chloride potassium carbonate buffer was used to lyse red blood cells and following several washes the cells were filtered through a 70 µm cell strainer. Peyer's patch lymphocytes were isolated by chopping up the Peyer's patches with fine surgical scissors and incubating the pieces in collagenase at 37° C. The collagenase step was repeated and the second suspension was isolated. After a second wash the cells were combined and filtered through a 70 µm cell strainer.

Flow cytometry. Immune cells from 2 mice were pooled for each biological replicate with a total of at least 4 biological replicates per group. Cells were stained using appropriate antibodies and a Cell Staining kit from EBIOSCIENCES™, Inc. (San Diego, Calif.). Briefly, tubes containing $1 \times 10^6$ cells were washed with Flow Cytometry Staining Buffer (FCSB; supplied in the kit) 2 times. Fc Block was added to each tube in FCSB for 10 min. For CD4 cell populations, cells were incubated with surface staining antibodies (anti-CD3-FITC, anti-CD4-APC-Cy7, anti-CD25-PerCP) at 4° C. for 30 min. After removing excess antibodies, Fixation/Permeabilization Buffer (FPB; supplied in the kit) was added and incubated overnight. Cells were washed with Permeabilization Buffer (PB, supplied in the kit) and again incubated for 10 min with Fc block. Internal cell antibodies (Gata3-PE, T-Bet-PE-Cy7, FoxP3-APC, IL-17-EFLUOR® 450) were then added and incubated for 30 min at 4° C. Finally, cells were washed and suspended in FCSB. For other immune cell populations, cells were incubated with surface staining antibodies (CD19-APC, CD3-FITC, CD49b-PE, F4/80-PeCy7, CD11c-PerCP-Cy5.5, CD8-APC-EFLUOR® 780, and CD45-EFLUOR® 450) at 4° C. for 30 minutes. After removing excess antibodies, FPB was added to the tubes and incubated overnight. Cells were then washed and resuspended in FCSB. Events ($1 \times 10^5$) were counted on a BD FACSCANTO™ II and analyzed with the BD FACSDIVA™ Software v6.1.3.

RNA isolation. Sections from the small intestine and distal colon were stored in RNALATER™ (Qiagen, Valencia, Calif.) at −20° C. until RNA was isolated. Colon tissue (approximately 14 mg) was placed in QIAzol lysis reagent in a 2.0 mL conical bottom centrifuge tube with Zirconia/Silica beads. A BEAD BUG™ (Denville Scientific Inc., Mass.) was used to homogenize the tissue. An RNEASY® Microarray Tissue Kit from Qiagen was used to purify the RNA from the tissue homogenate. RNA was stored at −80° C. until use.

Microarray gene expression analysis. Total RNA was amplified and labeled following the AFFYMETRIX™ (Santa Clara, Calif.) standard protocol for whole transcript expression analysis, followed by hybridization to AFFYMETRIX™ MOUSE GENE 2.0 ST® arrays. The arrays were processed following the manufacturer recommended wash and stain protocol on an AFFYMETRIX™ FS-450 fluidics station and scanned on an AFFYMETRIX™ GENECHIP® 7G scanner using Command Console 3.3. The resulting .cel files were imported into PARTEK® Genomics Suite 6.6 and transcripts were normalized at the gene level using RMA as normalization and background correction method. Contrasts in a one-way ANOVA were set up to compare the treatments of interest.

qRT-PCR. First strand cDNA was obtained from reverse transcription of 150 ng RNA using a SUPERSCRIPT VILO cDNA synthesis kit (Life Technologies) according to the manufacturer's instructions. Template cDNA were added to a reaction mixture containing 10 μl of 2× TAQMAN® Fast Advanced Master Mix (Life Technologies) and endonuclease free water to 20 μl and loaded in TAQMAN® Array Standard 96 well Plates (APPLIED BIOSYSTEMS™). These plates contain pre-spotted individual TAQMAN® Gene Expression probes for the detection of genes of interest as well as the house keeping genes 18S, 3-actin (ACTB), and GAPDH (Table 1). PCR amplification was carried out on a 7900HT Fast Real-Time PCR System (APPLIED BIOSYSTEMS™) with the following conditions: 950 C, 20 min; 40 cycles (95° C., 1 min); 20 min at 60° C. The 7500 Software v2.0.6 (APPLIED BIOSYSTEMS™) was used to determine the cycle threshold (Ct) for each reaction and derive the expression ratios relative to control. Wound healing pathway analysis was performed with a RT2 Profiler PCR Mouse Wound Healing Array (Qiagen) under the same conditions described above.

TABLE 1 Gene Identity for qRT-PCR Analysis.

TABLE 1

GENE IDENTITY FOR QRT-PCR ANALYSIS.

| Gene Name | Gene ID | Entrez Gene ID |
|---|---|---|
| Angiogenin, ribonuclease A family, member 4 | Ang4 | 219033 |
| Angiopoietin 1 | Angpt1 | 11600 |
| ATP-binding cassette, sub-family A (ABC1), member 1 | Abca1 | 11303 |
| Cathepsin K | Ctsk | 13038 |
| Collagen, type 1, alpha 1 | Col1a1 | 12842 |
| Collagen, type 1, alpha 2 | Col1a2 | 12843 |
| Collagen, type 3, alpha 1 | Col3a1 | 12825 |
| Collagen, type XIV, alpha 1 | Col14a1 | 12818 |
| Colony stimulating factor 2 (granulocyte-macrophage) | Csf2 | 12981 |
| Decorin | Dcn | 13179 |
| Interleukin 1 beta | Il1b | 16176 |
| Interleukin 33 | Il33 | 77125 |
| Malate dehydrogenase 1, NAD | Mdh1 | 17449 |
| Matrix Metallopeptidase 2 | Mmp2 | 17390 |
| Mitogen-activated protein kinase kinase kinase kinase 4 | Map4k4 | 26921 |
| NLR family, pyrin domain containing 3 | Nlrp3 | 216799 |
| SMAD family member 6 | Smad6 | 17130 |
| Tissue inhibitor of metalloproteinase 4 | Timp4 | 110595 |
| Transforming growth factor, beta 1 | Tgfb1 | 21803 |
| Transgelin | Tagln | 21345 |
| Tumor necrosis factor | Tnf | 21926 |

Caco2 wound healing assay. The Caco2 wound healing assay was performed using a modified method. Briefly, the cells were seeded and grown to confluence in 6 well plates (THERMO SCIENTIFIC™ NUJNC™ Cell-Culture Treated). The culture medium was discarded, two 0.5-1.0 mm across linear wounds were made per well with a 200 μL sterile beveled pipette tip (USA Scientific) and cells were washed with PBS to remove loose cells. PBS, CTBp (0.3-3 μM), TGFβ1 (0.2 nM), and/or an anti-TGFβ1,2,3 antibody (3.85 nM; ABCAM®) were subsequently added in fresh serum-deprived medium. Photomicrographs of the wounds were taken 0, 24 and 48 h after the wounding at 4× magnification. Quantification of the remaining cell-free area to the initial wound area was measured using the public domain software Image J and calculated as a mean percentage per well. The culture medium/supernatants were collected from each well 48 h after wounding and stored −80° C. until analysis. The culture supernatants were analyzed by a human Cytokine/Chemokine or TGFβ1,2,3 Magnetic Bead Panel (EMD Millipore). The panel was analyzed with a MILLIPLEX® MAP Kit on a MAGPIX® with LUMINEX® XMAP® technology.

Immunohistochemistry. Colons were removed and washed with PBS. A portion of the distal colon was fixed with paraformaldehyde overnight and stored in 70% ethanol until paraffin embedding and sectioning. Sections were deparaffinized with Citrisolv and rehydrated through several ethanol washing steps ending with incubation in distilled water. Antigen retrieval was performed overnight with a 2100 Retriever (Electron Microscopy Sciences) using Buffer B designed specifically for the Retriever. Tissue sections were blocked for endogenous peroxidase, avidin, biotin, and serum from the animal in which the secondary antibody was raised. Primary antibody (anti-F4/80; ABCAM®) was incubated with the tissue sections for 2 h at room temperature. The VECTASTAIN® Elite ABC kit (rabbit anti-goat; VECTOR® Labs) was used to label the primary antibody. F4/80+ cells were visualized with the IMMPACT™ DAB Substrate Kit (VECTOR® Labs) and then dehydrated through an ethanol gradient and finally incubated with Citrisolv. Sections were scanned using a Aperio ScanScope CS (Leica Biosystems) and positive cells were counted, in a blinded manner, in 10 representative sections (40× magnification) from each colon. The 10 sections were averaged and that was the score for each animal.

Histology. Colons were removed and washed with PBS. A portion of the distal colon was fixed with paraformaldehyde overnight and stored in 70% ethanol until paraffin embedding, sectioning and routine H&E staining. Inflammation scoring was performed using a scale that has been previously published. Tissue sections from 8 mice were scored in a blinded manner and averaged for each group. Masson's Trichrome Stain was performed using a kit purchased from Electron Microscopy Sciences (Masson's Trichrome for Connective Tissues).

Protein isolation and quantification. Distal colon tissue isolated at sacrifice was snap frozen in liquid nitrogen and pulverized with a Bessman Tissue Pulverizer and placed in T-PER (Thermo Scientific) with a protease inhibitor cocktail (Sigma-Aldrich). Total protein was isolated by gravity centrifugation of tissue fragments followed by collection of the buffer containing isolated protein, and storage at −80° C. until analysis. Protein sample concentrations were determined using a NANODROP™ 1000 (Thermo Scientific). Protein was normalized for all samples prior to loading on a Mouse Cytokine/Chemokine Magnetic Bead Panel (EMD Millipore). The panel was analyzed with a MILLIPLEX® MAP Kit on a MAGPIX® with LUMINEX® XMAP® technology.

Figure 43A:
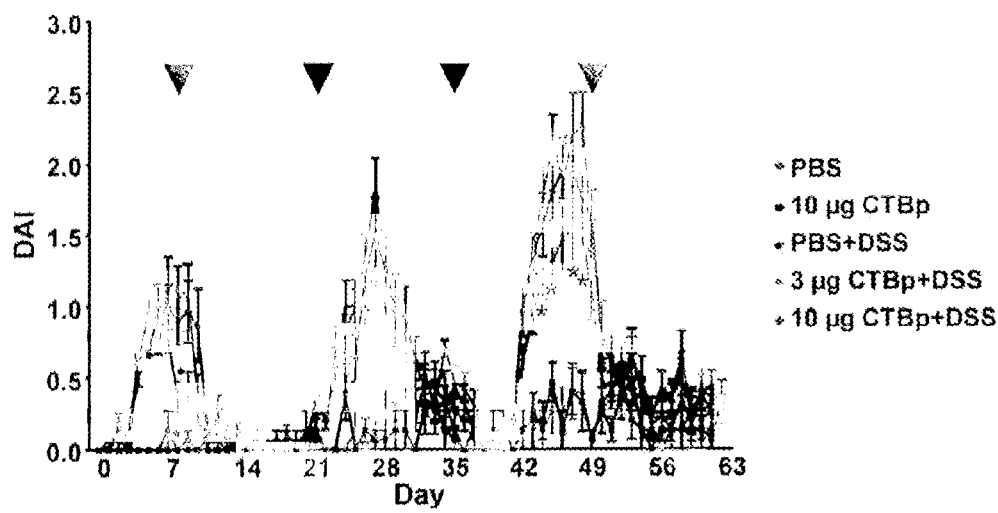
FIGS. 43A-43F include graphs and images showing biweekly oral therapy with CTBp can mitigate chronic colitis and colitis-associated tumorigenesis. Mice received azoxymethane (AOM) i.p. one week prior to DSS exposure. Mice were given water or 2% DSS water for 7 days followed by water for two weeks; the cycle was repeated two additional times. Mice were dosed orally with PBS, 3 µg CTBp or 10 µg CTBp on days 7, 21, 35, and 49 (black arrows).
Figure 43B:
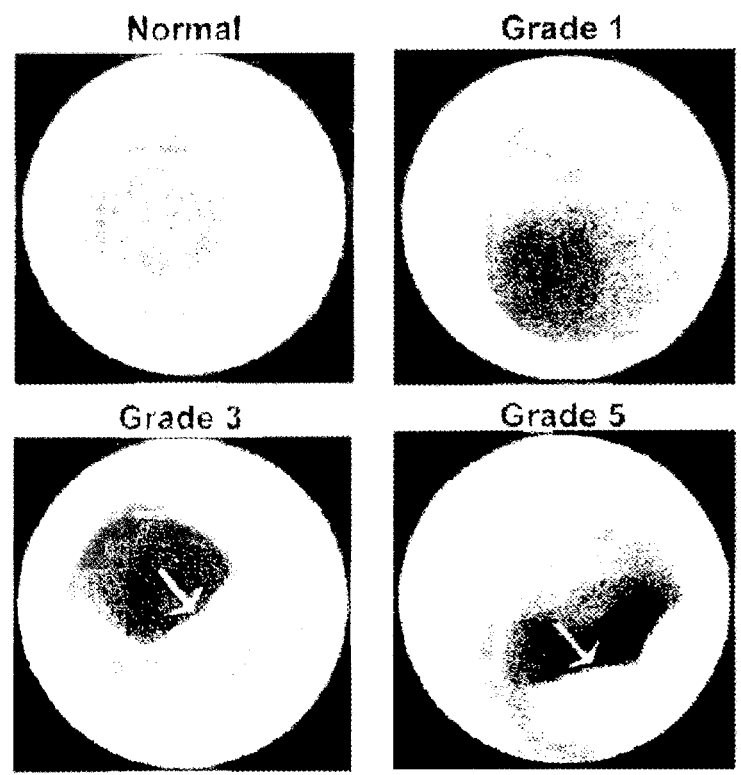

Tumor scoring. Tumors were scored via endoscopic analysis of the full length of the colon. Tumor scoring was based on the following rubric: 0 for no tumor, 1 is a very small but detectable tumor, 2 the tumor covers up to ⅛ colon circumference, 3 tumor covers ¼ of colon circumference, 4 tumor covers up to ½ of colon, and 5 tumor covers more than ½ of colon (FIG. 43B).

Microbiome analysis. Fecal samples were collected at the end of the acclimation period and at the time of study termination. Bacterial DNA was isolated using the POWERFECAL® DNA Isolation Kit (Mo Bio Laboratories, Inc.). Briefly, fecal samples were added to a bead tube with solution and lysed with a bead beater. Through a series of centrifugation and elution steps Fecal DNA was isolated. DNA concentration was determined using the Quant-iT dsDNA Broad-Range Kit (Life Technologies). Samples were then sent to Second Genome, Inc. for analysis. Upon arrival, samples were enriched for bacterial 16S V4 rDNA region by utilizing fuxion primers designed against conserved regions and tailed with sequences to incorporate Illumina flow cell adapters and indexing barcodes. Amplified products were concentrated using a solid-phase reversible immobilization method and quantified by electrophoresis using an Agilent 2100 BIOANALYZER®. Samples were loaded into a MISEQ® reagent cartridge and then loaded into the instrument. Amplicons were sequenced for 250 cycles with the MISEQ® instrument. Second Genome's PHYCA-STATS™ analysis software package was used to analyze the results.

Statistics. For all data, outliers were determined by statistical analysis using the Grubb's test (P<0.05) and excluded from further analysis. Graphs were prepared and analyzed using Graphpad Prism version 5.0 (Graphpad Software, La Jolla, Calif). To compare two data sets, an unpaired, two-tailed Student's t test was used. To compare three or more data sets, one-way ANOVA with Bonferroni's multiple-comparison post-test or Kruskal-Wallis test with Dunn's multiple-comparison post-test were performed. For body weights and DAI results, a two-way ANOVA with Bonferroni's multiple-comparison post-test was employed.

Figure 37A:
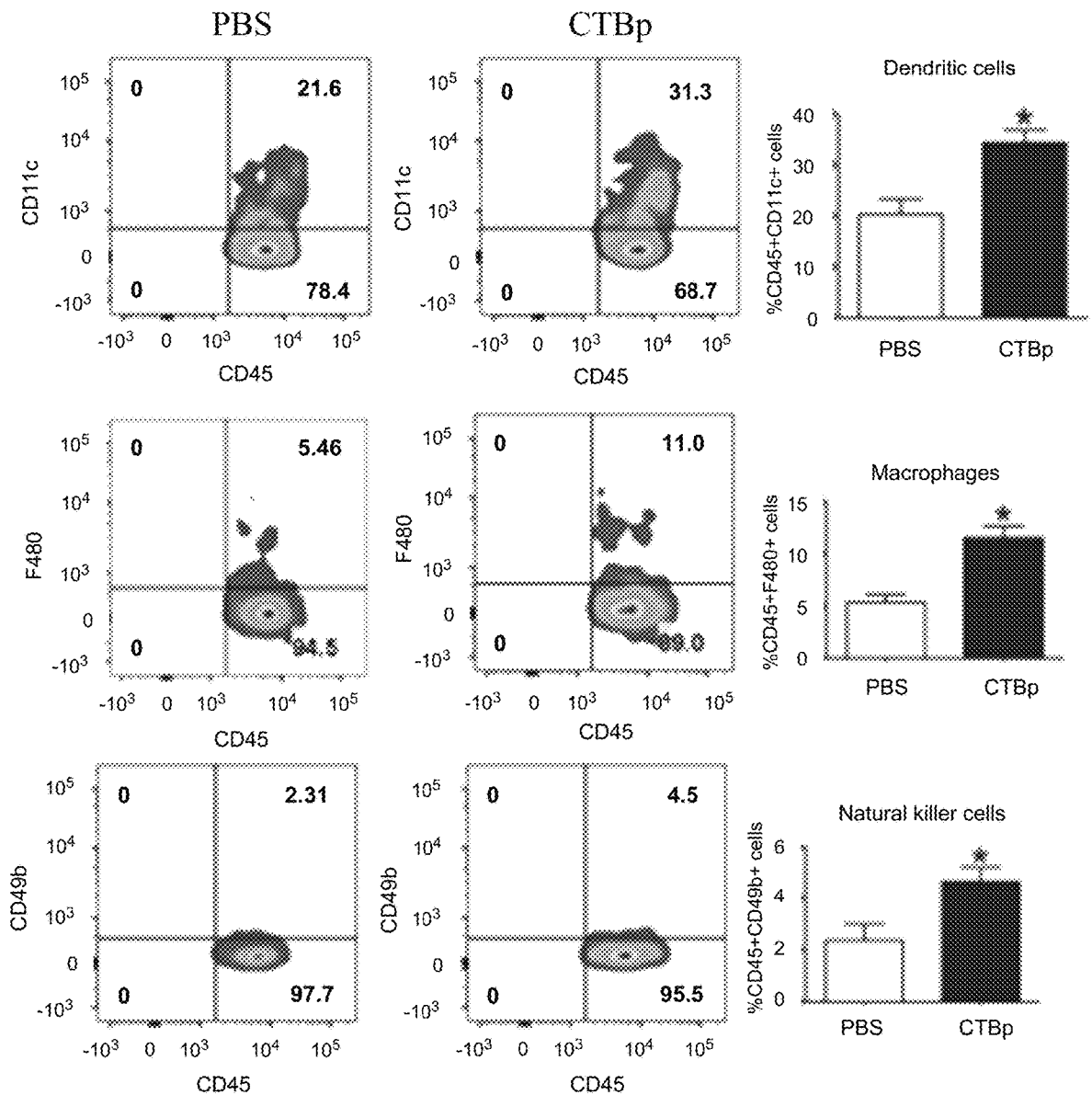
FIGS. 37A-37E include graphs and images showing CTBp significantly alters the immune cell profile in the colon. Animals were orally administered PBS or CTBp twice, at a two-week interval and two weeks later the mice were sacrificed. Colon lamina propria leukocytes were isolated and stained for surface and internal markers specific for immune cell subtypes. $CD4^+$ and $CD8^+$ cells gated on T lymphocyte subpopulation ($CD45^+CD3^+$). Additionally, $CD45^+$ cells were further divided into B ($CD19^+$), macrophage ($F4/80^+$), dendritic ($CD11c^+$) and natural killer ($CD49b^+$) subpopulations. Dot plots are representative samples from each group. Data presented as mean±standard error of the mean (SEM) of at least four biological replicates comprised of two pooled mice each. Unpaired t test was performed with *P<0.05 compared to PBS group.
Figure 37B:
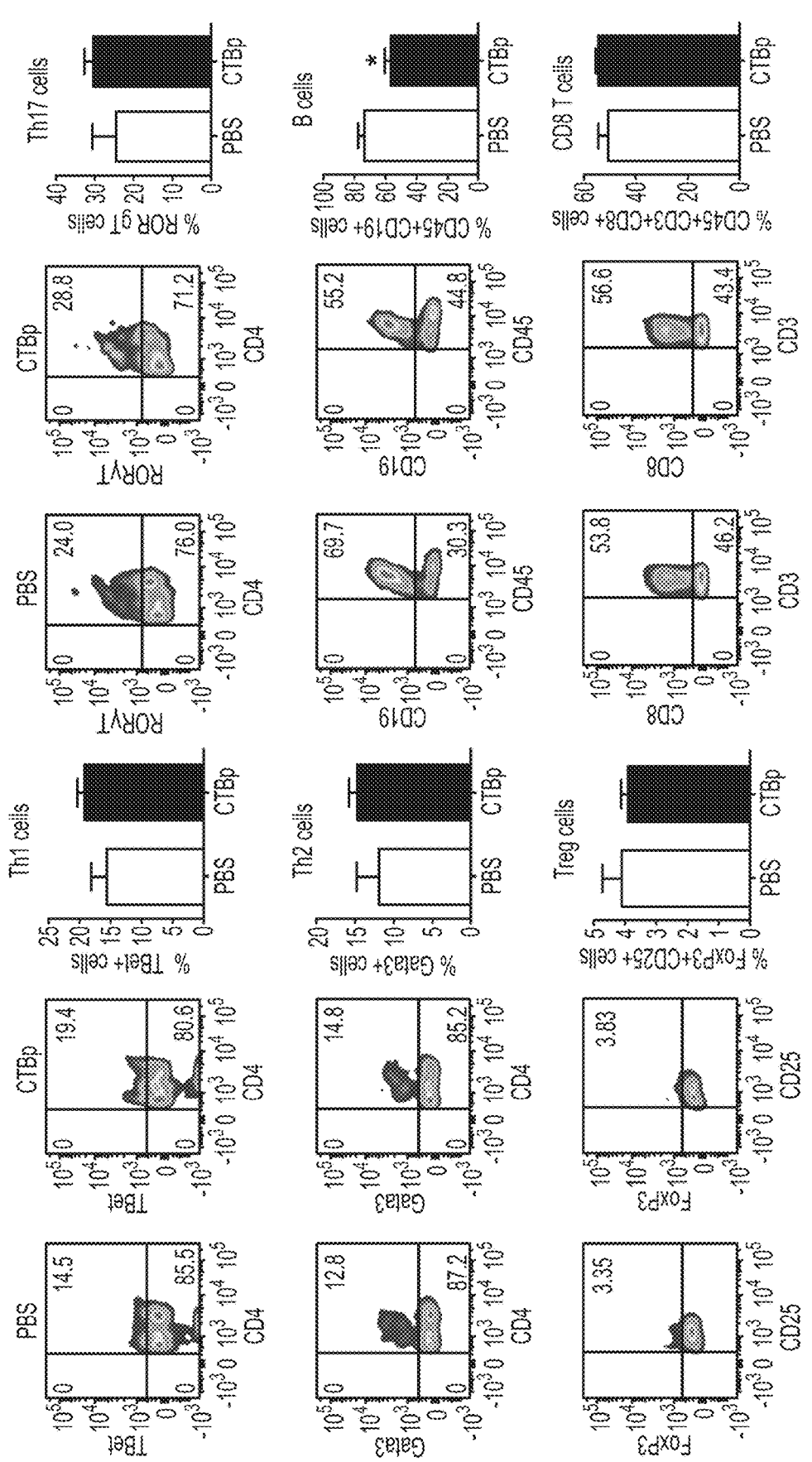
Figures 37C, 37D, 37E:
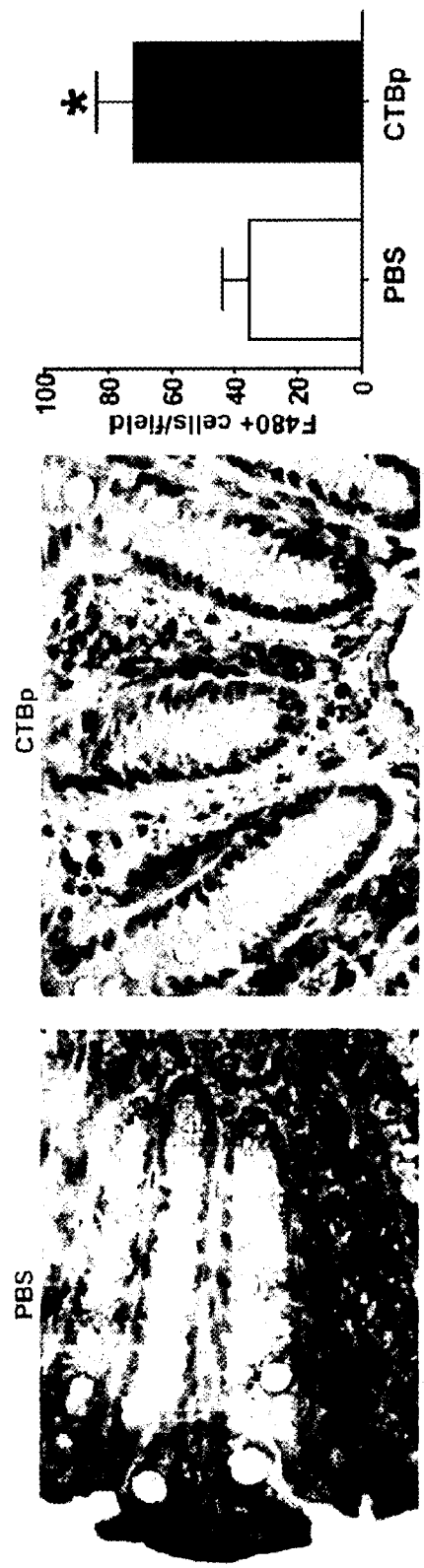
Figure 44:
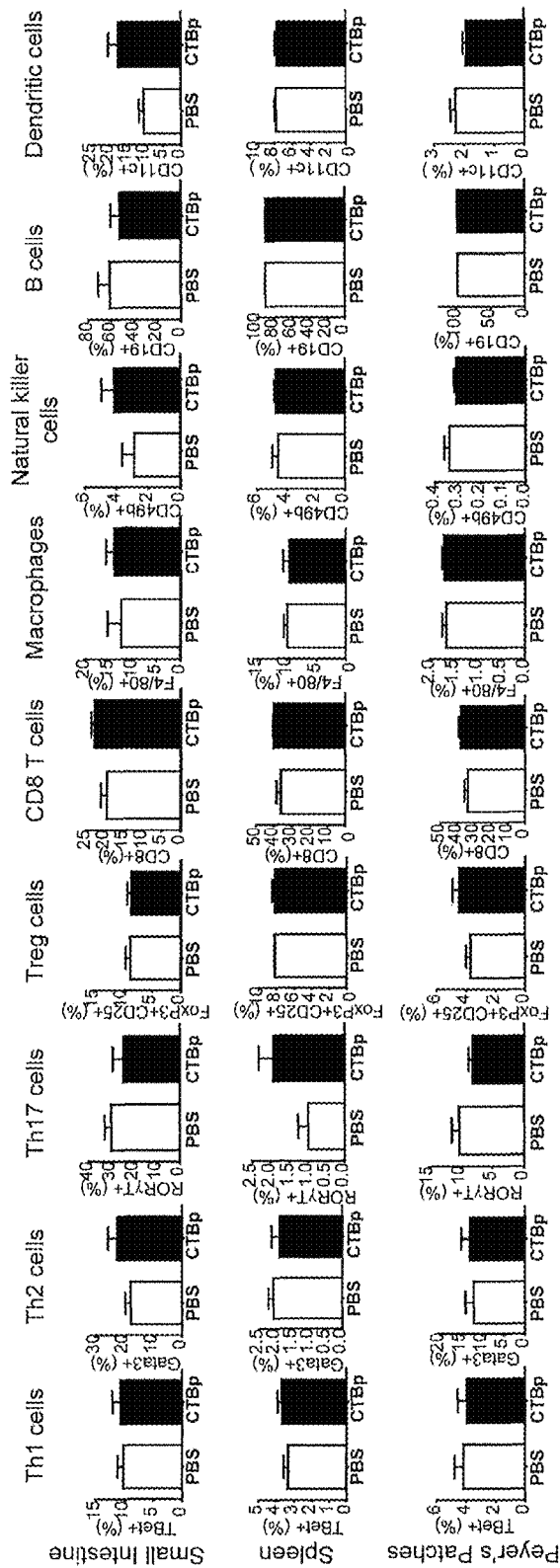
FIG. 44 includes graphs showing immune cell populations in different lymphoid tissues two weeks after the second CTBp or PBS oral administration. Animals were orally administered twice at a two-week interval with PBS or CTBp and two weeks later the mice were sacrificed. Small intestine, Peyer's patches, and spleen lymphocytes were isolated after several wash steps and collagenase incubation steps as necessary. $CD4^+$ and $CD8^+$ cells gated on gated on T lymphocyte subpopulation ($CD45^+$ $CD3^+$). Additionally, $CD45^+$ cells were further divided into B ($CD19^+$), macrophage ($F4/80^-$), dendritic ($CD11c^-$) and natural killer ($CD49b^+$) subpopulations. Dot plots are representative samples taken from each group. Data are presented as mean±standard error of the mean (SEM) of at least four biological replicates comprised of two pooled mice each. Unpaired t test was performed with *P<0.05 compared to PBS group. Colon lamina propria immune cell profiles are shown in FIG. 1.
Figure 45:
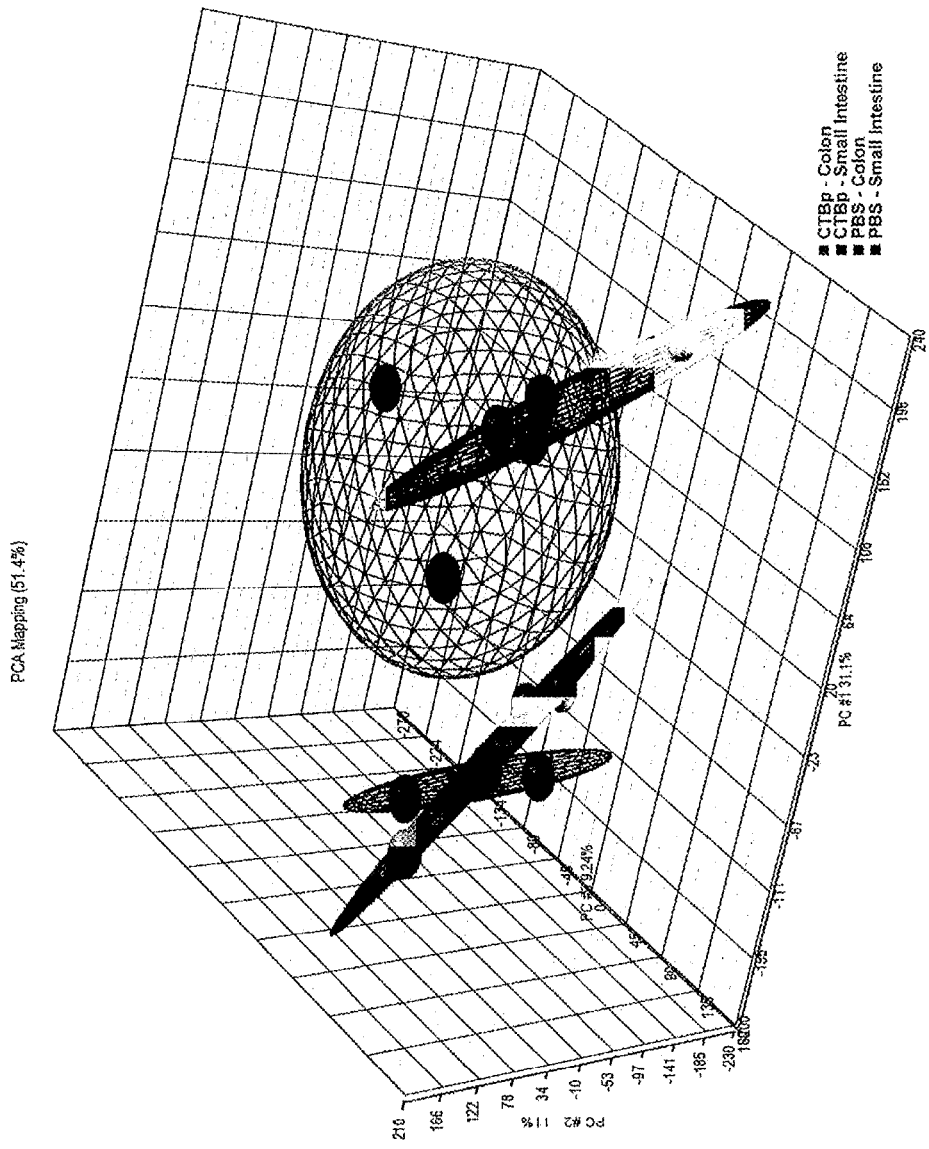
FIG. 45 is a graph showing a principal coordinate analysis that revealed separation of GI tract gene expression profiles of mice vaccinated with PBS and CTBp. PBS or CTBp were administered twice to mice at a two-week interval. Two weeks after the final dose animals were sacrificed and the small intestine and colon was removed. RNA was purified from small intestine and colon tissue sections. Total RNA was amplified and labeled then whole transcript expression analysis was performed as described in Materials and Methods. Principal coordinate analysis was performed using PARTEK® Genomics Suite 6.6 (St. Louis, Mo.). N=3 for all groups.

Example 14—Colon Lamina Propria Leukocyte Profile is Significantly Altered by CTBP Oral Administration Using flow cytometry, the immune cell populations of the lamina propria of small intestine and colon, Peyer's patches, and spleen was characterized in mice two weeks after CTBp oral administration. The analysis revealed that subsets of innate immune cell populations in the lamina propria of colon (FIGS. 37A-37E), but not of the small intestine (FIG. 44), significantly increased; macrophages (F4/80+), dendritic cells (DCs; CD11c+) and natural killer (NK) cells (CD49b+) were significantly increased when compared to the control PBS group (FIG. 37A). The increase of these cell types was associated with a relative decrease in B cells within the CD45+ cell population (FIG. 37B). Increased macrophage infiltration into colon lamina propria upon CTBp administration was confirmed by immunohistochemistry analysis (FIGS. 37C-37E). Despite the significant increase of macrophages, there was no abnormality or inflammation noted in the colon mucosa. Meanwhile, such a major shift in immune cell profiles was not observed in the small intestine lamina propria, Peyer's patches or spleen (FIG. 44), indicating compartmentalized impacts of orally administered CTBp on immune cells in different regions of the GI tract.

Figure 38A:
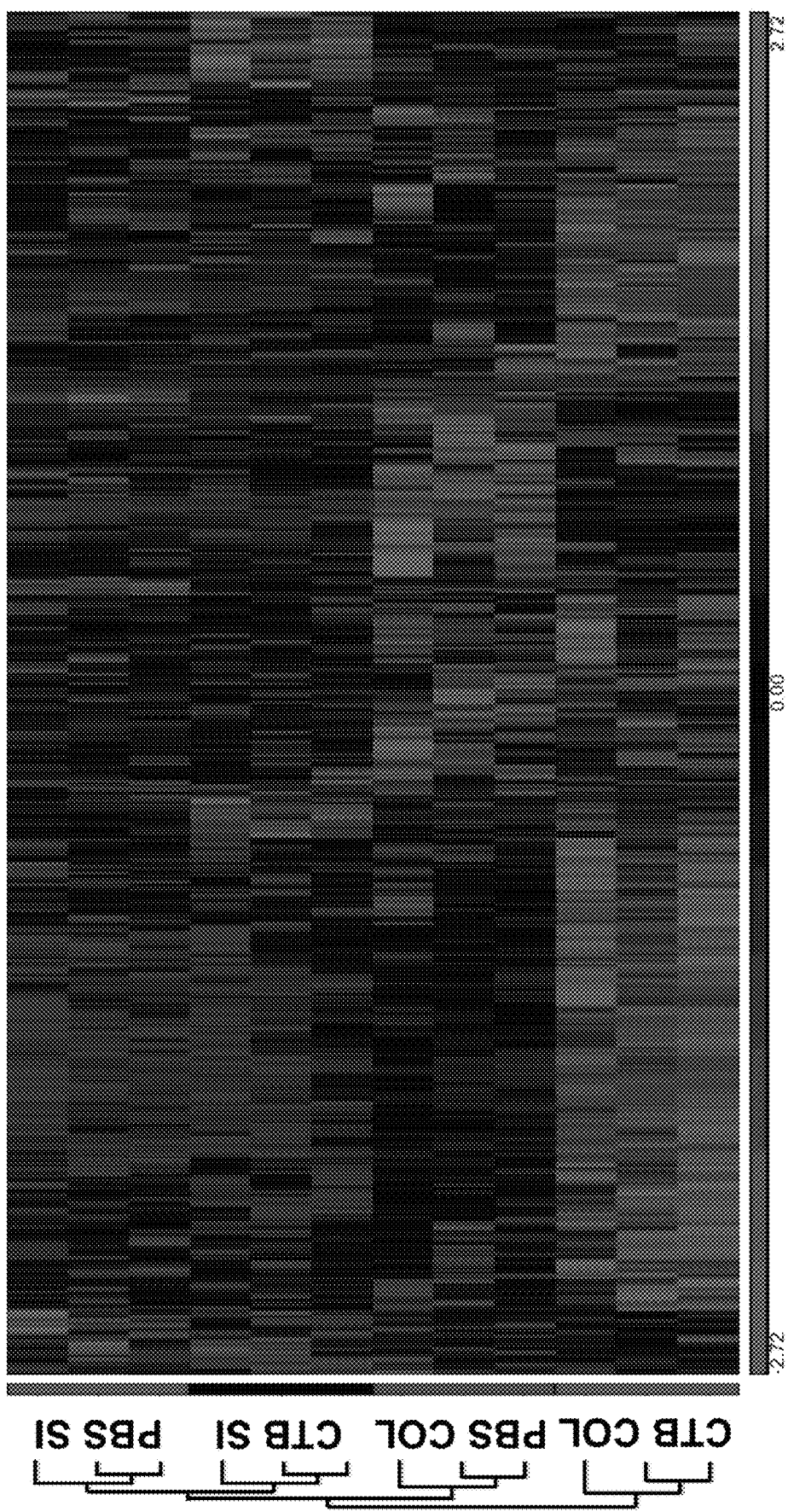
Figure 38B:
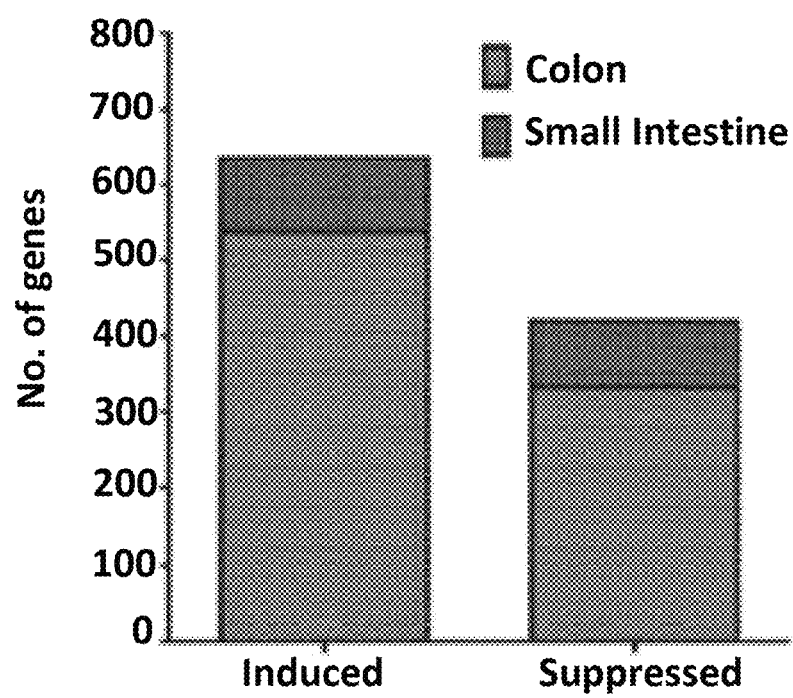

Example 15—CTBP Oral Administration has a More Pronounced Effect on Colon Gene Expression than Small Intestine To further evaluate the impacts of orally administered CTBp on the GI tract, microarray analysis of transcripts isolated from the small intestine and colon was performed. The protein had profound impacts on the gene expression profile of both upper and lower GI tract (FIGS. 38A-38C and FIG. 45). However, while gene expression profiles in small intestine samples clustered relatively tightly, colons from CTBp-treated mice showed a completely separated pattern compared with the control samples (FIG. 38A). At a global level, 871 genes were significantly altered in the colon between CTBp and PBS groups (P<0.01; one-way ANOVA), while about 5 fold less (i.e., 184) genes were significantly altered in the small intestine (FIG. 38B). Of these significantly altered genes, 539 were induced and 332 were suppressed in the colon. By comparison, the small intestine was fairly evenly split between induced and suppressed genes, with 97 and 87 altered genes, respectively, and there was no overlap with genes affected in the colon.

Example 16—CTBP Enhances TGFB-Associated Gene Expression Pathways in the Colon

Figure 46:
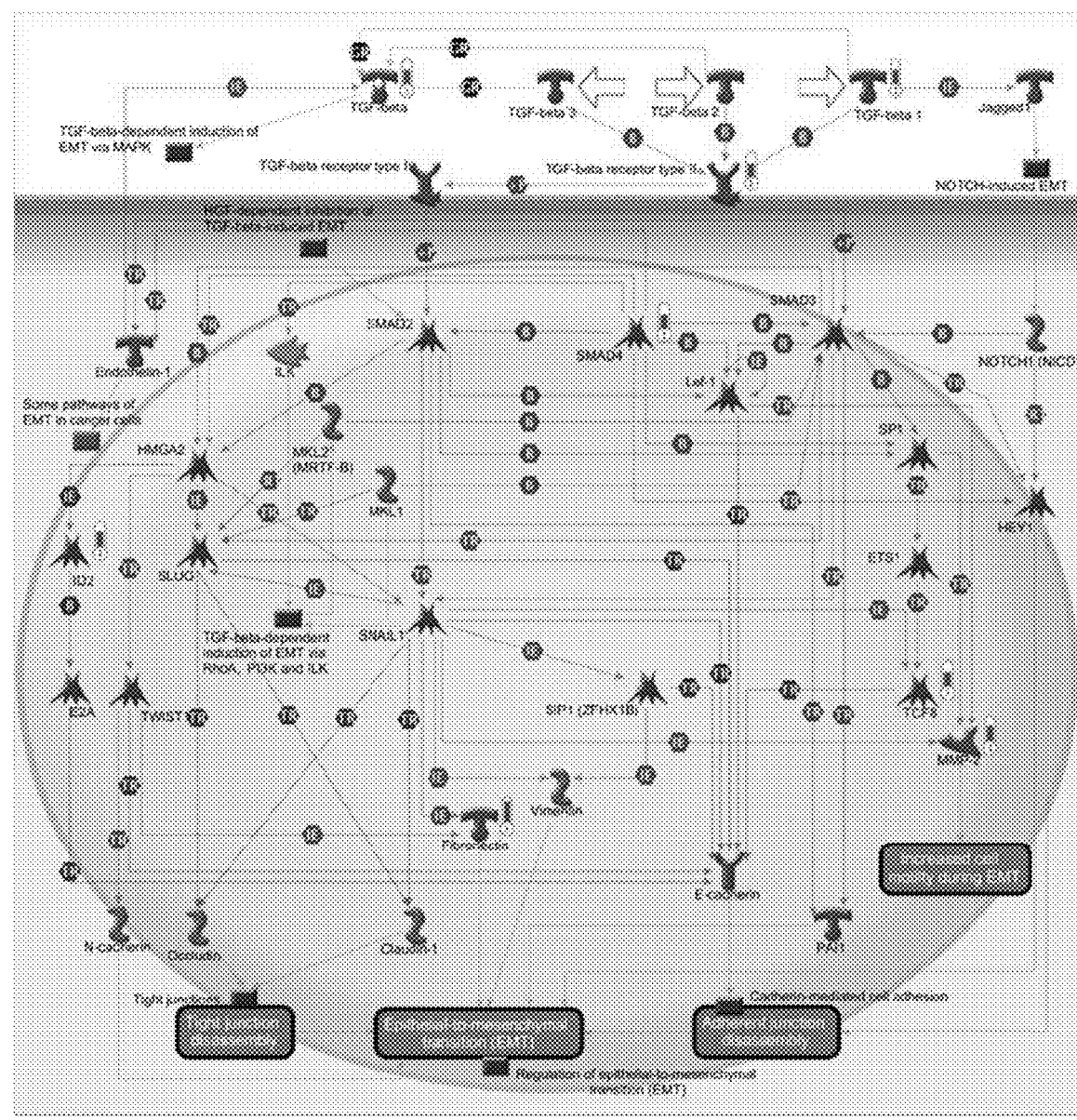
FIG. 46 is a schematic diagram showing TGFβ-associated gene expression pathways in the colon induced by CTBp oral administration. Pathway analysis of colon gene expression from microarray analysis is shown. Red bars are indicative of significant induction of the gene. Pathway analysis was performed by METACORE™ ontologies enrichment analysis using P<0.01 (one-way ANOVA) and a fold change of greater or less than 1.2. Definitions: EMT=epithelial to mesenchymal transition, MAPK=mitogen-activated protein kinase, HGF=hepatocyte growth factor.
Figure 48A:
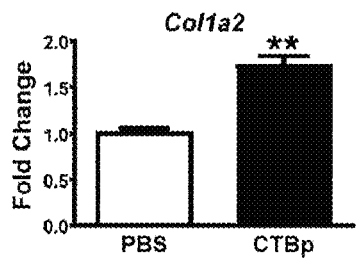
Figure 48B:
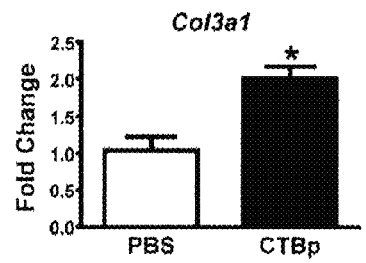
Figure 48C:
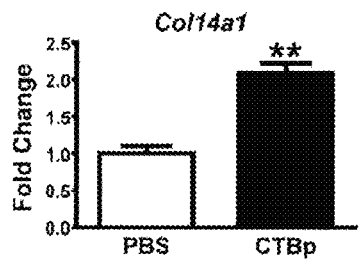
Figure 48D:
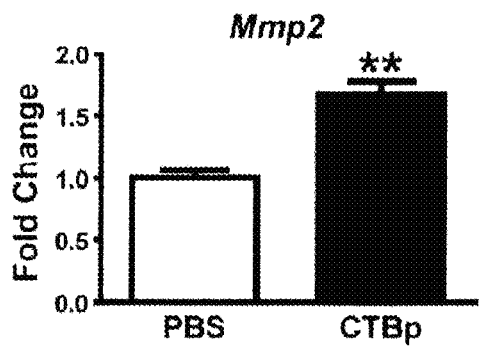
Figure 48E:
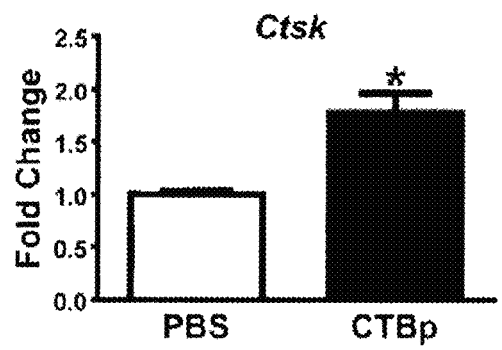
Figure 48F:
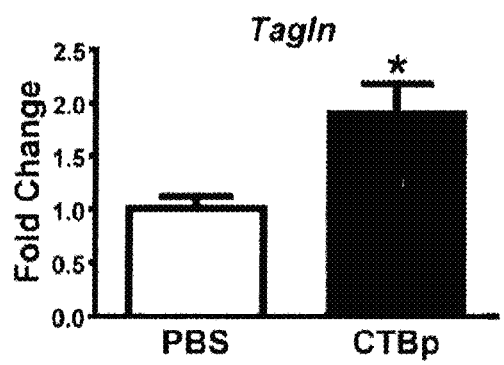
Figure 48G:
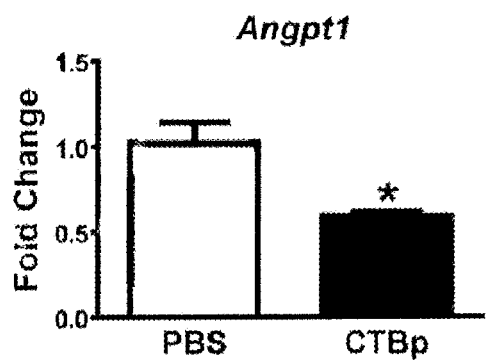

A gene expression pathway analysis (METACORE™ version 6.22 build 67265) revealed that extracellular matrix (ECM) remodeling and epithelial to mesenchymal transition (EMT) pathways were among the most significantly induced pathways in the colon upon CTBp oral administration. In particular, TGFβ-dependent pathways heavily populated the induced pathways (FIG. 38C). Indeed, when evaluating individual gene expression from the microarray analysis Tgfb1, TgfbII receptor and Smad4 were found to be significantly induced by CTBp (FIG. 46), which is indicative of epithelial wound healing activity. By contrast, such strong induction of TGFβ-related pathways was not observed in the small intestine. Suppressed pathways in the colon epithelium included several metabolic pathways, cystic fibrosis transmembrane conductance regulator (CFTR) pathways, and an apoptosis associated pathway. Genes associated with lipid, bile acid, pyruvate, and androstenedione and testosterone metabolic pathways were significantly blunted by CTBp. To confirm microarray data, quantitative real-time reverse-transcription PCR (qRT-PCR) was performed on selected induced, suppressed, or unaltered genes; a high agreement between microarray and qRT-PCR results was obtained (FIGS. 47A-47H). Notably, a wound healing pathway-focused qRT-PCR analysis revealed that many key genes, including Col1a1, Col1a2, Col3a1, Col14a, Mmp2, Ctsk, Tagln and Angptl, were significantly upregulated by CTBp oral administration.

Example 17—CTBP Enhances Wound Healing in Human Colonic Epithelial Cells

Figure 39A:
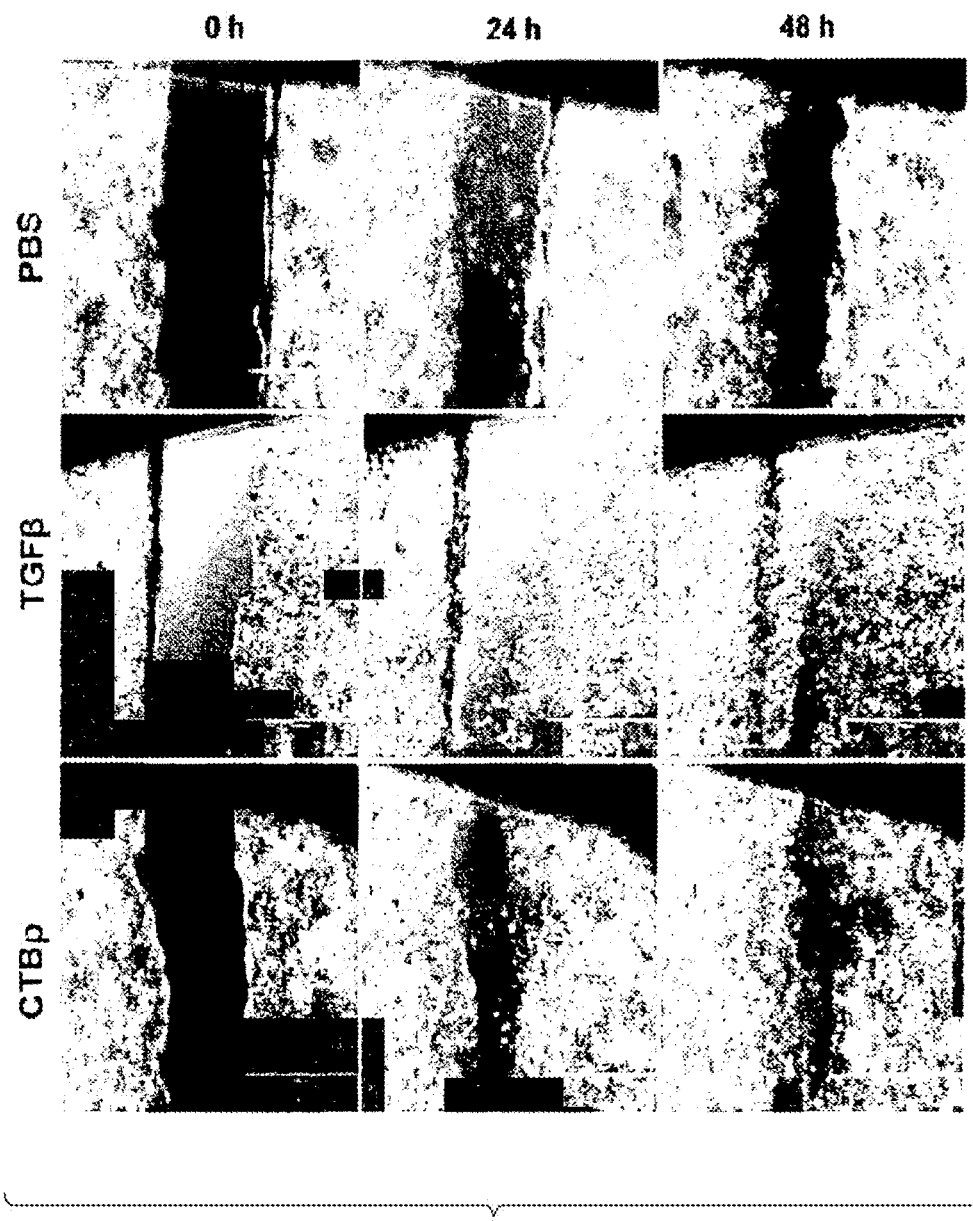
FIGS. 39A-39D includes graphs and images showing that CTBp enhances wound healing in a human colon epithelial model. Caco2 cells were grown to confluence and scratched with a pipette tip. Cells were then incubated with PBS, TGFβ1, anti-TGFβ1,2,3 antibody, and/or CTBp. The in vitro wound closure was recorded over 48 h and 4× magnification images were acquired with a EVOS® fl by Advanced Microscopy Group and mean percentage closure was determined by Image J software.
Figure 39B:
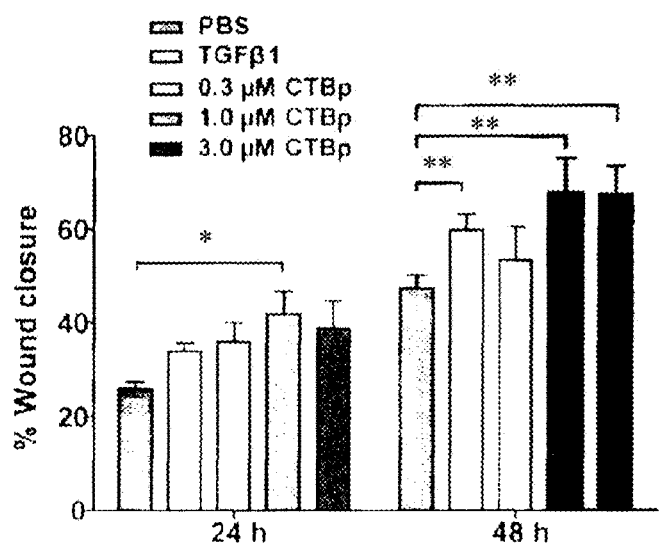
Figure 39C:
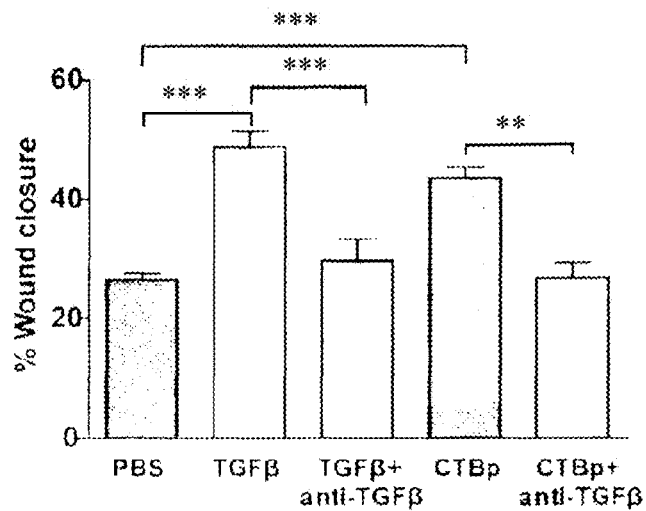
Figure 39D:
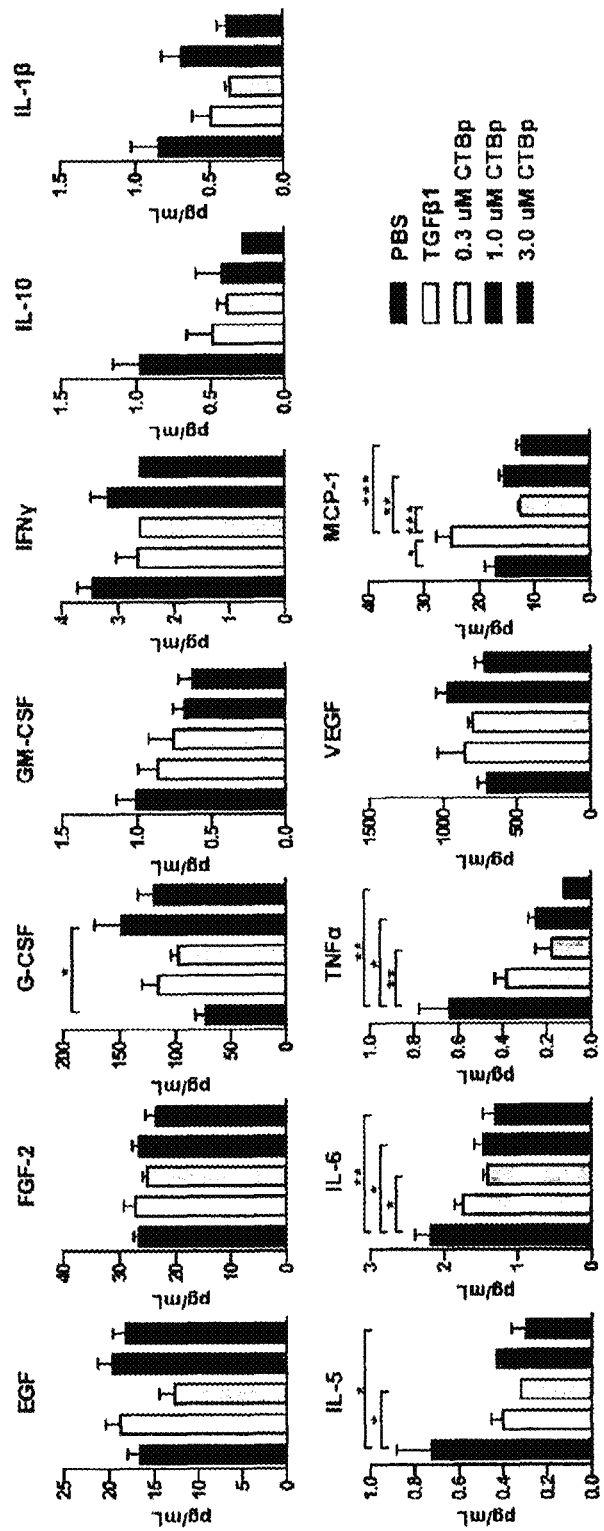
Figure 49:
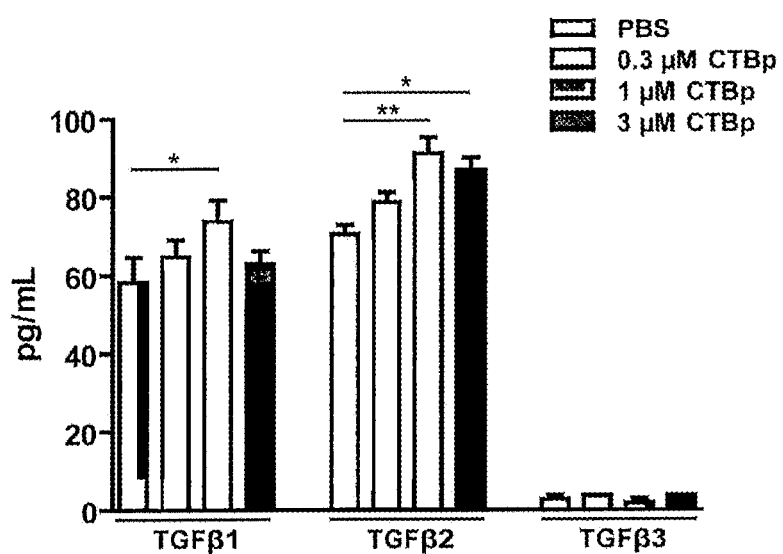
FIG. 49 is a graph showing that CTBp enhances TGFβ mediated wound healing in a human colon epithelial model. Caco2 cells were grown to confluence and scratched with a pipette tip. Cells were then incubated with PBS, TGFβ, Anti-TGFβ, and/or CTBp. The in vitro TGFβ levels were measured after 24 by a LUMINEX® Multiplex assay. Mean±SEM is shown (N=4, experimental replicates per group). *P<0.05, P<0.01, and *P<0.001; one-way ANOVA with Bonferroni's multiple comparison tests.

To investigate the mucosal wound healing potential of CTBp suggested by the gene expression analysis, the human colon epithelial cell line Caco2 wound healing model 14 was employed. As shown in FIGS. 39A-39B, CTBp (1.0 and 3.0 μM) significantly enhanced wound closure, similarly to the TGFβ1 control. Indeed, increased levels of TGFβ1 and TGFβ2 were noted 24 h post wounding in the culture supernatant of CTBp treated cells (Supplementary FIG. 49), and co-incubation of CTBp with an anti-TGFβ1,2,3 neutralizing antibody completely inhibited the wound healing activity (FIG. 39C). Analysis of inflammation and wound healing-related cytokines in the culture supernatant at 48 h revealed that CTBp and TGFβ1 had an overall similar cytokine profile (FIG. 39D); both produced similar levels of epidermal growth factor (EGF), fibroblast growth factor (FGF)-2, granulocyte-colony stimulating factor (G-CSF), granulocyte macrophage colony-stimulating factor (GM-CSF), interferon (IFN)-β, interleukin (IL)-10, IL-1β, IL-5, IL-6, tumor necrosis factor (TNF)α and vascular endothelial growth factor (VEGF), in contrast to the PBS control. An exception was monocyte chemoattractant protein (MCP)-1, which was significantly elevated only in TGFβ1-treated cells.

Example 18—CTBP Mitigates DSS-Induced Acute Colonic Injury and Inflammation

Figure 40A:
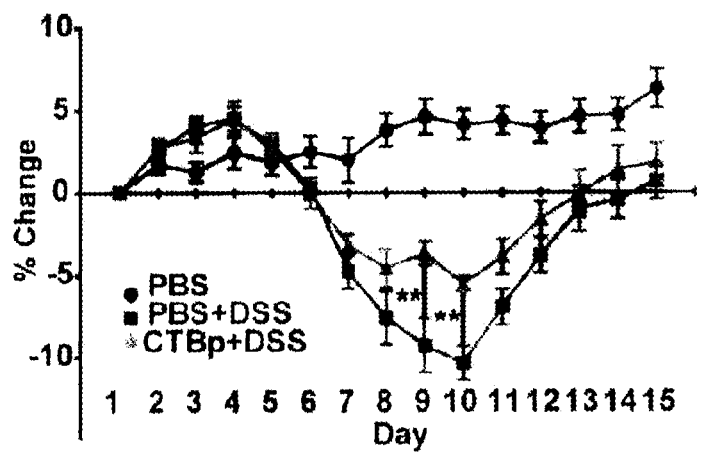
FIGS. 40A-40G includes graphs and images showing that oral administration of CTBp blunts DSS-induced colonic epithelial damage. Mice were orally administered PBS or CTBp twice at a two-week interval. Immediately after the second administration DSS exposure began and continued for 8 days. Colon tissues were isolated after a 6-day recovery for analyses. Mean±SEM is shown for each group. Animals per group: PBS (n=6), 30 µg CTBp+DSS=(n=8), and PBS+DSS (n=8).
Figure 40B:
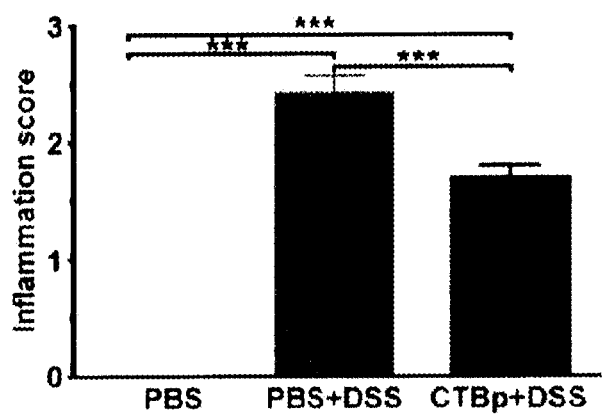
Figure 40C:
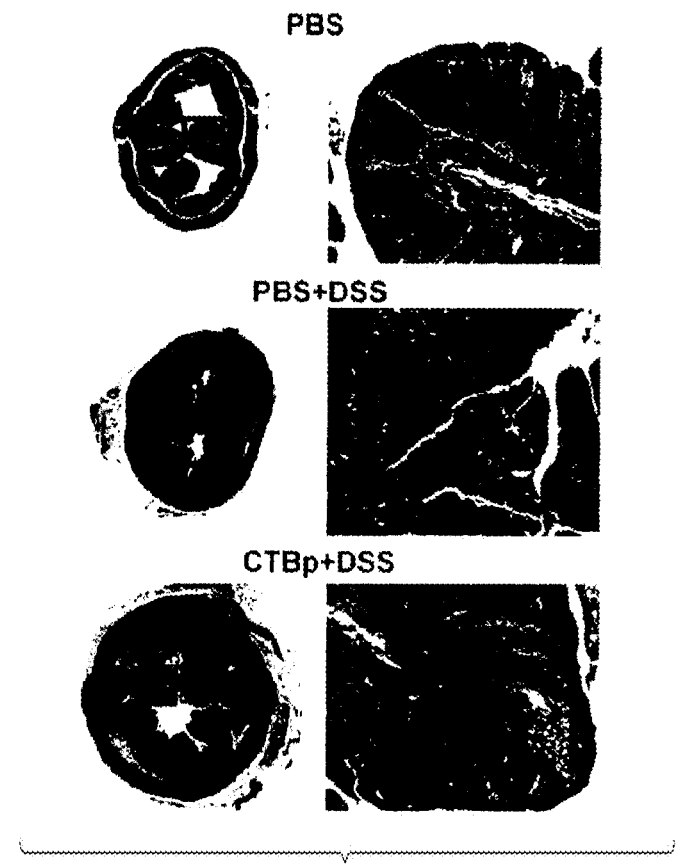
Figure 40D:
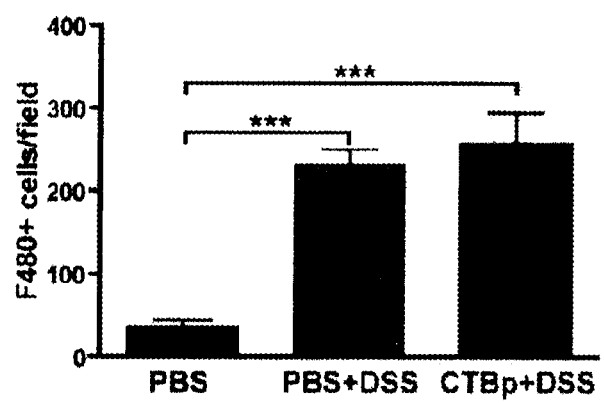
Figure 40E:
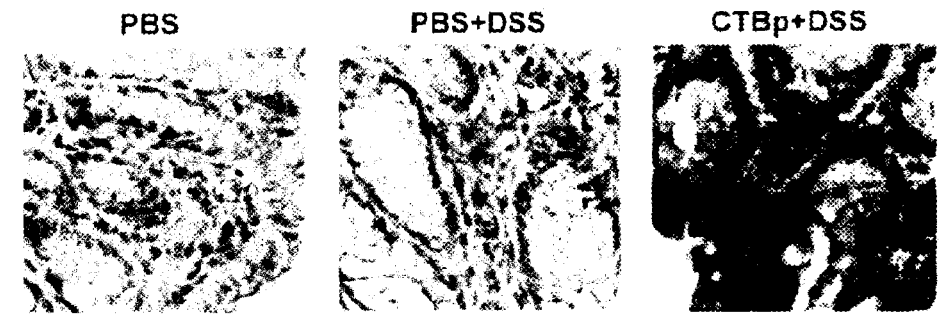
Figure 40F:
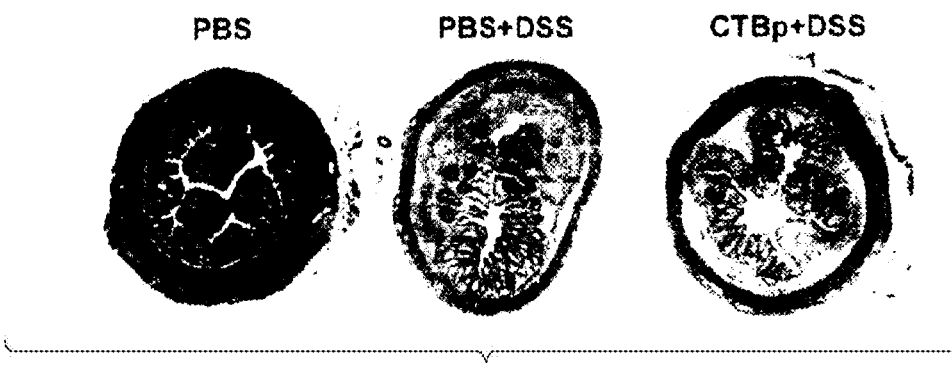
Figure 40G:
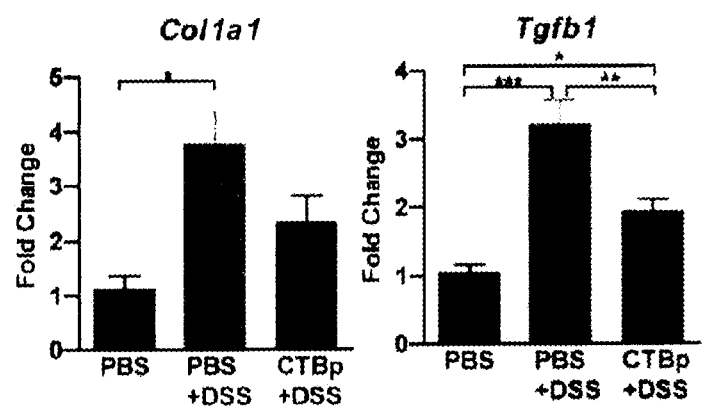
Figure 50:
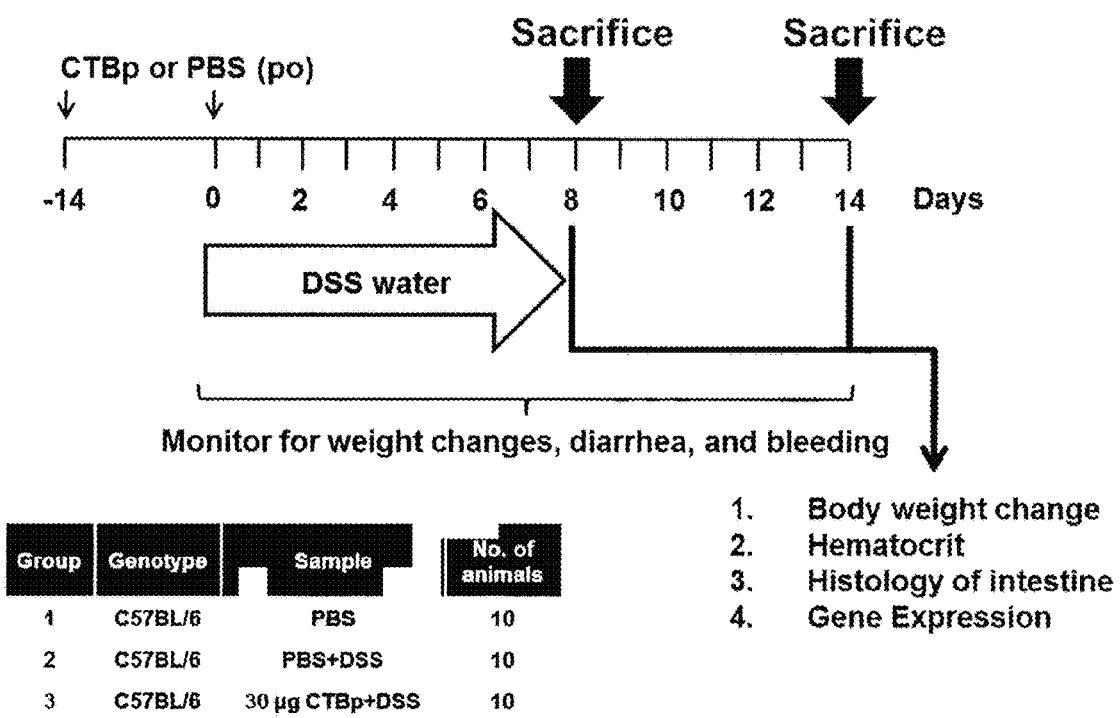
FIG. 50 is a schematic diagram showing study design for acute colitis experiments. Mice were orally administered PBS and CTBp twice at a two-week interval. Immediately after the second administration DSS exposure began for 8 days. Animals were sacrificed either immediately after the DSS exposure period or after a 6 day recovery.
Figure 51:
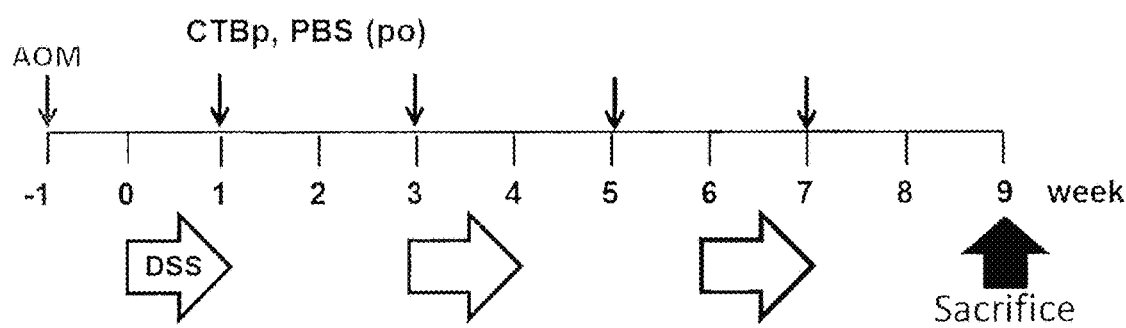
FIG. 51 is a schematic diagram showing chronic colitis study design. Animals in the indicated groups were injected i.p. with 10 mg/kg azoxymethane (AOM). DSS exposure began 1 week after AOM injection and continued for 1 week. Immediately after removal of DSS water, PBS or CTBp (3 or 10 µg per mouse) was administered to the respective groups and dosing was continued biweekly for a total of 4 doses. Animals were allowed to recover for 2 weeks prior to the beginning of a second DSS exposure period. The DSS exposure/2 week recovery cycle was repeated 2 additional times for a total of 3 cycles. Animals were sacrificed following the final 2 week recovery.

It was next determined if the in vitro mucosal healing activity of CTBp could be translated into a therapeutic effect in vivo. A well-established mouse DSS colitis model was employed, which induces injury and severe inflammation in the distal colon. In an initial study, the "vaccination" regimen that brought about the above-described biological effects implicated in mucosal protection was used (FIGS. 37A-37E and 38A-38C); PBS or 30 µg CTBp was orally administered twice at a 2 week interval to mice prior to DSS exposure (FIG. 50). As shown in FIG. 40A, CTBp significantly blunted the weight loss induced by DSS. Histopathological examination on hematoxylin and eosin (H&E)-stained distal colon tissue at 6 days post DSS exposure revealed that CTBp treatment prevented the aberrant loss of crypts and ulceration that were noted in the untreated control group; although shortening of basal crypts and mild inflammatory infiltrates were observed, the epithelial surface remained intact (FIG. 40B-40C). Despite the significantly less damage and inflammation in the colon of CTBp-administered mice, the numbers of macrophages infiltrated into the colon mucosa were similar between CTBp-treated and untreated groups, and significantly higher than that of the non-DSS-exposed control group (FIG. 40D-40E). Moreover, CTBp administration appeared to prevent fibrosis in the colon according to Masson's trichrome stain, while fibrosis was evident in the DSS-exposed vehicle control-administered group (FIG. 40F). Consistent with this, the major fibrotic genes Col1a1 and Tgfb116, 17 were significantly increased in the colon tissue of the DSS-exposed vehicle control-administered mice; CTBp treatment, on the other hand, showed lower levels of these transcripts (FIG. 40G).

Figure 41A:
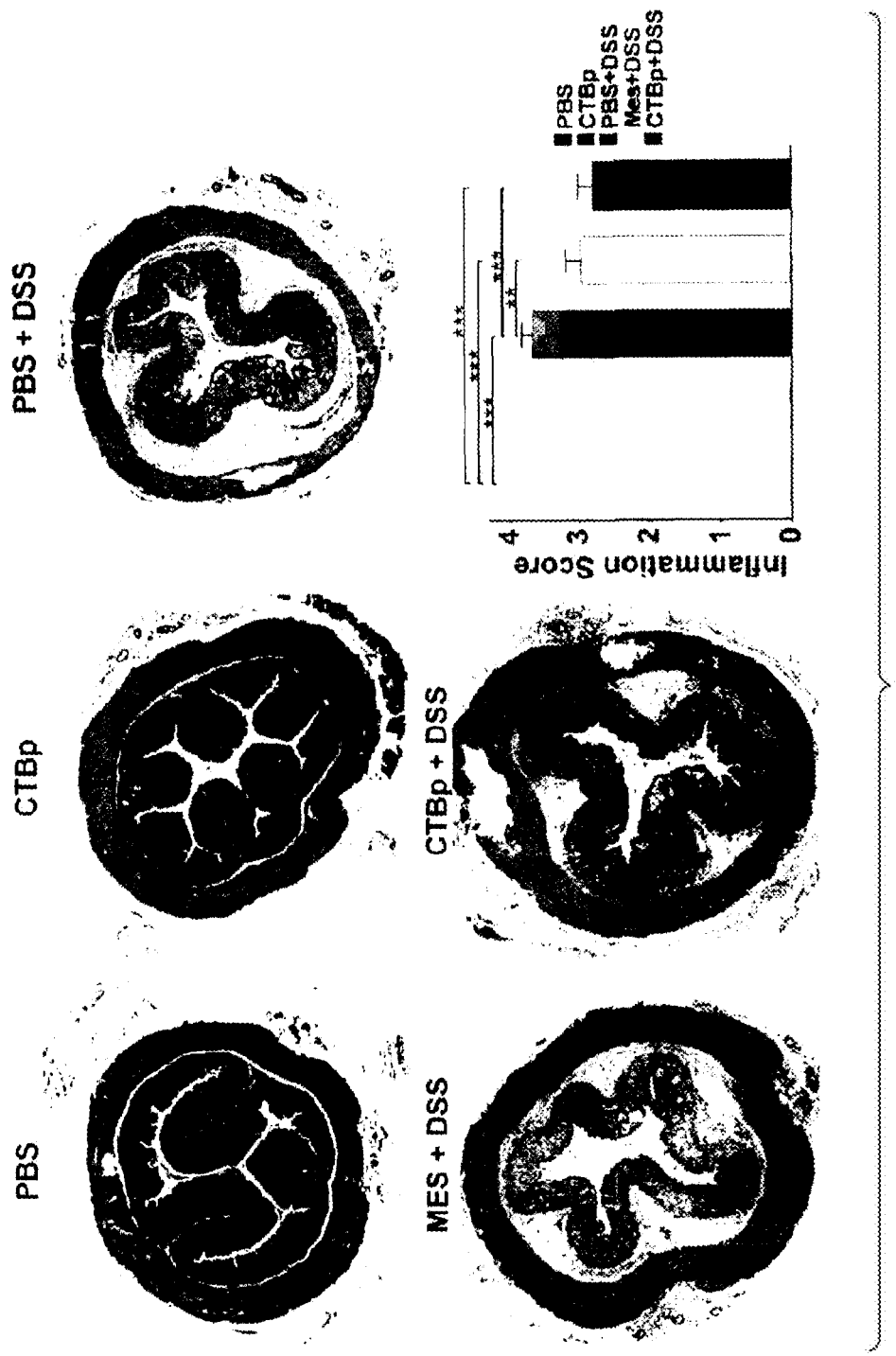
FIGS. 41A-41C include graphs and images showing that CTBp significantly reduces colon inflammation induced by DSS exposure. Mice were orally administered with PBS or CTBp and exposed to DSS as in FIG. 40. As a reference control, a group of mice were treated with oral administration of 100 µg mesalamine daily during the DSS exposure. Colon tissues were isolated immediately after the DSS exposure for analyses.
Figure 41B:
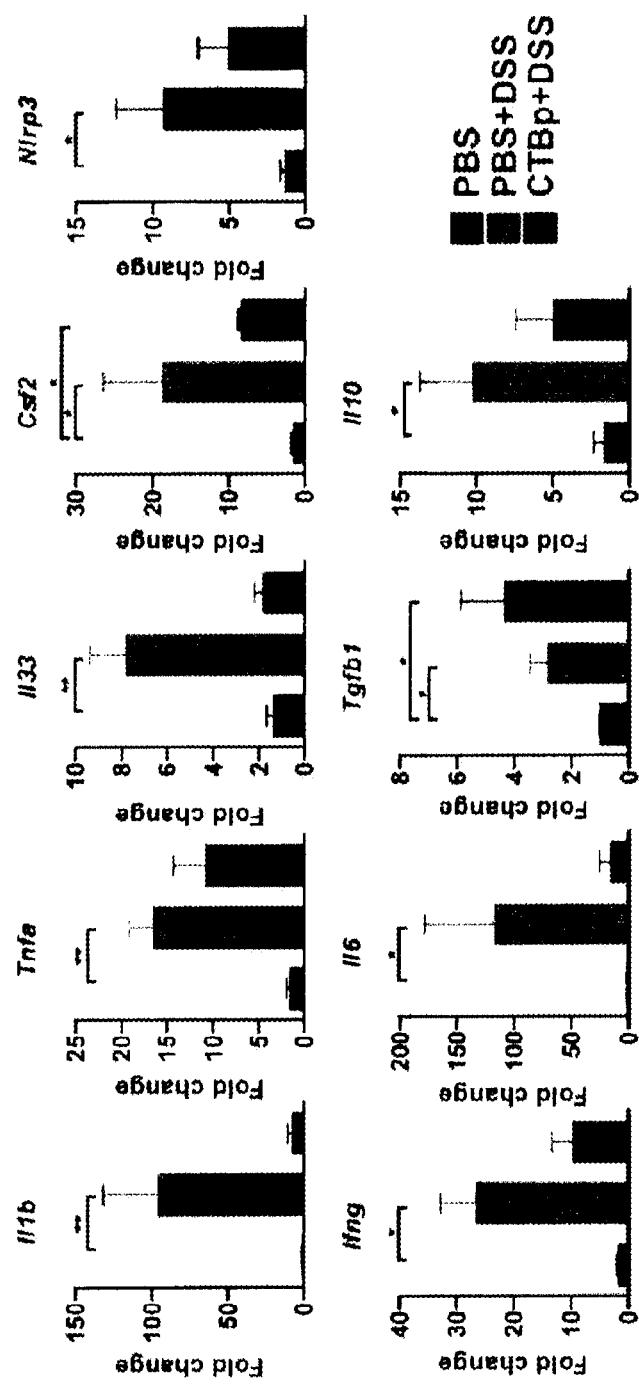
Figure 41C:
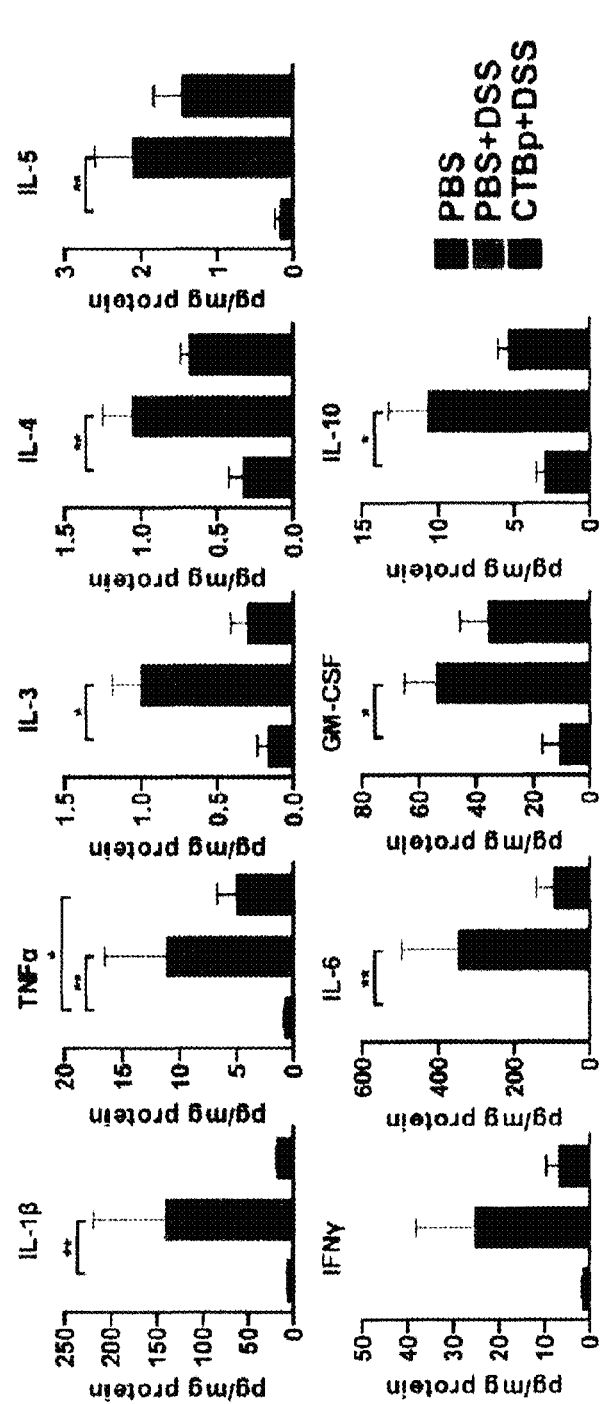
Figure 42A:
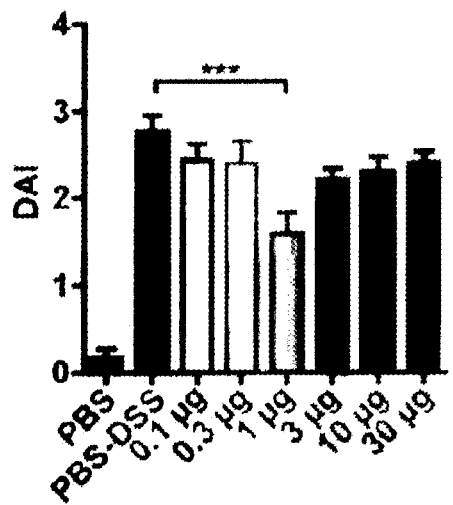
FIGS. 42A-42D include graphs and images showing the therapeutic dosing of CTBp is effective in ameliorating DSS-induced acute colitis. Mice were exposed to 3% DSS for seven days and orally administered with PBS or CTBp on the third and sixth day. Colon tissues were isolated after a two-day recovery for analyses. N=5 for PBS and N=10 for all other groups.
Figure 42B:
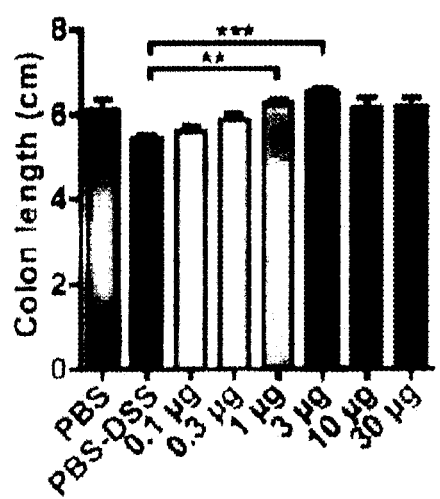
Figure 42C:
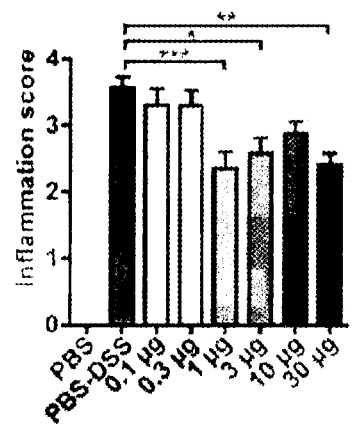
Figure 42D:
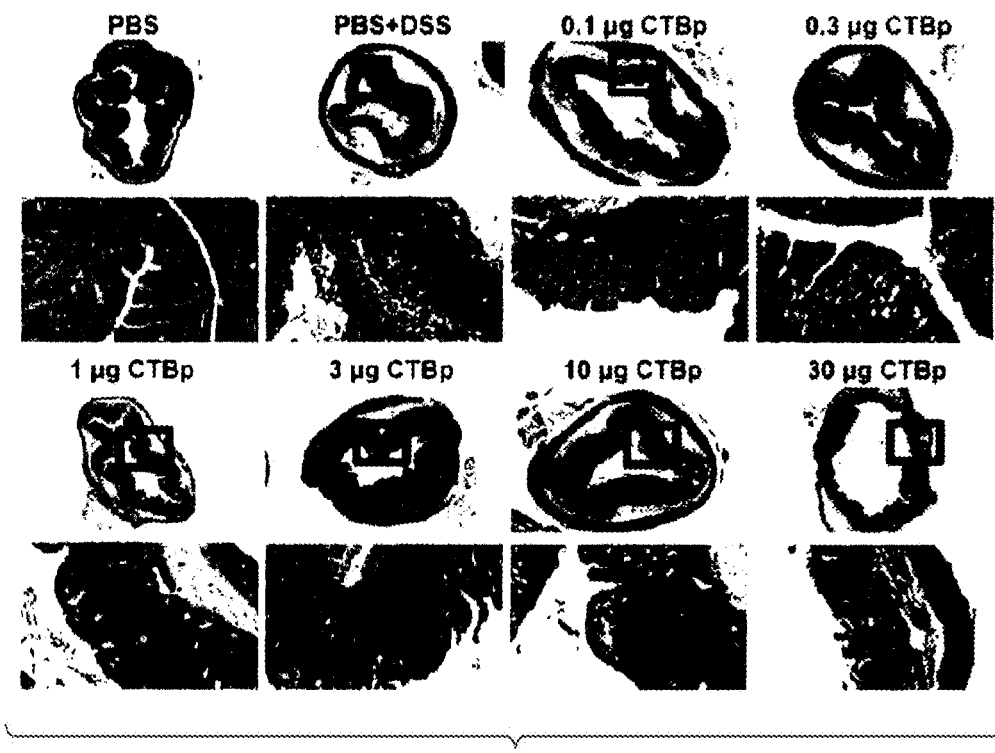

Given that CTBp significantly improved recovery from DSS-induced acute colitis, its effect immediately after DSS exposure was also investigated. At this maximum injury/inflammatory point, CTBp administration again significantly reduced the mucosal damage, characterized by shortened yet visible basal crypts, relatively mild inflammatory infiltrates in the mucosa and submucosa, and retention of the epithelial cell surface unlike the PBS control group. Meanwhile, daily oral administration of 100 µg mesalamine (MES) during the DSS exposure, which simulates a current treatment for ulcerative colitis in humans, showed similar protection observed with the CTBp regimen employed here (FIG. 41A). To further characterize CTBp's protective effect, qRT-PCR analysis was performed. CTBp treatment was shown to blunt the escalation of representative inflammatory marker expression induced by DSS exposure, including Il1b, Il33, Il6 and Infg (FIG. 41). Tgfb1, on the other hand, showed a significant increase in both CTBp-treated and vehicle control-administered mice following DSS exposure compared to healthy animals. Analysis of soluble inflammatory markers in the distal colon also showed that CTBp administration blunted the significant increase of major inflammatory proteins, including IL-1β, IL-3, IL-4, IL-5, IFN.gamma., IL-6 and GM-CSF (FIG. 41C). Of note, CTBp administration did not increase IL-10 either at the gene expression or protein levels, despite that IL-10 has previously been linked to the potential anti-inflammatory activity of CTB and CT.

Since CTBp "vaccination" was effective in DSS-induced acute colitis, we next examined the protein's therapeutic dosing effect. As shown in FIGS. 42A-42D, protection was evident as CTBp was dosed at the late phase of the DSS exposure (Day 3 and 6), when the onset of colonic epithelial damage had already taken place. This demonstrates that the protein does not require pre-emptive dosing for protection against DSS-induced colon epithelial insult. Conversely, CTBp's mucosal protective activity can take effect relatively quickly against ongoing epithelial damage and inflammation. A dose-ranging study (0.1-30 µg/mouse/dose) showed that the most effective dose of CTBp in this therapeutic regimen was as low as 1 µg/mouse/dose. Interestingly, the efficacy did not follow a dose-dependent pattern; 3, 10 and 30 µg were less effective than 1 µg, according to disease activity index (DAI) scores. Nevertheless, the highest dose still prevented the shortening of the colon length, showed a significantly lower inflammation score than the untreated control, and reduced epithelial damage and ulceration in the distal colon tissue, suggesting no adverse effects at this dose (FIGS. 42A-42D).

Figure 43C:
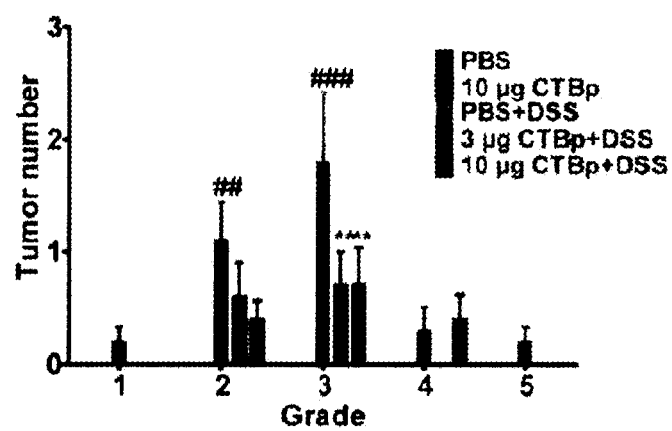

Example 19—CTBP Oral Administration can Protect Against Chronic Colitis and Colon Tumor Development in an AOM/DSS Model The significant protection seen in the acute colitis/colon injury model prompted an investigation into whether CTBp could also be effective in an AOM/DSS mouse model of chronic colitis and colon cancer. CTBp (3 or 10 µg) was given at the end of the first DSS exposure period followed by three additional doses every two weeks for a total of four doses (see FIG. 51). As shown in FIGS. 43A-43F, CTBp administration (3 µg) significantly decreased the DAI score immediately following the first dose and more dramatically during the 3rd DSS exposure period (FIG. 43A). Such a clear effect was not observed with the higher dose (10 µg) of CTBp. However, tumorigenesis was significantly reduced at both dose levels (FIG. 43C).

Figure 43D:
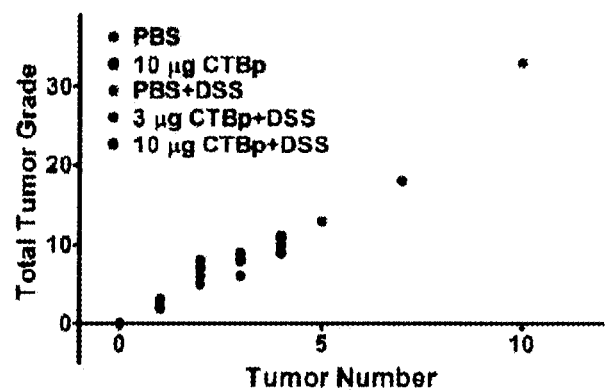

Tumor growth also appeared to be limited by CTBp, as indicated by the decreased number of grade 3-5 tumors and total tumor grade in CTBp-administered groups (FIGS. 43C-43D). Of note, CTBp administration (10 µg) without DSS exposure did not induce any sign of intestinal damage or tumor growth (FIG. 43A, 43C, 43D).

Figure 43E:
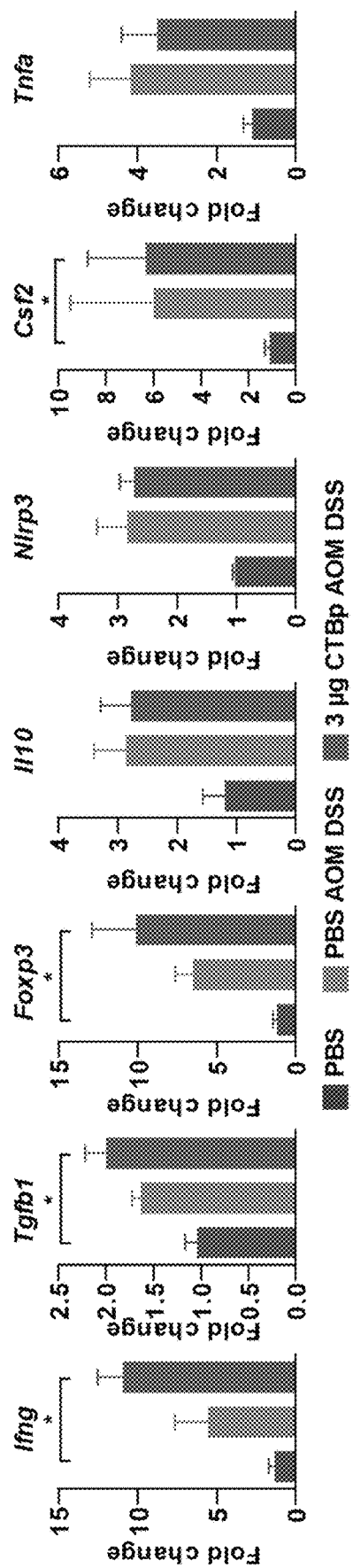
Figure 43F:
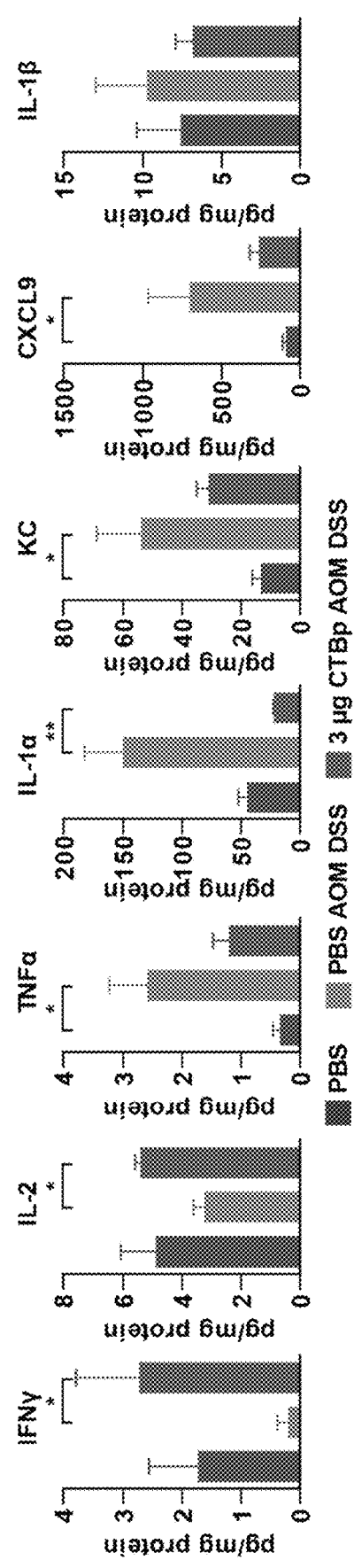

To further characterize the protection of 3 µg CTBp in the AOM/DSS model, markers associated with inflammation and cancer development were evaluated in the colon tissue two weeks following the final DSS exposure. Both DSS-exposed groups showed an increased level of Infg, Tgfb1, Foxp3, Il10, Nlrp3, Csf2 and Tnfa. However, CTBp administration resulted in a more significant increase in Tgfb1, Foxp3 and Ifng compared to healthy mice (FIG. 43E). Analysis of soluble markers showed that, although IL-1β had declined to a baseline level at this point, several inflammatory markers still showed a significantly higher level in the DSS-exposed, vehicle control-administered group compared to healthy mice, including TNFα, IL-1α, keratinocyte chemoattractant (KC), chemokine (C—X—C motif) ligand 9 (CXCL9) (FIG. 43F). CTBp administration blunted the elevation of these markers, most notably IL-1α, which is a key factor to exacerbate gut inflammation. Notably, CTBp-treatment completely blocked the AOM/DSS-induced decrease of IFN.gamma. and IL-2 levels, which could be linked to the reduced tumorigenesis in this group.

Discussion of Examples 14-19

Oral administration of CTB leads to a robust antibody response and an anti-inflammatory effect. The former represents the protein's most well-known biological activity, which has been exploited in cholera prevention (as a component of DUKORAL® vaccine). On the other hand, the utilization of CTB's anti-inflammatory activity in inflammatory disease therapy is yet to be achieved, in part due to its obscure underlying mechanisms. The present study revealed that oral administration of CTBp exhibits previously unidentified impacts on the distal part of the GI tract; recruitment of macrophages, DCs and NK cells into the colon lamina propria and upregulation of TGFβ pathways in the colon (FIGS. 37A-37E and FIGS. 38A-38C), which subsequently lead to the discovery that CTBp promotes mucosal healing in the colon (FIGS. 39A-39D-43A-43F). The use of CTBp was justified because it retains key molecular features of original CTB. Although CTB was previously shown to upregulate TGFβ in immune cells and blunt intestinal inflammation of Crohn's disease, the present studies demonstrated for the first time that orally administered CTB can facilitate TGFβ-driven mucosal wound healing in the colon. TGFβ has multifaceted functions including pivotal roles in gut homeostasis and intestinal wound healing. A recent study has shown that the suppression of TGFβ signaling in an injured and inflamed mucosa leads to invasive tumor development in the colon, showing that TGFβ-mediated mucosal repair plays a key role in colitis-associated colon tumor prevention. This is in line with our findings in the AOM/DSS study (FIGS. 43A-43F). However, TGFβ1 is also known to be elevated in collagenous colitis and connected to increased collagen deposition and fibrosis, indicating the dual nature of this cytokine in mucosal remodeling. In this regard, the fact that CTBp administration prevented fibrosis in the acute DSS colitis study (FIGS. 40F-40G) suggests that the CTBp dosing regimen did not overstimulate TGFβ signaling to a level causing adverse effects. Interestingly, the Caco2 study showed that CTBp did not dose-dependently induce TGFβ1 or TGFβ2 (FIG. 49), which might represent feedback inhibition by CTBp overdose. This may in turn explain why the higher doses of CTBp were not as effective as the lower dose in the acute and chronic DSS studies (FIGS. 42A-42D-43A-43F). Detailed investigation into CTBp's dose-effect relationship is warranted to define a therapeutic window for optimal mucosal healing.

Figure 52:
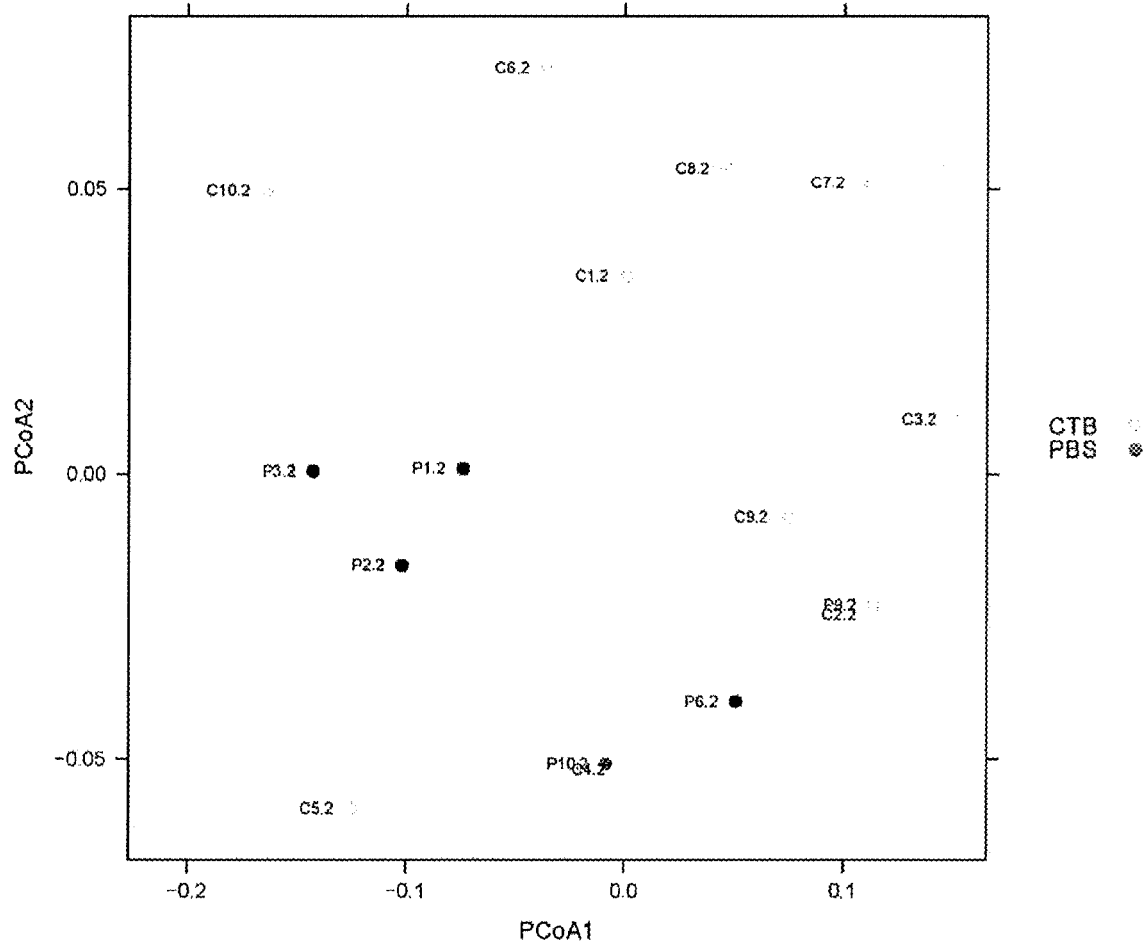
FIG. 52 is a graph showing principal coordinate analysis of gut microbiome two weeks following the second CTBp or PBS administration. Fecal samples were collected from each mouse 2 weeks after the final dose of PBS or CTBp. Following bacterial DNA isolation samples were analyzed. No significant alteration of overall microbiome was noted following CTBp administration. Weighted UniFrac metric was performed on 1,896 taxa. No significant change in overall microbiome was observed between the two groups.
Figure 53A:
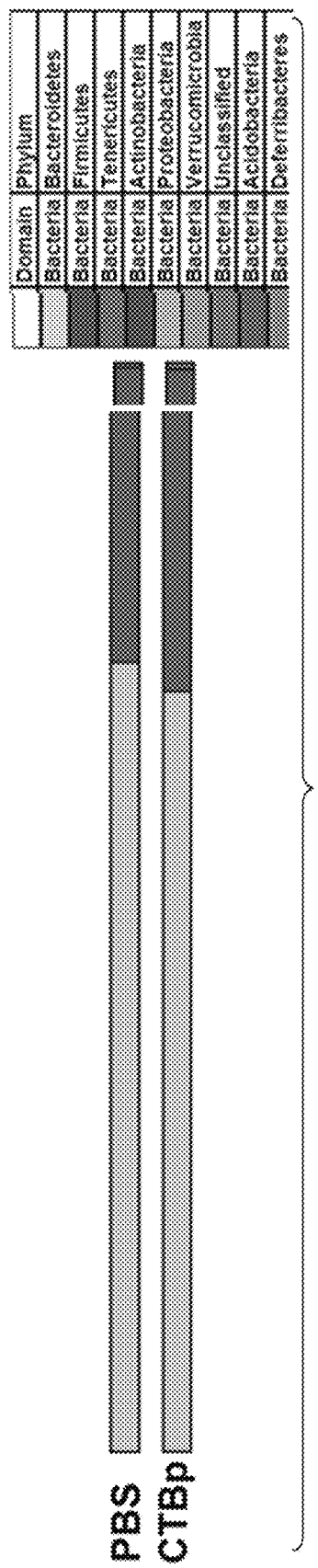
FIGS. 53A-53C include schematic diagrams and graphs showing gut microbiome analysis of mice administered with CTBp or PBS at the phylum and species levels. Fecal samples were collected from each mouse 2 weeks after the second dose of PBS or CTBp. Following bacterial DNA isolation samples were analyzed.
Figure 53B:
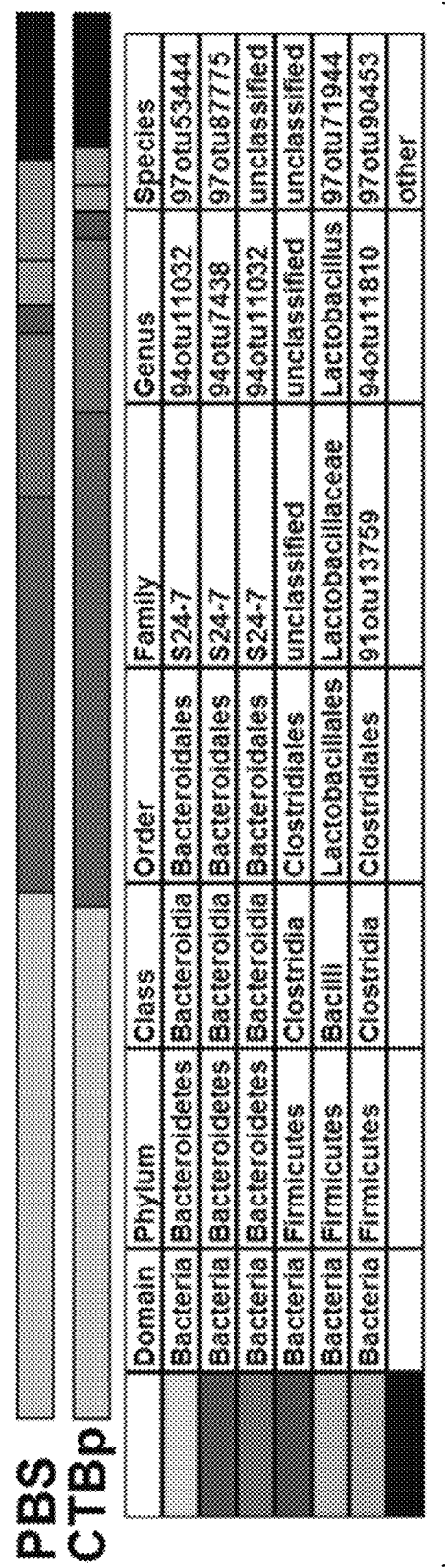
Figure 53C:
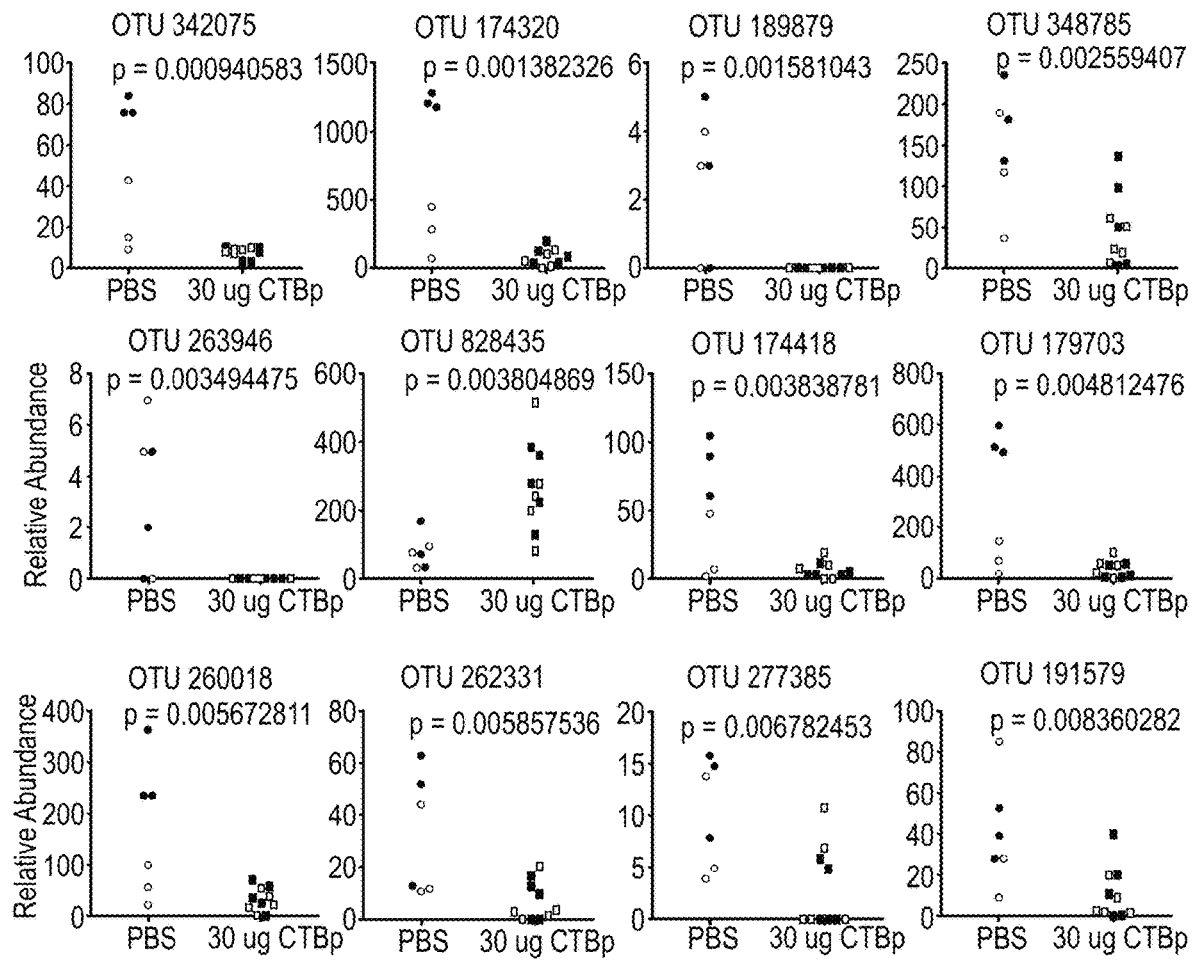

It is of interest to note that CTBp-induced TGFβ activation in the colon epithelium was accompanied by a significant increase of several innate immune cells in the same mucosa (FIGS. 37A-37E-38A-38C). CTB is known to alter the T cell profile under various conditions and affect DC maturation in vitro. However, the protein's impacts on immune cells in different regions of the GI tract, as shown in the present study, are unprecedented. At this point, the mechanism by which CTBp induced such compartmentalized effects on GI tract immune cells is not clear. A possible change in the gut microbiota was suspected. However, the overall fecal microbiome profile showed no discernible shift at the point when colon gene expression and immune cell profile changes were observed (FIG. 52). Bacteroidetes and Firmicutes spp. dominated at the phylum level (FIGS. 53A-53B), which is typical for C57BL/6J mice. There were significant changes at the species level in 12 Operational Taxonomic Units with 11 belonging to the Clostridiales order, but these constitute minor subpopulations in the gut flora (FIG. 53C). These results suggested that the gut microbiota was unlikely the cause of the drastic changes in the colon observed in the present study, although more detailed investigation is warranted to reveal possible impacts of CTBp on gut microbiota over a longer term. Meanwhile, the observation that CTBp concomitantly stimulated the activation of TGFβ signaling and the increase of the innate immune cells in the colon leads us to postulate that the latter effect might also play a role in the protein's mucosal healing effects. For example, lamina propria-resident DCs were previously shown to suppress the severity of DSS colitis. NK cells play a major role in tissue remodeling by clearing dead or dying cells. Macrophages can remove bacteria that penetrate the epithelium and damaged tissue and play an important role in enhancing late phase wound healing, which might explain our observation that CTBp markedly increased macrophage infiltration into the colon mucosa in DSS-exposed mice (FIGS. 40D-40E) while significantly reducing epithelial damage (FIGS. 40B-40C). Studies are currently underway to elucidate the mechanism and the potential contribution of CTBp-induced colonic immune cell profile in the context of mucosal healing.

In the mouse DSS model, CTBp oral administration significantly reduced ulceration in DSS-exposed colon epithelia (FIGS. 40A-40G and 42A-42D), which is indicative of enhanced mucosal healing. Additionally, the escalation of inflammatory markers was blunted independently of the strong anti-inflammatory cytokine IL-10, while Tgfb1 expression significantly increased (FIGS. 41B-41C). Coupled together, it was strongly suggested that CTBp's protective effect was primarily ascribed to the TGFβ-mediated mucosal healing activity demonstrated in the Caco2 wound healing assay (FIGS. 39A-39D). Since DSS colitis is pathologically similar to ulcerative colitis in humans, the data point to a possibility that CTBp is effective against ulcerative colitis, a major form of IBD along with Crohn's disease. In particular, mucosal healing has recently become an important target for ulcerative colitis therapy because it is associated with improved clinical outcomes. It should be noted that only two low oral doses of CTBp were as effective as mesalamine dosed daily during the 8-day DSS exposure in the acute colitis model (FIGS. 41A-41C), and biweekly dosing of CTBp also proved to be effective against chronic colitis and reduced colitis-associated colon tumorigenesis (FIGS. 43A-43F), highlighting the protein's remarkable therapeutic effect.

In summary, the foregoing work revealed a novel function of CTBp to enhance colonic mucosal healing through TGFβ pathways. Oral administration of CTBp provided protection against DSS-induced colonic injury and colitis. Although further investigations are required to carefully define the dose-effect relationship in mucosal remodeling and efficacy in other clinically relevant conditions such as Smad7 overexpression, an efficient bioproduction system already available for CTBp9 should significantly facilitate the protein's preclinical and clinical investigations towards its potential use to promote colonic mucosal health besides cholera prevention.

Figure 54A:
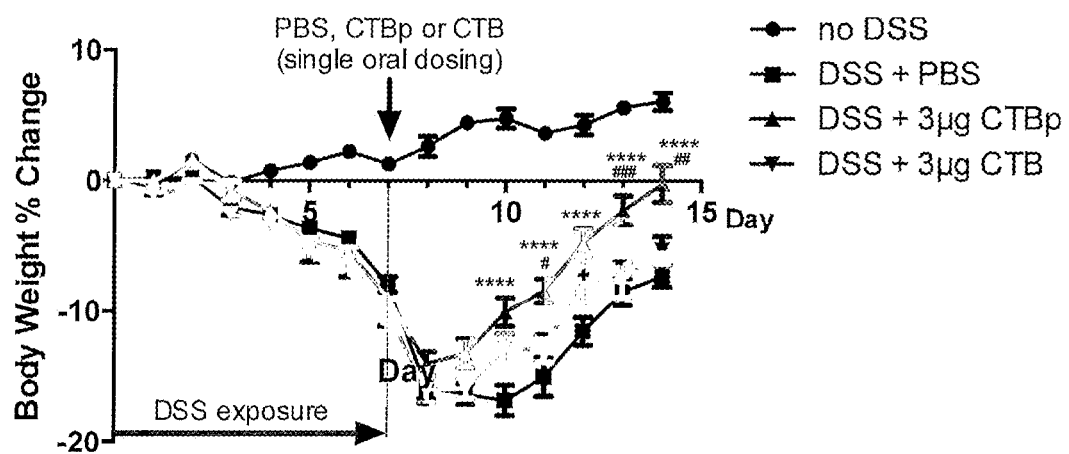
FIGS. 54A-54C are graphs showing a comparison of plant-produced N4S-CTB-SEKDEL (CTBp) with original CTB in an acute colitis mouse model.
Figure 54B:
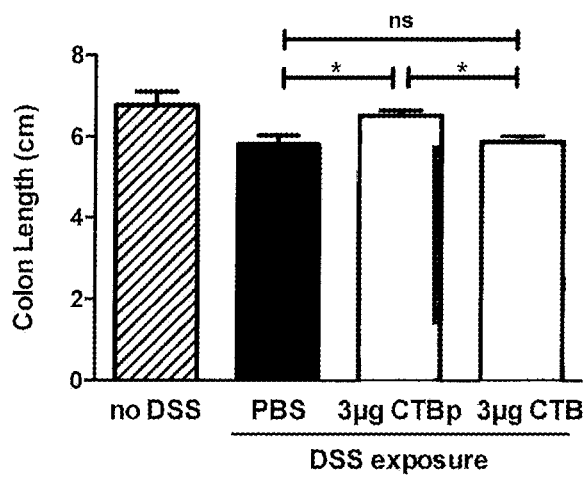
Figure 54C:
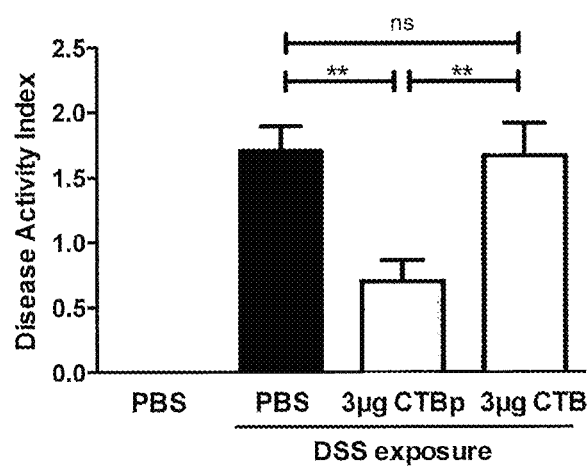

Example 20—Comparison of Plant-Produced
N4S-CTB-Sekdel (CTBP) with Original CTB in an
Acute Colitis Mouse Model The effects of therapeutic dosing of CTBp and CTB were investigated in C57b1/6 mice exposed to 3% dextran sodium sulfate (DSS) in drinking water for 7 days. At the end of DSS exposure, mice were orally administered with either 3 µg CTBp, 3 µg CTB, or PBS vehicle control once. Percent body weight change was monitored daily until sacrifice on day 14. As illustrated in FIGS. 54A-54C, the administration of CTBp significantly affected percent body weight change, colon length, and disease activity index (DAI) as compared to both PBS and original CTB. More specifically, as illustrated in FIG. 54A, administration of CTBp provided significant increases in percent body weight change as compared to both PBS and CTB. Additionally, as illustrated in FIGS. 54B and 54C, respectively, administration of CTBp provided a significant increase in colon length and a significant decrease in disease activity index as compared to both PBS and CTB. In contrast, there were no significant differences observed in colon length (FIG. 54B) or disease activity index (FIG. 54C) between original CTB and PBS. Thus, in some embodiments, CTBp provides increased wound healing and/or disease treatment as compared to original CTB and/or PBS.

Throughout this document, various references are mentioned. All such references are incorporated herein by reference, including the references set forth in the following list:

REFERENCES

1. J. Sanchez, J. Holmgren, Cholera toxin structure, gene regulation and pathophysiological and immunological aspects. Cell Mol Life Sci 65, 1347-1360 (2008).
2. R. G. Zhang et al., The 2.4 A crystal structure of cholera toxin B subunit pentamer: choleragenoid. Journal of molecular biology 251, 550-562 (1995).
3. T. Jelinek, H. Kollaritsch, Vaccination with Dukoral against travelers' diarrhea (ETEC) and cholera. Expert Rev Vaccines 7, 561-567 (2008).
4. J. Clemens, S. Shin, D. Sur, G. B. Nair, J. Holmgren, New-generation vaccines against cholera. Nature reviews. Gastroenterology & hepatology 8, 701-710 (2011).
5. J. Holmgren et al., Mucosal adjuvants and anti-infection and anti-immunopathology vaccines based on cholera toxin, cholera toxin B subunit and CpG DNA. Immunology letters 97, 181-188 (2005).
6. K. J. Baldauf, J. M. Royal, K. T. Hamorsky, N. Matoba, Cholera toxin B: one subunit with many pharmaceutical applications. Toxins (Basel) 7, 974-996 (2015).
7. J. B. Sun, C. Czerkinsky, J. Holmgren, Mucosally induced immunological tolerance, regulatory T cells and the adjuvant effect by cholera toxin B subunit. Scand J Immunol 71, 1-11 (2010).
8. H. H. Smits et al., Cholera toxin B suppresses allergic inflammation through induction of secretory IgA. Mucosal Immunol 2, 331-339 (2009).
9. M. Stanford et al., Oral tolerization with peptide 336-351 linked to cholera toxin B subunit in preventing relapses of uveitis in Behcet's disease. Clin Exp Immunol 137, 201-208 (2004).
10. K. T. Hamorsky et al., Rapid and scalable plant-based production of a cholera toxin B subunit variant to aid in mass vaccination against cholera outbreaks. PLoS neglected tropical diseases 7, e2046 (2013).
11. M. H. Kothary, E. F. Claverie, M. D. Miliotis, J. M. Madden, S. H. Richardson, Purification and characterization of a Chinese hamster ovary cell elongation factor of *Vibrio hollisae*. Infection and immunity 63, 2418-2423 (1995).
12. A. K. Gloudemans et al., The mucosal adjuvant cholera toxin B instructs non-mucosal dendritic cells to promote IgA production via retinoic acid and TGF-beta. PLoS One 8, e59822 (2013).
13. L. Guo et al., Prophylactic and therapeutic efficacy of the epitope vaccine CTB-UA against *Helicobacter pylori* infection in a BALB/c mice model. Applied microbiology and biotechnology 95, 1437-1444 (2012).
14. D. M. Gonzalez, D. Medici, Signaling mechanisms of the epithelial-mesenchymal transition. Science signaling 7, re8 (2014).
15. P. Biancheri et al., The role of transforming growth factor (TGF)-beta in modulating the immune response and fibrogenesis in the gut. Cytokine Growth Factor Rev 25, 45-55 (2014). 16. A. Sturm, A. U. Dignass, Epithelial restitution and wound healing in inflammatory bowel disease. World J Gastroenterol 14, 348-353 (2008).
17. P. Balogh, S. Katz, A. L. Kiss, The role of endocytic pathways in TGF-beta signaling. Pathol Oncol Res 19, 141-148 (2013).
18. G. Jego, A. Hazoume, R. Seigneuric, C. Garrido, Targeting heat shock proteins in cancer. Cancer Lett 332, 275-285 (2013).
19. G. D. Lianos et al., The role of heat shock proteins in cancer. Cancer Lett 360, 114-118 (2015).
20. T. Kayashima et al., Consumption of vitamin B6 reduces colonic damage and protein expression of HSP70 and HO-1, the anti-tumor targets, in rats exposed to 1,2-dimethylhydrazine. Oncol Lett 2, 1243-1246 (2011).
21. V. Khattar, J. Fried, B. Xu, J. V. Thottassery, Cks1 proteasomal degradation is induced by inhibiting Hsp90-mediated chaperoning in cancer cells. Cancer Chemother Pharmacol 75, 411-420 (2015).
22. J. S. Chen et al., Secreted heat shock protein 90alpha induces colorectal cancer cell invasion through CD91/LRP-1 and NF-kappaB-mediated integrin alphaV expression. The Journal of biological chemistry 285, 25458-25466 (2010).
23. S. Baindur-Hudson, A. L. Edkins, G. L. Blatch, Hsp70/Hsp90 organising protein (hop): beyond interactions with chaperones and prion proteins. Subcell Biochem 78, 69-90 (2015).
24. F. F. Anhe et al., A polyphenol-rich cranberry extract protects from diet-induced obesity, insulin resistance and intestinal inflammation in association with increased Akkermansia spp. population in the gut microbiota of mice. Gut 64, 872-883 (2015).
25. F. Gutierrez-Orozco et al., Intestinal microbial dysbiosis and colonic epithelial cell hyperproliferation by dietary alpha-mangostin is independent of mouse strain. Nutrients 7, 764-784 (2015).
26. P. Desreumaux, S. Ghosh, Review article: mode of action and delivery of 5-aminosalicylic acid—new evidence. Aliment Pharmacol Ther 24 Suppl 1, 2-9 (2006).
27. G. Bamias, G. Kaltsa, S. D. Ladas, Cytokines in the pathogenesis of ulcerative colitis. Discov Med 11, 459-467 (2011).
28. M. H. Zaki, M. Lamkanfi, T. D. Kanneganti, The Nlrp3 inflammasome: contributions to intestinal homeostasis. Trends Immunol 32, 171-179 (2011).
29. J. Dabritz et al., Reprogramming of monocytes by GM-CSF contributes to regulatory immune functions during intestinal inflammation. J Immunol 194, 2424-2438 (2015).
30. D. C. Lacey et al., Defining GM-CSF- and macrophage-CSF-dependent macrophage responses by in vitro models. J Immunol 188, 5752-5765 (2012).

31. I. Matos, A. F. Bento, R. Marcon, R. F. Claudino, J. B. Calixto, Preventive and therapeutic oral administration of the pentacyclic triterpene alpha,beta-amyrin ameliorates dextran sulfate sodium-induced colitis in mice: the relevance of cannabinoid system. Mol Immunol 54, 482-492 (2013).
32. S. Wirtz, C. Neufert, B. Weigmann, M. F. Neurath, Chemically induced mouse models of intestinal inflammation. Nature protocols 2, 541-546 (2007).
33. N. A. Williams, T. R. Hirst, T. O. Nashar, Immune modulation by the cholera-like enterotoxins: from adjuvant to therapeutic. Immunology today 20, 95-101 (1999).
34. N. A. Williams, Immune modulation by the cholera-like enterotoxin B-subunits: from adjuvant to immunotherapeutic. International journal of medical microbiology: IJMM 290, 447-453 (2000).
35. A. D'Ambrosio, M. Colucci, O. Pugliese, F. Quintieri, M. Boirivant, Cholera toxin B subunit promotes the induction of regulatory T cells by preventing human dendritic cell maturation. J Leukoc Biol 84, 661-668 (2008).
36. V. Burkart et al., Cholera toxin B pretreatment of macrophages and monocytes diminishes their proinflammatory responsiveness to lipopolysaccharide. J Immunol 168, 1730-1737 (2002).
37. M. Kaplan, B. B. Mentes, E. Tatlicioglu, B. Kayhan, C. Aybay, Effect of mucosal immunomodulation with fed cholera toxin on healing of experimental colonic anastomosis. Diseases of the colon and rectum 45, 819-825 (2002).
38. P. H. Kim, L. Eckmann, W. J. Lee, W. Han, M. F. Kagnoff, Cholera toxin and cholera toxin B subunit induce IgA switching through the action of TGF-beta 1. J Immunol 160, 1198-1203 (1998).
39. A. Hameedaldeen, J. Liu, A. Batres, G. S. Graves, D. T. Graves, FOXO1, TGF-beta regulation and wound healing. International journal of molecular sciences 15, 16257-16269 (2014).
40. Y. Jung, M. E. Rothenberg, Roles and regulation of gastrointestinal eosinophils in immunity and disease. J Immunol 193, 999-1005 (2014).
41. Y. Wang et al., Tumor-derived GM-CSF promotes inflammatory colon carcinogenesis via stimulating epithelial release of VEGF. Cancer Res 74, 716-726 (2014).
42. K. R. Cutroneo, TGF-beta-induced fibrosis and SMAD signaling: oligo decoys as natural therapeutics for inhibition of tissue fibrosis and scarring. Wound Repair Regen 15 Suppl 1, S54-60 (2007).
43. W. Liu et al., A novel benzo[d]imidazole derivate prevents the development of dextran sulfate sodium-induced murine experimental colitis via inhibition of NLRP3 inflammasome. Biochem Pharmacol 85, 1504-1512 (2013).
44. L. A. Dieleman et al., Chronic experimental colitis induced by dextran sulphate sodium (DSS) is characterized by Th1 and Th2 cytokines. Clin Exp Immunol 114, 385-391 (1998).
45. M. Yue, Z. Shen, C. H. Yu, H. Ye, Y. M. Li, The therapeutic role of oral tolerance in dextran sulfate sodium-induced colitis via Th1-Th2 balance and gammadelta T cells. Journal of digestive diseases 14, 543-551 (2013).
46. K. Karlinger, T. Gyorke, E. Mako, A. Mester, Z. Tarjan, The epidemiology and the pathogenesis of inflammatory bowel disease. European journal of radiology 35, 154-167 (2000). 47. G. Latella, C. Papi, Crucial steps in the natural history of inflammatory bowel disease. World J Gastroenterol 18, 3790-3799 (2012).
48. M. A. Engel, M. Khalil, M. F. Neurath, Highlights in inflammatory bowel disease—from bench to bedside. Clinical chemistry and laboratory medicine: CCLM/FESCC 50, 1229-1235 (2012).
49. G. Monteleone, R. Caruso, F. Pallone, Targets for new immunomodulation strategies in inflammatory bowel disease. Autoimmun Rev 13, 11-14 (2014).
50. A. Geremia, P. Biancheri, P. Allan, G. R. Corazza, A. Di Sabatino, Innate and adaptive immunity in inflammatory bowel disease. Autoimmun Rev 13, 3-10 (2014).
51. A. M. Globig et al., Comprehensive intestinal T helper cell profiling reveals specific accumulation of IFN-gamma IL-17 coproducing CD4$^+$ T cells in active inflammatory bowel disease. Inflamm Bowel Dis 20, 2321-2329 (2014).
52. R. Siegel, D. Naishadham, A. Jemal, Cancer statistics, 2012. CA Cancer J Clin 62, 10-29 (2012).
53. P. Munkholm, Review article: the incidence and prevalence of colorectal cancer in inflammatory bowel disease. Aliment Pharmacol Ther 18 Suppl 2, 1-5 (2003).
54. M. Doulberis et al., Cholera-toxin suppresses carcinogenesis in a mouse model of inflammation-driven sporadic colon cancer. Carcinogenesis 36, 280-290 (2015).
55. K. Bulut et al., Glucagon-like peptide 2 improves intestinal wound healing through induction of epithelial cell migration in vitro-evidence for a TGF-beta-mediated effect. Regul Pept 121, 137-143 (2004).
56. 56. H. S. Cooper, S. N. Murthy, R. S. Shah, D. J. Sedergran, Clinicopathologic study of dextran sulfate sodium experimental murine colitis. Laboratory investigation; a journal of technical methods and pathology 69, 238-249 (1993).
57. Jelinek, T., Kollaritsch, H. Vaccination with Dukoral against travelers' diarrhea (ETEC) and cholera. Expert Rev Vaccines. 5, 561-567 (2008).
58. Hamorsky, K. T., Kouokam, J. C., Bennett, L. J., Baldauf, K. J, Kajiura, H., Fujiyama, K., Matoba, N. Rapid and Scalable Plant-based Production of a Cholera Toxin B Subunit Variant to Aid in Mass Vaccination against Cholera Outbreaks. PLoS Negl Trop Dis. 7(3), e2046 (2013).
59. Smits, H H., Gloudemans, A K., van Nimwegen, M., Willart, M A., Soullie, T., Muskens, F., et al. Cholera toxin B suppresses allergic inflammation through induction of secretory IgA. Mucosal Immunol. 4, 331-339 (2009).
60. Stanford, M., Whittall, T., Bergmeier, L A., Lindblad, M., Lundin, S., Shinnick, T., et al. Oral tolerization with peptide 336-351 linked to cholera toxin B subunit in preventing relapses of uveitis in Behcet's disease. Clin Exp Immunol 137(1), 201-208 (2004).
61. Boirivant, M., Fuss, I J., Ferroni, L., Pascale, M D., & Strober, W. Oral administration of Recombinant Cholera Toxin Subunit B Inhibits IL-12-Mediated Murine Experimental (Trinitrobenzene Sulfonic Acid) Colitis. J Immunol. 166, 3522-3532 (2001).
62. Sun, J B., Czerkinsky, C., Holmgren, J. Mucosally induced immunological tolerance, regulatory T cells and the adjuvant effect by cholera toxin B subunit. Scand J Immunol. 71(1), 1-11 (2010).
63. Ordas, I., Eckmann, L., Talamini, M., Baumgart, D C., & Sandborn, W J. Ulcerative Colitis. Lancet. 380(9853), 1606-19 (2012).
64. Doulberis, M., Angelopoulou, K., Kaldrymidou, E., Tsingotjidou, A., Abas, Z., Erdman, S E., Poutahidis, T. Carcinogenesis. 36(2), 280-290 (2015).

65. Cooper, H. S., Murthy, S. N. S., Shah R. S., Sedergran, D J. Clinicopathologic Study of Dextran Sulfate Sodium Experimental Murine Colitis. Lab Invest. 69(2), 238-49.
66. Jelinek, T., Kollaritsch, H. Vaccination with Dukoral against travelers' diarrhea (ETEC) and cholera. Expert Rev Vaccines. 5, 561-567 (2008).
67. Smits, H H., Gloudemans, A K., van Nimwegan, M., Willart, M A., Soullie, T., Muskens, F., et al. Cholera toxin B suppresses allergic inflammation through induction of secretory IgA. Mucosal Immunol. 4, 331-339 (2009).
68. Stanford, M., Whittall, T., Bergmeier, L A., Lindblad, M., Lundin, S., Shinnick, T., et al. Oral tolerization with peptide 336-351 linked to cholera toxin B subunit in preventing relapses of uveitis in Behcet's disease. Clin Exp Immunol 137(1), 201-208 (2004).
69. Boirivant, M., Fuxx, I J., Ferroni, L., Pascale, M D., & Strober, W. Oral administration of Recombinant Cholera Toxin Subunit B Inhibits IL-12-Mediated Murine Experimental (Trinitrobenzene Sulfonic Acid) Colitis. J Immunol. 166, 3522-3532 (2001).
70. Sun, J B., Czerkinsky, C., Holmgren, J. Mucosally induced immunological tolerance, regulatory T cells and the adjuvant effect by cholera toxin B subunit. Scand J Immunol. 71(1), 1-11 (2010).
71. Ordas, I., Exckmann, L., Talamini, M., Baumgart, D C., & Sandborn, W J. Ulcerative Colitis. Lancet. 380(9853), 1606-19 (2012).
72. Hamorsky, K. T., Kouckam, J. C., Bennett, L. J., Baldauf, K. J., Kajiura, H., Fujiyama, K., Matoba, N. Rapid and Scalable Plant-based Production of a Cholera Toxin B Subunit Variant to Aid in Mass Vaccination against Cholera Outbreaks. PLoS Negl Trop Dis. 7(3), c2046 (2013).
73. J. Sanchez, J. Holmgren. Cholera toxin structure, gene regulation and pathophysiological and immunological aspects. Cell Mol Life Sci 65. 1347-1360 (2008).
74. R. G. Zhang, M. L. Westbrook, E. M. Westbrook, D. L. Scott, Z. Otwinowski, P. R. Maulik, R. A. Reed, G. G. Shipley. The 2.4 A crystal structure of cholera toxin B subunit pentamer: choleragenoid. Journal of molecular biology 251. 550-562 (1995).
75. T. Jelinek, H. Kollaritsch. Vaccination with Dukoral against travelers' diarrhea (ETEC) and cholera. Expert Rev Vaccines 7. 561-567 (2008).
76. J. Clemens, S. Shin, D. Sur, G. B. Nair, J. Holmgren. New-generation vaccines against cholera. Nature reviews. Gastroenterology & hepatology 8. 701-710 (2011).
77. J. Holmgren, J. Adamsson, F. Anjuere, J. Clemens, C. Czerkinsky, K. Eriksson, C. F. Flach, A. George-Chandy, A. M. Harandi, M. Lebens, T. Lehner, M. Lindblad, E. Nygren, S. Raghavan, J. Sanchez, M. Stanford, J. B. Sun, A. M. Svennerholm, S. Tengvall. Mucosal adjuvants and anti-infection and anti-immunopathology vaccines based on cholera toxin, cholera toxin B subunit and CpG DNA. Immunology letters 97. 181-188 (2005).
78. K. J. Baldauf, J. M. Royal, K. T. Hamorsky, N. Matoba. Cholera toxin B: one subunit with many pharmaceutical applications. Toxins (Basel) 7. 974-996 (2015).
79. J. B. Sun, C. Czerkinsky, J. Holmgren. Mucosally induced immunological tolerance, regulatory T cells and the adjuvant effect by cholera toxin B subunit. Scand J Immunol 71. 1-11 (2010).
80. H. H. Smits, A. K. Gloudemans, M. van Nimwegen, M. A. Willart, T. Soullie, F. Muskens, E. C. de Jong, L. Boon, C. Pilette, F. E. Johansen, H. C. Hoogsteden, H. Hammad, B. N. Lambrecht. Cholera toxin B suppresses allergic inflammation through induction of secretory IgA. Mucosal Immunol 2. 331-339 (2009).
81. M. Stanford, T. Whittall, L. A. Bergmeier, M. Lindblad, S. Lundin, T. Shinnick, Y. Mizushima, J. Holmgren, T. Lehner. Oral tolerization with peptide 336-351 linked to cholera toxin B subunit in preventing relapses of uveitis in Behcet's disease. Clin Exp Immunol 137. 201-208 (2004).
82. E. M. Coccia, M. E. Remoli, C. Di Giacinto, B. Del Zotto, E. Giacomini, G. Monteleone, M. Boirivant. Cholera toxin subunit B inhibits IL-12 and IFN-{gamma} production and signaling in experimental colitis and Crohn's disease. Gut 54. 1558-1564 (2005).
83. P. Stal, R. Befrits, A. Ronnblom, A. Danielsson, O. Suhr, D. Stahlberg, A. Brinkberg Lapidus, R. Lofberg. Clinical trial: the safety and short-term efficacy of recombinant cholera toxin B subunit in the treatment of active Crohn's disease. Aliment Pharmacol Ther 31. 387-395 (2010).
84. K. T. Hamorsky, J. C. Kouokam, L. J. Bennett, K. J. Baldauf, H. Kajiura, K. Fujiyama, N. Matoba. Rapid and scalable plant-based production of a cholera toxin B subunit variant to aid in mass vaccination against cholera outbreaks. PLoS neglected tropical diseases 7. e2046 (2013).
85. K. T. Hamorsky, J. C. Kouokam, J. M. Jurkiewicz, B. Nelson, L. J. Moore, A. S. Husk, H. Kajiura, K. Fujiyama, N. Matoba. N-glycosylation of cholera toxin B subunit in *Nicotiana benthamiana*: impacts on host stress response, production yield and vaccine potential. Sci Rep 5. 8003 (2015).
86. A. K. Gloudemans, M. Plantinga, M. Guilliams, M. A. Willart, A. Ozir-Fazalalikhan, A. van der Ham, L. Boon, N. L. Harris, H. Hammad, H. C. Hoogsteden, M. Yazdanbakhsh, R. W. Hendriks, B. N. Lambrecht, H. H. Smits. The mucosal adjuvant cholera toxin B instructs non-mucosal dendritic cells to promote IgA production via retinoic acid and TGF-beta. PLoS One 8. e59822 (2013).
87. A. Sturm, A. U. Dignass. Epithelial restitution and wound healing in inflammatory bowel disease. World J Gastroenterol 14. 348-353 (2008).
88. P. Balogh, S. Katz, A. L. Kiss. The role of endocytic pathways in TGF-beta signaling. Pathol Oncol Res 19. 141-148 (2013).
89. G. D. Lianos, G. A. Alexiou, A. Mangano, A. Mangano, S. Rausei, L. Boni, G. Dionigi, D. H. Roukos. The role of heat shock proteins in cancer. Cancer Lett 360. 114-118 (2015).
90. J. S. Chen, Y. M. Hsu, C. C. Chen, L. L. Chen, C. C. Lee, T. S. Huang. Secreted heat shock protein 90alpha induces colorectal cancer cell invasion through CD91/LRP-1 and NF-kappaB-mediated integrin alphaV expression. The Journal of biological chemistry 285. 25458-25466 (2010).
91. E. Ruckova, P. Muller, R. Nenutil, B. Vojtesek. Alterations of the Hsp70/Hsp90 chaperone and the HOP/CHIP co-chaperone system in cancer. Cell Mol Biol Lett 17. 446-458 (2012).
92. K. Bulut, J. J. Meier, N. Ansorge, P. Felderbauer, F. Schmitz, P. Hoffmann, W. E. Schmidt, B. Gallwitz. Glucagon-like peptide 2 improves intestinal wound healing through induction of epithelial cell migration in vitro-evidence for a TGF-beta-mediated effect. Regul Pept 121. 137-143 (2004).
93. S. Wirtz, C. Neufert, B. Weigmann, M. F. Neurath. Chemically induced mouse models of intestinal inflammation. Nature protocols 2. 541-546 (2007).
94. Y. L. Jones-Hall, M. B. Grisham. Immunopathological characterization of selected mouse models of inflammatory bowel disease: Comparison to human disease. Pathophysiology 21. 267-288 (2014).
95. P. Desreumaux, S. Ghosh. Review article: mode of action and delivery of 5-aminosalicylic acid—new evidence. Aliment Pharmacol Ther 24 Suppl 1. 2-9 (2006).
96. G. Bamias, G. Kaltsa, S. D. Ladas. Cytokines in the pathogenesis of ulcerative colitis. Discov Med 11. 459-467 (2011).
97. M. H. Zaki, M. Lamkanfi, T. D. Kanneganti. The Nlrp3 inflammasome: contributions to intestinal homeostasis. Trends Immunol 32. 171-179 (2011).
98. J. Dabritz, T. Weinhage, G. Varga, T. Wirth, K. Walscheid, A. Brockhausen, D. Schwarzmaier, M. Bruckner, M. Ross, D. Bettenworth, J. Roth, J. M. Ehrchen, D. Foell. Reprogramming of monocytes by GM-CSF contributes to regulatory immune functions during intestinal inflammation. J Immunol 194. 2424-2438 (2015).
99. D. C. Lacey, A. Achuthan, A. J. Fleetwood, H. Dinh, J. Roiniotis, G. M. Scholz, M. W. Chang, S. K. Beckman, A. D. Cook, J. A. Hamilton. Defining GM-CSF- and macrophage-CSF-dependent macrophage responses by in vitro models. J Immunol 188. 5752-5765 (2012). 100. J. B. Sun, C. Czerkinsky, J. Holmgren. B Lymphocytes Treated In Vitro with Antigen Coupled to Cholera Toxin B Subunit Induce Antigen-Specific Foxp3(+) Regulatory T Cells and Protect against Experimental Autoimmune Encephalomyelitis. Journal of Immunology 188. 1686-1697 (2012).
101. M. Doulberis, K. Angelopoulou, E. Kaldrymidou, A. Tsingotjidou, Z. Abas, S. E. Erdman, T. Poutahidis. Cholera-toxin suppresses carcinogenesis in a mouse model of inflammation-driven sporadic colon cancer. Carcinogenesis 36. 280-290 (2015).
102. D. Ma, D. Wolvers, A. M. Stanisz, J. Bienenstock. Interleukin-10 and nerve growth factor have reciprocal upregulatory effects on intestinal epithelial cells. Am J Physiol Regul Integr Comp Physiol 284. R1323-1329 (2003).
103. P. A. Phipps, M. R. Stanford, J. B. Sun, B. G. Xiao, J. Holmgren, T. Shinnick, A. Hasan, Y. Mizushima, T. Lehner. Prevention of mucosally induced uveitis with a HSP60-derived peptide linked to cholera toxin B subunit. Eur J Immunol 33. 224-232 (2003).
104. P. H. Kim, L. Eckmann, W. J. Lee, W. Han, M. F. Kagnoff. Cholera toxin and cholera toxin B subunit induce IgA switching through the action of TGF-beta 1. J Immunol 160. 1198-1203 (1998).
105. J. B. Sun, B. G. Xiao, M. Lindblad, B. L. Li, H. Link, C. Czerkinsky, J. Holmgren. Oral administration of cholera toxin B subunit conjugated to myelin basic protein protects against experimental autoimmune encephalomyelitis by inducing transforming growth factor-beta-secreting cells and suppressing chemokine expression. Int Immunol 12. 1449-1457 (2000).
106. J. B. Sun, B. L. Li, C. Czerkinsky, J. Holmgren. Enhanced immunological tolerance against allograft rejection by oral administration of allogeneic antigen linked to cholera toxin B subunit. Clin Immunol 97. 130-139 (2000).
107. C. Aspord, C. Thivolet. Nasal administration of CTB-insulin induces active tolerance against autoimmune diabetes in non-obese diabetic (NOD) mice. Clin Exp Immunol 130. 204-211 (2002).
108. P. Biancheri, P. Giuffrida, G. H. Docena, T. T. MacDonald, G. R. Corazza, A. Di Sabatino. The role of transforming growth factor (TGF)-beta in modulating the immune response and fibrogenesis in the gut. Cytokine Growth Factor Rev 25. 45-55 (2014).
109. M. F. Neurath. New targets for mucosal healing and therapy in inflammatory bowel diseases. Mucosal Immunol 7. 6-19 (2014).
110. H. Oshima, M. Nakayama, T. S. Han, K. Naoi, X. Ju, Y. Maeda, S. Robine, K. Tsuchiya, T. Sato, H. Sato, M. M. Taketo, M. Oshima. Suppressing TGFbeta signaling in regenerating epithelia in an inflammatory microenvironment is sufficient to cause invasive intestinal cancer. Cancer Res 75. 766-776 (2015).
111. M. Stahle-Backdahl, J. Maim, B. Veress, C. Benoni, K. Bruce, A. Egesten. Increased presence of eosinophilic granulocytes expressing transforming growth factor-beta1 in collagenous colitis. Scand J Gastroenterol 35. 742-746 (2000).
112. K. Suzuki, X. Sun, M. Nagata, T. Kawase, H. Yamaguchi, V. Sukumaran, Y. Kawauchi, H. Kawachi, T. Nishino, K. Watanabe, H. Yoneyama, H. Asakura. Analysis of intestinal fibrosis in chronic colitis in mice induced by dextran sulfate sodium. Pathol Int 61. 228-238 (2011).
113. N. A. Williams, T. R. Hirst, T. O. Nashar. Immune modulation by the cholera-like enterotoxins: from adjuvant to therapeutic. Immunology today 20. 95-101 (1999).
114. N. A. Williams. Immune modulation by the cholera-like enterotoxin B-subunits: from adjuvant to immunotherapeutic. International journal of medical microbiology: IJMM 290. 447-453 (2000).
115. A. D'Ambrosio, M. Colucci, O. Pugliese, F. Quintieri, M. Boirivant. Cholera toxin B subunit promotes the induction of regulatory T cells by preventing human dendritic cell maturation. J Leukoc Biol 84. 661-668 (2008).
116. V. Burkart, Y. E. Kim, B. Hartmann, I. Ghiea, U. Syldath, M. Kauer, W. Fingberg, P. Hanifi-Moghaddam, S. Muller, H. Kolb. Cholera toxin B pretreatment of macrophages and monocytes diminishes their proinflammatory responsiveness to lipopolysaccharide. J Immunol 168. 1730-1737 (2002).
117. F. F. Anhe, D. Roy, G. Pilon, S. Dudonne, S. Matamoros, T. V. Varin, C. Garofalo, Q. Moine, Y. Desjardins, E. Levy, A. Marette. A polyphenol-rich cranberry extract protects from diet-induced obesity, insulin resistance and intestinal inflammation in association with increased Akkermansia spp. population in the gut microbiota of mice. Gut 64. 872-883 (2015).
118. F. Gutierrez-Orozco, J. M. Thomas-Ahner, J. D. Galley, M. T. Bailey, S. K. Clinton, G. B. Lesinski, M. L. Failla. Intestinal microbial dysbiosis and colonic epithelial cell hyperproliferation by dietary alpha-mangostin is independent of mouse strain. Nutrients 7. 764-784 (2015).
119. J. M. Davies, M. T. Abreu. The innate immune system and inflammatory bowel disease. Scand J Gastroenterol 50. 24-33 (2015).
120. M. Gross, T. M. Salame, S. Jung. Guardians of the Gut-Murine Intestinal Macrophages and Dendritic Cells. Frontiers in immunology 6. 254 (2015).
121. G. Leoni, P. A. Neumann, R. Sumagin, T. L. Denning, A. Nusrat. Wound repair: role of immune-epithelial interactions. Mucosal Immunol 8. 959-968 (2015).
122. J. E. Qualls, H. Tuna, A. M. Kaplan, D. A. Cohen. Suppression of experimental colitis in mice by CD11c+ dendritic cells. Inflamm Bowel Dis 15. 236-247 (2009).
123. T. Lysakova-Devine, C. O'Farrelly. Tissue-specific NK cell populations and their origin. J Leukoc Biol 96. 981-990 (2014).

124. P. Kiesler, I. J. Fuss, W. Strober. Experimental Models of Inflammatory Bowel Diseases. Cell Mol Gastroenterol Hepatol 1. 154-170 (2015).
125. C. Bezzio, F. Furfaro, R. de Franchis, G. Maconi, A. K. Asthana, S. Ardizzone. Ulcerative colitis: current pharmacotherapy and future directions. Expert Opin Pharmacother 15. 1659-1670 (2014).
126. F. Furfaro, C. Bezzio, S. Ardizzone, A. Massari, R. de Franchis, G. Maconi. Overview of biological therapy in ulcerative colitis: current and future directions. J Gastrointestin Liver Dis 24. 203-213 (2015).
127. B. P. Vaughn, S. Shah, A. S. Cheifetz. The role of mucosal healing in the treatment of patients with inflammatory bowel disease. Curr Treat Options Gastroenterol 12. 103-117 (2014).
128. R. A. Irizarry, B. Hobbs, F. Collin, Y. D. Beazer-Barclay, K. J. Antonellis, U. Scherf, T. P. Speed. Exploration, normalization, and summaries of high density oligonucleotide array probe level data. Biostatistics 4. 249-264 (2003).
129. I. Matos, A. F. Bento, R. Marcon, R. F. Claudino, J. B. Calixto. Preventive and therapeutic oral administration of the pentacyclic triterpene alpha,beta-amyrin ameliorates dextran sulfate sodium-induced colitis in mice: the relevance of cannabinoid system. Mol Immunol 54. 482-492 (2013).
130. H. S. Cooper, S. N. Murthy, R. S. Shah, D. J. Sedergran. Clinicopathologic study of dextran sulfate sodium experimental murine colitis. Laboratory investigation; a journal of technical methods and pathology 69. 238-249 (1993).
131. Hamorsky, et al., "Rapid and Scalable Plant-based Production of a Cholera Toxin B Subunit Variant to Aid in Mass Vaccination against Cholera Outbreaks." PLoSNTD. March 2013. 7(3): e2046.
132. Doulberis, M., et al. Cholera-toxin suppresses carcinogenesis in a mouse model of inflammation-driven sporadic colon cancer. Carcinogenesis. 36(2). 280-290. (2015).
133. International Patent Application No. PCT/US12/29072.

It will be understood that various details of the presently-disclosed subject matter can be changed without departing from the scope of the subject matter disclosed herein. Furthermore, the foregoing description is for the purpose of illustration only, and not for the purpose of limitation.

What is claimed is:

1. A method of promoting mucosal wound healing, comprising administering to a subject in need thereof an effective amount of a cholera toxin B subunit variant comprising an endoplasmic reticulum (ER) retention sequence attached to its C-terminus.

2. The method of claim 1, wherein the C-terminal ER retention sequence comprises a hexapeptide sequence.

3. The method of claim 1, wherein the C-terminal ER retention sequence comprises SEKDEL (SEQ ID NO: 30), KDEL (SEQ ID NO: 31), or HDEL (SEQ ID NO: 32).

4. The method of claim 1, wherein the C-terminal ER retention sequence comprises KDEL (SEQ ID NO: 31).

5. The method of claim 1, wherein the cholera toxin B subunit variant further comprises an Asn4 to Ser mutation.

6. The method of claim 1, wherein the cholera toxin B subunit variant further comprises a secretory signal peptide selected from a rice alpha-amylase secretory signal peptide, a *Nicotiana plumbagenifolia* calreticulin secretory signal peptide, an apple pectinase secretory signal peptide, or a barley alpha-amylase secretory signal peptide.

7. The method of claim 6, wherein the secretory signal peptide comprises the rice alpha-amylase secretory signal peptide.

8. The method of claim 1, wherein the cholera toxin B subunit variant comprises two or more N-linked glycosylation sequons.

9. The method of claim 1, wherein the cholera toxin B subunit variant comprises an amino acid sequence selected from SEQ ID NO: 4, 5, 8, 10, 12, 14, 25, 26, 27, 28, or 29.

10. The method of claim 1, wherein the cholera toxin B subunit variant comprises the amino acid sequence of SEQ ID NO: 4.

11. The method of claim 1, wherein the cholera toxin B subunit variant is substantially immunologically identical to a cholera toxin B subunit.

12. The method of claim 1, wherein the composition is administered to the subject without significantly changing a fecal microbiome of the subject.

13. The method of claim 1, wherein the administering of the composition comprises oral administration.

14. The method of claim 1, wherein the administering of the composition decreases protein levels of tumor promoting cytokines.

15. The method of claim 1, wherein the method promotes mucosal wound healing in the colon.

16. The method of claim 15, wherein the C-terminal ER retention sequence comprises a hexapeptide sequence.

17. The method of claim 15, wherein the C-terminal ER retention sequence comprises SEKDEL (SEQ ID NO: 30), KDEL (SEQ ID NO: 31), or HDEL (SEQ ID NO: 32).

18. The method of claim 15, wherein the C-terminal ER retention sequence comprises KDEL (SEQ ID NO: 31).

19. The method of claim 15, wherein the cholera toxin B subunit variant comprises the amino acid sequence of SEQ ID NO: 4.

20. The method of claim 15, wherein the administering of the composition comprises oral administration.

* * * * *

SEQUENCE LISTING

```
<160> NUMBER OF SEQ ID NOS: 32

<210> SEQ ID NO 1
<211> LENGTH: 309
<212> TYPE: DNA
<213> ORGANISM: Vibrio cholerae

<400> SEQUENCE: 1
accccacaaa acatcactga cttgtgtgct gagtaccaca acacccaaat ccacaccctc     60
aatgacaaga tctttagcta caccgagagc cttgctggca agagggagat ggctatcatc    120
accttcaaga atggtgctac cttccaagtg gaggtgcctg gaagccaaca cattgatagc    180
caaaagaagg ccattgagag gatgaaggac acacttagga tagcttacct cactgaggct    240
aaggtggaga agctttgtgt gtggaacaac aagaccccc atgctattgc tgccatcagc    300
atggccaac                                                            309

<210> SEQ ID NO 2
<211> LENGTH: 103
<212> TYPE: PRT
<213> ORGANISM: Vibrio cholerae

<400> SEQUENCE: 2

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100
```

<210> SEQ ID NO 3
<211> LENGTH: 327
<212> TYPE: DNA
<213> ORGANISM: Artificial Sequence
<220> FEATURE:
<223> OTHER INFORMATION: Cholera Toxin B Subunit Polypeptide Variant
      Polypeptide

<400> SEQUENCE: 3

```
accccacaaa gcatcactga cttgtgtgct gagtaccaca cacccaaat ccacaccctc      60 aatgacaaga tctttagcta caccgagagc c

-continued

```
<210> SEQ ID NO 6
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 6

Thr Pro Gln Asn Ile Thr Asp Leu Cys Ala Glu Tyr His Asn Thr Gln
1               5                   10                  15

Ile His Thr Leu Asn Asp Lys Ile Phe Ser T

```
Lys Val Glu Lys Leu Cys Val Trp Asn Asn Lys Thr Pro His Ala Ile
            85                  90                  95

Ala Ala Ile Ser Met Ala Asn Val Thr Lys Asp Glu Leu
            100                 105

<210> SEQ ID NO 9
<211> LENGTH: 327
<212> TYPE: DNA
<213> ORGANISM: Artificial Sequence
<220> FEATURE:
<223> OTHER INFORMATION: Cholera Toxin B Subunit Polypeptide Variant
      Polypeptide

<400> SEQUENCE: 9
accccacaaa acatcactga cttgtgtgct gagtaccaca cacccaaat ccacaccctc     60 aatgacacta tctttagcta caccgagagc cttgctggca agaggagat ggctatcatc   120 accttcaaga atggtgctac cttccaagtg gaggtgcctg gaagccaaca cattgatagc   180
caaaagaagg ccattgagag gatgaaggac acacttagga tagcttacct cactgaggct   240
aaggtggaga agctttgtgt gtggaacaac aagacccccc atgctattgc tgccatcagc   300
atggccaact ccgagaagga tgaactc                                        327

<210> SEQ ID NO 10
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 10

Thr Pro Gln Asn Ile Thr Asp Leu Cys Ala Glu Tyr His Asn Thr Gln
1               5                   10                  15

Ile His Thr Leu Asn Asp Thr Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
            85                  90                  95

Ala Ala Ile Ser Met Ala Asn Ser Glu Lys Asp Glu Leu
            100                 105

<210> SEQ ID NO 11
<211> LENGTH: 327
<212> TYPE: DNA
<213> ORGANISM: Artificial Sequence
<220> FEATURE:
<223> OTHER INFORMATION: Cholera Toxin B Subunit Polypeptide Variant
      Polypeptide

<400> SEQUENCE: 11
accccacaaa acatcactga cttgtgtgct gagtaccaca cacccaaat ccacaccctc     60 aatgacacta tctttagcta caccgagagc cttgctggca agaggagat ggctatcatc   120 accttcaaga atggtgctac cttccaagtg gaggtgcctg gaagccaaca cattgatagc   180
```

```
caaaagaagg ccattgagag gatgaaggac acacttagga tagcttacct cactgaggct    240
aaggtggaga agctttgtgt gtggaacaac aagaccccc atgctattgc tgccatcagc    300
atggccaacg ttactaagga tgaactc                                        327
```

<210> SEQ ID NO 12
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 12

```
Thr Pro Gln Asn Ile Thr Asp Leu Cys Ala Glu Tyr His Asn Thr Gln
1               5                   10                  15

Ile His Thr Leu Asn Asp Thr Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Val Thr Lys Asp Glu Leu
            100                 105
```

<210> SEQ ID NO 13
<211> LENGTH: 345
<212> TYPE: DNA
<213> ORGANISM: Artificial Sequence
<220> FEATURE:
<223> OTHER INFORMATION: Cholera Toxin B Subunit Polypeptide Variant
      Polypeptide

<400> SEQUENCE: 13

```
accccacaaa acatcactga cttgtgtgct gagtaccaca acacccaaat ccacaccctc    60
aatgacacta tctttagcta caccgagagc cttgctggca agagggagat ggctatcatc    120
accttcaaga atggtgctac cttccaagtg gaggtgcctg gaagccaaca cattgatagc    180
caaaagaagg ccattgagag gatgaaggac acacttagga tagcttacct cactgaggct    240
aaggtggaga agctttgtgt gtggaacaac aagaccccc atgctattgc tgccatcagc    300
atggccaacg ttactggtgg tggaggatcc gagaaggatg aactc                    345
```

<210> SEQ ID NO 14
<211> LENGTH: 115
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 14

```
Thr Pro Gln Asn Ile Thr Asp Leu Cys Ala Glu Tyr His Asn Thr Gln
1               5                   10                  15

Ile His Thr Leu Asn Asp Thr Ile Phe Ser Tyr Thr Glu Ser Leu Ala
            20                  25                  30

Gly Lys Arg Glu Met Ala Ile Ile Thr Phe Lys Asn Gly Ala Thr Phe
```

```
                35                  40                  45
Gln Val Glu Val Pro Gly Ser Gln His Ile Asp Ser Gln Lys Lys Ala
 50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Val Thr Gly Gly Gly Ser Glu Lys
            100                 105                 110

Asp Glu Leu
        115

<210> SEQ ID NO 15
<211> LENGTH: 393
<212> TYPE: DNA
<213> ORGANISM: Artificial Sequence
<220> FEATURE:
<223> OTHER INFORMATION: Cholera Toxin B Subunit Polypeptide Variant
      Polypeptide

<400> SEQUENCE: 15
atggctatca agctcaagtt tggagtgttc ttcactgtgc tccttagctc tgcctatgca      60
catggcaccc cacaaaacat cactgacttg tgtgctgagt accacaacac ccaaatccac     120
accctcaatg acaagatctt tagctacacc gagagccttg ctggcaagag ggagatggct     180
atcatcacct tcaagaatgg tgctaccttc caagtggagg tgcctggaag ccaacacatt     240
gatagccaaa agaaggccat tgagaggatg aaggacacac ttaggatagc ttacctcact     300
gaggctaagg tggagaagct ttgtgtgtgg aacaacaaga ccccccatgc tattgctgcc     360
atcagcatgg ccaactccga aaggatgaa ctc                                   393

<210> SEQ ID NO 16
<211> LENGTH: 131
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 16

Met Ala Ile Lys Leu Lys Phe Gly Val Phe Phe Thr Val Leu Leu Ser
1               5                   10                  15

Ser Ala Tyr Ala His Gly Thr Pro Gln Asn Ile Thr Asp Leu Cys Ala
            20                  25                  30

Glu Tyr His Asn Thr Gln Ile His Thr Leu Asn Asp Lys Ile Phe Ser
        35                  40                  45

Tyr Thr Glu Ser Leu Ala Gly Lys Arg Glu Met Ala Ile Ile Thr Phe
    50                  55                  60

Lys Asn Gly Ala Thr Phe Gln Val Glu Val Pro Gly Ser Gln His Ile
65                  70                  75                  80

Asp Ser Gln Lys Lys Ala Ile Glu Arg Met Lys Asp Thr Leu Arg Ile
                85                  90                  95

Ala Tyr Leu Thr Glu Ala Lys Val Glu Lys Leu Cys Val Trp Asn Asn
            100                 105                 110

Lys Thr Pro His Ala Ile Ala Ala Ile Ser Met Ala Asn Ser Glu Lys
        115                 120                 125

Asp Glu Leu
        130
```

<210> SEQ ID NO 17
<211> LENGTH: 78
<212> TYPE: DNA
<213> ORGANISM: Oryza sativa

<400> SEQUENCE: 17

```
atggggaagc aaatggccgc cctgtgtggc tttctcctcg tggcgttgct ctggctcacg    60
cccgacgtcg cgcatggt                                                  78
```

<210> SEQ ID NO 18
<211> LENGTH: 26
<212> TYPE: PRT
<213> ORGANISM: Oryza sativa

<400> SEQUENCE: 18

```
Met Gly Lys Gln Met Ala Ala Leu Cys Gly Phe Leu Leu Val Ala Leu
 1               5                  10                  15

Leu Trp Leu Thr Pro Asp Val Ala His Gly
            20                  25
```

<210> SEQ ID NO 19
<211> LENGTH: 81
<212> TYPE: DNA
<213> ORGANISM: Nicotiana plumbaginifolia

<400> SEQUENCE: 19

```
atggctactc aacgaagggc aaaccctagc tctctccatc taattactgt attctctctg    60
ctcgtcgctg tcgtctcagg t                                              81
```

<210> SEQ ID NO 20
<211> LENGTH: 27
<212> TYPE: PRT
<213> ORGANISM: Nicotiana plumbaginifolia

<400> SEQUENCE: 20

```
Met Ala Thr Gln Arg Arg Ala Asn Pro Ser Ser Leu His Leu Ile Thr
 1               5                  10                  15

Val Phe Ser Leu Leu Val Ala Val Val Ser Gly
            20                  25
```

<210> SEQ ID NO 21
<211> LENGTH: 78
<212> TYPE: DNA
<213> ORGANISM: Malus domestica

<400> SEQUENCE: 21

```
atggcattga agacacagtt gttgtggtca ttcgtggttg tgttcgttgt gtccttcagt    60
acaacttcat gctcaggt                                                  78
```

<210> SEQ ID NO 22
<211> LENGTH: 26
<212> TYPE: PRT
<213> ORGANISM: Malus domestica

<400> SEQUENCE: 22

```
Met Ala Leu Lys Thr Gln Leu Leu Trp Ser Phe Val Val Val Phe Val
 1               5                  10                  15

Val Ser Phe Ser Thr Thr Ser Cys Ser Gly
            20                  25
```

<210> SEQ ID NO 23
<211> LENGTH: 72
<212> TYPE: DNA
<213> ORGANISM: Hordeum vulgare

<400> SEQUENCE: 23
atggcgaaca aacacttgtc cctctccctc ttcctcgtcc tccttggcct gtcggccagc    60
ttggcctcag gt                                                        72

<210> SEQ ID NO 24
<211> LENGTH: 24
<212> TYPE: PRT
<213> ORGANISM: Hordeum vulgare

<400> SEQUENCE: 24

Met Ala Asn Lys His Leu Ser Leu Ser Leu Phe Leu Val Leu Leu Gly
1               5                   10                  15

Leu Ser Ala Ser Leu Ala Ser Gly
            20

<210> SEQ ID NO 25
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 25

Thr Pro Gln Asn Ile Thr Asp Leu Cys Ala Glu Tyr His Asn Thr Gln
1               5                   10                  15

Ile His Thr Leu Asn Asp Lys Ile Phe Cys Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Cys Asn Ser Glu Lys Asp Glu Leu
            100                 105

<210> SEQ ID NO 26
<211> LENGTH: 135
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 26

Met Gly Lys Gln Met Ala Ala Leu Cys Gly Phe Leu Leu Val Ala Leu
1               5                   10                  15

Leu Trp Leu Thr Pro Asp Val Ala His Gly Thr Pro Gln Asn Ile Thr
            20                  25                  30

Asp Leu Cys Ala Glu Tyr His Asn Thr Gln Ile His Thr Leu Asn Asp
        35                  40                  45

Lys Ile Phe Ser Tyr Thr Glu Ser Leu Ala Gly Lys Arg Glu Met Ala

Ile Ile Thr Phe Lys Asn Gly Ala Thr Phe Gln Val Glu Val Pro Gly
65                  70                  75                  80

Ser Gln His Ile Asp Ser Gln Lys Lys Ala Ile Glu Arg Met Lys Asp
                85                  90                  95

Thr Leu Arg Ile Ala Tyr Leu Thr Glu Ala Lys Val Glu Lys Leu Cys
            100                 105                 110

Val Trp Asn Asn Lys Thr Pro His Ala Ile Ala Ala Ile Ser Met Ala
        115                 120                 125

Asn Ser Glu Lys Asp Glu Leu
    130                 135

<210> SEQ ID NO 27
<211> LENGTH: 136
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 27

Met Ala Thr Gln Arg Arg Ala Asn Pro Ser Ser Leu His Leu Ile Thr
1               5                   10                  15

Val Phe Ser Leu Leu Val Ala Val Ser Gly Thr Pro Gln Asn Ile
            20                  25                  30

Thr Asp Leu Cys Ala Glu Tyr His Asn Thr Gln Ile His Thr Leu Asn
            35                  40                  45

Asp Lys Ile Phe Ser Tyr Thr Glu Ser Leu Ala Gly Lys Arg Glu Met
    50                  55                  60

Ala Ile Ile Thr Phe Lys Asn Gly Ala Thr Phe Gln Val Glu Val Pro
65                  70                  75                  80

Gly Ser Gln His Ile Asp Ser Gln Lys Lys Ala Ile Glu Arg Met Lys
                85                  90                  95

Asp Thr Leu Arg Ile Ala Tyr Leu Thr Glu Ala Lys Val Glu Lys Leu
            100                 105                 110

Cys Val Trp Asn Asn Lys Thr Pro His Ala Ile Ala Ala Ile Ser Met
        115                 120                 125

Ala Asn Ser Glu Lys Asp Glu Leu
    130                 135

<210> SEQ ID NO 28
<211> LENGTH: 135
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 28

Met Ala Leu Lys Thr Gln Leu Leu Trp Ser Phe Val Val Phe Val
1               5                   10                  15

Val Ser Phe Ser Thr Thr Ser Cys Ser Gly Thr Pro Gln Asn Ile Thr
            20                  25                  30

Asp Leu Cys Ala Glu Tyr His Asn Thr Gln Ile His Thr Leu Asn Asp
            35                  40                  45

Lys Ile Phe Ser Tyr Thr Glu Ser Leu Ala Gly Lys Arg Glu Met Ala
    50                  55                  60

Ile Ile Thr Phe Lys Asn Gly Ala Thr Phe Gln Val Glu Val Pro Gly 65                  70                  75                  80
Ser Gln His Ile Asp Ser Gln Lys Lys Ala Ile Glu Arg Met Lys Asp
                    85                  90                  95
Thr Leu Arg Ile Ala Tyr Leu Thr Glu Ala Lys Val Glu Lys Leu Cys
                100                 105                 110
Val Trp Asn Asn Lys Thr Pro His Ala Ile Ala Ala Ile Ser Met Ala
            115                 120                 125
Asn Ser Glu Lys Asp Glu Leu
        130                 135

<210> SEQ ID NO 29
<211> LENGTH: 133
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 29

Met Ala Asn Lys His Leu Ser Leu Ser Leu Phe Leu Val Leu Leu Gly
1               5                   10                  15
Leu Ser Ala Ser Leu Ala Ser Gly Thr Pro Gln Asn Ile Thr Asp Leu
            20                  25                  30
Cys Ala Glu Tyr His Asn Thr Gln Ile His Thr Leu Asn Asp Lys Ile
        35                  40                  45
Phe Ser Tyr Thr Glu Ser Leu Ala Gly Lys Arg Glu Met Ala Ile Ile
    50                  55                  60
Thr Phe Lys Asn Gly Ala Thr Phe Gln Val Glu Val Pro Gly Ser Gln
65                  70                  75                  80
His Ile Asp Ser Gln Lys Lys Ala Ile Glu Arg Met Lys Asp Thr Leu
                85                  90                  95
Arg Ile Ala Tyr Leu Thr Glu Ala Lys Val Glu Lys Leu Cys Val Trp
            100                 105                 110
Asn Asn Lys Thr Pro His Ala Ile Ala Ala Ile Ser Met Ala Asn Ser
        115                 120                 125
Glu Lys Asp Glu Leu
    130

<210> SEQ ID NO 30
<211> LENGTH: 6
<212> TYPE: PRT
<213> ORGANISM: Artificial Sequence
<220> FEATURE:
<223> OTHER INFORMATION: Endoplasmic Reticulum Retention Signal

<400> SEQUENCE: 30

Ser Glu Lys Asp Glu Leu
1               5

<210> SEQ ID NO 31
<211> LENGTH: 4
<212> TYPE: PRT
<213> ORGANISM: Artificial Sequence
<220> FEATURE:
<223> OTHER INFORMATION: Endoplasmic Reticulum Retention Signal

<400> SEQUENCE: 31

Lys Asp Glu Leu
1

```
<210> SEQ ID NO 32
<211> LENGTH: 4
<212> TYPE: PRT
<213> ORGANISM: Artificial Sequence
<220> FEATURE:
<223> OTHER INFORMATION: Endoplasmic Reticulum Retention Signal

<400> SEQUENCE: 32

His Asp Glu Leu
1
```